(12) United States Patent
Chesworth et al.

(10) Patent No.: US 9,540,380 B2
(45) Date of Patent: Jan. 10, 2017

(54) IMIDAZOTRIAZINONE COMPOUNDS

(71) Applicant: Ironwood Pharmaceuticals, Inc., Cambridge, MA (US)

(72) Inventors: Richard Chesworth, Concord, MA (US); Gerhard Koenig, Newton, MA (US); Amy Ripka, Reading, MA (US); Gideon Shapiro, Gainesville, FL (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 129 days.

(21) Appl. No.: 14/334,073

(22) Filed: Jul. 17, 2014

(65) Prior Publication Data

US 2014/0330014 A1 Nov. 6, 2014

Related U.S. Application Data

(63) Continuation of application No. 13/237,795, filed on Sep. 20, 2011, now abandoned.

(60) Provisional application No. 61/384,694, filed on Sep. 20, 2010.

(51) Int. Cl.
  C07D 487/04 (2006.01)
  A61K 31/53 (2006.01)

(52) U.S. Cl.
  CPC ................... *C07D 487/04* (2013.01)

(58) Field of Classification Search
  CPC ................... A61K 31/53; A61K 25/88
  See application file for complete search history.

(56) References Cited

U.S. PATENT DOCUMENTS

| 2004/0067945 A1 | 4/2004 | Niewohner et al. |
| 2004/0220186 A1 | 11/2004 | Bell et al. |
| 2004/0254187 A1 | 12/2004 | Alonso-Alija et al. |
| 2006/0264624 A1 | 11/2006 | Heim-Riether et al. |
| 2009/0030003 A1 | 1/2009 | Verhoest et al. |
| 2009/0163521 A1 | 6/2009 | Tadiparthi et al. |
| 2011/0183976 A1 | 7/2011 | Ripka et al. |
| 2012/0157458 A1 | 6/2012 | Ripka et al. |
| 2015/0191476 A1 | 7/2015 | Bursavich et al. |

FOREIGN PATENT DOCUMENTS

| EP | 039051 A2 | 11/1981 |
| JP | 2005535646 A | 11/2005 |
| WO | WO-03037432 A1 | 5/2003 |
| WO | WO-2004078163 A2 | 9/2004 |
| WO | WO-2004096811 A1 | 11/2004 |
| WO | WO-2008139293 A1 | 11/2008 |
| WO | WO-PCT/CN2012/070718 | 1/2012 |
| WO | WO-PCT/CN2012/080208 | 8/2012 |
| WO | WO-2013110768 A1 | 8/2013 |
| WO | WO-2013142269 A1 | 9/2013 |

OTHER PUBLICATIONS

Fisher, Douglas A. et al. "Isolation and Characterization of PDE9A, a Novel Human cGMP-specific Phosphodiesterase." The Journal of Biological Chemistry. vol. 273, No. 25, Dec. 22, 1997. pp. 15559-15564. 7 pages.
Hutson, P.H. et al. "The Selective Phosphodiesterase 9 (PDE9) Inhibitor PF-04447943 (6-[3S,4S)-4-methyl-1-(pyrimidin-2ylmethyl)pyrrolidon-3-yl]-1-(tetrahydro-2H-pyran-4-yl)-1,5-dihydro-4H-pyrazolo[3,4-d]pyrimidin-4-one) Enhances Synaptic Plasticity and Cognitive Function in Rodents." Neuropharmacology. May 2011. pp. 665-676. 12 pages.
International Search Report and Written Opinion for International Application No. PCT/US13/31516 mailed May 24, 2013. 32 pages.
International Search Report and Written Opinion for International Application No. PCT/US2011/052399 mailed Nov. 24, 2011. 11 pages.
Van Der Staay, F. Josef et al. "The Novel Selective PDE9 Inhibitor BAY 73-6691 Improves Learning and Memory in Rodents." Nueropharmacology. Jul. 4, 2008. pp. 908-918. 11 pages.
Wermuth, C.G. :Molecular Variations Based on Isosteric Replacements. Practice of Medicinal Chemistry XP-002190259. No Month Listed. 1996, p. 203-237.
EESR 13763450.7 dated Aug. 21, 2015.
Lazorthes et al., "Advances in Drug Delivery Systems and Applications in Neurosurgery" Advances and Technical Standards in Neurosurgery, vol. 18, Springer-Verlag, Wien New York, pp. 143-192, 1991.
Minto et al., "Pharmacokinetics and Pharmacodynamics of Nandrolone Esters in Oil Vehicle; Effects of Ester, Injection Site and Injection Volume" J. Pharmacol. & Exp. Therapy, vol. 281 (1):93-102, 1997.
Ommaya, A., "Implantable Devices for Chronic Access and Drug Delivery to the Cnetral Nervous System" Cancer Drug Delivery, vol. 1(2):169-179, 1984.

*Primary Examiner* — Kendra D Carter
(74) *Attorney, Agent, or Firm* — McCarter & English, LLP; Andrej Barbic

(57) ABSTRACT

The present invention provides imidazotriazinone compounds which are inhibitors of phosphodiesterase 9. The present invention further provides processes, pharmaceutical compositions, pharmaceutical preparations and pharmaceutical use of the compounds in the treatment of PDE9 associated diseases or disorders in mammals, including humans.

1 Claim, No Drawings

IMIDAZOTRIAZINONE COMPOUNDS

RELATED APPLICATIONS

This application is a continuation of U.S. patent application Ser. No. 13/237,795, filed Sep. 20, 2011 which claims the benefit of U.S. Provisional Application No. 61/384,694, filed Sep. 20, 2010, which are hereby expressly incorporated by reference in their entirety.

The phosphodiesterases (PDEs) are a superfamily of enzymes with eleven members encoded by 21 genes that regulate intracellular cyclic nucleotide signaling (i.e., cyclic adenosine monophosphate (cAMP) and cyclic guanosine monophosphate (cGMP)). The PDEs contain a variable N-terminal regulatory domain and a highly conserved C-terminal catalytic domain and differ in their substrate specificity, expression and localization in cellular and tissue compartments, including the CNS. In neurons these cyclic nucleotides serve as second messengers in the signaling cascade of G-protein coupled receptors and lead to the activation of kinases which, in turn, will phosphorylate proteins involved in the regulation of synaptic transmission and homeostasis.

The PDE9 enzyme selectively hydrolyzes cGMP over cAMP and has the highest affinity of any PDE for cGMP, $K_m$ ~170 nM (Fisher et al., *Journal of Biological Chemistry* 1998, 273 (25), 15559-15564). PDE9 is found to be present in a variety of human tissues including prostate, colon, small intestine, spleen, kidney, brain and skeletal muscle. Specifically, PDE9 mRNA is found in the hippocampal formation further suggesting a role in learning and memory. Studies have also implicated cGMP pathways in synaptic plasticity. In PDE9 knockout mice, long term potentiation (LTP) is enhanced suggesting that PDE9 inhibition can improve learning and memory. Indeed, a selective PDE9 inhibitor was shown to potentiate LTP at the Schaeffer collateral/CA1 synapse, a region of the hippocampus known to be involved in learning and memory (Van der Staay et al., *Neuropharmacology*, 2008, 55 (5), 908-918; Huttson et al., *Neuropharmacology*, 2011, 61 (4), 665-676). In multiple studies, selective PDE9 inhibitors were effective in attenuating the deficits observed in passive avoidance, novel object recognition, social recognition, and T-maze behavioral assays (Van der Staay et al., *Neuropharmacology*, 2008, 55 (5), 908-918). Furthermore, in two studies, neurite outgrowth, a measure of synaptic plasticity, was increased following PDE9 inhibition (Huttson et al., *Neuropharmacology*, 2011, 61 (4), 665-676; Menitti, ICAD, 2009). Overall the data suggest that modulation of neuronal cGMP via inhibition of PDE9 can alter synaptic processes including learning and memory.

As such, there remains a strong need for novel PDE9 inhibitors for use in increasing synaptic plasticity and synaptic processes, for example, involved in learning, memory, as well as CNS diseases or disorders related to modulation of cGMP levels.

SUMMARY OF THE INVENTION

The present invention provides imidazotriazinone compounds which are inhibitors of phosphodiesterase 9. The present invention further provides processes, pharmaceutical compositions, pharmaceutical preparations and pharmaceutical use of the compounds in the treatment of PDE9 associated diseases or disorders in mammals, including human(s). In particular embodiments, the compounds of the invention are useful for treating central nervous system (CNS) diseases and disorders, as well as other disorders that may affect CNS function, which are related to the modulation of cGMP levels. In a specific embodiment, the compounds of the invention are useful for treating diseases or disorders that would benefit from increased synaptic plasticity and synaptic processes, including learning and memory.

Accordingly, one aspect of the invention provides compounds of Formula (I)

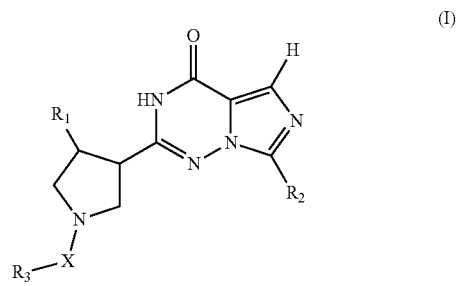

or a pharmaceutically acceptable salt thereof, wherein:

X is selected from a bond, C(O) or $S(O)_2$;

$R_1$ is independently selected from the group consisting of H, $(C_1-C_6)$ alkyl, $(C_1-C_6)$ alkoxy; $(C_3-C_7)$cycloalkyl, $(C_3-C_7)$cycloalkyl$(C_1-C_4)$ alkyl, $(C_3-C_7)$cycloalkyloxy, heterocycloalkyl, heterocycloalkyl$(C_1-C_4)$alkyl and heterocycloalkyloxy, each of which may be optionally substituted with one or more substituents selected from the group consisting of halogen, —$S(O)_2(C_1-C_4)$alkyl, OH, —C(O)—$(C_1-C_4)$alkyl, oxo, CN, $(C_1-C_6)$alkyl, $(C_1-C_4)$alkoxy, $(C_3-C_7)$cycloalkyl, —C(O)NH$(C_1-C_4)$alkyl, —C(O)N[$(C_1-C_4)$alkyl$(C_1-C_4)$alkyl], $(C_1-C_4$ alkyl)-C(O)—, $(C_1-C_4)$alkylsulfonyl-, —$S(O)_2$NH$(C_1-C_4)$alkyl, and —$S(O)_2$N[$(C_1-C_4)$alkyl$(C_1-C_4)$alkyl];

$R_2$ is independently selected from the group consisting of $(C_1-C_6)$ alkyl, $(C_3-C_{10})$cycloalkyl, $(C_3-C_7)$cycloalkyl$(C_1-C_4)$ alkyl, heterocycloalkyl, heterocycloalkyl$(C_1-C_4)$alkyl, heteroaryl, heteroaryl$(C_1-C_4)$alkyl, restricted phenyl and restricted phenyl$(C_1-C_4)$alkyl, each of which may be optionally substituted with one or more substituents selected from the group consisting of halogen, —$S(O)_2(C_1-C_4)$alkyl, OH, —C(O)—$(C_1-C_4)$alkyl, oxo, CN, $(C_1-C_6)$alkyl, $(C_1-C_4)$alkoxy, $(C_3-C_7)$cycloalkyl, —C(O)NH$(C_1-C_4)$alkyl, —C(O)N[$(C_1-C_4)$alkyl$(C_1-C_4)$alkyl], $(C_1-C_4$ alkyl)-C(O)—, $(C_1-C_4)$alkylsulfonyl-, —$S(O)_2$NH$(C_1-C_4)$alkyl, and —$S(O)_2$N[$(C_1-C_4)$alkyl$(C_1-C_4)$alkyl]; and $R_3$ is independently selected from the group consisting of $(C_1-C_6)$ alkyl, $(C_3-C_7)$cycloalkyl, $(C_3-C_7)$cycloalkyl$(C_1-C_4)$alkyl, heterocycloalkyl, heterocycloalkyl$(C_1-C_4)$alkyl, heteroaryl, heteroaryl$(C_1-C_4)$alkyl, restricted phenyl and restricted phenyl$(C_1-C_4)$alkyl, each of which may be optionally substituted with one or more substituents selected from the group consisting of halogen, —$S(O)_2(C_1-C_4)$alkyl, OH, —C(O)—$(C_1-C_4)$alkyl, oxo, CN, $(C_1-C_6)$alkyl, $(C_1-C_4)$alkoxy, $(C_3-C_7)$cycloalkyl, —C(O)NH$(C_1-C_4)$alkyl, —C(O)N[$(C_1-C_4)$alkyl$(C_1-C_4)$alkyl], $(C_1-C_4$ alkyl)-C(O)—, $(C_1-C_4)$alkylsulfonyl-, —$S(O)_2$NH$(C_1-C_4)$alkyl, and —$S(O)_2$N[$(C_1-C_4)$alkyl$(C_1-C_4)$alkyl].

Another aspect of the invention provides a compound of Formula (I)

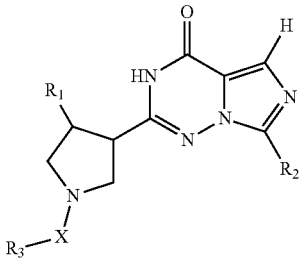

or a pharmaceutically acceptable salt thereof, wherein:

X is selected from a bond, C(O) and S(O)$_2$;

R$_1$ is (C$_1$-C$_6$) alkyl;

R$_2$ is selected from the group consisting of heterocycloalkyl, (C$_3$-C$_{10}$)cycloalkyl, e.g., adamantyl, and restricted phenyl, each of which may be optionally substituted with one or more substituents selected from the group consisting of halogen, —S(O)$_2$(C$_1$-C$_4$)alkyl, OH, —C(O)—(C$_1$-C$_4$) alkyl, CN, (C$_1$-C$_6$)alkyl, and (C$_1$-C$_4$)alkoxy; and R$_3$ is selected from the group consisting of a mono or bicyclic heteroaryl(C$_1$-C$_4$)alkyl and restricted phenyl(C$_1$-C$_4$)alkyl, each of which may be optionally substituted with one or more substituents selected from the group consisting of halogen, —S(O)$_2$(C$_1$-C$_4$)alkyl, OH, —C(O)—(C$_1$-C$_4$) alkyl, CN, (C$_1$-C$_6$)alkyl, and (C$_1$-C$_4$)alkoxy.

In another aspect, the invention provides a compound of Formula (I)

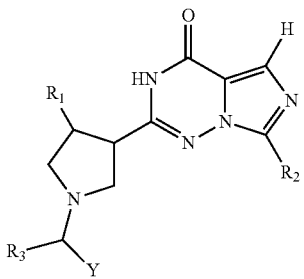

or a pharmaceutically acceptable salt thereof, wherein:

Y is H or (C$_1$-C$_3$) alkyl;

R$_1$ is (C$_1$-C$_6$) alkyl;

R$_2$ is selected from the group consisting of heterocycloalkyl, (C$_3$-C$_{10}$)cycloalkyl, e.g., adamantyl, and restricted phenyl, each of which may be optionally substituted with one or more substituents selected from the group consisting of halogen, —S(O)$_2$(C$_1$-C$_4$)alkyl, OH, —C(O)—(C$_1$-C$_4$) alkyl, CN, (C$_1$-C$_6$)alkyl, and (C$_1$-C$_4$)alkoxy; and R$_3$ is selected from the group consisting of a mono or bicyclic heteroaryl and restricted phenyl, each of which may be optionally substituted with one or more substituents selected from the group consisting of halogen, —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

In yet another aspect, the present invention provides a compound selected from the following:

(−)-2-((3,4-trans)-1-benzyl-4-methylpyrrolidin-3-yl)-7-(tetrahydro-2H-pyran-4-yl)imidazo[1,5-f][1,2,4]triazin-4(3H)-one (+)-2-((3,4-trans)-1-benzyl-4-methylpyrrolidin-3-yl)-7-(tetrahydro-2H-pyran-4-yl)imidazo[1,5-f][1,2,4]triazin-4(3H)-one (+)-2-((3,4-trans)-1-(imidazo[1,2-b]pyridazin-2-ylmethyl)-4-methylpyrrolidin-3-yl)-7-(tetrahydro-2H-pyran-4-yl) imidazo[5,1-f][1,2,4]triazin-4(3H)-one (+)-2-((3,4-trans)-1-(imidazo[1,2-b]pyridazin-6-ylmethyl)-4-methylpyrrolidin-3-yl)-7-(tetrahydro-2H-pyran-4-yl) imidazo[5,1-f][1,2,4]triazin-4(3H)-one (−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one (+)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one (+)-3-(((3,4-trans)-3-methyl-4-(4-oxo-7-(tetrahydro-2H-pyran-4-yl)-3,4-dihydroimidazo[5,1-f][1,2,4]triazin-2-yl) pyrrolidin-1-yl)methyl)benzonitrile (−)-4-(((3,4-trans)-3-methyl-4-(4-oxo-7-(tetrahydro-2H-pyran-4-yl)-3,4-dihydroimidazo[5,1-f][1,2,4]triazin-2-yl) pyrrolidin-1-yl)methyl)benzonitrile (+)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one (+)-2-(((3,4-trans)-3-methyl-4-(4-oxo-7-(tetrahydro-2H-pyran-4-yl)-3,4-dihydroimidazo[5,1-f][1,2,4]triazin-2-yl) pyrrolidin-1-yl)methyl)benzonitrile (+)-2-((3,4-trans)-4-methyl-1-(pyridin-2-ylmethyl) pyrrolidin-3-yl)-7-(tetrahydro-2H-pyran-4-yl) imidazo[5,1-f][1,2,4]triazin-4(3H)-one (+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one (+)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one (−)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one (+)-7-((1s,3R)-adamantan-1-yl)-2-((3,4-trans)-1-benzyl-4-methylpyrrolidin-3-yl)imidazo[5,1-f][1,2,4]triazin-4(3H)-one (−)-7-((1s,3R)-adamantan-1-yl)-2-((3,4-trans)-1-benzyl-4-methylpyrrolidin-3-yl)imidazo[5,1-f][1,2,4]triazin-4(3H)-one (−)-2-((3,4-trans)-1-benzyl-4-methylpyrrolidin-3-yl)-7-(5-chloro-2-methylphenyl)imidazo[5,1-f][1,2,4]triazin-4(3H)-one (+)-2-((3,4-trans)-1-benzyl-4-methylpyrrolidin-3-yl)-7-(5-chloro-2-methylphenyl)imidazo[5,1-f][1,2,4]triazin-4(3H)-one (+)-2-((3,4-trans)-1-benzyl-4-methylpyrrolidin-3-yl)-7-(4-fluoro-2-methylphenyl)imidazo[5,1-f][1,2,4]triazin-4(3H)-one (−)-2-((3,4-trans)-1-benzyl-4-methylpyrrolidin-3-yl)-7-(4-fluoro-2-methylphenyl)imidazo[5,1-f][1,2,4]triazin-4(3H)-one (+)-2-((3,4-trans)-1-benzyl-4-methylpyrrolidin-3-yl)-7-(4,4-difluorocyclohexyl)imidazo[5,1-f][1,2,4]triazin-4(3H)-one (−)-2-((3,4-trans)-1-benzyl-4-methylpyrrolidin-3-yl)-7-(4,4-difluorocyclohexyl)imidazo[5,1-f][1,2,4]triazin-4(3H)-one (−)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one (−)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one (−)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one (−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one (+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one (−)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one (+)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one (+)-7-((1s,3R)-adamantan-1-yl)-2-((3,4-trans)-4-methyl-1-(pyrimidin-2-ylmethyl)pyrrolidin-3-yl)imidazo[5,1-f][1,2,4]triazin- -continued 4(3H)-one
2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 1
2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 2
2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 3
(+)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one
(−)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one
(−)-7-(4-fluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one
(+)-7-(4,4-difluorocyclohexyl)-2-((3,4-trans)-4-methyl-1-(pyrimidin-2-ylmethyl)pyrrolidin-3-yl)imidazo[5,1-f][1,2,4]triazin-4(3H)-one
(−)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one
(+)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one
(−)-7-(5-chloro-2-methylphenyl)-2-((3,4-trans)-4-methylpyrrolidin-3-yl)imidazo[5,1-f][1,2,4]triazin-4(3H)-one
(+)-2-((3,4-trans)-1-benzyl-4-methylpyrrolidin-3-yl)-7-(furan-3-yl)imidazo[5,1-f][1,2,4]triazin-4(3H)-one
(−)-2-((3,4-trans)-1-benzyl-4-methylpyrrolidin-3-yl)-7-(furan-3-yl)imidazo[5,1-f][1,2,4]triazin-4(3H)-one
(−)-7-(1-acetylpiperidin-4-yl)-2-((3,4-trans)-1-benzyl-4-methylpyrrolidin-3-yl)imidazo[5,1-f][1,2,4]triazin-4(3H)-one
(+)-7-(1-acetylpiperidin-4-yl)-2-((3,4-trans)-1-benzyl-4--methylpyrrolidin-3yl)imidazo[5,1-f][1,2,4]triazin-4(3H)-one
(−)-2-((3,4-trans)-1-benzyl-4-methylpyrrolidin-3-yl)-7-(2-hydroxypropan-2-yl)imidazo[5,1-f][1,2,4]triazin-4(3H)-one
(+)-2-((3,4-trans)-1-benzyl-4-methylpyrrolidin-3-yl)-7-(2-hydroxypropan-2-yl)imidazo[5,1-f][1,2,4]triazin-4(3H)-one
(+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one
(−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one
(−)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one
(+)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one
(+)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one
(−)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one or a pharmaceutically acceptable salt thereof.

Another aspect of the invention provides a pharmaceutical composition comprising a compound of the invention, e.g., a compound of Formula (I), and a pharmaceutically acceptable carrier or excipient.

Another aspect of the invention provides a method for treating a PDE9 associated disease or disorder comprising administering to a subject an effective amount of a compound of the invention, e.g., in a pharmaceutical composition of the invention, such that the PDE9 associated disease or disorder is treated.

In another aspect, the invention provides a method of inhibiting PDE9 in a subject, wherein the method comprises administering to the subject a therapeutically effective amount of a compound of the invention, e.g., a compound of Formula (I), such that PDE9 is inhibited in the subject.

DETAILED DESCRIPTION OF THE INVENTION

The present invention provides imidazotriazinone compounds which are inhibitors of phosphodiesterase 9. The present invention further provides processes, pharmaceutical compositions, pharmaceutical preparations and pharmaceutical use of the compounds in the treatment of PDE9 associated diseases or disorders in mammals, including human(s). The present invention, including compounds, methods, and pharmaceutical compositions will be described with reference to the following definitions that, for convenience, are set forth below. Unless otherwise specified, the below terms used herein are defined as follows:

I. Definitions

As used herein, the teen "a," "an," "the" and similar terms used in the context of the present invention (especially in the context of the claims) are to be construed to cover both the singular and plural unless otherwise indicated herein or clearly contradicted by the context.

As used herein, the language "PDE9 associated diseases or disorders" describes the class of disorders associated with abnormal PDE9 activity, or aberrant levels of cGMP. In certain embodiments, the PDE9 associated disease or disorder is a central nervous system (CNS) disease or disorder, a neurodegeneration disorder, or a disorder that may affect CNS function, wherein each of these diseases or disorders is related to the modulation of cGMP levels. In certain embodiments, the PDE9 associated disease or disorder is a disease or disorder caused by a relative reduction in synaptic plasticity and synaptic processes, e.g., as in learning or memory. In a particular embodiment, the compounds of the invention serve to treat these disorders by acting to increase synaptic plasticity and synaptic processes, wherein the language increasing synaptic plasticity and synaptic process includes induction of synaptic plasticity and synaptic processes.

Exemplary CNS disorders include Alzheimer's disease, amyotrophic lateral sclerosis (ALS or Lou Gerig's disease), Binswanger's dementia (subcortical arteriosclerotic encephalopathy), bipolar disorders, Down's syndrome, frontotemporal lobar degeneration or dementia, glaucoma, Huntington's disease (chorea), HIV-associated dementia, Lewy body dementia, multiple sclerosis, multiple system atrophy, Parkinson's disease, presenile dementia (mild cognitive impairment), schizophrenia, spinocerebellar ataxies, Steel-Richardson-Olszewski disease (progressive supranuclear palsy), vascular dementia, attention deficit disorder (ADD) and attention deficit hyperactivity disorder (ADHD). Exemplary neurodegeneration disorders include either traumatic (closed or open, penetrating head injuries) or non-traumatic (stroke, aneurism, hypoxia) injury to the brain. In certain embodiments, PDE9 associated diseases or disorders characterized by aberrant levels of cGMP may also include dystonia, including for example, generalized, focal, segmental, sexual, intermediate, acute dystonic reaction, and genetic/primary; and dyskinesia, including for example, acute, pharmacological, chronic/tardive, and non-motor. In certain embodiments, PDE9 associated diseases or disorders characterized by a relative reduction in synaptic plasticity and synaptic processes include, for example, obsessive compulsive disorder, Fragile X, Rhett's, Williams syndrome, Renpenning's syndrome, autism spectrum disorders, including autism, Asperger's syndrome, pervasive development disorder, Rhett's syndrome, and childhood disintegrative disorder As used herein, the term "modulation" refers to a relative increase or decrease in the levels of a particular cellular indicator, e.g., cGMP. In this respect, the diseases/disorders described herein are characterized by relatively decreased levels of cGMP levels, wherein the compounds of the present invention serve to increase the level of cGMP through inhibition of PDE9.

As used herein, the term "pharmaceutically acceptable" refers to salts prepared from pharmaceutically acceptable non-toxic bases and acids, including inorganic and organic bases and inorganic and organic acids. Salts derived from inorganic bases include, but are not limited to lithium, sodium, potassium, magnesium, calcium and zinc. Salts derived from organic bases include, but are not limited to ammonia, primary (e.g. Tromethamine), secondary and tertiary amines, and amino acids (e.g. Lysine). Salts derived from inorganic acids include, but are not limited to sulfuric, hydrochloric, phosphoric, methanesulfonic, hydrobromic. Salts derived from organic acids include, but are not limited to $C_{1-6}$ alkyl carboxylic acids, di-carboxylic acids and tri-carboxylic acids such as acetic acid, propionic acid, fumaric acid, maleic acid, succinic acid, tartaric acid, adipic acid and citric acid, and alkylsulfonic acids such as methanesulfonic and aryl sulfonic acids such as para-toluene sulfonic acid and benzene sulfonic acid. For detailed list of slats see P. H. Stahl and C. G. Wermuth (eds.) "Handbook of Pharmaceutical Salts, Properties, Selection and Use" Wiley-VCH (ISBN 3-906390-26-8)

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the advancement or worsening of the disease or disorder resulting from the administration of a compound of the invention to a patient with such a disease or disorder. In some embodiments, the terms refer to the administration of a compound provided herein, with or without other additional active agents, after the onset of symptoms of the particular disease. The terms "treating", "treatment", or the like, as used herein covers the treatment of a disease-state in a subject, e.g., a mammal, and includes at least one of: (i) inhibiting the disease-state, i.e., partially or completely halting its progression; (ii) relieving the disease-state, i.e. causing regression of symptoms of the disease-state, or ameliorating a symptom of the disease; and (iii) reversal or regression of the disease-state, preferably eliminating or curing of the disease. In a particular embodiment the terms "treating", "treatment", or the like, covers the treatment of a disease-state in a mammal, e.g., a primate, e.g., a human, and includes at least one of (i), (ii), and (iii) above. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

As used herein, the terms "subject", and "patient" are used interchangeably. The terms "subject" and "patient" refer to an animal (e.g., a bird such as a chicken, quail or turkey) or a mammal including non-primates (e.g., a cow, pig, horse, sheep, rabbit, guinea pig, rat, cat, dog, and mouse) and primates (e.g., a monkey, chimpanzee and a human). In a particular embodiment, the subject is a human.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the administration of a compound provided herein to a subject, with or without other additional active compound, prior to the onset of symptoms, particularly to patients at risk of diseases or disorders provided herein. The terms encompass the inhibition or reduction of a symptom of the particular disease. Subjects with familial history of a disease in particular are candidates for preventive regimens in certain embodiments. In addition, subjects who have a history of recurring symptoms are also potential candidates for the prevention. In this regard, the term "prevention" may be interchangeably used with the term "prophylactic treatment." In certain embodiments, the prevention is achieved by administration of a prophylactically effective amount of a compound of the invention.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent e.g. cholinesterase inhibitors, donepezil, rivastigmine, galantamine and/or memantine.

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Alkyl is meant to denote a linear or branched saturated or unsaturated aliphatic $C_1$-$C_8$ hydrocarbon, unless some other number of carbon atoms is specified. Unsaturation in the form of a double or triple carbon-carbon bond may be internal or terminally located and, in the case of a double bond, both cis and trans isomers are included. An optionally substituted alkyl can be independently substituted with one or more substituents selected from F, oxo, OH, $(C_1$-$C_4)$ alkoxy, $(C_3$-$C_6)$cycloalkyloxy, $(C_1$-$C_4)$alkylthio, $(C_3$-$C_6)$cycloalkylthio-, —C(O)NH$_2$, —C(O)NH$(C_1$-$C_4)$alkyl, —C(O)N[$(C_1$-$C_4)$alkyl$(C_1$-$C_4)$alkyl], $(C_1$-$C_4$ alkyl)-C(O)—, $(C_1$-$C_4)$alkylsulfonyl-, —S(O)$_2$NH$_2$, —S(O)$_2$NH$(C_1$-$C_4)$alkyl, —S(O)$_2$N[$(C_1$-$C_4)$alkyl$(C_1$-$C_4)$alkyl]. Examples of alkyl groups include, but are not limited to, methyl, trifluoromethyl, ethyl, trifluoroethyl, isobutyl, neopentyl, cis- and trans-2-butenyl, isobutenyl and propargyl. $C_1$-$C_4$ alkyl is the subset of alkyl limited to a total of up to 4 carbon atoms. In other cases, an optionally substituted alkyl can be independently substituted with one or more substituents selected from F, OH, oxo, and ($C_1$-$C_4$)alkoxy. In other cases, an optionally substituted alkyl can be independently substituted with up to three fluorines.

In each case in which a size range for the number of atoms in a ring or chain is disclosed, all subsets are disclosed. Thus, $C_x$-$C_y$ includes all subsets, e.g., $C_1$-$C_4$ includes $C_1$-$C_2$, $C_2$-$C_4$, and $C_1$-$C_3$ as well as $C_1$, $C_2$, $C_3$ and $C_4$.

Acyl is an alkyl-C(O)— group wherein alkyl is as defined above. Examples of acyl groups include but are not limited to acetyl and proprionyl.

Alkoxy is an alkyl-O— group wherein alkyl is as defined above, including the optional substitutions. $C_1$-$C_4$ alkoxy is the subset of alkyl-O— where the subset of alkyl is limited to a total of up to 4 carbon atoms. Examples of alkoxy groups include, but are not limited to, methoxy, trifluoromethoxy, ethoxy, trifluoroethoxy, and propoxy.

Alkoxyalkyl is an alkyl-O—($C_1$-$C_4$ alkyl)- group wherein alkyl is as defined above. Examples of alkoxyalkyl groups include, but are not limited to, methoxymethyl and ethoxymethyl.

Alkoxyalkyloxy is an alkoxy-alkyl-O— group wherein alkoxy and alkyl are as defined above. Examples of alkoxyalkyloxy groups include, but are not limited to, methoxymethyloxy ($CH_3OCH_2O$—) and methoxyethyloxy ($CH_3OCH_2CH_2O$—) groups.

Alkylthio is alkyl-S— group wherein alkyl is as defined above. $C_1$-$C_4$ alkylthio is the subset of alkyl-S— where the subset of alkyl is limited to a total of up to 4 carbon atoms.

Alkylsulfonyl is alkyl-$SO_2$— wherein alkyl is as defined above. Examples of alkylsulfonyl groups include, but are not limited to, methanesulfonyl and isopropylsulfonyl.

Alkylamino is alkyl-NH— wherein alkyl is as defined above.

Dialkylamino is $(alkyl)_2$-N— wherein alkyl is as defined above.

Amido is $H_2NC(O)$—

Alkylamido is alkyl-NHC(O)— wherein alkyl is as defined above.

Dialkylamido is $(alkyl)_2$-NC(O)— wherein alkyl is as defined above.

Aromatic is heteroaryl or aryl wherein heteroaryl and aryl are as defined below.

Aryl is a phenyl or napthyl group. An optionally substituted aryl can be independently substituted with one or more substituents selected from halogen, $CF_3$, CN, OH, ($C_1$-$C_4$)alkoxy, ($C_1$-$C_4$)alkylthio, ($C_3$-$C_7$)cycloalkylthio, ($C_3$-$C_7$)cycloalkyloxy, aryloxy, ($C_1$-$C_4$)alkoxy($C_1$-$C_4$)alkyloxy, hetero($C_3$-$C_7$)cycloalkyloxy, heteroaryloxy, —OC(O)$R_a$, —OC(O)NH$R_a$, —OC(O)N($R_a$)($R_b$), —S(O)$R_a$, —NH$R_a$, —N($R_a$)($R_b$), —NHC(O)$R_a$, —N($R_a$)C(O)$R_b$, —NHC(O)OR$_a$, —N($R_a$)C(O)OR$_b$, —N($R_a$)—C(O)—NH($R_b$), —N($R_a$)—C(O)—N($R_b$)$_2$, —C(O)NH$_2$, —C(O)NH$R_a$, —C(O)N($R_a$)($R_b$), —$CO_2$H, —$CO_2R_a$, —COR$_a$ and $R_c$ wherein $R_a$, $R_b$ and $R_c$ are independently chosen from ($C_1$-$C_6$)alkyl, ($C_1$-$C_4$)alkoxy($C_1$-$C_4$)alkyl, —$CH_2CH_2OH$, —$CH_2CH_2OMe$, ($C_3$-$C_7$)cycloalkyl, ($C_3$-$C_7$)cycloalkyl($C_1$-$C_4$)alkyl, aryl, arylalkyl, heteroaryl, heteroarylalkyl, hetero($C_3$-$C_7$)cycloalkyl, and hetero($C_3$-$C_7$)cycloalkyl($C_1$-$C_4$)alkyl, each of which is optionally and independently substituted with up to three groups selected from halogen, ($C_1$-$C_6$)alkyl, ($C_3$-$C_7$)cycloalkyl, ($C_3$-$C_7$)cycloalkyloxy, ($C_3$-$C_7$)cycloalkylalkoxy, CN, $CHF_2$, $CF_3$, $CH_2CF_3$, NHMe, $NMe_2$, piperidnyl, morpholinyl, N-Me-piperazinyl, piperazinyl, $OCF_3$, $OCHF_2$, $OCH_2CF_3$, SMe, each of which are attached via carbon-carbon or carbon-nitrogen or carbon-oxygen single bonds, and none of which are substituted; or $R_a$ and $R_b$ taken together with the atom(s) to which they are attached form a 5-6 membered ring. In other cases, an optionally substituted aryl can be independently substituted with one or more substituents selected from halogen, $CF_3$, CN, ($C_1$-$C_6$)alkyl, ($C_3$-$C_7$)cycloalkyl, ($C_1$-$C_4$)alkoxy, ($C_3$-$C_7$)cycloalkylthio, ($C_3$-$C_7$)cycloalkyloxy, hetero($C_3$-$C_7$)cycloalkyl, C(O)$NH_2$, —C(O)NH$R_a$, —C(O)N($R_a$)($R_b$) wherein $R_a$ and $R_b$ are defined as above. In further cases, an optionally substituted aryl can be independently substituted with one or more substituents selected from halogen, $CF_3$, CN, ($C_1$-$C_6$)alkyl, ($C_3$-$C_7$)cycloalkyl, ($C_3$-$C_7$)cycloalkyloxy, and hetero($C_3$-$C_7$)cycloalkyl.

Arylalkyl is an aryl-alkyl- group wherein aryl and alkyl are as defined above, including the optional substitutions.

Aryloxy is an aryl-O— group wherein aryl is as defined above, including the optional substitutions.

Arylalkoxy is an aryl-($C_1$-$C_4$ alkyl)-O— group wherein aryl is as defined above, including the optional substitutions.

Carboxy is a $CO_2H$ or $CO_2R_d$ group wherein $R_d$ is independently chosen from ($C_1$-$C_6$)alkyl, ($C_3$-$C_7$)cycloalkyl, aryl($C_1$-$C_3$)alkyl, ($C_3$-$C_7$)cycloalkyl($C_1$-$C_3$)alkyl, and alkoxyalkyl, wherein alkyl, cycloalkyl, aryl and alkoxy are as defined above, including the optional substitutions.

Cycloalkyl is a $C_3$-$C_{10}$ cyclic non-aromatic hydrocarbon, e.g., a $C_3$-$C_7$, cyclic non-aromatic hydrocarbon, which may contain a single double bond. An optionally substituted cycloalkyl can be independently substituted with one or more substituents selected from F, oxo, OH, ($C_1$-$C_6$)alkyl, ($C_1$-$C_4$)alkoxy, —($C_3$-$C_7$)cycloalkyl, ($C_3$-$C_7$)cycloalkylalkyl, ($C_3$-$C_7$)cycloalkyloxy, ($C_1$-$C_4$)alkylthio, ($C_3$-$C_6$)cycloalkylthio-, —C(O)$NH_2$, —C(O)NH($C_1$-$C_4$)alkyl, —C(O)N[($C_1$-$C_4$)alkyl($C_1$-$C_4$)alkyl], ($C_1$-$C_4$ alkyl)-C(O)—, ($C_1$-$C_4$)alkylsulfonyl-, —$S(O)_2NH_2$, —$S(O)_2NH$($C_1$-$C_4$)alkyl, —$S(O)_2N$[($C_1$-$C_4$)alkyl($C_1$-$C_4$)alkyl]. In other cases, an optionally substituted cycloalkyl can be independently substituted with one or more substituents selected from F, oxo, ($C_1$-$C_4$)alkoxy, ($C_3$-$C_7$)cycloalkyl, —C(O)NH($C_1$-$C_4$)alkyl, —C(O)N[($C_1$-$C_4$)alkyl($C_1$-$C_4$)alkyl], ($C_1$-$C_4$ alkyl)-C(O)—, ($C_1$-$C_4$)alkylsulfonyl-, —$S(O)_2$ NH($C_1$-$C_4$)alkyl, —$S(O)_2N$[($C_1$-$C_4$)alkyl($C_1$-$C_4$)alkyl]. In further cases, an optionally substituted cycloalkyl can be independently substituted with one substituent selected from oxo, OH, ($C_1$-$C_6$)alkyl, ($C_1$-$C_4$)alkoxy, ($C_3$-$C_7$)cycloalkylalkyl, ($C_3$-$C_7$)cycloalkyloxy, ($C_1$-$C_4$)alkylthio, ($C_3$-$C_6$)cycloalkylthio-, —C(O)$NH_2$, —C(O)NH($C_1$-$C_4$)alkyl, —C(O)N[($C_1$-$C_4$)alkyl($C_1$-$C_4$)alkyl], ($C_1$-$C_4$ alkyl)-C(O)—, ($C_1$-$C_4$)alkylsulfonyl-, —$S(O)_2NH_2$, —$S(O)_2$ NH($C_1$-$C_4$)alkyl, —$S(O)_2N$ [($C_1$-$C_4$)alkyl($C_1$-$C_4$) alkyl]. In other cases, an optionally substituted cycloalkyl can be independently substituted with one substituent selected from oxo, OH, ($C_1$-$C_6$)alkyl, ($C_1$-$C_4$)alkoxy, ($C_3$-$C_7$)cycloalkylalkyl and ($C_3$-$C_7$)cycloalkyloxy.

Examples of cycloalkyl groups include, but are not limited to, cyclopropyl, cyclobutyl, cyclopentyl, cyclohexyl, cyclopentenyl, and adamantyl.

Cycloalkyloxy is a cycloalkyl-O— group wherein cycloalkyl is as defined above, including the optional substitutions. Examples include but are not limited to, cyclopropyloxy, cyclobutyloxy and cyclopentyloxy. $C_3$-$C_6$ cycloalkyloxy is the subset of cycloalkyl-O— where cycloalkyl contains 3-6 carbon atoms.

Cycloalkylthio is a cycloalkyl-S— group wherein cycloalkyl is as defined above, including the optional substitutions. Examples include but are not limited to cyclopropylthio, cyclobutylthio and cyclopentylthio.

Cycloalkylalkyl is a cycloalkyl-($C_1$-$C_4$ alkyl)- group wherein cycloalkyl and alkyl are defined above, including the optional substitutions. Examples include but are not limited to cyclopropylmethyl, cyclopropylethyl, cyclohexylmethyl and cyclohexylethyl.

Cycloalkylalkoxy is a cycloalkyl-($C_1$-$C_4$ alkyl)-O— group wherein cycloalkyl and alkoxy are as defined above, including the optional substitutions. Examples of cycloalkylalkoxy groups include but are not limited to cyclopropylmethoxy, cyclopentylmethoxy and cyclohexylmethoxy.

Cycloalkylalkylthio is a cycloalkyl-($C_1$-$C_4$)alkyl-S— group wherein cycloalkyl and alkyl are as defined above. Examples of cycloalkylalkylthio groups include but are not limited to cyclopropylmethanethio, cyclobutylmethanethio and cyclopentylmethanethio.

Halogen is F, Cl, Br or I. In particular embodiments, halogens are F, Cl and Br. In a specific embodiment, the halogen is F.

A heteroaryl group can be: (a) a tetrazole, (b) 1,2,3,4-oxatriazole, (c) 1,2,3,5-oxatriazole, or (d) a mono or bicyclic aromatic ring system, or a heterobicyclic ring system with one aromatic ring having 5 to 10 ring atoms independently selected from C, N, O and S, provided that not more than 3 ring atoms in any single ring are other than C. Examples of heteroaryl groups include but are not limited to thiophenyl, furanyl, thiazolyl, isothiazolyl, oxazolyl, isoxazolyl, 1,2,4-oxadiazolyl, 1,3,4-oxadiazolyl, pyrazolyl, imidazolyl, 1,2,3-triazolyl, 1,3,4-triazolyl, pyrimidinyl, pyrazinyl, indolyl, quinolyl, tetrahydroquinolyl, isoquinolyl, tetrahydroisoquinolyl, indazolyl, benzthiadiazololyl, benzoxadiazolyl and benzimidazolyl. An optionally substituted heteroaryl can be independently substituted with one or more substituents selected from halogen, $CF_3$, CN, OH, ($C_1$-$C_4$)alkoxy, ($C_1$-$C_4$)alkylthio, ($C_3$-$C_7$)cycloalkylthio, ($C_3$-$C_7$)cycloalkyloxy, aryloxy, ($C_1$-$C_4$)alkoxy($C_1$-$C_4$)alkyloxy, hetero($C_3$-$C_7$)cycloalkyloxy, heteroaryloxy, —OC(O)$R_a$, —OC(O)NH$R_a$, —OC(O)N($R_a$)($R_b$), —S(O)$R_a$, —NH$_2$, —NHR$_a$, —N($R_a$)($R_b$), —NHC(O)$R_a$, —N($R_a$)C(O)$R_b$, —NHC(O)O$R_a$, —N($R_a$)C(O)O$R_b$, —N($R_a$)—C(O)—NH($R_b$), —N($R_a$)—C(O)—N($R_b$)$_2$, —C(O)NH$_2$, —C(O)NH$R_a$, —C(O)N($R_a$)($R_b$), —CO$_2$H, —CO$_2$$R_a$, —COR$_a$ and $R_c$ wherein $R_a$, $R_b$ and $R_c$ are independently chosen from ($C_1$-$C_6$)alkyl, ($C_1$-$C_4$)alkoxy($C_1$-$C_4$)alkyl, —CH$_2$CH$_2$OH, —CH$_2$CH$_2$OMe, ($C_3$-$C_7$)cycloalkyl, ($C_3$-$C_7$)cycloalkyl($C_1$-$C_4$)alkyl, aryl, arylalkyl, heteroaryl, heteroarylalkyl, hetero($C_3$-$C_7$)cycloalkyl, and hetero($C_3$-$C_7$)cycloalkyl($C_1$-$C_4$)alkyl, each of which is optionally and independently substituted with up to three groups selected from halogen, ($C_1$-$C_6$)alkyl, ($C_3$-$C_7$)cycloalkyl, ($C_3$-$C_7$)cycloalkyloxy, ($C_3$-$C_7$)cycloalkylalkoxy, CN, NO$_2$, NH$_2$, CHF$_2$, CF$_3$, CH$_2$CF$_3$, NHMe, NMe$_2$, piperidnyl, morpholinyl, N-Me-piperazinyl, piperazinyl, OCF$_3$, OCHF$_2$, OCH$_2$CF$_3$, SMe, each of which are attached via carbon-carbon or carbon-nitrogen or carbon-oxygen single bonds, and none of which are substituted; or $R_a$ and $R_b$ taken together with the atom(s) to which they are attached form a 5-6 membered ring. In other cases, an optionally substituted heteroaryl can be independently substituted with one or more substituents selected from halogen CF$_3$, CN, ($C_1$-$C_6$) alkyl, ($C_3$-$C_7$)cycloalkyl, ($C_1$-$C_4$)alkoxy, ($C_3$-$C_7$)cycloalkylthio, ($C_3$-$C_7$)cycloalkyloxy, hetero($C_3$-$C_7$)cycloalkyl, C(O)NH$_2$, —C(O)NH$R_a$, —C(O)N($R_a$)($R_b$) wherein $R_a$ and $R_b$ are defined as above. In further cases, an optionally substituted heteroaryl can be independently substituted with one or more substituents selected from halogen, CF$_3$, CN, ($C_1$-$C_6$)alkyl, ($C_3$-$C_7$)cycloalkyl, ($C_3$-$C_7$)cycloalkyloxy, and hetero($C_3$-$C_7$)cycloalkyl.

Heteroarylalkyl is a heteroaryl-($C_1$-$C_4$ alkyl)- group wherein heteroaryl and alkyl are as defined above, including the optional substitutions. Examples of heteroarylalkyl groups include but are not limited to 4-pyridinylmethyl and 4-pyridinylethyl.

Heteroaryloxy is a heteroaryl-O group wherein heteroaryl is as defined above, including the optional substitutions.

Heteroarylalkoxy is a heteroaryl-($C_1$-$C_4$ alkyl)-O— group wherein heteroaryl and alkoxy are as defined above, including the optional substitutions. Examples of heteroarylalkyl groups include but are not limited to 4-pyridinylmethoxy and 4-pyridinylethoxy.

Heterobicyclic ring system is a bicyclic ring system having 8-10 atoms independently selected from C, N, O and S, provided that not more than 3 ring atoms in any single ring are other than carbon and provided that at least one of the rings is aromatic. An optionally substituted heterobicyclic ring system can be independently substituted with one or more substituents selected from ($C_1$-$C_6$)alkyl, ($C_1$-$C_4$) alkoxy, ($C_3$-$C_7$)cycloalkyl, ($C_3$-$C_7$)cycloalkyloxy, ($C_3$-$C_7$) cycloalkyl($C_1$-$C_3$)alkyl, halogen, alkylsulfonyl and cyano. In other cases, an optionally substituted heterobicyclic ring system can be independently substituted with one or more substituents selected from ($C_1$-$C_6$)alkyl, ($C_3$-$C_7$)cycloalkyl, ($C_3$-$C_7$)cycloalkyloxy, halogen and cyano. Examples of 8-10 membered heterobicyclic ring systems include but are not limited to 1,5-naphthyridyl, 1,2,3,4-tetrahydro-1,5-naphthyridyl 1,6-naphthyridyl, 1,2,3,4-tetrahydro-1,6-naphthyridyl 1,7-naphthyridyl, 1,2,3,4-tetrahydro-1,7-naphthyridinyl 1,8-naphthyridyl, 1,2,3,4-tetrahydro-1,8-naphthyridyl, 2,6-naphthyridyl, 2,7-naphthyridyl, cinnolyl, isoquinolyl, tetrahydroisoquinolinyl, phthalazyl, quinazolyl, 1,2,3,4-tetrahydroquinazolinyl, quinolyl, tetrahydroquinolinyl, quinoxalyl, tetrahydroquinoxalinyl, benzo[d][1,2,3]triazyl, benzo[e][1,2,4]triazyl, pyrido[2,3-b]pyrazyl, pyrido[2,3-c]pyridazyl, pyrido[2,3-d]pyrimidyl, pyrido[3,2-b] pyrazyl, pyrido[3,2-c]pyridazyl, pyrido[3,2-d]pyrimidyl, pyrido[3,4-b]pyrazyl, pyrido[3,4-c]pyridazyl, pyrido[3,4-d] pyrimidyl, pyrido[4,3-b]pyrazyl, pyrido[4,3-c]pyridazyl, pyrido[4,3-d]pyrimidyl, quinazolyl, 1H-benzo[d][1,2,3]triazoyl, 1H-benzo[d]imidazoyl, 1H-indazoyl, 1H-indoyl, 2H-benzo[d][1,2,3]triazoyl, 2H-pyrazolo[3,4-b]pyridinyl, 2H-pyrazolo[4,3-b]pyridinyl, [1,2,3]triazolo[1,5-a]pyridinyl, [1,2,4]triazolo[1,5-a]pyridinyl, [1,2,4]triazolo[4,3-a] pyridinyl, benzo[b]thienyl, benzo[c][1,2,5]oxadiazyl, benzo [c][1,2,5]thiadiazolyl, benzo[d]isothiazoyl, benzo[c/] isoxazoyl, benzo[d]oxazoyl, benzo[d]thiazoyl, benzofuryl, imidazo[1,2-a]pyrazyl, imidazo[1,2-a]pyridinyl, imidazo[1, 2-a]pyrimidyl, imidazo[1,2-b]pyridazyl, imidazo[1,2-c]pyrimidyl, imidazo[1,5-a]pyrazyl, imidazo[1,5-a]pyridinyl, imidazo[1,5-c]pyrimidyl, imidazo[1,5-b]pyridazyl, imidazo [1,5-c]pyrimidyl, indolizyl, pyrazolo[1,5-a]pyrazyl, pyrazolo[1,5-a]pyridinyl, pyrazolo[1,5-a]pyrimidyl, pyrazolo[1, 5-b]pyridazine, pyrazolo[1,5-c]pyrimidine, pyrrolo[1,2-c] pyrazine, pyrrolo[1,2-a]pyrimidyl, pyrrolo[1,2-b]pyridazyl, pyrrolo[1,2-c]pyrimidyl, 1H-imidazo[4,5-b]pyridinyl, 1H-imidazo[4,5-c]pyridinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-c]pyridinyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, 2H-indazoyl, 3H-imidazo[4,5-b]pyridinyl, 3H-imidazo[4,5-c]pyridinyl, benzo[c]isothiazyl, benzo[c]isoxazyl, furo[2,3-b]pyridinyl, furo[2,3-c] pyridinyl, furo[3,2-b]pyridinyl, furo[3,2-c]pyridinyl, isothiazolo[4,5-b]pyridinyl, isothiazolo[4,5-c]pyridinyl, isothiazolo[5,4-b]pyridinyl, isothiazolo[5,4-c]pyridinyl, isoxazolo[4,5-b]pyridinyl, isoxazolo[4,5-c]pyridinyl, isoxazolo

[5,4-b]pyridinyl, isoxazolo[5,4-c]pyridinyl, oxazolo[4,5-b] pyridinyl, oxazolo[4,5-c]pyridinyl, oxazolo[5,4-b]pyridinyl, oxazolo[5,4-c]pyridinyl, thiazolo[4,5-b]pyridinyl, thiazolo [4,5-c]pyridinyl, thiazolo[5,4-b]pyridinyl, thiazolo[5,4-c] pyridinyl, thieno[2,3-b]pyridinyl, thieno[2,3-c]pyridinyl, thieno[3,2-b]pyridinyl and thieno[3,2-c]pyridinyl. In some cases, an optionally substituted heterobicyclic system can be independently substituted on carbon with one or more substituents selected from halogen, $CF_3$, CN, $(C_1-C_6)$alkyl, $(C_1-C_4)$alkoxy, $(C_3-C_7)$cycloalkyl, $(C_3-C_7)$cycloalkyloxy, and hetero$(C_3-C_7)$cycloalkyl.

Heterocycloalkyl is a non-aromatic, monocyclic or bicyclic saturated or partially unsaturated ring system comprising 5-10 ring atoms selected from C, N, O and S, provided that not more than 2 ring atoms in any single ring are other than C. An optionally substituted heterocycloalkyl can be independently substituted on a carbon atom with one or more substituents selected from OH, $(C_1-C_6)$alkyl and $(C_1-C_4)$alkoxy groups and up to two oxo groups. In one case where the heterocycloalkyl group contains a nitrogen, an optionally substituted heterocycloalkyl can be independently substituted on said nitrogen with one or more substituents selected from $(C_1-C_6)$alkyl, $(C_3-C_7)$cycloalkyl, $(C_3-C_7)$cycloalkyl$(C_1-C_3)$alkyl, acyl, —C(O)O—$(C_1-C_4)$alkyl, —C(O)NH—$(C_1-C_4)$alkyl or a —C(O)N($(C_1-C_4)$alkyl$)_2$ group. In other cases where the heterocycloalkyl group contains a nitrogen, an optionally substituted heterocycloalkyl can be independently substituted on said nitrogen with one or more substituents selected from $(C_1-C_6)$alkyl, $(C_3-C_7)$cycloalkyl, $(C_3-C_7)$cycloalkyl$(C_1-C_3)$alkyl and acyl. Heterocycloalkyl groups may be linked to the rest of the molecule via either carbon or nitrogen ring atoms. Examples of heterocycloalkyl groups include tetrahydrofuranyl, tetrahydrothienyl, tetrahydro-2H-pyranyl, tetrahydro-2H-thiopyranyl, pyrrolidinyl, pyrrolidonyl, succinimidyl, piperidinyl, piperazinyl, N-methylpiperazinyl, morpholinyl, morpholin-3-one, thiomorpholinyl, thiomorpholin-3-one, 2,5-diazabicyclo[2.2.2]octanyl, 2,5-diazabicyclo[2.2.1]heptanyl, 2-azabicyclo[2.2.2]octane, 2-azabicyclo[2.2.1]heptane and octahydro-1H-pyrido[1,2-a]pyrazine.

Heterocycloalkylalkyl is a heterocycloalkyl-$(C_1-C_4$ alkyl)- group wherein heterocycloalkyl and alkyl are as defined above, including the optional substitutions.

Heterocycloalkyloxy is a heterocycloalkyl-O— group wherein heterocycloalkyl is as defined above, including the optional substitutions.

Heterocycloalkylalkoxy is a heterocycloalkyl-$(C_1-C_4$ alkyl)-O— group wherein heterocycloalkyl and alkyl are as defined above, including the optional substitutions.

Oxo is a —C(O)— group.

Phenyl is a benzene ring. An optionally substituted phenyl can be independently substituted with one or more substituents selected from halogen, $CF_3$, CN, OH, $(C_1-C_4)$alkoxy, $(C_1-C_4)$alkylthio, $(C_3-C_7)$cycloalkylthio, $(C_3-C_7)$cycloalkyloxy, aryloxy, $(C_1-C_4)$alkoxy$(C_1-C_4)$alkyloxy, hetero$(C_3-C_7)$cycloalkyloxy, heteroaryloxy, —OC(O)$R_a$, —OC(O)NH$R_a$, —OC(O)N($R_a$)($R_b$), —S(O)$R_a$, —NH$R_a$, —N($R_a$)($R_b$), —NHC(O)$R_a$, —N($R_a$)C(O)$R_b$, —NHC(O)O$R_a$, —N($R_a$)C(O)O$R_b$, —N(R)—C(O)—NH($R_b$), —N($R_a$)—C(O)—N($R_b$)$_2$, —C(O)NH$_2$, —C(O)NH$R_a$, —C(O)N($R_a$)($R_b$), —CO$_2$H, —CO$_2R_a$, —COR$_a$ and $R_c$ wherein, $R_a$, $R_b$ and $R_c$ are independently chosen from $(C_1-C_6)$alkyl, $(C_1-C_4)$alkoxy$(C_1-C_4)$alkyl, —CH$_2$CH$_2$OH, —CH$_2$CH$_2$OMe, $(C_3-C_7)$cycloalkyl, $(C_3-C_7)$cycloalkyl$(C_1-C_4)$alkyl, aryl, arylalkyl, heteroaryl, heteroarylalkyl, hetero$(C_3-C_7)$cycloalkyl, and hetero$(C_3-C_7)$cycloalkyl$(C_1-C_4)$alkyl, each of which is optionally and independently substituted with up to three groups selected from halogen, $(C_1-C_6)$alkyl, $(C_3-C_7)$cycloalkyl, $(C_3-C_7)$cycloalkyloxy, $(C_3-C_7)$cycloalkylalkoxy, CN, NO$_2$, NH$_2$, CHF$_2$, CF$_3$, CH$_2$CF$_3$, NHMe, NMe$_2$, piperidinyl, morpholinyl, N-Me-piperazinyl, piperazinyl, OCF$_3$, OCHF$_2$, OCH$_2$CF$_3$, SMe, each of which are attached via carbon-carbon or carbon-nitrogen or carbon-oxygen single bonds, and none of which are substituted; or $R_a$ and $R_b$ taken together with the atom(s) to which they are attached form a 5-6 membered ring. In other cases, an optionally substituted phenyl can be independently substituted with one or more substituents selected from halogen $CF_3$, CN, $(C_1-C_6)$alkyl, $(C_3-C_7)$cycloalkyl, $(C_1-C_4)$alkoxy, $(C_3-C_7)$cycloalkylthio, $(C_3-C_7)$cycloalkyloxy, hetero$(C_3-C_7)$cycloalkyl, C(O)NH$_2$, —C(O)NH$R_a$, —C(O)N($R_a$)($R_b$) wherein $R_a$ and $R_b$ are defined as above. In further cases, an optionally substituted phenyl can be independently substituted with one or more substituents selected from halogen, $CF_3$, CN, $(C_1-C_6)$alkyl, $(C_3-C_7)$cycloalkyl, $(C_3-C_7)$cycloalkyloxy, and hetero$(C_3-C_7)$cycloalkyl.

Restricted phenyl is a optionally substituted benzene ring which can be independently substituted with up to three groups selected from halogen, $CF_3$, CN, $(C_1-C_4)$alkoxy, $(C_1-C_4)$alkylthio, $(C_3-C_7)$cycloalkylthio, $(C_3-C_7)$cycloalkyloxy, $(C_1-C_4)$alkoxy$(C_1-C_4)$alkyloxy, hetero$(C_3-C_7)$cycloalkyloxy, —OC(O)NH$R_a$, —OC(O)N($R_a$)($R_b$), —C(O)NH$_2$, —C(O)NH$R_a$, —C(O)N($R_a$)($R_b$), —COR$_a$ and $R_c$ wherein $R_a$, $R_b$ and $R_c$ are independently chosen from $(C_1-C_6)$alkyl, $(C_1-C_4)$alkoxy$(C_1-C_4)$alkyl, —CH$_2$CH$_2$OH, —CH$_2$CH$_2$OMe, $(C_3-C_7)$cycloalkyl, $(C_3-C_7)$cycloalkyl$(C_1-C_4)$alkyl, aryl, arylalkyl, heteroaryl, heteroarylalkyl, hetero$(C_3-C_7)$cycloalkyl, and hetero$(C_3-C_7)$cycloalkyl$(C_1-C_4)$alkyl, each of which is optionally and independently substituted with up to three groups selected from halogen, $(C_1-C_6)$alkyl, $(C_3-C_7)$cycloalkyl, $(C_3-C_7)$cycloalkyloxy, $(C_3-C_7)$cycloalkylalkoxy, CN, CHF$_2$, CF$_3$, CH$_2$CF$_3$, piperidnyl, morpholinyl, N-Me-piperazinyl, piperazinyl, OCF$_3$, OCHF$_2$, OCH$_2$CF$_3$, SMe, each of which are attached via carbon-carbon or carbon-nitrogen or carbon-oxygen single bonds, and none of which are substituted; or $R_a$ and $R_b$ taken together with the atom(s) to which they are attached form a 5-6 membered ring.

Restricted phenylalkyl is a restricted phenyl-$(C_1-C_4$ alkyl)- group wherein restricted phenyl and alkyl are as defined above, including the optional substitutions. Examples of restricted phenylalkyl groups include but are not limited to 4-cyano-phenylmethyl and 3-chloro-phenylethyl.

Abbreviations used in the following examples and preparations include:

Ac Acyl (Me-C(O)—)
AcN Acetonitrile
ACN Acetonitrile
BINAP 2,2'-bis(diphenylphosphino)-1,1'-binaphthyl
Bn Benzyl
Celite® Diatomaceous earth
DABCO 1,4-diazabicyclo[2.2.2]octane
DBU 1,8-Diazabicyclo[5.4.0]undec-7-ene
DCC N.N', Dicyclohexylcarbodiimide
DCM Dichloromethane
DIEA Di-isopropylethyl amine
DIPEA Di-isopropylethyl amine
DMAP 4-Dimethylaminopyridine
DMF Dimethylformamide
DMP Dess Martin Periodinane
DMSO Dimethyl sulfoxide
Dppf 1,4-Bis(diphenylphosphino) ferrocene EDC 1-(3-Dimethylaminopropyl)-3-ethylcarbodiimide Hydrochloride
Et₃N Triethylamine
g gram(s)
h Hour(s)
hr Hour(s)
HATU 2-(7-Aza-1H-benzotriazole-1-yl)-1,1,3,3-tetramethyluronium hexafluorophosphate
HMDS Hexamethyldisilazide
HOBt 1-Hydroxybenzotriazole
HPLC High Pressure Liquid Chromatography
HRMS High resolution mass spectrometry
i.v. Intravenous
KHMDS Potassium Hexamethydisilazide
LDA Lithium Di-isopropylamide
IPA Isopropyl alcohol
m Multiplet
m- meta
MEM Methoxyethoxymethyl
MeOH Methyl Alcohol or Methanol
min Minute(s)
mmol millimoles
mmole millimoles
Ms Mesylate
MS Mass Spectrometry
MW Molecular Weight
NBS N-Bromosuccinamide
NIS N-Iodosuccinamide
NMR Nuclear Magnetic Resonance
NMM N-Methyl Morpholine
NMP N-Methyl-2-pyrrolidone
o ortho
o/n overnight
p para
PCC Pyridinium Chlorochromate
PEPPSI 1,3-Bis(2,6-diisopropylphenyl)imidazolidene)(3-chloropyridinyl) palladium(II) dichloride
PhNTf₂ 1,1,1-trifluoro-N-phenyl-N-(trifluoromethylsulfonyl)methanesulfonamide
POPd Dihydrogen dichlorobis(di-tert-butylphosphinito-kp)palladate (2-)
p.s.i. Pounds per square inch
PPA Polyphosphoric acid
PPAA 1-Propanephosphonic Acid Cyclic Anhydride
PTSA p-Toluenesulfonic acid
PyBOP® Benzotriazol-1-yl-oxytripyrrolidinophosphonium hexafluorophosphate
RT (or rt) room temperature (about 20-25° C.)
s Singlet
sat. Saturated
SuOH N-hydroxy succinimide
t Triplet
TBAF Tetra-butyl ammonium fluoride
TEA Triethylamine
TFA Trifluoroacetic Acid
THF Tetrahydrofuran
TLC Thin layer chromatography
TMS Trimethylsilyl
Tf Triflate
Tof-MS Time of Flight Mass Spectrometry
Ts Tosylate
v/v volume/volume
wt/v weight/volume II. Compounds of the Invention In one embodiment, the invention provides compounds of Formula (I)

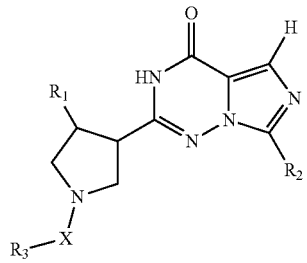

or a pharmaceutically acceptable salt thereof,
wherein:
X is selected from a bond, C(O) or S(O)₂;
$R_1$ is independently selected from the group consisting of H, $(C_1-C_6)$ alkyl, $(C_1-C_6)$ alkoxy, $(C_3-C_7)$cycloalkyl, $(C_3-C_7)$cycloalkyl$(C_1-C_4)$ alkyl, $(C_3-C_7)$cycloalkyloxy, heterocycloalkyl, heterocycloalkyl$(C_1-C_4)$alkyl and heterocycloalkyloxy, each of which may be optionally substituted with one or more substituents selected from the group consisting of halogen (e.g., F or Cl), —S(O)₂$(C_1-C_4)$alkyl, OH, —C(O)—$(C_1-C_4)$alkyl, oxo, CN, $(C_1-C_6)$alkyl, $(C_1-C_4)$alkoxy, $(C_3-C_7)$cycloalkyl, —C(O)NH$(C_1-C_4)$alkyl, —C(O)N[$(C_1-C_4)$alkyl$(C_1-C_4)$alkyl], $(C_1-C_4$ alkyl)-C(O)—, $(C_1-C_4)$alkylsulfonyl-, —S(O)₂NH$(C_1-C_4)$alkyl, and —S(O)₂N[$(C_1-C_4)$alkyl$(C_1-C_4)$alkyl];

$R_2$ is independently selected from the group consisting of $(C_1-C_6)$ alkyl, $(C_3-C_{10})$cycloalkyl, $(C_3-C_7)$cycloalkyl$(C_1-C_4)$ alkyl, heterocycloalkyl, heterocycloalkyl$(C_1-C_4)$alkyl, heteroaryl, heteroaryl$(C_1-C_4)$alkyl, restricted phenyl and restricted phenyl$(C_1-C_4)$alkyl, each of which may be optionally substituted with one or more substituents selected from the group consisting of halogen (e.g., F or Cl), —S(O)₂$(C_1-C_4)$alkyl, OH, —C(O)—$(C_1-C_4)$alkyl, oxo, CN, $(C_1-C_6)$alkyl, $(C_1-C_4)$alkoxy, $(C_3-C_7)$cycloalkyl, —C(O)NH$(C_1-C_4)$alkyl, —C(O)N[$(C_1-C_4)$alkyl$(C_1-C_4)$alkyl], $(C_1-C_4$ alkyl)-C(O)—, $(C_1-C_4)$alkylsulfonyl-, —S(O)₂NH$(C_1-C_4)$alkyl, and —S(O)₂N[$(C_1-C_4)$alkyl$(C_1-C_4)$alkyl]; and $R_3$ is independently selected from the group consisting of $(C_1-C_6)$ alkyl, $(C_3-C_7)$cycloalkyl, $(C_3-C_7)$cycloalkyl$(C_1-C_4)$alkyl, heterocycloalkyl, heterocycloalkyl$(C_1-C_4)$alkyl, heteroaryl, heteroaryl$(C_1-C_4)$alkyl, restricted phenyl and restricted phenyl$(C_1-C_4)$alkyl, each of which may be optionally substituted with one or more substituents selected from the group consisting of halogen (e.g., F or Cl), —S(O)₂$(C_1-C_4)$alkyl, OH, —C(O)—$(C_1-C_4)$alkyl, oxo, CN, $(C_1-C_6)$alkyl, $(C_1-C_4)$alkoxy, $(C_3-C_7)$cycloalkyl, —C(O)NH$(C_1-C_4)$alkyl, —C(O)N[$(C_1-C_4)$alkyl$(C_1-C_4)$alkyl], $(C_1-C_4$ alkyl)-C(O)—, $(C_1-C_4)$alkylsulfonyl-, —S(O)₂NH$(C_1-C_4)$alkyl, and —S(O)₂N[$(C_1-C_4)$alkyl$(C_1-C_4)$alkyl]. In certain embodiments the substituents are selected from halogen (e.g., F or Cl), CN, $(C_1-C_6)$alkyl, and $(C_1-C_4)$alkoxy. In certain embodiments, $R_1$ is selected from $(C_1-C_6)$ alkyl, e.g., methyl. In certain embodiments, $R_2$ is selected from the group consisting of heterocycloalkyl, e.g., tetrahydropyranyl or piperidinyl, $(C_3-C_{10})$cycloalkyl, e.g., adamantyl, and restricted phenyl, which may be optionally substituted with one or more substituents selected from the group consisting of halogen, —S(O)₂$(C_1-C_4)$alkyl, OH, —C(O)—$(C_1-C_4)$alkyl, CN, $(C_1-C_6)$alkyl, and $(C_1-C_4)$alkoxy. In certain embodiments, $R_3$ is selected from the group consisting of a mono or bicyclic heteroaryl$(C_1-C_4)$alkyl and restricted phenyl$(C_1-C_4)$alkyl, which may be optionally substituted with one or more substituents selected from the group consisting of halogen, —S(O)$_2$(C$_1$-C$_4$)alkyl, OH, —C(O)—(C$_1$-C$_4$) alkyl, CN, (C$_1$-C$_6$)alkyl, and (C$_1$-C$_4$)alkoxy. In certain embodiments, X is a bond. In certain embodiments, R$_3$ is pyrimidinylmethyl-, which may be optionally substituted with one or more substituents selected from the group consisting of halogen (e.g., F or Cl), —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy. In certain alternative embodiments, R$_3$ is (restricted phenyl)methyl-, which may be optionally substituted with one or more substituents selected from the group consisting of halogen (e.g., F or Cl), —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

In another embodiment, the invention provides compounds of Formula (I)

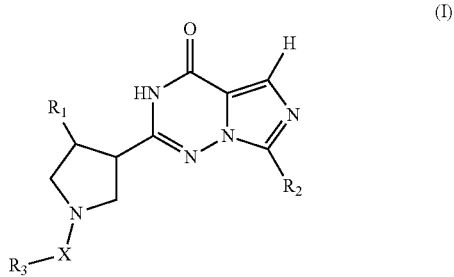

(I)

wherein:

X is selected from a bond, C(O) and S(O)$_2$;

R$_1$ is independently selected from H, (C$_1$-C$_6$) alkyl, (C$_1$-C$_6$) alkoxy, (C$_3$-C$_7$)cycloalkyl, (C$_3$-C$_7$)cycloalkyl (C$_1$-C$_4$)alkyl, (C$_3$-C$_7$)cycloalkyloxy, heterocycloalkyl, heterocycloalkyl(C$_1$-C$_4$)alkyl and heterocycloalkyloxy all of which may be optionally substituted;

R$_2$ is independently selected from (C$_1$-C$_6$) alkyl, (C$_3$-C$_7$) cycloalkyl, (C$_3$-C$_7$)cycloalkyl (C$_1$-C$_4$) alkyl, heterocycloalkyl, heterocycloalkyl(C$_1$-C$_4$)alkyl, heteroaryl, heteroaryl(C$_1$-C$_4$)alkyl, restricted phenyl and restricted phenyl (C$_1$-C$_4$) alkyl, all of which can be optionally substituted; and R$_3$ is independently selected from (C$_1$-C$_6$) alkyl, (C$_3$-C$_7$) cycloalkyl, (C$_3$-C$_7$)cycloalkyl (C$_1$-C$_4$) alkyl, heterocycloalkyl, heterocycloalkyl(C$_1$-C$_4$)alkyl, heteroaryl, heteroaryl(C$_1$-C$_4$)alkyl, restricted phenyl and restricted phenyl (C$_1$-C$_4$) alkyl, all of which can be optionally substituted. In a further embodiment, the compound may be a pharmaceutically acceptable salt thereof.

In yet another embodiment, the invention provides compounds of Formula (I)

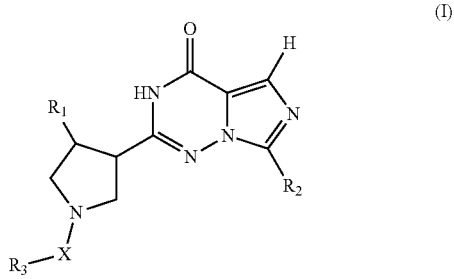

(I)

or a pharmaceutically acceptable salt thereof, wherein:

X is selected from a bond, C(O) and S(O)$_2$;

R$_1$ is (C$_1$-C$_6$) alkyl, e.g., methyl;

R$_2$ is selected from the group consisting of heterocycloalkyl, e.g., tetrahydropyranyl or piperidinyl, (C$_3$-C$_{10}$) cycloalkyl, e.g., adamantyl, and restricted phenyl, each of which may be optionally substituted with one or more substituents selected from the group consisting of halogen (e.g., F or Cl), —S(O)$_2$(C$_1$-C$_4$)alkyl, OH, —C(O)—(C$_1$-C$_4$) alkyl, CN, (C$_1$-C$_6$)alkyl, and (C$_1$-C$_4$)alkoxy; and R$_3$ is selected from the group consisting of a mono or bicyclic heteroaryl(C$_1$-C$_4$)alkyl and restricted phenyl(C$_1$-C$_4$)alkyl, each of which may be optionally substituted with one or more substituents selected from the group consisting of halogen (e.g., F or Cl), —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

A further embodiment of Formula (I) may be represented as

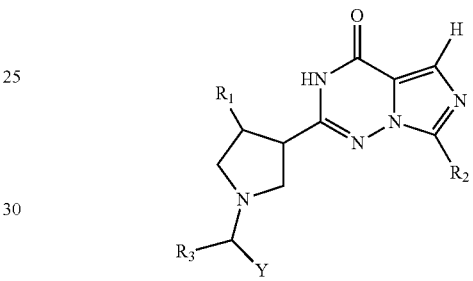

or a pharmaceutically acceptable salt thereof, wherein:

Y is H or (C$_1$-C$_3$) alkyl, e.g., methyl or ethyl;

R$_1$ is (C$_1$-C$_6$) alkyl, e.g., methyl;

R$_2$ is selected from the group consisting of heterocycloalkyl, e.g., tetrahydropyranyl or piperidinyl, (C$_3$-C$_{10}$) cycloalkyl, e.g., adamantyl, and restricted phenyl, each of which may be optionally substituted with one or more substituents selected from the group consisting of halogen (e.g., F or Cl), —S(O)$_2$(C$_1$-C$_4$)alkyl, e.g., —S(O)$_2$CH$_2$CH$_3$, OH, —C(O)—(C$_1$-C$_4$)alkyl, e.g., —C(O)CH$_3$, CN, (C$_1$-C$_6$) alkyl, and (C$_1$-C$_4$)alkoxy; and R$_3$ is selected from the group consisting of a mono or bicyclic heteroaryl and restricted phenyl, each of which may be optionally substituted with one or more substituents selected from the group consisting of halogen (e.g., F or Cl), —S(O)$_2$(C$_1$-C$_4$)alkyl, e.g., —S(O)$_2$CH$_2$CH$_3$, OH, —C(O)—(C$_1$-C$_4$)alkyl, e.g., —C(O)CH$_3$, CN, (C$_1$-C$_6$)alkyl, and (C$_1$-C$_4$)alkoxy. In certain embodiments, R$_3$ is pyrimidinyl, which may be optionally substituted with one or more substituents selected from the group consisting of halogen (e.g., F or Cl), —S(O)$_2$(C$_1$-C$_4$)alkyl, e.g., —S(O)$_2$CH$_2$CH$_3$, OH, —C(O)—(C$_1$-C$_4$)alkyl, e.g., —C(O)CH$_3$, CN, (C$_1$-C$_6$) alkyl, and (C$_1$-C$_4$)alkoxy. In certain alternative embodiments, R$_3$ is restricted phenyl, which may be optionally substituted with one or more substituents selected from the group consisting of halogen (e.g., F or Cl), —S(O)$_2$(C$_1$-C$_4$) alkyl, e.g., —S(O)$_2$CH$_2$CH$_3$, OH, —C(O)—(C$_1$-C$_4$)alkyl, e.g., —C(O)CH$_3$, CN, (C$_1$-C$_6$)alkyl, and (C$_1$-C$_4$)alkoxy.

In certain embodiments of the invention, where R$_1$ is H, the compound of the invention is the trans (−) stereoisomer.

In certain embodiments of the invention, where R$_1$ is H, the compound of the invention is the trans (+) stereoisomer.

A. Additional Embodiments of the Invention

In one embodiment, alkyl groups are fully saturated whether present on their own or as part of another group (e.g. alkylamino).

In certain embodiments, substituent groups are not further substituted.

In various embodiments, any group that is defined as being optionally substituted can be independently singly or multiply optionally substituted.

In one embodiment, compounds of the invention contain one alkyl group which is substituted with 1-3 fluorine atoms.

In another embodiment, compounds of the invention contain one alkyl group which contains a double bond.

In one embodiment compounds of the invention contain two alkyl groups which are substituted with 1-3 fluorine atoms.

In another embodiment, compounds of the invention contain one alkyl group which contains a triple bond.

In another embodiment, compounds of the invention contain one alkyl group which is substituted with an oxo group.

In another embodiment, compounds of the invention contain one alkyl group which is substituted with a hydroxyl group.

In another embodiment, compounds of the invention contain one alkyl group which is substituted with a ($C_1$-$C_4$) alkoxy group.

In another embodiment, compounds of the invention contain one alkyl group which is substituted with a ($C_1$-$C_4$) alkylsulfonyl group.

In another embodiment, compounds of the invention contain one alkoxy group which is substituted with 1-3 fluorine atoms In one embodiment, saturated monocyclic heterocycloalkyl groups are substituted on carbon with up to 2 groups selected from OH, ($C_1$-$C_6$)alkyl or ($C_1$-$C_4$)alkoxy group.

In one embodiment, saturated monocyclic heterocycloalkyl groups are substituted on nitrogen with a group selected from —S(O)$_2$($C_1$-$C_4$)alkyl, e.g., —S(O)$_2$ethyl, and —C(O)—($C_1$-$C_4$)alkyl, e.g., —C(O)CH$_3$.

In one embodiment, saturated monocyclic heterocycloalkyl groups are substituted on nitrogen with groups selected from ($C_1$-$C_6$)alkyl, acyl, —C(O)O—($C_1$-$C_4$)alkyl, —C(O)NH—($C_1$-$C_4$)alkyl, C(O)N(($C_1$-$C_4$)alkyl)$_2$ and ($C_1$-$C_4$)alkylsulfonyl-.

In one embodiment heteroaryl groups are substituted on carbon with 1-3 groups selected from halogen, CN, OH, ($C_1$-$C_4$)alkyl, ($C_3$-$C_6$)cycloalkyl, ($C_1$-$C_4$)alkoxy and ($C_1$-$C_4$)alkylsulfonyl.

In one embodiment restricted phenyl groups are substituted with 1-3 groups selected from halogen, CN, OH, ($C_1$-$C_4$)alkyl, ($C_3$-$C_6$)cycloalkyl, ($C_1$-$C_4$)alkoxy and ($C_1$-$C_4$)alkylsulfonyl.

In various embodiments, heteroaryl may be defined as tetrazolyl, thiophenyl, furanyl, thiazolyl, isothiazolyl, oxazolyl, isoxazolyl, 1,2,4-oxadiazolyl, 1,3,4-oxadiazolyl, pyrazolyl, imidazolyl, 1,2,3-triazolyl, 1,3,4-triazolyl, pyrimidinyl and pyrazinyl, all of which may be optionally substituted. In a particular embodiment, the heteroaryl is pyrimidinyl.

In other embodiments, heteroaryl may be defined as 1,5-naphthyridyl, 1,2,3,4-tetrahydro-1,5-naphthyridyl 1,6-naphthyridyl, 1,2,3,4-tetrahydro-1,6-naphthyridyl 1,7-naphthyridyl, 1,2,3,4-tetrahydro-1,7-naphthyridinyl 1,8-naphthyridyl, 1,2,3,4-tetrahydro-1,8-naphthyridyl, 2,6-naphthyridyl, 2,7-naphthyridyl, cinnolyl, isoquinolyl, tetrahydroisoquinolinyl, phthalazyl, quinazolyl, 1,2,3,4-tetrahydroquinazolinyl, quinolyl, tetrahydroquinolinyl, quinoxalyl and tetrahydroquinoxalinyl, all of which may be optionally substituted.

In further embodiments, heteroaryl may be defined as benzo[d][1,2,3]triazyl, benzo[e][1,2,4]triazyl, pyrido[2,3-b]pyrazyl, pyrido[2,3-c]pyridazyl, pyrido[2,3-d]pyrimidyl, pyrido[3,2-b]pyrazyl, pyrido[3,2-c]pyridazyl, pyrido[3,2-d]pyrimidyl, pyrido[3,4-b]pyrazyl, pyrido[3,4-c]pyridazyl, pyrido[3,4-d]pyrimidyl, pyrido[4,3-b]pyrazyl, pyrido[4,3-c]pyridazyl, pyrido[4,3-d]pyrimidyl, quinazolyl, 1H-benzo[d][1,2,3]triazolyl, 1H-benzo[d]imidazolyl, 1H-indazoyl, 1H-indoyl, 2H-benzo[d][1,2,3]triazoyl, 2H-pyrazolo[3,4-b]pyridinyl, 2H-pyrazolo[4,3-b]pyridinyl, [1,2,3]triazolo[1,5-a]pyridinyl, [1,2,4]triazolo[1,5-a]pyridinyl and [1,2,4]triazolo[4,3-a]pyridinyl, all of which may be optionally substituted.

In yet other embodiments, heteroaryl may be defined as benzo[b]thienyl, benzo[c][1,2,5]oxadiazyl, benzo[c][1,2,5]thiadiazolyl, benzo[d]isothiazoyl, benzo[d]isoxazoyl, benzo[d]oxazoyl, benzo[d]thiazoyl, benzofuryl, imidazo[1,2-a]pyrazyl, imidazo[1,2-a]pyridinyl, imidazo[1,2-a]pyrimidyl imidazo[1,2-b]pyridazyl, imidazo[1,2-c]pyrimidyl, imidazo[1,5-a]pyrazyl, imidazo[1,5-a]pyridinyl, imidazo[1,5-a]pyrimidyl, imidazo[1,5-b]pyridazyl, imidazo[1,5-c]pyrimidyl, indolizyl, pyrazolo[1,5-a]pyrazyl, pyrazolo[1,5-c]pyridinyl, pyrazolo[1,5-a]pyrimidyl, pyrazolo[1,5-b]pyridazine, pyrazolo[1,5-c]pyrimidine, pyrrolo[1,2-a]pyrazine, pyrrolo[1,2-a]pyrimidyl, pyrrolo[1,2-b]pyridazyl, pyrrolo[1,2-c]pyrimidyl, 1H-imidazo[4,5-b]pyridinyl, 1H-imidazo[4,5-c]pyridinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-c]pyridinyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, 2H-indazoyl, 3H-imidazo[4,5-b]pyridinyl and 3H-imidazo[4,5-c]pyridinyl, all of which may be optionally substituted.

In further embodiments, heteroaryl may be defined as benzo[c]isothiazyl, benzo[c]isoxazyl, furo[2,342]pyridinyl, furo[2,3-c]pyridinyl, furo[3,2-b]pyridinyl, furo[3,2-c]pyridiyl, isothiazolo[4,5-b]pyridinyl, isothiazolo[4,5-c]pyridinyl, isothiazolo[5,4-b]pyridinyl, isothiazolo[5,4-c]pyridinyl, isoxazolo[4,5-b]pyridinyl, isoxazolo[4,5-c]pyridinyl, isoxazolo[5,4-b]pyridinyl, isoxazolo[5,4-c]pyridinyl, oxazolo[4,5-b]pyridinyl, oxazolo[4,5-c]pyridinyl, oxazolo[5,4-b]pyridinyl, oxazolo[5,4-c]pyridinyl, thiazolo[4,5-b]pyridiyl, thiazolo[4,5-c]pyridinyl, thiazolo[5,4-b]pyridinyl, thiazolo[5,4-c]pyridinyl, thieno[2,3-b]pyridinyl, thieno[2,3-c]pyridinyl, thieno[3,2-b]pyridinyl and thieno[3,2-c]pyridinyl, all of which may be optionally substituted.

In one embodiment, X is selected from C(O) and S(O)$_2$.

In another embodiment, X is C(O).

In a further embodiment, X is S(O)$_2$.

In another embodiment, X is a bond.

In another embodiment, Y is H.

In another embodiment, Y is ($C_1$-$C_3$) alkyl, e.g., methyl or ethyl.

In one embodiment, R$_1$ is selected from H, ($C_1$-$C_6$) alkyl, ($C_3$-$C_7$)cycloalkyl and ($C_3$-$C_7$)cycloalkyl ($C_1$-$C_4$) alkyl.

In another embodiment, R$_1$ is selected from ($C_1$-$C_6$) alkyl, ($C_3$-$C_7$)cycloalkyl and ($C_3$-$C_7$)cycloalkyl ($C_1$-$C_4$) alkyl.

In another embodiment, R$_1$ is selected from ($C_1$-$C_6$) alkoxy and ($C_3$-$C_7$)cycloalkyloxy.

In another embodiment, R$_1$ is selected from ($C_1$-$C_6$) alkyl and ($C_1$-$C_6$) alkoxy.

In a further embodiment, R$_1$ is selected from ($C_1$-$C_6$) alkyl and ($C_3$-$C_7$)cycloalkyl.

In a further embodiment, $R_1$ is selected from heterocycloalkyl, heterocycloalkyl($C_1$-$C_4$)alkyl and heterocycloalkyloxy.

In another embodiment, $R_1$ is H.
In another embodiment, $R_1$ is ($C_1$-$C_6$) alkyl.
In another embodiment, $R_1$ is ($C_1$-$C_3$) alkyl.
In another embodiment, $R_1$ is methyl.
In an additional embodiment, $R_1$ is ($C_1$-$C_6$) alkoxy.
In an additional embodiment, $R_1$ is ($C_1$-$C_3$) alkoxy.
In a further embodiment, $R_1$ is ($C_3$-$C_7$)cycloalkyl.
In a further embodiment, $R_1$ is ($C_3$-$C_5$)cycloalkyl.
In another embodiment, $R_1$ is ($C_3$-$C_7$)cycloalkyl ($C_1$-$C_4$) alkyl.
In another embodiment, $R_1$ is ($C_3$-$C_5$)cycloalkyl ($C_1$-$C_2$) alkyl.
In another embodiment, $R_1$ is ($C_3$-$C_7$)cycloalkyloxy.
In another embodiment, $R_1$ is ($C_3$-$C_5$)cycloalkyloxy.
In another embodiment, $R_1$ is heterocycloalkyl.
In a further embodiment $R_1$ is heterocycloalkyl having only 6 ring atoms. Examples include but are not limited to morpholino, piperidinyl, piperazinyl N-Me-piperazinyl and pyranyl.
In another embodiment. $R_1$ is heterocycloalkyl having only 5 ring atoms. Examples include but are not limited to tetrahydrofuranyl and pyrrolidinyl.
In another embodiment, $R_1$ is a heterocycloalkyl group selected from Formulas B1-B16 depicted below:

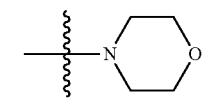
B1

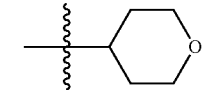
B2

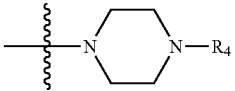
B3

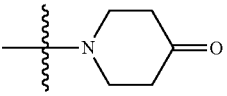
B4

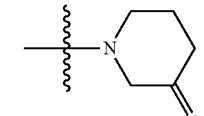
B5

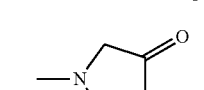
B6

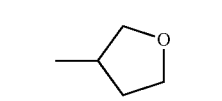
B7

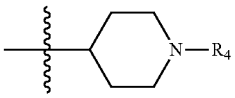
B8

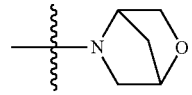
B9

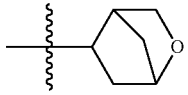
B10

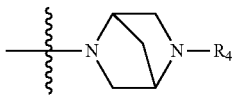
B11

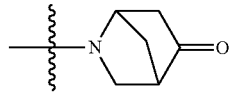
B12

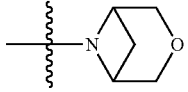
B13

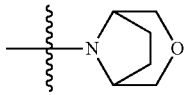
B14

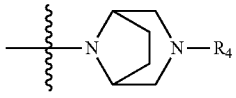
B15

B16 wherein $R_4$ is selected from hydrogen, $C_1$-$C_6$ alkyl, $C_3$-$C_6$ cycloalkyl and $C_3$-$C_6$ cycloalkylalkyl.

In another embodiment, $R_1$ is heterocycloalkyl($C_1$-$C_4$) alkyl.
In a further embodiment, $R_1$ is heterocycloalkyloxy.
In one embodiment, $R_2$ is selected from ($C_1$-$C_6$) alkyl, ($C_3$-$C_{10}$)cycloalkyl and ($C_3$-$C_7$)cycloalkyl ($C_1$-$C_4$) alkyl.
In one embodiment, $R_2$ is selected from ($C_1$-$C_6$) alkyl, ($C_3$-$C_7$)cycloalkyl and ($C_3$-$C_7$)cycloalkyl ($C_1$-$C_4$) alkyl.
In one embodiment, $R_2$ is selected from the group consisting of heterocycloalkyl, ($C_3$-$C_{10}$)cycloalkyl, and restricted phenyl.
In another embodiment, $R_2$ is selected from heterocycloalkyl and heterocycloalkyl($C_1$-$C_4$)alkyl.
In a further embodiment, $R_2$ is selected from restricted phenyl, restricted phenyl($C_1$-$C_4$)alkyl, heteroaryl and heteroaryl($C_1$-$C_4$)alkyl.
In a further embodiment, $R_2$ is selected from heteroaryl and heteroaryl($C_1$-$C_4$)alkyl.
In another embodiment, $R_2$ is selected ($C_3$-$C_7$)cycloalkyl, heterocycloalkyl, heteroaryl and restricted phenyl.
In another embodiment, $R_2$ is selected ($C_3$-$C_7$)cycloalkyl, heterocycloalkyl and heteroaryl.
In another embodiment, $R_2$ is ($C_1$-$C_6$) alkyl.
In another embodiment, $R_2$ is ($C_1$-$C_3$) alkyl.
In an additional embodiment, $R_2$ is ($C_3$-$C_7$)cycloalkyl.
In an additional embodiment, $R_2$ is ($C_3$-$C_7$)cycloalkyl substituted with one or two fluoro.

In an additional embodiment, $R_2$ is $(C_3-C_{10})$cycloalkyl.

In an additional embodiment, $R_2$ is $(C_3-C_{10})$cycloalkyl substituted with one or two fluoro.

In an additional embodiment, $R_2$ is $(C_3-C_5)$cycloalkyl.

In an additional embodiment, $R_2$ is $(C_3-C_7)$cycloalkyl $(C_1-C_4)$ alkyl.

In an additional embodiment, $R_2$ is $(C_3-C_5)$cycloalkyl $(C_1-C_2)$ alkyl.

In another embodiment, $R_2$ is heterocycloalkyl.

In a further embodiment $R_2$ is heterocycloalkyl having only 6 ring atoms. Examples include but are not limited to morpholino, piperidinyl, piperazinyl N-Me-piperazinyl and pyranyl. Additional examples include 4-piperidinyl, 3-tetrahydropyranyl and 4-tetrahydropyranyl, which may be optionally substituted with one or more groups selected from the group consisting of halogen (e.g., F or Cl), —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy In another embodiment $R_2$ is heterocycloalkyl having only 5 ring atoms. Examples include but are not limited to tetrahydrofuranyl and pyrrolidinyl.

In another embodiment, $R_2$ is a heterocycloalkyl group selected from Formulas B1-B16 depicted below:

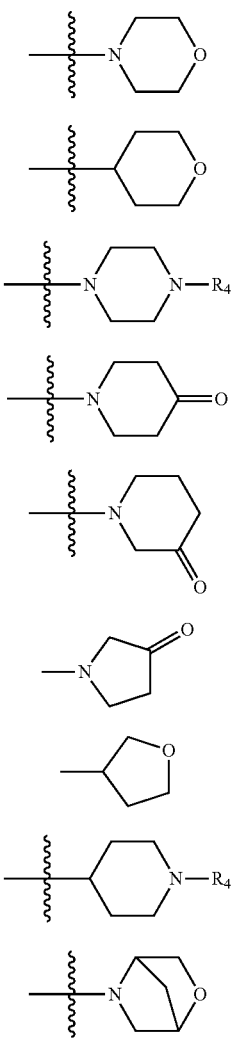

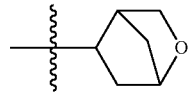

B10

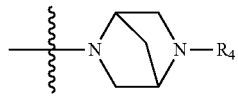

B11

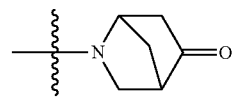

B12

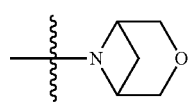

B13

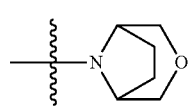

B14

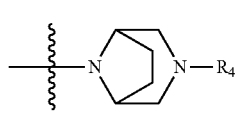

B15

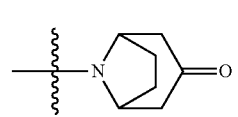

B16 wherein $R_4$ is selected from hydrogen, $C_1$-$C_6$ alkyl, $C_3$-$C_6$ cycloalkyl and $C_3$-$C_6$ cycloalkylalkyl.

In another embodiment, $R_2$ is heterocycloalkyl($C_1$-$C_4$) alkyl.

In an additional embodiment, $R_2$ is heteroaryl.

In a further embodiment $R_2$ is a heterobicyclic ring system.

In another embodiment, $R_2$ is a monocyclic aromatic ring having 5-6 atoms selected from C, O, S and N provided that not more than 3 ring atoms are not C and where said ring may be optionally and independently substituted with up to two groups selected from $C_1$-$C_4$ alkyl, cycloalkyl, cycloalkyloxy, $C_1$-$C_4$ alkoxy, CF$_3$, carboxyl, alkoxyalkyl, cycloalkylalkoxy, amino, alkylamino, dialkylamino, amido, alkylamido, dialkylamido, thioalkyl, halogen, cyano, and nitro.

In a further embodiment, $R_2$ is a monocyclic aromatic ring containing 5 atoms selected from C, O, S, and N provided that not more than 3 ring atoms are not C and where said ring may be optionally and independently substituted with up to two groups selected from $C_1$-$C_4$ alkyl, cycloalkyl, cycloalkyloxy, alkoxy, CF$_3$, carboxyl, alkoxyalkyl, $C_1$-$C_4$ cycloalkylalkoxy, amino, alkylamino, dialkylamino, amido, alkylamido, dialkylamido, thioalkyl, halogen, cyano, and nitro.

In a further embodiment, $R_2$ is a monocyclic aromatic ring containing 6 atoms selected from C and N provided that not more than 3 ring atoms are not C and where said ring may be optionally and independently substituted with up to two groups selected from $C_1$-$C_4$ alkyl, e.g., methyl, cycloalkyl, cycloalkyloxy, $C_1$-$C_4$ alkoxy, CF$_3$, carboxyl, alkoxyalkyl, cycloalkylalkoxy, amino, alkylamino, dialkylamino, amido, alkylamido, dialkylamido, thioalkyl, halogen (e.g., F or Cl), cyano, and nitro.

In a further embodiment, $R_2$ is heteroaryl($C_1$-$C_4$)alkyl.
In a further embodiment, $R_2$ is restricted phenyl.
In another embodiment, $R_2$ is restricted phenyl($C_1$-$C_4$) alkyl.

In one embodiment, $R_3$ is selected from ($C_1$-$C_6$) alkyl, ($C_3$-$C_7$)cycloalkyl, heterocycloalkyl, heteroaryl and restricted phenyl.

In one embodiment, $R_3$ is selected from ($C_1$-$C_6$) alkyl, ($C_3$-$C_7$)cycloalkyl, heterocycloalkyl and heteroaryl.

In another embodiment, $R_3$ is selected from ($C_3$-$C_7$) cycloalkyl ($C_1$-$C_4$) alkyl, heterocycloalkyl($C_1$-$C_4$)alkyl and heteroaryl($C_1$-$C_4$)alkyl.

In a further embodiment, $R_3$ is selected from heterocycloalkyl($C_1$-$C_4$)alkyl and heteroaryl($C_1$-$C_4$)alkyl.

In a further embodiment, $R_3$ is selected from heterocycloalkyl and heteroaryl.

In another embodiment, $R_3$ is ($C_1$-$C_6$) alkyl.
In another embodiment, $R_3$ is ($C_1$-$C_3$) alkyl.
In an additional embodiment, $R_3$ is ($C_3$-$C_7$)cycloalkyl.
In an additional embodiment, $R_3$ is ($C_3$-$C_5$)cycloalkyl.
In a further embodiment, $R_3$ is ($C_3$-$C_7$)cycloalkyl ($C_1$-$C_4$) alkyl.
In a further embodiment, $R_3$ is ($C_3$-$C_5$)cycloalkyl ($C_1$-$C_2$) alkyl.
In an additional embodiment $R_3$ is heterocycloalkyl.
In a further embodiment $R_3$ is heterocycloalkyl having only 6 ring atoms. Examples include but are not limited to morpholino, piperidinyl, piperazinyl N-Me-piperazinyl and pyranyl.

In another embodiment $R_3$ is heterocycloalkyl having only 5 ring atoms. Examples include but are not limited to tetrahydrofuranyl and pyrrolidinyl.

In another embodiment, $R_3$ is a heterocycloalkyl group selected from Formulas B1-B16 depicted below:

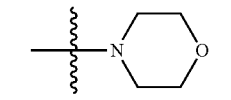
B1

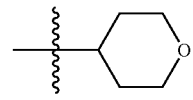
B2

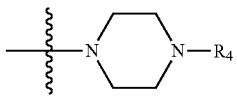
B3

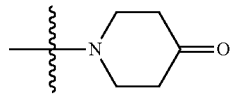
B4

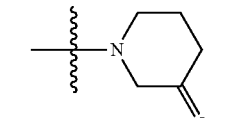
B5

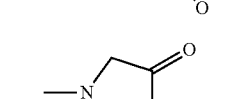
B6

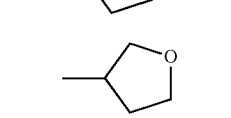
B7

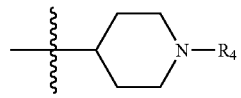
B8

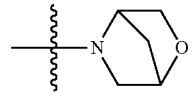
B9

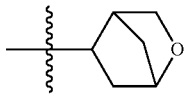
B10

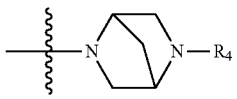
B11

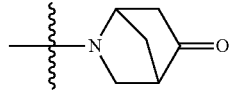
B12

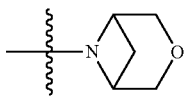
B13

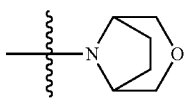
B14

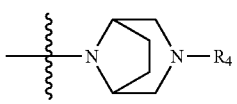
B15

B16 wherein $R_4$ is selected from hydrogen, $C_1$-$C_6$ alkyl, $C_3$-$C_6$ cycloalkyl and $C_3$-$C_6$ cycloalkylalkyl.

In another embodiment, $R_3$ is selected from the group consisting of a mono or bicyclic heteroaryl and restricted phenyl In another embodiment, $R_3$ is pyrimidinylmethyl-, which may be optionally substituted with one or more substituents selected from the group consisting of halogen (e.g., F or Cl), —S(O)$_2$($C_1$-$C_4$)alkyl, OH, —C(O)—($C_1$-$C_4$)alkyl, CN, ($C_1$-$C_6$)alkyl, and ($C_1$-$C_4$)alkoxy.

In another embodiment, $R_3$ is (restricted phenyl)methyl-, which may be optionally substituted with one or more substituents selected from the group consisting of halogen (e.g., F or Cl), —S(O)$_2$($C_1$-$C_4$)alkyl, OH, —C(O)—($C_1$-$C_4$) alkyl, CN, ($C_1$-$C_6$)alkyl, and ($C_1$-$C_4$)alkoxy.

In another embodiment $R_3$ is heterocycloalkyl($C_1$-$C_4$) alkyl.

In another embodiment $R_3$ is heteroaryl, e.g., mono or bicyclic heteroaryl.

In a further embodiment $R_3$ is a heterobicyclic ring system.

In another embodiment, $R_3$ is a monocyclic aromatic ring having 5-6 atoms selected from C, O, S and N provided that not more than 3 ring atoms are not C and where said ring may be optionally and independently substituted with up to two groups selected from C₁-C₄ alkyl, cycloalkyl, cycloalkyloxy, C₁-C₄ alkoxy, CF₃, carboxyl, alkoxyalkyl, C₁-C₄ cycloalkylalkoxy, amino, alkylamino, dialkylamino, amido, alkylamido, dialkylamido, thioalkyl, halogen, cyano, and nitro.

In a further embodiment, R₃ is a monocyclic aromatic ring containing 5 atoms selected from C, O, S, and N provided that not more than 3 ring atoms are not C and where said ring may be optionally and independently substituted with up to two groups selected from C₁-C₄ alkyl, cycloalkyl, cycloalkyloxy, C₁-C₄ alkoxy, CF₃, carboxyl, alkoxyalkyl, C₁-C₄ cycloalkylalkoxy, amino, alkylamino, dialkylamino, amido, alkylamido, dialkylamido, thioalkyl, halogen, cyano, and nitro.

In a further embodiment, R₃ is a monocyclic aromatic ring containing 6 atoms selected from C and N provided that not more than 3 ring atoms are not C and where said ring may be optionally and independently substituted with up to two groups selected from C₁-C₄ alkyl, cycloalkyl, cycloalkyloxy, C₁-C₄ alkoxy, e.g., —OMe, CF₃, carboxyl, alkoxyalkyl, C₁-C₄ cycloalkylalkoxy, amino, alkylamino, dialkylamino, amido, alkylamido, dialkylamido, thioalkyl, halogen, e.g., F, cyano, and nitro.

In another embodiment, R₃ is selected from the group consisting of a mono or bicyclic heteroaryl(C₁-C₄)alkyl and restricted phenyl(C₁-C₄)alkyl.

In another embodiment, R₃ is pyrimidinyl, which may be optionally substituted with one or more substituents selected from the group consisting of halogen (e.g., F or Cl), —S(O)₂(C₁-C₄)alkyl, OH, —C(O)—(C₁-C₄)alkyl, CN, (C₁-C₆)alkyl, and (C₁-C₄)alkoxy.

In another embodiment, R₃ is restricted phenyl, which may be optionally substituted with one or more substituents selected from the group consisting of halogen (e.g., F or Cl), —S(O)₂(C₁-C₄)alkyl, OH, —C(O)—(C₁-C₄)alkyl, CN, (C₁-C₆)alkyl, and (C₁-C₄)alkoxy.

In a further embodiment R₃ is heteroaryl(C₁-C₄)alkyl.

In a further embodiment, R₂ is heteroaryl-CH₂—.

In a further embodiment R₃ is restricted phenyl.

In a further embodiment R₃ is restricted phenyl(C₁-C₄)alkyl.

In a further embodiment R₃ is restricted phenyl-CH₂—.

In certain embodiments, the substituents are selected from halogen, CN, (C₁-C₆)alkyl, and (C₁-C₄)alkoxy.

In certain embodiments, heterocycloalkyl is tetrahydropyranyl.

In certain embodiments, heterocycloalkyl is piperidinyl.

In certain embodiments, halogen is F or Cl.

In a particular embodiment, the compound of the invention is selected from one of the following list of individual compounds, each of which is intended to be a separate embodiment, and which is provided in table/list format solely as a convenience:

(−)-2-((3,4-trans)-1-benzyl-4-methylpyrrolidin-3-yl)-7-(tetrahydro-2H-pyran-4-yl)imidazo[1,5-f][1,2,4]triazin-4(3H)-one
(+)-2-((3,4-trans)-1-benzyl-4-methylpyrrolidin-3-yl)-7-(tetrahydro-2H-pyran-4-yl)imidazo[1,5-f][1,2,4]triazin-4(3H)-one
(+)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one
(+)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one
(−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one
(+)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one
(+)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile
(−)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile
(+)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one
(+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile
(+)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one
(+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one
(+)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one
(−)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one
(+)-7-((1s,3R)-adamantan-1-yl)-2-((3,4-trans)-1-benzyl-4-methylpyrrolidin-3-yl)imidazo[5,1-f][1,2,4]triazin-4(3H)-one
(−)-7-((1s,3R)-adamantan-1-yl)-2-((3,4-trans)-1-benzyl-4-methylpyrrolidin-3-yl)imidazo[5,1-f][1,2,4]triazin-4(3H)-one
(−)-2-((3,4-trans)-1-benzyl-4-methylpyrrolidin-3-yl)-7-(5-chloro-2-methylphenyl)imidazo[5,1-f][1,2,4]triazin-4(3H)-one
(+)-2-((3,4-trans)-1-benzyl-4-methylpyrrolidin-3-yl)-7-(5-chloro-2-methylphenyl)imidazo[5,1-f][1,2,4]triazin-4(3H)-one
(+)-2-((3,4-trans)-1-benzyl-4-methylpyrrolidin-3-yl)-7-(4-fluoro-2-methylphenyl)imidazo[5,1-f][1,2,4]triazin-4(3H)-one
(−)-2-((3,4-trans)-1-benzyl-4-methylpyrrolidin-3-yl)-7-(4-fluoro-2-methylphenyl)imidazo[5,1-f][1,2,4]triazin-4(3H)-one
(+)-2-((3,4-trans)-1-benzyl-4-methylpyrrolidin-3-yl)-7-(4,4-difluorocyclohexyl)imidazo[5,1-f][1,2,4]triazin-4(3H)-one
(−)-2-((3,4-trans)-1-benzyl-4-methylpyrrolidin-3-yl)-7-(4,4-difluorocyclohexyl)imidazo[5,1-f][1,2,4]triazin-4(3H)-one
(−)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one
(−)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one
(−)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one
(−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one
(+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one
(−)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one
(+)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one
(+)-7-((1s,3R)-adamantan-1-yl)-2-((3,4-trans)-4-methyl-1-(pyrimidin-2-ylmethyl)pyrrolidin-3-yl)imidazo[5,1-f][1,2,4]triazin-4(3H)-one
2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 1
2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 2
2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 3
(+)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one
(−)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one
(−)-7-(4-fluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one
(+)-7-(4,4-difluorocyclohexyl)-2-((3,4-trans)-4-methyl-1-(pyrimidin-2-ylmethyl)pyrrolidin-3-yl)imidazo[5,1-f][1,2,4]triazin-4(3H)-one
(−)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one
(+)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one
(−)-7-(5-chloro-2-methylphenyl)-2-((3,4-trans)-4-methylpyrrolidin-3-yl)imidazo[5,1-f][1,2,4]triazin-4(3H)-one
(+)-2-((3,4-trans)-1-benzyl-4-methylpyrrolidin-3-yl)-7-(furan-3-yl)imidazo[5,1-f][1,2,4]triazin-4(3H)-one
(−)-2-((3,4-trans)-1-benzyl-4-methylpyrrolidin-3-yl)-7-(furan-3-yl)imidazo[5,1-f][1,2,4]triazin-4(3H)-one
(−)-7-(1-acetylpiperidin-4-yl)-2-((3,4-trans)-1-benzyl-4-methylpyrrolidin-3-yl)imidazo[5,1-f][1,2,4]triazin-4(3H)-one
(+)-7-(1-acetylpiperidin-4-yl)-2-((3,4-trans)-1-benzyl-4-methylpyrrolidin-3-yl)imidazo[5,1-f][1,2,4]triazin-4(3H)-one (−)-2-((3,4-trans)-1-benzyl-4-methylpyrrolidin-3-yl)-7-(2-hydroxypropan-2-yl)imidazo[5,1-f][1,2,4]triazin-4(3H)-one
(+)-2-((3,4-trans)-1-benzyl-4-methylpyrrolidin-3-yl)-7-(2-hydroxypropan-2-yl)imidazo[5,1-f][1,2,4]triazin-4(3H)-one
(+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one
(−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one
(−)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one
(+)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one
(+)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one
(−)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one or a pharmaceutically acceptable salt thereof In a further embodiment of Formula (I), the compounds of the disclosure are embodied by the examples listed in the table below, each of which is intended to be a separate embodiment, and which is provided in table/list format solely as a convenience:

| R1 | R2 | R3 |
|---|---|---|
| Me | 4-pyran | 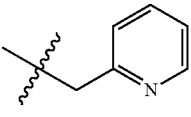 [SMILES: *Cc1ccccn1] |
| Me | 4-pyran | 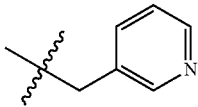 [SMILES: *Cc1cccnc1] |
| Me | 4-pyran | 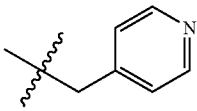 [SMILES: *Cc1ccncc1] |
| Me | 4-pyran | 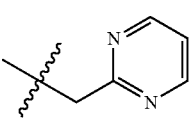 |
| Me | 4-pyran | 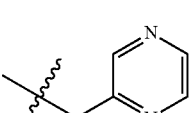 |
| Me | 4-pyran |  |
| Me | 4-pyran | 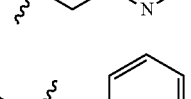 |
| Me | 4-pyran | 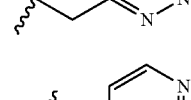 |
| Me | 4-pyran | 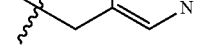 |
| Me | 4-pyran | 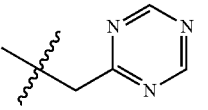 |
| Me | 4-pyran | 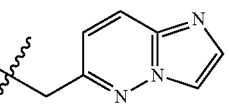 |
| Me | 4-pyran | 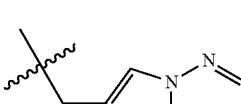 |
| Me | 4-pyran | 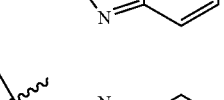 |
| Me | 4-pyran | 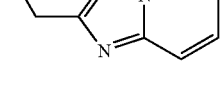 |
| Me | 4-pyran | 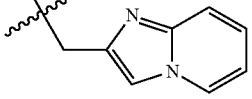 |
| Me | 4-pyran | 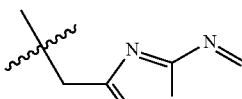 |
| Me | 4-pyran | 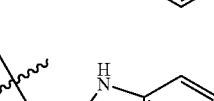 |
| Me | 4-pyran | 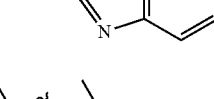 |
| Me | 4-pyran | 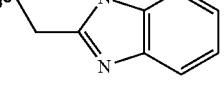 |
| Me | 4-pyran | 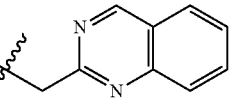 |
| Me | 4-pyran | 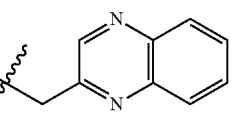 |
| Me | 4-pyran |  |

-continued

| R1 | R2 | R3 |
|----|----|----|
| Me | 4-pyran | quinoxalin-6-ylmethyl |
| Me | 4-pyran | quinazolin-6-ylmethyl |
| Me | 4-pyran | quinazolin-7-ylmethyl |
| Me | 4-pyran | benzyl |

The present invention is intended to include any novel compound or composition, e.g., pharmaceutical composition, described herein. In addition, in certain embodiments of the invention, the present invention includes all active metabolites of the compounds of the invention, e.g., N-oxide derivatives of the compounds of Formula (I).

Compounds in the disclosure, e.g., compounds of Formula (I), may be in the form of pharmaceutically acceptable salts. The phrase "pharmaceutically acceptable" refers to salts prepared from pharmaceutically acceptable non-toxic bases and acids, including inorganic and organic bases and inorganic and organic acids. Salts derived from inorganic bases include, but are not limited to lithium, sodium, potassium, magnesium, calcium and zinc. Salts derived from organic bases include, but are not limited to ammonia, primary (e.g. Tromethamine), secondary and tertiary amines, and amino acids (e.g. Lysine). Salts derived from inorganic acids include, but are not limited to sulfuric, hydrochloric, phosphoric, methanesulfonic, hydrobromic. Salts derived from organic acids include, but are not limited to $C_{1-6}$ alkyl carboxylic acids, di-carboxylic acids and tri-carboxylic acids such as acetic acid, propionic acid, fumaric acid, maleic acid, succinic acid, tartaric acid, adipic acid and citric acid, and alkylsulfonic acids such as methanesulfonic and aryl sulfonic acids such as para-toluene sulfonic acid and benzene sulfonic acid. For detailed list of slats see P. H. Stahl and C. G. Wermuth (eds.) "Handbook of Pharmaceutical Salts, Properties, Selection and Use" Wiley-VCH (ISBN 3-906390-26-8)

As noted herein, the present invention also includes enantiomers, diastereomers or racemates of the compound. Enantiomers are a pair of stereoisomers that are non-superimposable mirror images of each other. A 1:1 mixture of a pair of enantiomers is a racemic mixture. The term "enantiomers" is used to designate a racemic mixture where appropriate. Diastereoisomers are stereoisomers that have at least two asymmetric atoms, but which are not mirror-images of each other. The absolute stereochemistry may be specified according to the Cahn-Ingold-Prelog R-S system. When a compound is a pure enantiomer the stereochemistry at each chiral carbon may be specified by either R or S. Resolved compounds can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

In addition, compounds in the invention may exist in tautomeric forms which can be in equilibrium with each other. All tautomeric forms of Formula (I) are encompassed in the invention.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the tetra "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. For example, substitution with heavier isotopes such as deuterium ($^2H$) may offer certain therapeutic advantages resulting from greater metabolic stability which could be preferable and lead to longer in vivo half-life or dose reduction in a mammal or human. The invention includes various isotopically labeled compounds as defined herein, for example those into which radioactive isotopes, such as $^3H$, $^{13}C$, and $^{14}C$, are present. Such isotopically labeled compounds may also be useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of Formula (I) can generally be prepared by conventional techniques known to those skilled in the art or by processes analogous to those described in the accompanying Examples and Preparations using an appropriate isotopically-labeled reagents in place of the non-labeled reagent previously employed.

Compounds in the disclosure may exist in different crystal forms. Crystal forms include single-component crystal forms and multiple-component crystal forms, and include, but are not limited to, polymorphs, solvates, hydrates, and/or other molecular complexes. In certain embodiments, a crystalline form is substantially pure, isolated or enriched in one crystalline form, and/or is substantially free of amorphous forms and/or other crystal forms.

Furthermore, in certain embodiments, compounds and pharmaceutically acceptable salts thereof may be in the form of a solvate. i.e., a substance formed by chemical union of two or more elements or ingredients in definite proportion by weight. In certain embodiments, this occurs when a compound of Formula (I) crystallize in a manner that it incorporates solvent molecules into the crystal lattice. Examples of solvents forming solvates are water (hydrates), MeOH, EtOH, iPrOH, and acetone. Formula (I) covers all solvates of the depicted compounds. Pharmaceutically acceptable solvates in accordance with the invention also include those wherein the solvent of crystallization may be isotopically substituted, e.g. $D_2O$, $d_6$-acetone, $d_6$-DMSO.

Compounds of the invention, i.e. compounds of Formula (I) that contain groups capable of acting as donors and/or acceptors for hydrogen bonds may be capable of forming co-crystals with suitable co-crystal formers. These co-crystals may be prepared from compounds of Formula (I) by known co-crystal forming procedures. Such procedures include grinding, heating, co-subliming, co-melting, or contacting in solution compounds of Formula (I) with the co-crystal former under crystallization conditions and isolating co-crystals thereby formed. Suitable co-crystal formers include those described in WO 2004/078163. Hence the invention further provides co-crystals comprising a compound of Formula (I).

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that convert in vivo to the compounds of the present invention. A pro-drug is a compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)); and hydroxy groups have been masked as esters and ethers. EP 039,051 (Sloan and Little) discloses Mannich-base hydroxamic acid prodrugs, their preparation and use.

Practitioners of the art will recognize that certain electrophilic ketones, may exist in a hydrated form. The scope of this disclosure is to include all such hydrated forms. For example, a trifluoromethyl ketone may exist in a hydrated form via addition of water to the carbonyl group. This is depicted in figure below. This example is not meant to be limiting in the scope of hydrated forms.

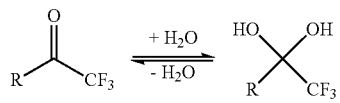

Other therapeutic agents may be administered either simultaneously with, before, or after compounds of the present invention. The compounds of the present invention may be administered separately, by the same or different route of administration, or together in the same pharmaceutical composition as the other agent(s).

In one embodiment, the invention provides a product comprising a compound of Formula (I) and at least one other therapeutic agent as a combined preparation for simultaneous, separate, or sequential use in therapy. In one embodiment, the therapy is the treatment of a disease or condition mediated by PDE9 or cGMP levels. Products provided as a combined preparation include a composition comprising the compound of Formula (I) and the other therapeutic agent(s) together in the same pharmaceutical composition, or the compound of Formula (I) and the other therapeutic agent(s) in separate form, e.g., in the form of a kit.

Compounds of the disclosure may also be used in mammals and humans in conjunction with conventional cognition enhancing or neuroprotective medications including donepezil, rivastigmine, galantamine and memantine. Additional medications could include additional cholinesterase inhibitors, NMDA receptor antagonists, nicotinic agonists (including ca agonists), muscarinic agonists (including $M_1$ agonists) and 5-$HT_6$ antagonists. The combination of a compound of Formula (I) with a subtherapeutic dose of an aforementioned conventional cognition enhancer or neuroprotective medication may afford certain treatment advantages including improved side effect profiles and lower dosing requirements.

III. Methods of the Invention

Compounds in the disclosure and their pharmaceutically acceptable salts, prodrugs, as well as metabolites of the compounds, may also be used to treat PDE9 associated diseases or disorders, e.g., CNS disorders and conditions, urogenital disorders and cardiovascular disorders. In certain embodiments, the imidazotriazinone compounds of Formula (I) are useful as inhibitors of at least one phosphodiesterase 9. Moreover, in particular embodiments, a compound of Formula (I) selectively inhibits PDE9A.

Another aspect of the invention provides a method for treating a PDE9 associated disease or disorder comprising administering to a subject an effective amount of a compound of the invention, e.g., in a pharmaceutical composition of the invention.

In another aspect, the invention provides a method of inhibiting PDE9 in a subject, wherein the method comprises administering to the subject a therapeutically effective amount of a compound of the invention, e.g., a compound of Formula (I), A. Methods of Use Another embodiment of the invention provides a method of treating a PDE9 associated disease or disorder comprising administering to a subject an effective amount of a compound of the invention, e.g., in a pharmaceutical composition of the invention, such that PDE9 is inhibited in the subject. The PDE9 associated diseases or disorders that may be treated by the compounds of the invention are those disorders or diseases associated with abnormal PDE9 activity, or aberrant levels of cGMP. In certain embodiments, the PDE9 associated disease or disorder is a central nervous system (CNS) disease or disorder, a neurodegeneration disorder, or a disorder that may affect CNS function, wherein each of these diseases or disorders is related to the modulation of cGMP levels. In certain embodiments, the PDE9 associated disease or disorder is a disease or disorder caused by a relative reduction in synaptic plasticity and synaptic processes, e.g., as in learning or memory. In a particular embodiment, the compounds of the invention serve to treat these disorders by acting to increase synaptic plasticity and synaptic processes.

Exemplary CNS disorders include Alzheimer's disease, amyotrophic lateral sclerosis (ALS or Lou Gerig's disease), Binswanger's dementia (subcortical arteriosclerotic encephalopathy), bipolar disorders, Down's syndrome, frontotemporal lobar degeneration or dementia, glaucoma, Huntington's diseases (chorea), HIV-associated dementia, Lewy body dementia, multiple sclerosis, multiple system atrophy, Parkinson's disease, presenile dementia (mild cognitive impairment), schizophrenia, spinocerebellar ataxies, Steel-Richardson-Olszewski disease (progressive supranuclear palsy), vascular dementia, attention deficit disorder (ADD) and attention deficit hyperactivity disorder (ADHD). Exemplary neurodegeneration disorders include either traumatic (closed or open, penetrating head injuries) or non-traumatic (stroke, aneurism, hypoxia) injury to the brain. In certain embodiments, PDE9 associated diseases or disorders characterized by aberrant levels of cGMP may also include dystonia, including for example, generalized, focal, segmental, sexual, intermediate, acute dystonic reaction, and genetic/primary; and dyskinesia, including for example, acute, chronic/tardive, and non-motor. In certain embodiments, PDE9 associated diseases or disorders characterized by a relative reduction in synaptic plasticity and synaptic processes include, for example, obsessive compulsive disorder, Fragile X, Rhett's, Williams syndrome, Renpenning's syndrome, autism spectrum disorders, including autism, Asperger's syndrome, pervasive development disorder, Rhett's syndrome, and childhood disintegrative disorder In one embodiment the treatment of PDE9 associated diseases or disorders by the compounds of the disclosure can include Alzheimer's disease, amyotrophic lateral sclerosis (ALS or Lou Gerig's disease), Binswanger's dementia (subcortical arteriosclerotic encephalopathy), bipolar disorders, Down's syndrome, frontotemporal lobar degeneration or dementia, glaucoma, Huntington's diseases (chorea), HIV-associated dementia, Lewy body dementia, multiple sclerosis, multiple system atrophy, Parkinson's disease, presenile dementia (mild cognitive impairment), schizophrenia, spinocerebellar ataxies, Steel-Richardson-Olszewski disease (progressive supranuclear palsy), vascular dementia, attention deficit disorder (ADD) and attention deficit hyperactivity disorder (ADHD).

In another embodiment the treatment of CNS disorders and conditions by the compounds of the disclosure can include Alzheimer's disease, amyotrophic lateral sclerosis (ALS or Lou Gehrig's disease), bipolar disorders, frontotemporal dementia, multiple system atrophy, Parkinson's disease, presenile dementia (mild cognitive impairment) and vascular dementia.

In another embodiment, compounds of the disclosure may be used for the treatment of neurodegeneration disorders caused by either traumatic (closed or open, penetrating head injuries) or non-traumatic (stroke, aneurism, hypoxia) injury to the brain. The present invention may also be useful for the treatment of cognitive impairment or dysfunction resulting from brain injuries or neurogenerative disorders.

In another embodiment of the invention provides a method of treating a PDE9 associated disease or disorder comprising administering to a subject an effective amount of a compound of the invention, e.g., in a pharmaceutical composition of the invention, in combination with a second therapeutic agent suitable to offer advantages of single administration, including for example, improved therapeutic effectiveness and reduction of therapeutic dose of the compound of the invention. In particular embodiments, the methods of the present invention may include an additional step of administering the second therapeutic agent. Compounds of the disclosure may also be used, e.g., in mammals and humans, in conjunction with conventional cognition enhancing or neuroprotective medications including donepezil, rivastigmine, galantamine and memantine. Additional medications could include additional cholinesterase inhibitors, NMDA receptor antagonists, nicotinic agonists (including $\alpha_7$ agonists), muscarinic agonists (including $M_1$ agonists) and $5\text{-HT}_5$ antagonists. The combination of a compound of Formula (I) with a subtherapeutic dose of an aforementioned conventional cognition enhancer or neuroprotective medication may afford certain treatment advantages including improved side effect profiles and lower dosing requirements.

In certain embodiments, the subject has been diagnosed with Alzheimer's disease or pre-Alzheimer's disease. In certain embodiments, the subject has been diagnosed with mild to moderate Alzheimer's disease. In certain embodiments, the subject has been diagnosed with moderate to severe Alzheimer's disease. In certain embodiments, the subject has been diagnosed with schizophrenia or schizoaffective disorder.

In any of the methods described herein, the method may improve one or more facets of cognition impairment, for example, related to Alzheimer's disease, selected from, but not limited to learning, delayed memory, attention, working memory, visual learning, speed of processing, vigilance, verbal learning, visual motor function, social cognition, long term memory or executive function.

In another embodiment, the methods described herein may be used to treat Alzheimer's disease (AD), also called Alzheimer disease, senile dementia of the Alzheimer type, primary degenerative dementia of the Alzheimer's type, or simply Alzheimer's, which is the most common form of dementia. It is a degenerative disease most often diagnosed in subjects over 65 years old. Without wishing to be bound by theory, the first symptoms of Alzheimer's are often mistaken as related to aging and stress. The early symptoms can affect most daily living activities, including feeding oneself, bathing, dressing, grooming, work, homemaking, leisure activity, and memory loss. This pre-dementia period has also been termed mild Alzheimer's (a term well known in the art), or mild cognitive impairment, and includes subtle problems with executive functions of attentiveness, planning, flexibility, and abstract thinking, as well as impairments in semantic memory. Moderate AD (a term also well known in the art) is characterized by speech difficulties, impairment of reading and writing skills, and complex motor sequences becoming less coordinated making the risk of falling increasingly higher. During moderate AD, memory problems worsen, and the subject may fail to recognize close relatives. Long term memory also becomes impaired. Moderate AD often leads to advanced, or severe AD (both terms well known in the art), where the subject is completely dependent on caregivers. Language is reduced to simple phrases or even single words, eventually leading to complete loss of speech. Despite the loss of verbal language abilities, subjects can often understand and return emotional signals. Although aggressiveness can still be present, extreme apathy and exhaustion are much more common results. Subjects will ultimately not be able to perform even the simplest tasks without assistance. Muscle mass and mobility deteriorate to the point where they are bedridden, and they lose the ability to feed themselves.

In another embodiment, the invention provides a method of inhibiting PDE9 in a subject, wherein the method comprises administering to the subject a therapeutically effective amount of a compound of the invention, e.g., a compound of Formula (I), such that PDE9 is inhibited in the subject.

In an additional embodiment, the compounds of the present invention may be used to improve or enhance PDE9 related function, for example, related to memory and cognition, through modulation of cGMP levels.

B. Methods of Preparation

Certain compounds of the present invention were prepared using novel methods of the invention as shown herein in the schemes and description of the Exemplification section. Such methods are intended to be included with the present invention, including minor variations as would be understood by the skilled artisan, and which would not involve undue experimentation, for example, minor modifications in general reaction controls of temperature, reaction time, and relative amounts of starting materials, as well as minor modifications to any purification, separation, or isolation techniques.

IV. Pharmaceutical Compositions of the Invention

The present invention also provides pharmaceutical compositions for treating a subject having a PDE9 associated disease or disorder.

In one embodiment, the present invention provides a pharmaceutical composition for treating a PDE9 associated disease or disorder comprising a therapeutically effective amount of a compound of the invention, e.g., a compound of Formula (I), or a pharmaceutically acceptable salt thereof, and a pharmaceutically acceptable excipient, carrier or diluent.

The pharmaceutical compositions can be administered in a variety of dosage forms including, but not limited to, a solid dosage form or in a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension or combinations thereof. The dosage can be an oral dosage form that is a controlled release dosage form. The oral dosage form can be a tablet or a caplet. The compounds can be administered, for example, by oral or parenteral routes, including intravenous, intramuscular, intraperitoneal, subcutaneous, transdermal, airway (aerosol), rectal, vaginal and topical (including buccal and sublingual) administration. In one embodiment, the compounds or pharmaceutical compositions comprising the compounds are delivered to a desired site, such as the brain, by continuous injection via a shunt.

In another embodiment, the compound can be administered parenterally, such as intravenous (i.v.) administration. The formulations for administration will commonly comprise a solution of the compound of the Formula (I) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of compound of Formula (I) in these formulations can vary widely, and will be selected primarily based on fluid volumes, viscosities, body weight, and the like, in accordance with the particular mode of administration selected and the patient's needs. For i.v. administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In one embodiment, a compound of Formula (I) can be administered by introduction into the central nervous system of the subject, e.g., into the cerebrospinal fluid of the subject. The formulations for administration will commonly comprise a solution of the compound of Formula (I) dissolved in a pharmaceutically acceptable carrier. In certain aspects, the compound of Formula (I) is introduced intrathecally, e.g., into a cerebral ventricle, the lumbar area, or the cisterna magna. In another aspect, the compound of Formula (I) is introduced intraocularly, to thereby contact retinal ganglion cells.

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

In one embodiment, the pharmaceutical composition comprising a compound of Formula (I) is administered into a subject intrathecally. As used herein, the term "intrathecal administration" is intended to include delivering a pharmaceutical composition comprising a compound of Formula (I) directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a compound of Formula (I) to any of the above mentioned sites can be achieved by direct injection of the pharmaceutical composition comprising the compound of Formula (I) or by the use of infusion pumps. For injection, the pharmaceutical compositions can be formulated in liquid solutions, preferably in physiologically compatible buffers such as Hank's solution or Ringer's solution. In addition, the pharmaceutical compositions may be formulated in solid form and re-dissolved or suspended immediately prior to use. Lyophilized forms are also included. The injection can be, for example, in the form of a bolus injection or continuous infusion (e.g., using infusion pumps) of pharmaceutical composition.

In one embodiment, the pharmaceutical composition comprising a compound of Formula (I) is administered by lateral cerebro ventricular injection into the brain of a subject. The injection can be made, for example, through a burr hole made in the subject's skull. In another embodiment, the encapsulated therapeutic agent is administered through a surgically inserted shunt into the cerebral ventricle of a subject. For example, the injection can be made into the lateral ventricles, which are larger, even though injection into the third and fourth smaller ventricles can also be made.

In yet another embodiment, the pharmaceutical composition is administered by injection into the cisterna magna, or lumbar area of a subject.

For oral administration, the compounds will generally be provided in unit dosage forms of a tablet, pill, dragee, lozenge or capsule; as a powder or granules; or as an aqueous solution, suspension, liquid, gels, syrup, slurry, etc. suitable for ingestion by the patient. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include, but are not limited to sodium and calcium carbonate, sodium and calcium phosphate, and lactose, while corn starch and alginic acid are suitable disintegrating agents. Binding agents may include, but are not limited to starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutical preparations for oral use can be obtained through combination of a compound of Formula (I) with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For transmucosal administration (e.g., buccal, rectal, nasal, ocular, etc.), penetrants appropriate to the barrier to be permeated are used in the formulation. Such penetrants are generally known in the art.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. For intramuscular, intraperitoneal, subcutaneous and intravenous use, the compounds will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The suppositories for rectal administration of the drug can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds can be delivered transdermally, by a topical route, formulated as applicator sticks, solutions, suspensions, emulsions, gels, creams, ointments, pastes, jellies, paints, powders, or aerosols.

The compounds may also be presented as aqueous or liposome formulations. Aqueous suspensions can contain a compound of Formula (I) in admixture with excipients suitable for the manufacture of aqueous suspensions. Such excipients include, but are not limited to a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a compound of Formula (I) in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In general a suitable dose will be in the range of 0.001 to 150 mg per kilogram body weight of the recipient per day, e.g., in the range of 0.01 to 100 mg per kilogram body weight of the recipient per day, e.g., in the range of 0.2 to 10 mg per kilogram body weight per day. In a particular embodiment, the desired dose is presented once daily, but may be dosed as two, three, four, five, six or more sub-doses administered at appropriate intervals throughout the day.

The compounds can be administered as the sole active agent, or in combination with other known therapeutics to be beneficial in the treatment of neurological disorders. In any event, the administering physician can provide a method of treatment that is prophylactic or therapeutic by adjusting the amount and timing of drug administration on the basis of observations of one or more symptoms (e.g., motor or cognitive function as measured by standard clinical scales or assessments) of the disorder being treated.

Details on techniques for formulation and administration are well described in the scientific and patent literature, see, e.g., the latest edition of Remington's Pharmaceutical Sciences, Maack Publishing Co, Easton Pa. ("Remington's After a pharmaceutical composition has been formulated in an acceptable carrier, it can be placed in an appropriate container and labeled for treatment of an indicated condition. For administration of the compounds of Formula (I), such labeling would include, e.g., instructions concerning the amount, frequency and method of administration.

EXEMPLIFICATION

The present invention is illustrated by the following examples, which are not intended to be limiting in any way.

I. Biological Assays

Example 1

Phosphodiesterase Enzyme Screening Assay

Compounds of the invention were screened against PDE1A, PDE1B, PDE2A, PDE3A, PDE3B, PDE4A1A, PDE4B1, PDE4D3, PDE5A1, PDE6C, PDE7A, PDE8A1, PDE9A2, PDE10A2 AND PDE11A isoforms of the phosphodiesterase enzyme to determine activity and overall selectivity through comparative analysis. The assay generally consists of testing the compounds of the invention at 10 concentrations. Where 8-methoxy-IBMX and Zaprinast were used as reference inhibitors.
Materials and Methods:

The phosphodiesterase enzyme isoforms were obtained from a commercial retailer (Reaction Biology Corporation, Malvern, Pa.) for use in the instant screening assay.

The analysis was completed using the Caliper LabChip 3000 and a 12-sipper LabChip. LabChip assays are separations-based, meaning that the product and substrate are electrophoretically separated, thereby minimizing interferences and yielding the highest data quality available on any screening platform. Z' factors for both the EZ Reader and LC3000 enzymatic assays are routinely in the 0.8 to 0.9 range. High Z' values, few false positives, few false negatives and analytical quality reproducibility are the reasons cited for the increasing reliance on the LabChip assays.

The off-chip incubation mobility-shift phosphodiesterase assay uses a microfluidic chip to measure the conversion of a fluorescent cyclic AMP substrate to a 5'-AMP product, or a cyclic GMP substrate to a 5'-GMP product. The reaction mixture, from a microtiter plate well, is introduced through a capillary sipper onto the chip, where the fluorescent substrate and product are separated by electrophoresis and detected via laser-induced fluorescence. The signature of the fluorescence signal over time reveals the extent of the reaction. The precision of microfluidics allows researchers to detect subtle interactions between drug candidates and therapeutic targets. The technology is able to detect both strong and weak inhibitors with high accuracy, and routinely identifies drug candidates that conventional techniques miss.
Experimental:

Reactions were carried out in 100 mM HEPES (pH 7.5), 5 mM MgCl2, 1 mM DTT, 0.003% Brij, 4.0 µM cGMP substrate. The reaction was started by addition of cGMP or cAMP and incubated for 1 hour at R.T. The reaction was terminated by the addition of stop buffer containing 100 mM HEPES (pH 7.5), 15 mM EDTA, 0.015% Brij-35, 5% DMSO. Cyclic AMP/GMP substrate and 5'-AMP/5'-GMP product were separated by charge using electrophoretic mobility shift. Product formed was compared to control wells to determine inhibition or enhancement of enzyme activity.

One or more reference compounds, depending on phosphodiesterase isoform, selected from 8-methoxy-IBMX, Zaprinast, Trequinsin, Pentoxifyline, Rolipram, and Vinpocetine, Dipyridamole, and BRL-50481 were run alongside client samples to ensure data quality. The resulting IC50 is compared against the historical average and must be within 3-fold of this average.

Data points were averages of quadruplicate wells and error bars represented the SEM for each point. IC50s were determined using GraphPad Prism Version 5.01 and the log (inhibitor) vs. response variable slope curve fit. Selectivity values shown in the table below were made by comparison of IC50 values for the various isoforms, and calculated, for example, as a ratio of the IC50 of PDE9A2 to the IC50 of PDE1A or PDE 1B; wherein a value greater than 1 indicates a greater selectivity for PDE9A2.

TABLE 1

| Example name | Band (PDE9A2 IC50) | PDE1A selectivity (versus PDE9A2) | PDE1B selectivity (versus PDE9A2) |
| --- | --- | --- | --- |
| (+)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one | A | 1005 | 1413 |
| (+)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one | A | 232 | 633 |
| (−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one | A | 1110 | 1140 |
| (+)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one | A | 664 | 714 |

TABLE 1-continued

| Example name | Band (PDE9A2 IC50) | PDE1A selectivity (versus PDE9A2) | PDE1B selectivity (versus PDE9A2) |
| --- | --- | --- | --- |
| (+)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile | A | 942 | 343 |
| (−)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile | A | 640 | 1445 |
| (+)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one | A | 300 | 442 |
| (+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile | A | 241 | 220 |
| (+)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one | A | 373 | 470 |
| (+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one | A | 621 | 1400 |
| (+)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one | A | 973 | 1360 |
| (−)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one | A | 56 | 48 |
| (+)-7-((1s,3R)-adamantan-1-yl)-2-((3,4-trans)-1-benzyl-4-methylpyrrolidin-3-yl)imidazo[5,1-f][1,2,4]triazin-4(3H)-one | A | N/A | N/A |
| (−)-7-((1s,3R)-adamantan-1-yl)-2-((3,4-trans)-1-benzyl-4-methylpyrrolidin-3-yl)imidazo[5,1-f][1,2,4]triazin-4(3H)-one | C | N/A | N/A |
| (−)-2-((3,4-trans)-1-benzyl-4-methylpyrrolidin-3-yl)-7-(5-chloro-2-methylphenyl)imidazo[5,1-f][1,2,4]triazin-4(3H)-one | B | N/A | N/A |
| (+)-2-((3,4-trans)-1-benzyl-4-methylpyrrolidin-3-yl)-7-(5-chloro-2-methylphenyl)imidazo[5,1-f][1,2,4]triazin-4(3H)-one | A | 276 | 142 |
| (+)-2-((3,4-trans)-1-benzyl-4-methylpyrrolidin-3-yl)-7-(4-fluoro-2-methylphenyl)imidazo[5,1-f][1,2,4]triazin-4(3H)-one | A | 257 | 225 |
| (−)-2-((3,4-trans)-1-benzyl-4-methylpyrrolidin-3-yl)-7-(4-fluoro-2-methylphenyl)imidazo[5,1-f][1,2,4]triazin-4(3H)-one | C | N/A | N/A |
| (+)-2-((3,4-trans)-1-benzyl-4-methylpyrrolidin-3-yl)-7-(4,4-difluorocyclohexyl)imidazo[5,1-f][1,2,4]triazin-4(3H)-one | A | 309 | 496 |
| (−)-2-((3,4-trans)-1-benzyl-4-methylpyrrolidin-3-yl)-7-(4,4-difluorocyclohexyl)imidazo[5,1-f][1,2,4]triazin-4(3H)-one | A | N/A | N/A |
| (−)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one | A | 1213 | 2000 |
| (−)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one | A | 8 | 12 |
| (−)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one | A | N/A | N/A |

TABLE 1-continued

| Example name | Band (PDE9A2 IC50) | PDE1A selectivity (versus PDE9A2) | PDE1B selectivity (versus PDE9A2) |
|---|---|---|---|
| (−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one | C | N/A | N/A |
| (+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one | A | 393 | 386 |
| (−)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one | B | N/A | N/A |
| (+)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one | A | 202 | 178 |
| (+)-7-((1s,3R)-adamantan-1-yl)-2-((3,4-trans)-4-methyl-1-(pyrimidin-2-ylmethyl)pyrrolidin-3-yl)imidazo[5,1-f][1,2,4]triazin-4(3H)-one | A | N/A | N/A |
| 2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 1 | A | 28 | 38 |
| 2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 2 | B | N/A | N/A |
| 2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 3 | B | N/A | N/A |
| (+)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one | A | 579 | 571 |
| (−)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one | B | N/A | N/A |
| (−)-7-(4-fluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one | A | 132 | 175 |
| (+)-7-(4,4-difluorocyclohexyl)-2-((3,4-trans)-4-methyl-1-(pyrimidin-2-ylmethyl)pyrrolidin-3-yl)imidazo[5,1-f][1,2,4]triazin-4(3H)-one | A | 165 | 313 |
| (−)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one | A | N/A | N/A |
| (+)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one | A | 51 | 99 |
| (−)-7-(5-chloro-2-methylphenyl)-2-((3,4-trans)-4-methylpyrrolidin-3-yl)imidazo[5,1-f][1,2,4]triazin-4(3H)-one | B | N/A | N/A |
| (+)-2-((3,4-trans)-1-benzyl-4-methylpyrrolidin-3-yl)-7-(furan-3-yl)imidazo[5,1-f][1,2,4]triazin-4(3H)-one | A | N/A | N/A |
| (−)-2-((3,4-trans)-1-benzyl-4-methylpyrrolidin-3-yl)-7-(furan-3-yl)imidazo[5,1-f][1,2,4]triazin-4(3H)-one | B | N/A | N/A |
| (−)-7-(1-acetylpiperidin-4-yl)-2-((3,4-trans)-1-benzyl-4-methylpyrrolidin-3-yl)imidazo[5,1-f][1,2,4]triazin-4(3H)-one | C | N/A | N/A |
| (+)-7-(1-acetylpiperidin-4-yl)-2-((3,4-trans)-1-benzyl-4-methylpyrrolidin-3-yl)imidazo[5,1-f][1,2,4]triazin-4(3H)-one | A | N/A | N/A |
| (−)-2-((3,4-trans)-1-benzyl-4-methylpyrrolidin-3-yl)-7-(2-hydroxypropan-2-yl)imidazo[5,1-f][1,2,4]triazin-4(3H)-one | C | N/A | N/A |

TABLE 1-continued

| Example name | Band (PDE9A2 IC50) | PDE1A selectivity (versus PDE9A2) | PDE1B selectivity (versus PDE9A2) |
|---|---|---|---|
| (+)-2-((3,4-trans)-1-benzyl-4-methylpyrrolidin-3-yl)-7-(2-hydroxypropan-2-yl)imidazo[5,1-f][1,2,4]triazin-4(3H)-one | B | N/A | N/A |
| (+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one | A | N/A | N/A |
| (−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one | C | N/A | N/A |
| (−)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one | C | N/A | N/A |
| (+)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one | B | N/A | N/A |
| (+)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one | B | N/A | N/A |
| (−)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one | C | N/A | N/A |

A <1 μM
B 1 μM-10 μM
C >10 μM
N/A Not Available

II. Synthetic Preparation of Compounds of the Invention

A. Synthesis of Building Blocks i. 2,5-dioxopyrrolidin-1-yl tetrahydro-2H-pyran-4-carboxylate

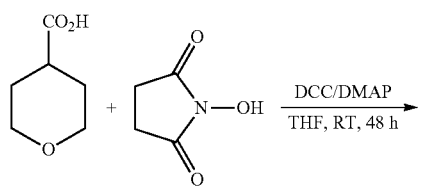

Synthesis of 2,5-dioxopyrrolidin-1-yl tetrahydro-2H-pyran-4-carboxylate

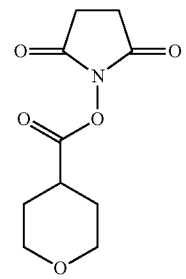 [SMILES: O=C(ON1C(=O)CCC1=O)C1CCOCC1]

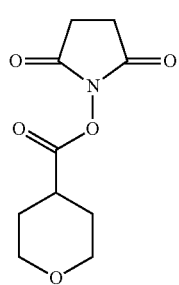

Typical experimental procedure: To a solution of tetrahydro-pyran-4-carboxylic acid (11.28 g, 86.7 mmol), N-hydroxysuccinimide (10.97 g, 95.3 mmol), and DMAP (1.16 g, 0.95 mmol) in THF (430 mL) was added. DCC (19.67 g, 95.3 mmol) slowly under argon atmosphere at RT. The reaction mixture was stirred at RT for 48 h. The reaction mixture cooled in a freezer and was then filtered and the filter cake was rinsed with dichloromethane (2×100 mL). The combined filtrates were concentrated under reduced pressure to give a light yellow solid (24.50 g). Flash chromatography (50% EtOAc/heptane—ETOAc only) provided 2,5-dioxopyrrolidin-1-yl tetrahydro-2H-pyran-4-carboxylate (17.24 g, 84%) as white solid. $^1$H NMR (300 MHz, CDCl$_3$) δ 4.02 (t, 1H, J=3.8 Hz), 3.98 (t, 1H, J=3.8 Hz), 3.56-3.46 (m, 2H), 2.99-2.86 (m, 1H), 2.85 (s, 3H), 2.04-1.87 (m, 4H); $^{13}$C NMR (75 MHz, CDCl$_3$) δ 169.4, 168.9, 66.5, 37.6, 28.3, 25.6.

ii. 2-(chloromethyl)pyrimidine

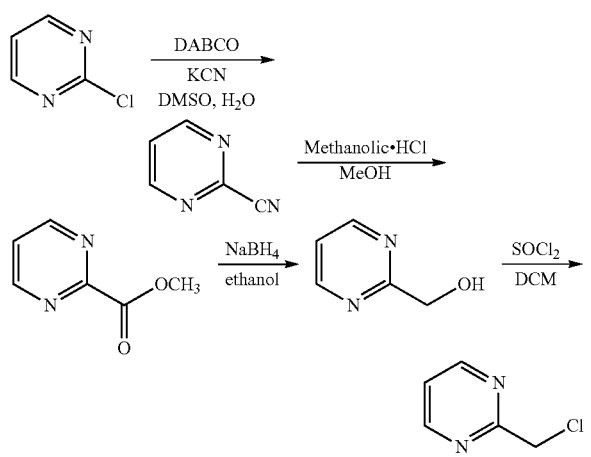

Synthesis of Pyrimidine-2-carbonitrile

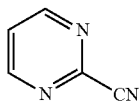

To a stirred solution of 2-chloropyrimidine (20.0 g, 174.6 mmol) in DMSO (40 mL) were added DABCO (3.72 g, 33.17 mmol), KCN (12.48 g, 192 mmol) and dropwise addition of H$_2$O (15 mL) at RT. The resulting solution was stirred at RT for 48 h. After consumption of starting material by TLC, the reaction mixture was diluted with water and extracted with EtOAc. Combined organic layer was dried over sodium sulphate, filtered and concentrated in vacuo to obtain the crude product. The crude material was triturated with Hexane to afford pyrimidine-2-carbonitrile (12 g, 65%) as dark brown solid. $^1$H-NMR (DMSO-d$_6$, 400 MHz): δ 9.04 (s, 2H), 8.92 (d, 1H); LC-MS: 99.41%; 107.6 (M+2); (column; X-bridge C-18, (50×3.0 mm, 3.5μ); RT 1.14 min. 0.1% Aq TFA: ACN; 0.8 ml/min); TLC: 30% EtOAc/Hexane (Rf: 0.2)

Synthesis of methyl pyrimidine-2-carboxylate

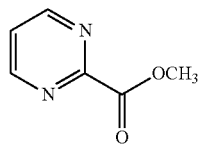

To a stirred solution of pyrimidine-2-carbonitrile (12.0 g, 114.28 mmol) in MeOH (20 mL) was added methanolic.HCl (180 mL) at 0° C. and stirred for 16 h. After completion of starting material by TLC, the volatiles were evaporated under reduced pressure. The residue was neutralized with saturated NaHCO$_3$ solution and extracted with EtOAc. The combined organic layer was dried over sodium sulphate, filtered and concentrated in vacuo to obtain the crude product. The crude material was triturated with Hexane to afford methyl pyrimidine-2-carboxylate (10.0 g, crude) as yellow solid. $^1$H-NMR (DMSO-d$_6$, 400 MHz): δ 9.08 (d, 2H), 7.76 (t, 1H), 3.92 (s, 3H); LC-MS: 94.32%; 139 (M$^+$+1) (column; Chromolith RP-18, (100×4.6 mm); RT 2.85 min. 5 mM NH$_4$OAc: ACN; 0.8 ml/min); TLC: 70% EtOAc/Hexane (Rf: 0.2).

Synthesis of pyrimidin-2-ylmethanol

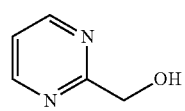

To a stirred solution of methyl pyrimidine-2-carboxylate (10.0 g, 72.46 mmol) in EtOH (100 mL) was added NaBH$_4$ (3.85 g, 101.31 mmol) portion wise at 0° C. under inert atmosphere. The reaction mixture was warmed to RT and stirred for 2 h. After completion of starting material by TLC, the volatiles were evaporated under reduced pressure. The residue was diluted with saturated K$_2$CO$_3$ solution and extracted with EtOAc. The combined organic layer was dried over sodium sulphate, filtered and concentrated in vacuo to afford pyrimidin-2-ylmethanol (4.5 g, crude) as yellow semi-solid. $^1$H-NMR (DMSO-d$_6$, 400 MHz): δ 8.76 (d, 2H), 7.42 (t, 1H), 5.29 (br s, 1H), 4.61 (s, 2H); LC-MS: 94.12%; 111 (M$^+$+1) (column; Chromolith RP-18, (100×4.6 mm); RT 2.24 min. 5 mM NH$_4$OAc: ACN; 0.8 ml/min); TLC: 100% EtOAc (Rf: 0.2).

Synthesis of 2-(chloromethyl)pyrimidine

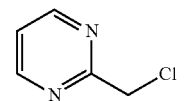

To a stirred solution of pyrimidin-2-ylmethanol (4.5 g 40.90 mmol) in DCM (50 mL) was added SOCl$_2$ (10 mL) at 0° C. under inert atmosphere. The reaction mixture was heated up to 50° C. and stirred for 2 h. After completion of starting material (by TLC), the volatiles were evaporated under reduced pressure. The residue was quenched with ice cold water followed by saturated NaHCO$_3$ and extracted with EtOAc. Combined organic layer was dried over sodium sulphate, filtered and concentrated in vacuo to obtain the crude product. The crude material was purified by silica gel column chromatography to afford 2-(chloromethyl)pyrimidine (960 mg, 18%) as brown liquid. $^1$H-NMR (DMSO-d$_6$, 400 MHz): δ 8.84 (d, 2H), 7.52 (t, 1H), 4.82 (s, 2H); Mass (ESI): 128.5 [M+1]; LC-MS: 95.09%; 129 (M$^+$+1) (column; Chromolith RP-18, (100×4.6 mm); RT 3.86 min. 5 mM NH$_4$OAc: ACN; 0.8 ml/min); TLC: 70% EtOAc/Hexane (Rf: 0.6).

iv. 2-(chloromethyl)pyrimidine

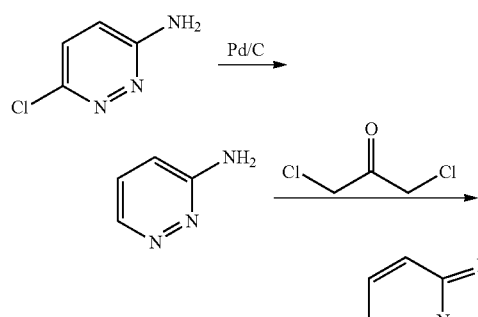

Synthesis of pyridazin-3-amine

To a stirred solution of 6-chloropyridazin-3-amine (10 g, 77.19 mmol) in MeOH (100 mL) was added 10% Pd—C (2.5 g), diethyl amine (16.0 mL, 154.38 mmol) and stirred at RT for 16 h under $H_2$ atmosphere (balloon pressure). The reaction mixture was passed through a pad of celite and washed with MeOH (10 mL). Volatiles were dried in vacuo to afford pyridazin-3-amine (7.3 g) as a crude. This was used for next step without further purification. $^1$H-NMR (DMSO $d_6$, 500 MHz): δ 8.84 (br s, 2H), 8.41-8.38 (m, 1H), 7.22-7.18 (m, 1H), 6.74 (d, 1H); LC-MS: 78.43%; 95.9 (M$^+$+1); (column; X-bridge C-18, (50×3.0 mm, 3.5μ); RT 0.68 min. 5 mM AA in water: ACN; 0.5 ml/min); TLC: 100% EtOAc (Rf: 0.2).

Synthesis of 2-(chloromethyl)imidazo[1,2-b]pyridazine

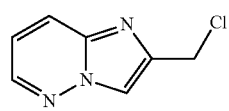

To a stirred solution of pyridazin-3-amine (7.3 g, 77.65 mmol) in ACN (100 mL) was added 1,3-dichloropropan-2-one (19.7 g, 155.3 mmol) at RT under inert atmosphere. The reaction mixture was stirred under reflux for 16 h. After full consumption of starting material (by TLC), the reaction mixture was cooled to RT and volatiles were evaporated under reduced pressure. The residue was neutralized with NaHCO$_3$ solution and extracted with EtOAc. The combined organic layer was dried over sodium sulphate, filtered and concentrated in vacuo to obtain the crude product. The crude material was purified by silica gel column chromatography to afford 2-(chloromethyl)imidazo[1,2-b]pyridazine (1.5 g, 12%) as a red solid. $^1$H-NMR (DMSO $d_6$, 500 MHz): δ 8.57-8.54 (m, 1H), 8.38 (s, 1H), 8.17 (d, 1H), 7.25-7.21 (m, 1H), 4.96 (s, 2H); LC-MS: 98.16%; 168.0 (M$^+$+1); (column; X-bridge C-18, (50×3.0 mm, 3.5μ); RT 2.02 min. 5 mM AA in water: ACN; 0.8 ml/min); TLC: 100% EtOAc (Rf: 0.6).

v. 6-(chloromethyl)imidazo[1,2-b]pyridazine

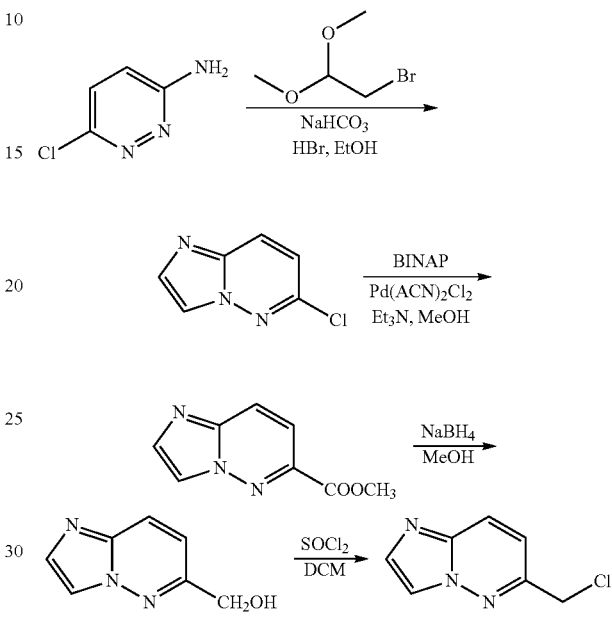

Synthesis of 6-Chloroimidazo[1,2-b]pyridazine

A mixture of 2-bromo-1,1-dimethoxyethane (45.67 mg, 0.27 mmol) and 48% of aqueous HBr (9 mL) was heated up to 120° C. and stirred for 30 min under inert atmosphere. The reaction mixture was cooled to 0° C., NaHCO$_3$ (10 g, 119.69 mmol) and a solution of 6-chloropyridazin-3-amine (5.0 g, 38.61 mmol) in EtOH (250 mL) was added to the reaction mixture at 0° C. The resultant reaction mixture was heated up to 80° C. and stirring was continued for another 2 h. After consumption of starting material by TLC, the volatiles were removed under reduced pressure. The residue was diluted with NaHCO$_3$ solution and extracted with EtOAc. Combined organic layer was dried over sodium sulphate, filtered and concentrated in vacuo to obtain the crude product. The crude material was purified by silica gel column chromatography to afford 6-chloroimidazo[1,2-b]pyridazine (3 g, 50%) as white solid. $^1$H-NMR (DMSO-$d_6$, 400 MHz): δ 8.32 (s, 1H), 8.18 (d, 1H), 7.81 (s, 1H), 7.34 (d, 1H); LC-MS: 99.59%; 154.0 (M+1); (column; X-bridge C-18, (50×3.0 mm, 3.5μ); RT 2.60 min. 5 mM NH$_4$OAc in water: ACN; 0.8 ml/min); TLC: 70% EtOAc/Hexane (Rf: 0.5).

Synthesis of methyl imidazo[1,2-b]pyridazine-6-carboxylate

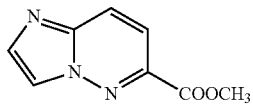

To a stirred solution of 6-chloroimidazo[1,2-b]pyridazine (2.0 g, 13.15 mmol) in ACN:MeOH (60 mL, 1:1) under $N_2$ bubbling atmosphere were added BINAP (818 mg, 1.31 mmol), $Pd(ACN)_2Cl_2$ (341 mg, 1.31 mmol) and $Et_3N$ (1.60 g, 15.78 mmol) in a steel bomb. The resultant reaction mixture was agitated under CO atmosphere (150 psi) at 100° C. for 16 h. After full consumption of starting material by TLC, the reaction was diluted with water and extracted with EtOAc. The combined organic layer was dried over sodium sulphate, filtered and concentrated in vacuo to obtain the crude product. The crude material was purified by silica gel column chromatography to afford imidazo[1,2-b]pyridazine-6-carboxylate (1.3 g, 65%) as brown solid. $^1$H-NMR (DMSO-$d_6$, 500 MHz): δ 8.51 (s, 1H), 8.27 (d, 1H), 7.94 (s, 1H), 7.72 (d, 1H), 3.97 (s, 3H); LC-MS: 91.14%; 178 ($M^+$+1) (column; X-bridge C-18, (50×3.0 mm, 3.5μ; RT 2.28 min. 5 mM $NH_4OAc$: ACN; 0.8 ml/min); TLC: 70% EtOAc/Hexane (Rf: 0.5).

Synthesis of imidazo[1,2-b]pyridazin-6-ylmethanol

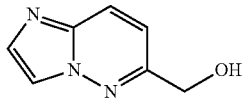 [SMILES: OCc1ccc2nccn2n1]

To a stirred solution of imidazo[1,2-b]pyridazine-6-carboxylate (3.5 g, 22.77 mmol) in MeOH:THF (45 mL, 1:2) was added $NaBH_4$ (1.72 g, 45.26 mmol) portion wise at 0° C. and stirred for 2 h. After full consumption of starting material by TLC, the reaction was diluted with saturated $Na_2CO_3$ solution and extracted with EtOAc. The combined organic layer was dried over sodium sulphate, filtered and concentrated in vacuo to obtain the crude product. The crude material was washed with 50% EtOAc/Hexane to afford crude imidazo[1,2-b]pyridazin-6-ylmethanol (2.5 g). $^1$H-NMR (DMSO-$d_6$, 400 MHz): δ 8.21 (s, 1H), 8.06 (d, 1H), 7.21 (s, 1H), 7.24 (d, 1H), 5.68 (br s, 1H), 4.59 (s, 2H); LC-MS: 85, 80%; 149.6 ($M^+$+1) (column; X-Select C-18, (50×3.0 mm, 3.5μ); RT 0.72 min, 5 mM $NH_4OAc$ in water: ACN; 0.8 ml/min); TLC: 100% EtOAc (Rf: 0.2).

Synthesis of 6-(chloromethyl)imidazo[1,2-b]pyridazine

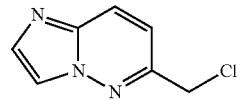

To a stirred solution of imidazo[1,2-b]pyridazin-6-ylmethanol (2.5 g 16.77 mmol) in DCM (20 mL) was added $SOCl_2$ (8 mL) at 0° C. under inert atmosphere. The reaction mixture was heated up to 50° C. and stirred for 3 h. After complete consumption of starting material (by TLC), the volatiles were evaporated under reduced pressure. The residue was quenched with ice cold water followed by saturated $Na_2SO_4$ and extracted with EtOAc, Combined organic layer was dried over sodium sulphate, filtered and concentrated in vacuo to obtain the crude product. The crude material was purified by silica gel column chromatography to afford 6-(chloromethyl)imidazo[1,2-b]pyridazine (1.4 g, 50%) as an off-white solid. $^1$H-NMR (DMSO-$d_6$, 500 MHz): δ 8.31 (s, 1H), 8.18 (d, 1H), 7.82 (s, 1H), 7.36 (d, 1H), 4.92 (s, 2H); LC-MS: 83.93%; 167.6 ($M^4$+1) (column X-Select C-18, (50×3.0 mm, 3.5μ); RT 2.29 min. 5 mM $NH_4OAc$ in water: ACN; 0.8 ml/min); UPLC (purity): 92.54%; (column; Acquity UPLC HSS T3, 2.1×100 mm, 1.7μ); RT 2.93 min. 0.025% Aq TFA: ACN; 0.3 ml/min.; TLC: 70% EtOAc/Hexane (Rf 0.6).

vi. 6-(chloromethyl)imidazo[1,2-b]pyridazine

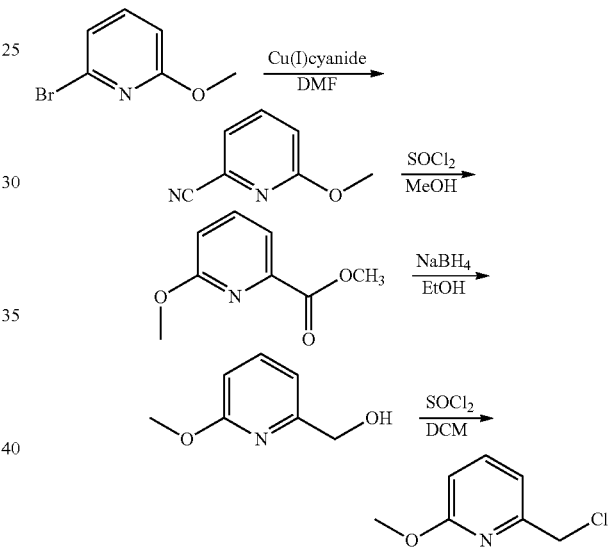

Synthesis of 6-methoxypicolinonitrile

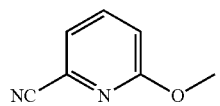

To a stirred solution of 2-bromo-6-methoxypyridine (5.0 g, 26.59 mmol) in DMF (50 mL) was added. Cu(I)cyanide (7.14 g, 79.77 mmol) at room temperature. The resulting reaction mixture was heated at 100° C. and stirred for 16 h. The reaction mixture was diluted with water, filtered through a pad of celite and the filtrate was extracted with EtOAc. Combined organic layer was dried over sodium sulphate, filtered and concentrated in vacuo to obtain the crude product. The crude material was purified by silica gel column chromatography to afford 6-methoxypicolinonitrile (1.4 g, 39%) as white solid. $^1$H-NMR (DMSO $d_5$, 400 MHz): δ 7.94 (t, 1H), 7.64 (d, 1H), 7.18 (d, 1H), 3.92 (s, 3H);

LC-MS: 99.14%; 135.8 (M⁺+1); (column; X-bridge C-18, (50×3.0 mm, 3.5μ); RT 3.31 min. 0.1% Aq TFA: ACN; 0.8 ml/min); TLC: 10% EtOAc/Hexane (Rf: 0.3).

Synthesis of methyl 6-methoxypicolinate

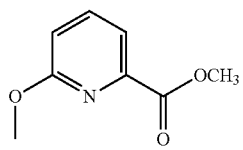

To a stirred solution of 6-methoxypicolinonitrile (1.4 g 10.44 mmol) in MeOH (30 mL) was added SOCl₂ (4 mL) at 0° C. The resultant reaction mixture was heated at 70° C. for 16 h. After full consumption of starting material (by TLC), the volatiles were evaporated under reduced pressure. The residue was quenched with ice cold water and saturated NaHCO₃ and extracted with EtOAc. Combined organic layer was dried over sodium sulphate, filtered and concentrated in vacuo to afford methyl 6-methoxypicolinate (1.2 g) as crude. LC-MS: 79.02%; 167.5 (M⁺+1); (column; X-select C-18, (50×3.0 mm, 3.50; RT 3.39 min. 5 mM NH₄OAc in water: ACN; 0.50 ml/min); TLC: 10% EtOAc/Hexane (Rf: 0.4).

Synthesis of (6-methoxypyridin-2-yl)methanol

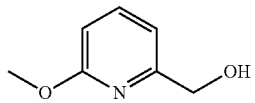

To a stirred solution of methyl 6-methoxypicolinate (1.2 g, 7.18 mmol) in ethanol (30 mL) was added NaBH₄ (409 mg, 10.77 mmol) portion wise at 0° C. and stirred for 3 h at RT. Progress of the reaction was monitored by TLC. Volatiles were evaporated under reduced pressure. The residue was diluted with water and extracted with EtOAc (2×25 mL). Combined organic layer was dried over sodium sulphate, filtered and concentrated in vacuo to afford crude (6-methoxypyridin-2-yl)methanol (0.7 g). LC-MS: 52.48%; 139.5 (M⁺+1); (column; X-select C-18, (50×3.0 mm, 3.5μ); RT 2.55 min. 5 mM NH₄OAc in water: ACN; 0.50 ml/min); TLC: 20% EtOAc/Hexane (Rf: 0.2).

Synthesis of 2-(chloromethyl)-6-methoxypyridine

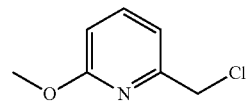

To a stirred solution of (6-methoxypyridin-2-yl)methanol (0.7 g 5.03 mmol) in CH₂Cl₂ (20 mL) was added SOCl₂ (2 mL) at 0° C. under inert atmosphere. The resultant reaction mixture was heated up to 50° C. and stirred for 2 h. After completion of starting material (by TLC), the volatiles were evaporated under reduced pressure. The residue was quenched with ice cold water and saturated NaHCO₃ and extracted with EtOAc. Combined organic layer was dried over sodium sulphate, filtered and concentrated in vacuo. The crude material was purified by silica gel column chromatography to afford 2-(chloromethyl)-6-methoxypyridine (180 mg, 24%) as a liquid. ¹H-NMR (DMSO d₆, 500 MHz): δ 7.72 (t, 1H), 7.12 (d, 1H), 6.87 (d, 1H), 4.64 (s, 2H), 3.82 (s, 3H); LC-MS: 98.62%; 158.0 (M⁺+1); (column; X-select C-18, (50×3.0 mm, 3.5μ); RT 4.12 min, 5 mM NH₄OAc in water: ACN; 0.50 ml/min); TLC: 10% EtOAc/Hexane (Rf: 0.6).

vii. (R)-(1-Chloroethyl)benzene

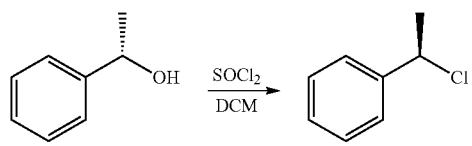

Synthesis of (R)-(1-Chloroethyl)benzene

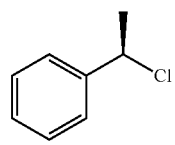

To a stirred solution of (S)-1-phenylethanol (0.5 g 4.09 mmol) in DCM (5 mL) was added SOCl₂ (1.48 mL, 20.49 mmol) at 0° C. under inert atmosphere. The resultant reaction mixture was heated up to 50° C. and stirred for 2 h. After complete consumption of starting material (by TLC), the volatiles were evaporated under reduced pressure. The residue was quenched with saturated NaHCO₃ and extracted with EtOAc. Combined organic layer was dried over sodium sulphate, filtered and concentrated in vacuo to afford (R)-(1-Chloroethyl)benzene (0.4 g, crude) as pale yellow liquid. ¹H-NMR (DMSO d₆, 400 MHz): δ 7.51-7.47 (m, 2H), 7.38-7.29 (m, 3H), 5.38-5.31 (m, 1H), 1.89 (d, 3H); TLC: 10% EtOAc/Hexane (Rf: 0.7).

viii. (S)-(1-Chloroethyl)benzene

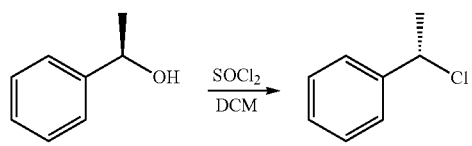

Synthesis of (S)-(1-chloroethyl)benzene

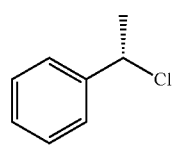

To a stirred solution of (R)-1-phenylethanol (0.5 g 4.09 mmol) in DCM (10 mL) was added SOCl$_2$ (2.438 g, 20.49 mmol) at 0° C. under inert atmosphere. The resultant reaction mixture was heated up to 50° C. and stirred for 3 h. After completion of starting material (by TLC), the volatiles were evaporated under reduced pressure. The residue was quenched with saturated NaHCO$_3$ and extracted with EtOAc. Combined organic layer was dried over sodium sulphate, filtered and concentrated in vacuo to afford (S)-(1-chloroethyl)benzene (0.38 g, 66%) as pale yellow liquid. $^1$H-NMR (DMSO d$_6$, 400 MHz): δ 7.48-7.46 (m, 2H), 7.38-7.29 (m, 3H), 5.36-5.32 (m, 1H), 1.87 (d, 3H); TLC: 10% EtOAc/Hexane (Rf: 0.7).

ix. methyl pyrazine-2-carboxylate

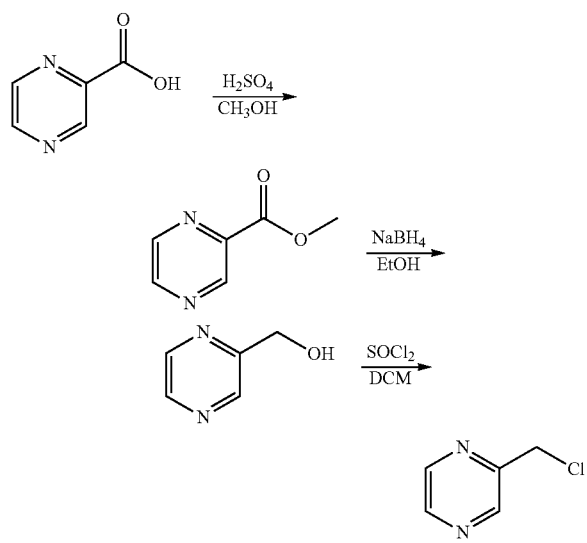

Synthesis of methyl pyrazine-2-carboxylate

To a stirred solution of pyrazine-2-carboxylic acid (5 g, 40.29 mmol) in MeOH (20 mL) was added concentrated H$_2$SO$_4$ (1 mL) drop wise and stirred under reflux for 5 h. The reaction mixture was cooled to RT; volatiles were evaporated under reduced pressure. The residue was diluted with water and basified to pH 8.5 using NaHCO$_3$ and extracted with EtOAc. Combined organic layer was dried over sodium sulphate, filtered and concentrated in vacuo to afford methyl pyrazine-2-carboxylate (3.5 g, 63.63%) as an off-white solid. $^1$H-NMR (DMSO d$_6$, 400 MHz): δ 9.21 (s, 1H), 8.91 (d, 1H), 8.82 (d, 1H), 3.92 (s, 3H); TLC: 50% EtOAc/Hexane (Rf: 0.4).

Synthesis of pyrazin-2-ylmethanol

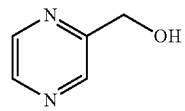

To a stirred solution of methyl pyrazine-2-carboxylate (0.5 g, 3.62 mmol) in H$_2$O (10 mL) was added NaBH$_4$ (685 g, 18.02 mmol) portion wise at 0° C., and the reaction mixture was allowed to warm to RT and stirred for 30 min under inert atmosphere. To this saturated K$_2$CO$_3$ (10 mL) and EtOH (5 mL) was added and stirring was continued for another 1 h at RT. The progress of the reaction was monitored by TLC; the reaction mixture was extracted with EtOAc. The combined organic layer was dried over sodium sulphate, filtered and concentrated in vacuo to afford crude pyrazin-2-ylmethanol (0.3 g). LC-MS: 99.91%; 111.9 (M$^+$+1) (column; X-bridge C-18, (50×3.0 mm, 3.5μ); RT 0.72 min. 0.1% TFA in water: ACN; 0.8 ml/min); TLC: 100% EtOAc (Rf: 0.2).

Synthesis of 2-(chloromethyl)pyrazine

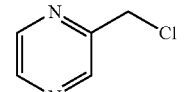

To a stirred solution of pyrazin-2-ylmethanol (0.3 g 2.72 mmol) in DCM (10 mL) was added SOCl$_2$ (1 mL) at 0° C. under inert atmosphere. The reaction mixture was heated up to 50° C. and stirred for 2 h. After completion of starting material (by TLC), the volatiles were evaporated under reduced pressure. The residue was quenched with ice cold water followed by saturated NaHCO$_3$ and extracted with EtOAc. Combined organic layer was dried over sodium sulphate, filtered and concentrated in vacuo to obtain the crude product. The crude material was purified by silica gel column chromatography to afford 2-(chloromethyl)pyrazine (110 mg, 20.4%) as liquid. $^1$H-NMR (CDCl$_3$, 400 MHz): δ 8.74 (s, 1H), 8.58-8.56 (m, 2H), 4.71 (s, 2H); LC-MS: 98.86%; 129 (M$^+$+1) (column; Eclipse XDB C-18, (150×4.6 mm, 5.0μ); RT 4.83 min. 5 mM NH$_4$OAc: ACN; 1.0 ml/min); TLC: 70% EtOAc/Hexane (Rf: 0.6).

x. (3r,5r,7r)-2,5-dioxopyrrolidin-1-yl adamantane-1-carboxylate

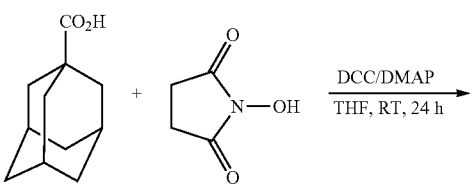

Synthesis of (3r,5r,7r)-2,5-dioxopyrrolidin-1-yl adamantane-1-carboxylate

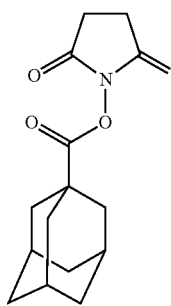

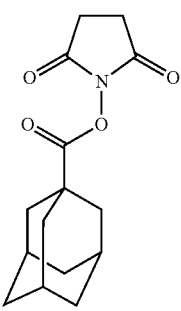 [SMILES: O=C1CCC(=O)N1OC(=O)C12CC3CC(CC(C3)C1)C2]

To a stirred solution of adamantine-1-carboxylic acid (1.80 g, 10 mmol), N-hydroxysuccinimide (1.15 g, 10 mmol), and DMAP (0.12 g, 1.0 mmol) in dry THF (40 mL) was added DCC (2.27 g, 11 mmol) slowly under argon atmosphere at RT. The reaction mixture was stirred at RT for 24 h. The resulting suspension was filtered through a Celite pad and the filter cake was rinsed with dichloromethane. The combined filtrates were concentrated under reduced pressure to give a white solid. This solid was redissolved in dichloromethane (20 mL) and filtered. The filtrate was concentrated under reduced pressure to give crude product (3.19 g) as white solid. Flash chromatography (10-60% ETOAc/heptane) provided (3r,5r,7r)-2,5-dioxopyrrolidin-1-yl adamantane-1-carboxylate as white solid (2.12 g, 77% yield). $^1$H NMR (300 MHz, CDCl$_3$) δ 2.82 (s, 4H), 2.08 (br s, 9H), 1.76 (br s, 6H); $^{13}$C NMR (75 MHz, CDCl$_3$) δ 172.1, 169.1, 40.4, 38.4, 36.2, 27.6, 25.7.

x. 5-chloro-2-methylbenzoyl chloride

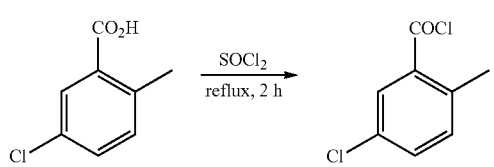

Synthesis of 5-chloro-2-methylbenzoyl chloride

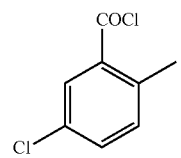

A suspension of 5-chloro-2-methyl-benzoic acid (2.00 g, 11.7 mmol) in thionyl chloride (10 mL) was heated to reflux for 2 h. After this time the mixture was cooled to RT and evaporated to dryness. Toluene (20 mL) was added and the resulting mixture was evaporated to dryness again to give 5-chloro-2-methylbenzoyl chloride (1.73 g, 78% yield) as brown oil. 1H NMR (300 MHz, CDCl3) δ 8.16 (s, 1H), 7.47 (s, 1H), 7.24 (s, 1H), 2.53 (s, 3H); 13C NMR (75 MHz, CDCl3) δ 166.4, 139.4, 133.9, 133.6, 133.1, 132.0, 21.5.

xi. 4-fluoro-2-methylbenzoyl chloride

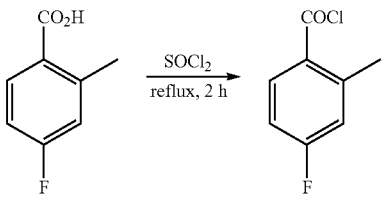

Synthesis of 4-fluoro-2-methylbenzoyl chloride

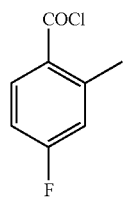

A suspension of 4-fluoro-2-methylbenzoic acid (1.54 g, 10 mmol) in thionyl chloride (10 mL) was heated to reflux for 2 h. After this time the mixture was cooled to RT. The excess thionyl chloride was evaporated and the residue was rotovaped twice with toluene (2×20 mL) to give 1.74 g crude 6 (3:1 molar ratio of 6 with toluene, 86% yield) as brown oil. $^1$H NMR (300 MHz, CDCl$_3$) δ 8.32-8.24 (m, 1H), 7.07-6.95 (m, 2H), 2.58 (s, 3H); $^{13}$C NMR (75 MHz, CDCl$_3$) δ 166.1, 165.6 (d, J=257 Hz), 145.2 (d, J=9.5 Hz), 137.1 (d, J=10 Hz), 128.5, 118.8 (d, J=22 Hz), 113.5 (d, J=22 Hz), 22.4.

xii. 2,5-dioxopyrrolidin-1-yl 4,4-difluorocyclohexanecarboxylate

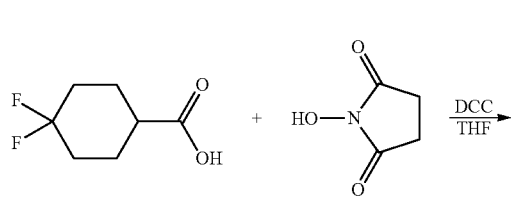

Synthesis of 2,5-dioxopyrrolidin-1-yl 4,4-difluorocyclohexanecarboxylate

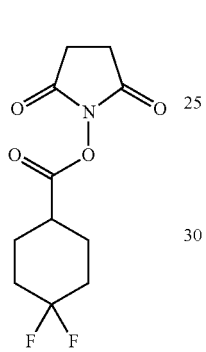

DCC (1.38 g, 6.7 mmol) was added to 4,4-difluorocyclohexanecarboxylic acid (1.0 g, 6.1 mmol) in THF (50 mL) at 0° C. The reaction mixture was stirred at room temperature for 1 h and cooled down to 0° C. N-Hydroxysuccinimide (0.77 g, 6.7 mmol) was added and stirring was continued overnight at room temperature. The reaction mixture was filtered, the solvent was evaporated, the residue was purified by column chromatography (silica gel, EtOAc/Hept, 1:1-1:0) to prepare 2,5-dioxopyrrolidin-1-yl 4,4-difluorocyclohexanecarboxylate (1.5 g, 94% yield). $^1$H NMR (300 MHz, CDCl$_3$/TMS): δ 2.81 (s, 4H), 2.2-1.8 (m, 8H), 1.2 (m, 1H).

xiii. 2,5-dioxopyrrolidin-1-yl furan-3-carboxylate

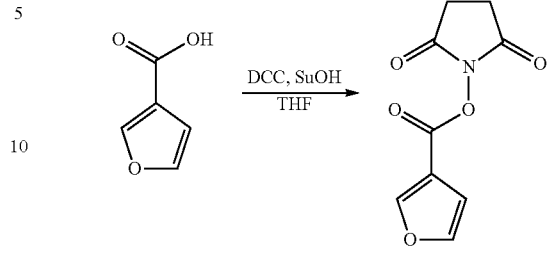

Synthesis of 2,5-dioxopyrrolidin-1-yl furan-3-carboxylate

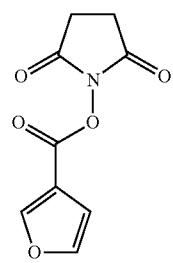 [SMILES: O=C(ON1C(=O)CCC1=O)c1ccoc1]

DCC (6.8 g, 33 mmol) was added to furan-3-carboxylic acid (3.36 g, 30 mmol) in THF (70 mL) at 0° C. The reaction mixture was stirred at room temperature for 1 h and cooled down to 0° C. N-hydroxysuccinimide (3.8 g, 33 mmol) was added and stirring was continued overnight at room temperature. The reaction mixture was filtered, the solvent was evaporated, the residue was purified by column chromatography (silica gel, EtOAc/Hept, 1:1) to prepare 2,5-dioxopyrrolidin-1-yl furan-3-carboxylate (2.7 g, 43% yield). $^1$H NMR (300 MHz, CDCl$_3$/TMS): δ 8.21 (s, 1H), 7.51 (s, 1H), 6.80 (s, 1H), 2.83 (s, 4H).

xiv. 1(((9H-fluoren-9-yl)methoxy)carbonyl)piperidine-4-carboxylic acid

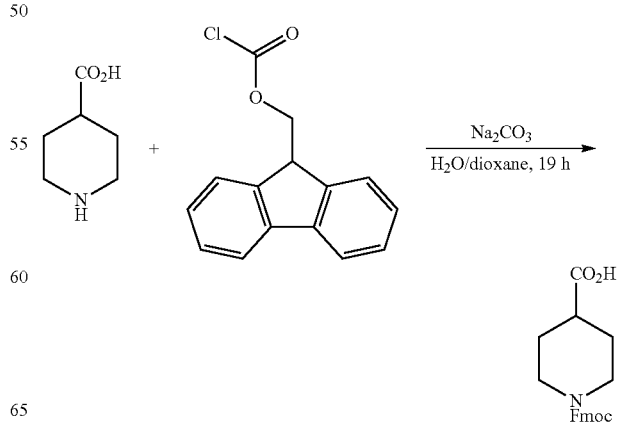

Synthesis of 1-(((9H-fluoren-9-yl)methoxy)carbonyl)piperidine-4-carboxylic acid

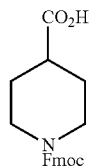

Fmoc chloride (3.30 g, 12.8 mmol) in dioxane (50 mL) was added to a solution of isonipecotic acid (1.50 g, 11.6 mmol) and sodium carbonate (6.15 g, 58.0 mmol) in water (50 mL) at RT. The resulting white suspension was stirred at RT for 19 h. After this time the mixture was diluted with water (75 mL), and extracted with ether (3×90 mL). The aqueous layer was acidified with 2N HCl aqueous solution to pH=2, and was extracted with EtOAc (3×100 mL). The combined organic phase was washed with brine (50 mL), dried over MgSO$_4$. Filtration, concentration and dried over high vacuum gave 1-(((9H-fluoren-9-yl)methoxy)carbonyl)piperidine-4-carboxylic acid (3.90 g, 95% yield) as white solid. $^1$H NMR (300 MHz, CDCl$_3$) δ 7.76 (d, 2H, 0.1=7.2 Hz), 7.57 (d, 2H, 0.1=6.9 Hz), 7.39 (t, 2H, J=7.4 Hz), 7.31 (t, 2H, J=7.4 Hz), 4.43 (s, 2H), 4.24 (t, 1H, J=6.5 Hz), 4.09-3.94 (m, 2H), 2.95 (t, 2H, J=11.4 Hz), 2.51 (t, 1H, J=10.4 Hz), 1.90 (br s, 2H), 1.64 (br s, 2H); $^{13}$C NMR (75 MHz, CDCl$_3$) δ 179.6, 155.0, 143.8, 141.2, 127.6, 126.9, 124.8, 119.9, 67.3, 47.4, 43.2, 40.6, 27.6.

xv. (9H-fluoren-9-yl)methyl 4-(chlorocarbonyl)piperidine-1-carboxylate

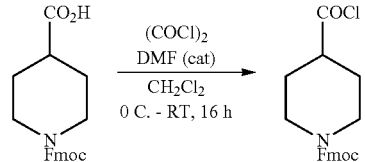

Synthesis of (9H-fluoren-9-yl)methyl 4-(chlorocarbonyl)piperidine-1-carboxylate

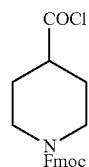

To a stirred suspension of 1-(((9H-fluoren-9-yl)methoxy)carbonyl)piperidine-4-carboxylic acid (3.88 g, 11 mmol) and DMF (0.4 mL) in CH$_2$Cl$_2$ (50 mL) was added oxalyl chloride (2.80 g, 22 mmol) drop-wise at 0° C. The reaction mixture turned to clear solution in 5 min, and then stirred for 16 h at RT. The reaction mixture was then concentrated at reduced pressure to afford (9H-fluoren-9-yl)methyl 4-(chlorocarbonyl)piperidine-1-carboxylate (4.07 g) as light yellow oily wax, which was used without further purification.

xvi. 2,5-dioxopyrrolidin-1-yl 2-(benzyloxy)-2-methylpropanoate

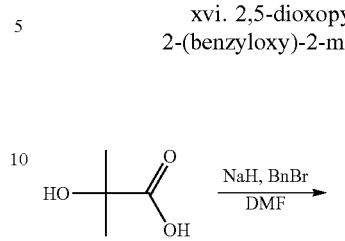

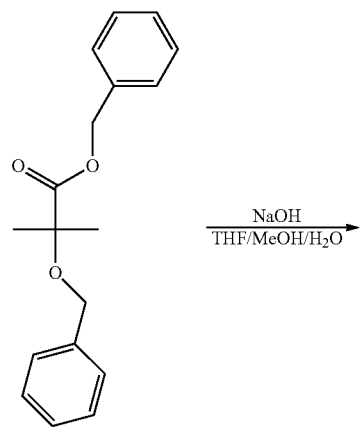

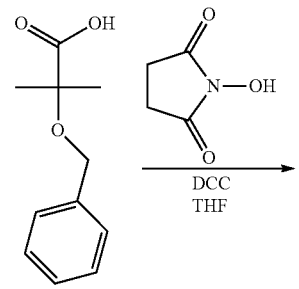

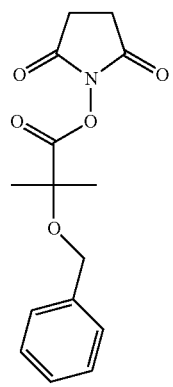

Synthesis of benzyl 2-(benzyloxy)-2-methylpropanoate

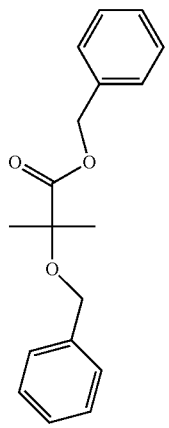 [SMILES: CC(C)(OCc1ccccc1)C(=O)OCc1ccccc1]

Sodium hydride (2.64 g, 60% in oil, 66 mmol) was added to 2-hydroxy-2-methyl-propionic acid (3.12 g, 30 mmol) in DMF (30 mL) at 0° C. The reaction mixture was stirred for 30 min at room temperature. Benzyl bromide (10.03 g, 60 mmol) was added and the reaction mixture was stirred at room temperature over night. The reaction mixture was quenched with HCl (1 M) and extracted with Et2O (3×50 mL). The organic solution was washed with water, brine, and dried over MgSO$_4$. The solvent was evaporated and residue was purified by column to prepare benzyl 2-(benzyloxy)-2-methylpropanoate (3.6 g, 42% yield). 1H NMR (300 MHz, CDCl3/TMS): δ 7.39-7.29 (m, 10H), 5.24 (s, 2H), 4.49 (s, 2H), 1.58 (s, 6H).

Synthesis of benzyl 2-(benzyloxy)-2-methylpropanoic acid

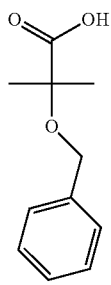

The benzyl 2-(benzyloxy)-2-methylpropanoate (3.6 g, 13 mmol) was refluxed in aqueous THF/MeOH/NaOH solution (2.0 g, 40/40/40 mL) for 1 h. The reaction mixture was acidified with HCl to pH=2 and extracted with CH$_2$Cl$_2$ (2×50 mL). The CH$_2$Cl$_2$ was evaporated, the residue was dissolved in aqueous NaOH (1 M, 40 mL). The aqueous solution was extracted with chloroform (2×30 mL). The aqueous solution was again acidified with HCl to pH=2 and extracted with chloroform. The organic solution was washed with water, brine, dried over MgSO$_4$, and evaporated to prepare benzyl 2-(benzyloxy)-2-methylpropanoic acid (2.4 g, 99% yield). $^1$H NMR (300 MHz, CDCl$_3$/TMS): δ 7.45-7.28 (m, 5H), 4.58 (s, 2H), 1.62 (s, 6H).

Synthesis of benzyl 2,5-dioxopyrrolidin-1-yl 2-(benzyloxy)-2-methylpropanoate

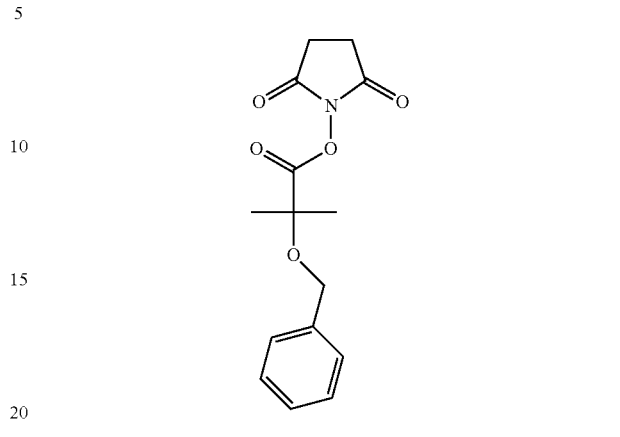

DCC (2.79 g, 13.5 mmol) was added to benzyl 2-(benzyloxy)-2-methylpropanoic acid (2.4 g, 12.3 mmol) in THF (70 mL) at 0° C. The reaction mixture was stirred at room temperature for 1 h and cooled down to 0° C. N-Hydroxysuccinimide (1.56 g, 13.5 mmol) was added and stirring was continued overnight at room temperature. The reaction mixture was filtered, the solvent was evaporated, the residue was purified by column chromatography (silica gel, EtOAc/Hept, 1:1) to prepare 2,5-dioxopyrrolidin-1-yl 2-(benzyloxy)-2-methylpropanoate (2.2 g, 61% yield). 1H NMR (300 MHz, CDCl3/TMS): δ 7.42-7.24 (m, 5H), 4.59 (s, 2H), 2.81 (s, 4H), 1.67 (6H).

xvii. 2,5-dioxopyrrolidin-1-yl tetrahydro-2H-pyran-3-carboxylate

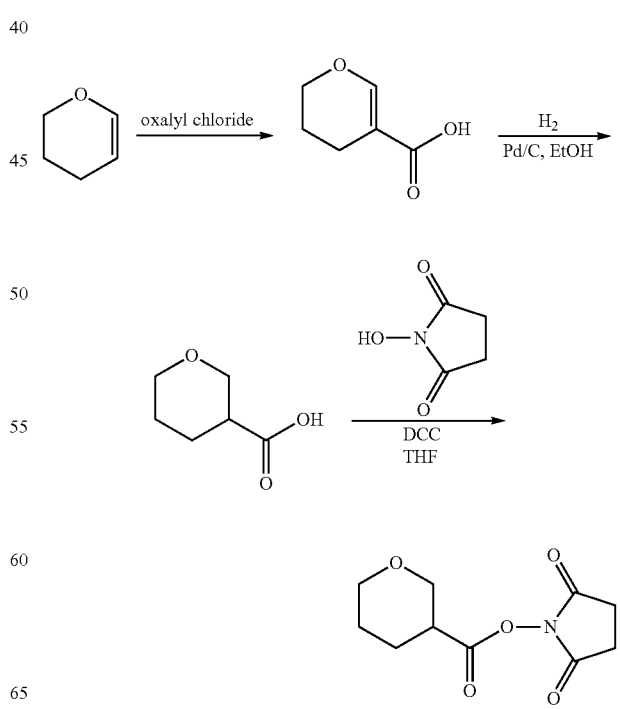

Synthesis of 3,4-dihydro-2H-pyran-5-carboxylic acid

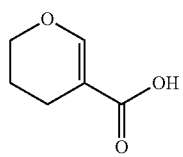

3,4-dihydro-2H-pyran-5-carboxylic acid was prepared as described in *J. Het. Chem.*, 2010, 47, p. 1171. Oxalyl chloride (7.2 mL, 83 mmol) was cooled to 0° C. and 3.4-dihydro-2H-pyrane (5.0 mL, 55.4 mmol) was added. The solution was slowly warmed to ambient temperature and stirring was continued for 1 h. Excess oxalyl chloride was evaporated in vacuo at 30° C. The mixture was then heated to 120° C. for 0.5 h, cooled to ambient temperature, and poured into ice-cold aqueous solution of $Na_2CO_3$. The alkaline solution was extracted with $CH_2Cl_2$ and then acidified with HCl (6 M). The aqueous layer was extracted with $CH_2Cl_2$ and the organic solution was dried over $MgSO_4$, filtered, and evaporated to yield 3,4-dihydro-2H-pyran-5-carboxylic acid (5.1 g, 67% yield). $^1$H NMR (300 MHz, $CDCl_3$/TMS): δ 11.4 (br s, 1H), 7.70 (s, 1H), 4.08 (t, J=5 Hz, 2H), 2.26 (t, J=7 Hz, 2H), 1.89 (m, 2H).

Synthesis of tetrahydro-2H-pyran-3-carboxylic acid

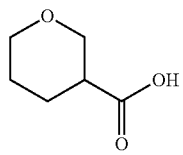

3,4-dihydro-2H-pyran-5-carboxylic acid (5.0 g, 39 mmol) was hydrogenated with $H_2$ under Pd/C (30%, 500 mg) in EtOH (100 mL) for 2 days at room temperature. The solution was filtered, EtOH was evaporated, and crude tetrahydro-2H-pyran-3-carboxylic acid (4.5 g) was used for next step without purification. $^1$H NMR (300 MHz, $CDCl_3$/TMS): δ 11.0 (br s, 1H), 4.00 (m, 1H), 3.78 (m, 1H), 3.60 (1H), 3.45 (m, 1H), 2.59 (m, 1H), 1.99 (m, 1H), 1.76-1.59 (m, 3H).

Synthesis of tetrahydro-2H-pyran-3-carboxylic acid

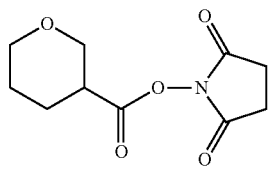 [SMILES: O=C(ON1C(=O)CCC1=O)C1CCCOC1]

DCC (7.85 g, 38.1 mmol) was added to tetrahydro-2H-pyran-3-carboxylic acid (4.5 g, 34.6 mmol) in THF (100 mL) at 0° C. The reaction mixture was stirred at room temperature for 1 h and cooled down to 0° C. N-Hydroxysuccinimide (4.78 g, 41.5 mmol) was added and stirring was continued overnight at room temperature. The reaction mixture was filtered, the solvent was evaporated, and the residue was purified by column chromatography (silica gel, EtOAc/Hept, 1:1-1:0) to prepare 2,5-dioxopyrrolidin-1-yl tetrahydro-2H-pyran-3-carboxylate (6.5 g, 83% yield). $^1$H NMR (300 MHz, $CDCl_3$/TMS): δ 4.14-4.06 (m, 1H), 3.88-3.79 (m, 1H), 3.71-3.64 (m, 1H), 3.54-3.44 (m, 1H), 2.99-2.89 (m, 1H), 2.81 (s, 4H), 22.2-2.14 (m, 1H), 1.95-1.84 (m, 1H), 1.78-1.64 (m, 3H).

B. Synthesis of Final Products i. Asymmetric synthesis of 2-((3S,4S)-1-benzyl-4-methylpyrrolidin-3-yl)-7-(tetrahydro-2H-pyran-4-yl)imidazo[5,1-f][1,2,4]triazin-4(3H)-one

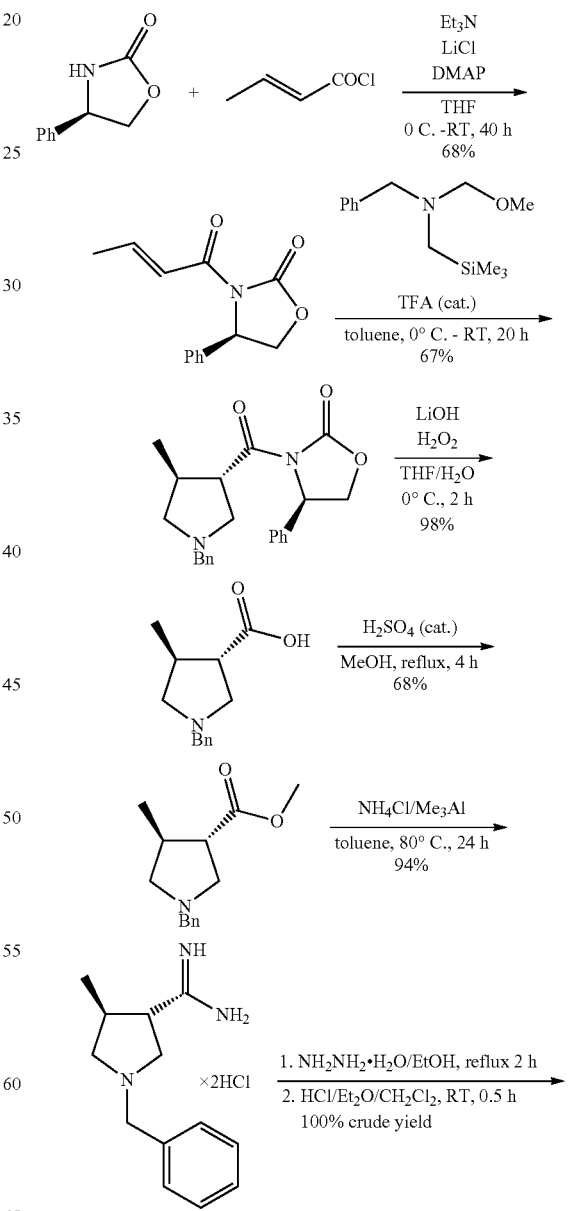

-continued

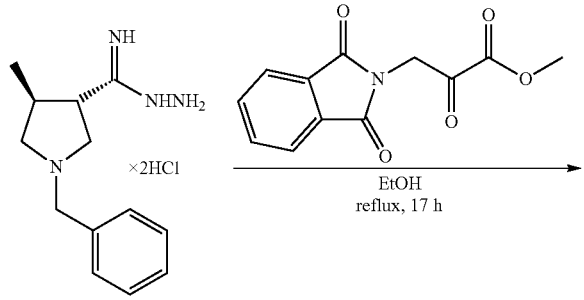

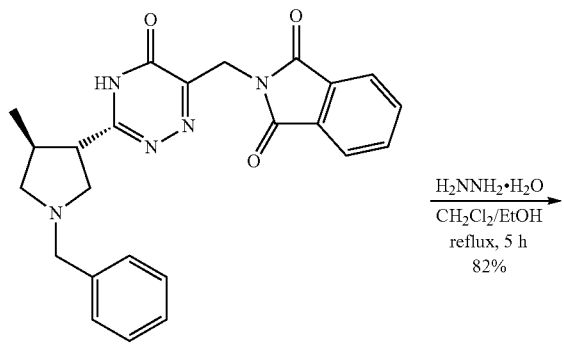

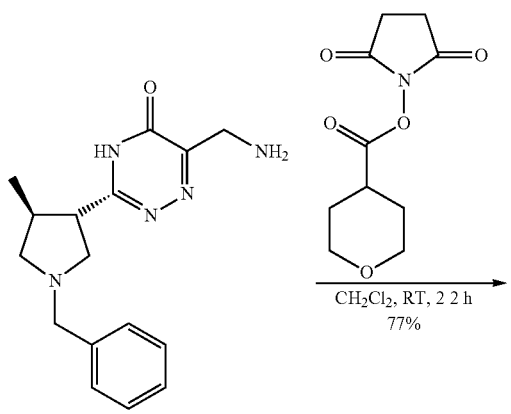

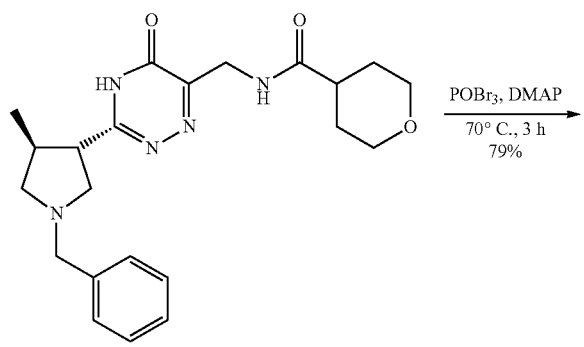

-continued

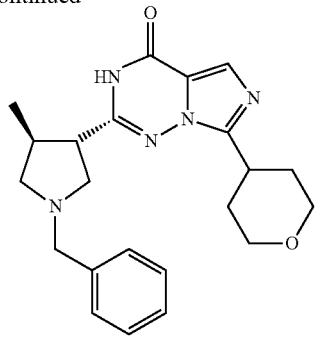

Synthesis of (R,E)-3-but-2-enoyl-4-phenyloxazolidin-2-one

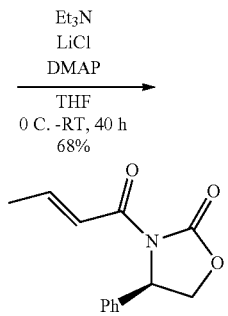

To a solution of (R)-4-phenyloxazolidin-2-one (8.30 g, 50.9 mmol) in anhydrous THF (80 mL) were added LiCl (2.48 g, 58.5 mmol) and triethylamine (10.30 g, 101.8 mmol). The resulting solution was stirred at RT for 20 minutes, and was then cooled by an ice-water bath. DMAP (0.63 g, 5.1 mmol) was added followed by drop-wise addition of (E)-but-2-enoyl chloride (6.11 g, 58.5 mmol). The resulting yellow suspension was stirred at 0° C. for 0.5 h, then at RT for 16 h. Water (160 mL) was added to quench the reaction, and the mixture was extracted with EtOAc (1×150 mL, 2×100 mL). The combined organic phases were washed with brine (50 mL), dried over magnesium sulfate. The solvent was removed under reduced pressure to give crude product as yellowish oily wax, which was purified by chromatography (0-50% EtOAc/heptane) to obtain (R,E)-3-but-2-enoyl-4-phenyloxazolidin-2-one as light yellow wax (8.0 g, 68%). $^1$H NMR (300 MHz, CDCl$_3$/TMS): δ 7.50-7.20 (m, 6H), 7.18-7.00 (m, 1H), 5.48 (dd, 1H, J=8.7, 3.9 Hz), 4.69 (t, 1H, J=8.7 Hz), 4.27 (dd, 1H, J=8.7, 3.9 Hz), 1.93 (dd, 3H, J=6.7, 1.3 Hz); $^{13}$C NMR (75 MHz, CDCl$_3$/TMS): δ 164.2, 153.5, 146.9, 138.9, 128.9, 128.3, 125.7, 121.5, 69.8, 57.6, 18.5.

Synthesis of (R)-3-((3S,4S)-1-benzyl-4-methylpyrrolidine-3-carbonyl)-4-phenyloxazolidin-2-one

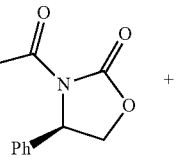 +

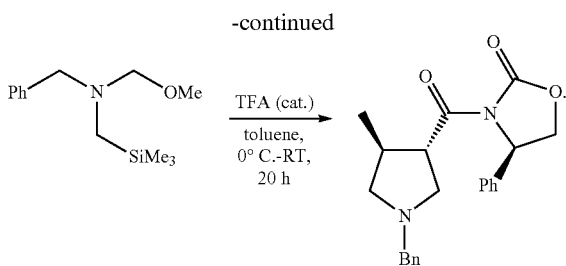

A solution of (R,E)-3-but-2-enoyl-4-phenyloxazolidin-2-one (8.04 g, 34.8 mmol) in dry toluene (150 mL) was flushed with argon. To this solution was added N-benzyl-1-methoxy-N-((trimethylsilyl)methyl)methanamine (9.92 g, 41.8 mmol) at 0° C., and the resulting solution was stirred at this temperature for 0.5 h. A solution of TFA in CH$_2$Cl$_2$ (1M, 3.5 mL) was added drop-wise over 10 minutes at 0° C. After addition was complete, the reaction mixture was stirred at 0° C. for 0.5 h and then at room temperature under argon for 20 h. The reaction mixture was washed with 5% NaHCO$_3$ aqueous solution (100 mL), brine (50 mL), and dried over magnesium sulfate. The solvent was removed under reduced pressure to give crude product as yellowish oily wax, which was separated by chromatography (10-100% EtOAc/heptane) to obtain (R)-3-((3S,4S)-1-benzyl-4-methylpyrrolidine-3-carbonyl)-4-phenyloxazolidin-2-one (8.10 g, 64%) and (R)-3-((3R,4R)-1-benzyl-4-methylpyrrolidine-3-carbonyl)-4-phenyloxazolidin-2-one (2.10 g, 17%).

(R)-3((3S,4S)-1-benzyl-4-methylpyrrolidine-3-carbonyl)-4-phenyloxazolidin-2-one: light yellow oily wax; $[\alpha]_D^{22}$—69.7 (c 0.9, CHCl$_3$); $^1$H NMR (300 MHz, CDCl$_3$/TMS): δ 7.60-7.10 (m, 10H), 5.42 (dd, 1H, J=8.7, 3.9 Hz), 4.65 (t, 1H, J=9.0 Hz), 4.20 (dd, 1H, J=8.7, 3.9 Hz), 3.76-3.66 (m, 1H), 3.64 (d, 1H, j=13.5 Hz), 3.46 (d, 1H, J=12.9 Hz), 2.99 (t, 1H, J=9.3 Hz), 2.88 (t, 1H, J=8.0 Hz), 2.83-2.72 (m, 1H), 2.66 (dd, 1H, J=10.0, 5.2 Hz), 2.25-2.10 (m, 1H), 1.06 (d, 3H, J=6.6 Hz); $^{13}$C NMR (75 MHz, CDCl$_3$/TMS): δ 173.4, 153.2, 138.8, 129.0, 128.4, 128.3, 127.9, 126.6, 125.5, 69.7, 61.6, 59.7, 57.7, 57.2, 50.2, 34.4, 19.0.

(R)-3-((3R,4R)-1-benzyl-4-methylpyrrolidine-3-carbonyl)-4-phenyloxazolidin-2-one: light yellow oily wax; $^1$H NMR (300 MHz, CDCl$_3$/TMS): δ 7.40-7.15 (m, 10H), 5.36 (dd, 1H, =8.4, 3.9 Hz), 4.58 (t, 1H, J=8.8 Hz), 4.17 (dd, 1H, J=8.8, 3.9 Hz), 3.86-3.75 (m, 1H), 3.63 (d, 1H, J=13.2 Hz), 3.53 (d, 1H, I=12.9 Hz), 2.94 (t, 1H, J=9.4 Hz), 2.88-2.75 (m, 2H), 2.61-2.49 (m, 1H), 2.25-2.10 (m, 1H), 1.02 (d, 3H, J=6.9 Hz); $^{13}$C NMR (75 MHz, CDCl$_3$/TMS): δ 173.7, 153.3, 138.9, 138.8, 128.9, 128.4, 127.9, 126.6, 125.5, 69.6, 61.4, 59.8, 57.8, 57.0, 49.6, 36.2, 18.8.

Synthesis of (3S,4S)-1-benzyl-4-methylpyrrolidine-3-carboxylic acid

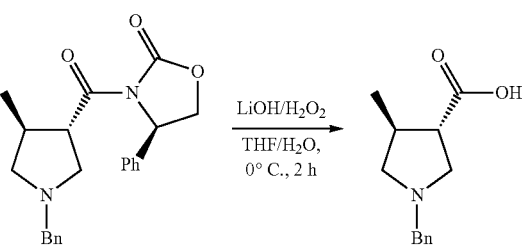 [SMILES: C[C@@H]1CN(Cc2ccccc2)C[C@H]1C(=O)N1C(=O)OC[C@H]1c1ccccc1 ; C[C@@H]1CN(Cc2ccccc2)C[C@H]1C(=O)O]

A solution of LiOH (1.32 g, 54.9 mmol) and H$_2$O$_2$ (35%, 426 g, 43.8 mmol) in water (35 mL) was added to a solution of (R)-3-((3S,4S)-1-benzyl-4-methylpyrrolidine-3-carbonyl)-4-phenyloxazolidin-2-one (8.00 g, 21.9 mmol) in THF (120 mL) dropwise at 0° C., and the resulting mixture was stirred at this temperature for 2 h, then diluted with water (150 mL). Sodium sulfite (5.77 g, 45.8 mmol) was added, and the solution was extracted with EtOAc (2×50 mL). The aqueous phase was adjusted to pH 4.6 with NaH$_2$PO$_4$.H$_2$O (10.3 g, 73 mmol) and 10% HCl, tehn saturated with NaCl. The solution was extracted with i-PrOH/CH$_2$Cl$_2$ (1:3, 5×120 mL). The combined organic phase was washed with brine (100 mL), dried over magnesium sulfate. The solvent was removed under reduced pressure to give crude (3S,4S)-1-benzyl-4-methylpyrrolidine-3-carboxylic acid (4.33 g, 90%) as highly hygroscopic, yellowish wax, which was used for next step without further purification; $^1$H NMR (300 MHz, CD$_3$OD/TMS): δ 7.55-7.45 (m, 5H), 4.39 (s, 2H), 3.68 (dd, 1H, J=12.3, 7.2 Hz), 3.61-3.51 (m, 2H), 3.00 (t, 1H, J=10.8 Hz), 2.90 (dd, 1H, J=16.5, &7 Hz), 2.67-3.55 (m, 1H), 1.26 (d, 3H, J=6.6 Hz); $^{13}$C NMR (75 MHz, CD$_3$OD/TMS): δ 174.6, 131.6, 131.3, 131.0, 130.3, 61.1, 59.9, 56.7, 50.3, 38.0, 17.2.

Synthesis of (3S,4S)-methyl 1-benzyl-4-methylpyrrolidine-3-carboxylate

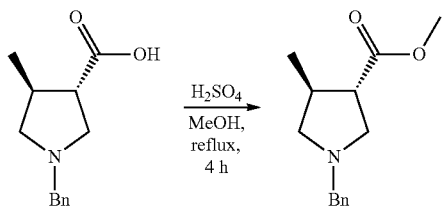

To a solution of (3S,4S)-1-benzyl-4-methylpyrrolidine-3-carboxylic acid (4.30 g, 19.6 mmol) in anhydrous methanol (100 mL) was added conc. H$_2$SO$_4$ (3 mL) at RT, and the resulting solution was stirred and heated under reflux for 4 h. The solvent was removed under reduced pressure, and the residue was dissolved in EtOAc (200 mL), treated with saturated NaHCO$_3$ aqueous solution (100 mL). The phases were separated, and the aqueous phase was extracted with EtOAc (2×50 mL). The combined organic phase was washed with brine (50 mL), and dried over magnesium sulfate. The solvent was removed under reduced pressure to give crude product as yellowish oil, which was purified by chromatography (0.1/6/94-0.5/15/85 Et$_3$N/EtOAc/heptane) to obtain (3S,4S)-methyl 1-benzyl-4-methylpyrrolidine-3-carboxylate (3.51 g, 68%) as light yellow oil. $^1$H NMR (300 MHz, CDCl$_3$/TMS): δ 7.38-7.20 (m, 5H), 3.67 (s, 3H), 3.64 (d, 1H, J=12.9 Hz), 3.56 (d, 1H, J=12.9 Hz), 2.91-2.73 (m, 3H), 2.60-2.42 (m, 2H), 2.21 (dd, 1H, J=8.7, 6.6 Hz), 1.13 (d, 3H, J=6.6 Hz); $^{13}$C NMR (75 MHz, CDCl$_3$/TMS): δ 174.8, 138.6, 128.5, 128.0, 126.7, 61.5, 60.0, 56.6, 51.7, 50.4, 36.7, 19.7.

Synthesis of (3S,4S)-1-benzyl-4-methylpyrrolidine-3-carboximidamide hydrochloride

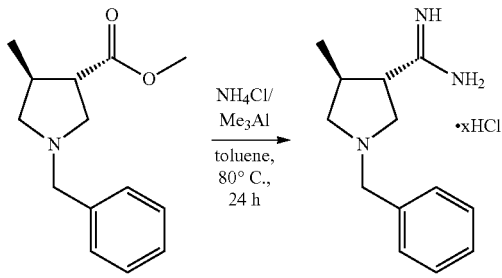

Ammonium chloride (4.01 g, 7.5 mmol) was suspended in dry toluene (90 mL) and the mixture was then cooled to 0° C. under argon. A solution of trimethylaluminum in heptane (37.5 mL, 2.0 M, 7.5 mmol) was added drop-wise and the resulting mixture was stirred at room temperature until no more evolution of gas was observed. (about 2 hours). After addition of (3S,4S)-methyl 1-benzyl-4-methylpyrrolidine-3-carboxylate (3.50 g, 1.5 mmol) at RT, resulting reaction mixture was stirred at RT for 0.5 h, then heated at 80° C. for 24 h. The reaction mixture was cooled to 0° C., quenched by slow addition of methanol (75 mL) and then stirred vigorously at room temperature for one hour. The mixture was filtered and the filter cake was washed with methanol (2×20 mL). The combined filtrates were concentrated under reduced pressure to give a yellow solid. The solid was triturated with dichloromethane/methanol (1:1, 50 mL), and filtered. The filtrate was concentrated under reduced pressure to give crude (3S,4S)-1-benzyl-4-methylpyrrolidine-3-carboximidamide hydrochloride as yellow wax (4.10 g, 94%). This compound was used for next step without further purification. $^1$H NMR (300 MHz, CD$_3$OD): δ 7.60-7.25 (m, 5H), 4.06 (br s, 2H), 3.46-3.16 (m, 3H), 2.94 (br s, 1H), 2.62 (br s, 2H), 1.19 (d, 3H, 6.3 Hz); $^{13}$C NMR (75 MHz, CDCl$_3$) δ 173.4, 135.8, 130.8, 129.9, 129.7, 61.3, 60.1, 57.3, 50.0, 40.3, 18.1.

Synthesis of (3S,4S)-1-benzyl-4-methylpyrrolidine-3-carboximidhydrazide hydrochloride

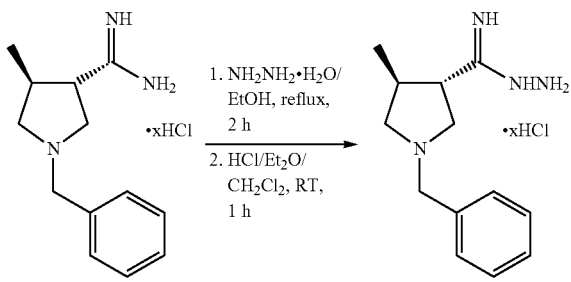

A solution of hydrazine monohydrate (0.69 g, 13.7 mmol) in EtOH (2 mL) was added slowly to a solution of (3S,4S)-1-benzyl-4-methylpyrrolidine-3-carboximidamide hydrochloride (3.98 g, 13.7 mmol) in ethanol (58 mL) at RT. The resulting light yellow suspension was stirred at reflux for 2 h. The reaction mixture was cooled to RT and the white solid was filtered. The filtrate was concentrated under reduced pressure to give a light pink wax. The material was dissolved in a minimum CH$_2$Cl$_2$ (10 mL), and to this stick solution was added 2M HCl in ether (18 mL) dropwise at RT with stirring. Then anhydrous ether (20 mL) was added. The resulting yellow suspension was stirred at RT under argon for 0.5 h. The solid was filtered and rinsed with ether, dried over high vacuum to provide crude (3S,4S)-1-benzyl-4-methylpyrrolidine-3-carboximidhydrazide hydrochloride (4.20 g, 100%). This material was used for next step without further purification.

Synthesis of 2-((3-((3S,4S)-1-benzyl-4-methylpyrrolidin-3-yl)-5-oxo-4,5-dihydro-1,2,4-triazin-6-yl)methyl)isoindoline-1,3-dione

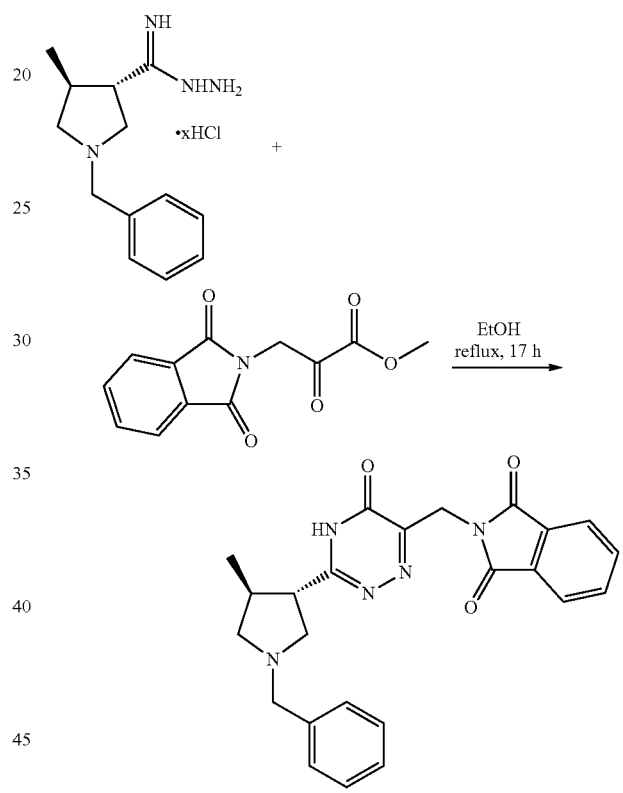

The mixture of (3S,4S)-1-benzyl-4-methylpyrrolidine-3-carboximidhydrazide hydrochloride (4.00 g, 13.1 mmol) and methyl 3-(1,3-dioxoisoindolin-2-yl)-2-oxopropanoate (3.24 g, 13.1 mmol) in anhydrous ethanol (45 mL) was heated under reflux and argon for 17 h. The cooled reaction mixture was concentrated under reduced pressure and the residue was dissolved in CHCl$_3$ (100 mL), and the pH value was adjusted to 8 with saturated NaHCO$_3$. The organic phase was separated from aqueous phase, and the latter was extracted with CHCl$_3$ (2×20 mL). The combined organic phase was dried over MgSO$_4$. After concentration the residue purified by flash chromatography over silica gel column (0.1/1.5/98.4-0.5/7.5/92 NH$_4$OH/MeOH/CH$_2$Cl$_2$) to give 2-((3-((3S,4S)-1-benzyl-4-methylpyrrolidin-3-yl)-5-oxo-4,5-dihydro-1,2,4-triazin-6-yl)methyl)isoindoline-1,3-dione (2.14 g, 38%) as yellow solid. $^1$H NMR (300 MHz, CDCl$_3$/TMS) δ 9.81 (br s, 1H), 7.86 (dd, 2H, J=5.6, 2.8 Hz), 7.72 (dd, 2H, J=5.3, 3.1 Hz), 7.30 (m, 5H), 5.01 (s, 2H), 3.97 (br s, 1H), 3.81 (d, 1H, J=10.5 Hz), 3.40-3.00 (m, 4H), 2.60-

2.50 (m, 2H), 0.95 (d, 3H, J=6.0 Hz); $^{13}$C NMR (75 MHz, CDCl$_3$/TMS) δ 167.8, 165.0, 162.6, 148.7, 133.7, 132.2, 129.3, 128.7, 128.5, 123.1, 60.2, 59.3, 56.5, 50.3, 38.5, 37.6, 17.6.

Synthesis of 6-(aminomethyl)-3-((3S,4S)-1-benzyl-4-methylpyrrolidin-3-yl)-1,2,4-triazin-5(4H)-one

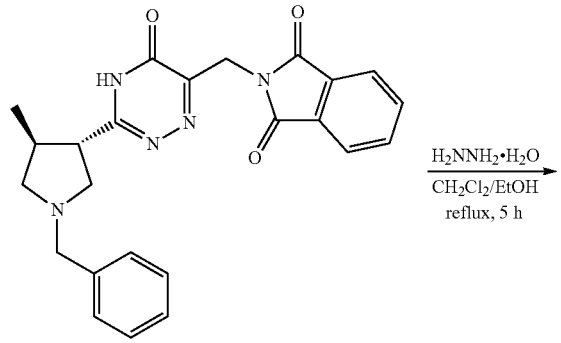

To a mixture of 2-((3-((3S,4S)-1-benzyl-4-methylpyrrolidin-3-yl)-5-oxo-4,5-dihydro-1,2,4-triazin-6-yl)methyl)isoindoline-1,3-dione (2.10 g, 4.88 mmol) in dichloromethane/ethanol (1:1, 80 mL) was added hydrazine monohydrate (0.62 g, 12.2 mmol) at RT, and the resulting solution was stirred and heated to reflux for 5 h. The cooled reaction mixture was filtered and the filter cake was rinsed with dichloromethane/ethanol (1:1, 60 mL). The combined filtrates were concentrated under reduced pressure to give crude mixture, which was purified by flash chromatography column (0.5/7.5/92-1/15/84 NH$_4$OH/MeOH/CH$_2$Cl$_2$) to provide 6-(aminomethyl)-3-((3S,4S)-1-benzyl-4-methylpyrrolidin-3-yl)-1,2,4-triazin-5(4H)-one (1.19 g, 81%) as yellow wax. $^1$H NMR (300 MHz, CD$_3$OD) δ 7.40-7.22 (m, 5H), 4.04 (s, 2H), 3.86 (d, 1H, J=12.6 Hz), 3.78 (d, 1H, J=12.6 Hz), 3.20-2.92 (m, 4H), 2.64-2.53 (m, 2H), 1.08 (d, 3H, J=6.3 Hz); $^{13}$C NMR (75 MHz, CD$_3$OD/TMS) δ 170.0, 166.5, 150.3, 138.0, 130.6, 129.5, 128.8, 62.5, 61.3, 60.2, 53.3, 41.4, 39.9, 18.8.

Synthesis of N-((3-((3S,4S)-1-benzyl-4-methylpyrrolidin-3-yl)-5-oxo-4,5-dihydro-1,2,4-triazin-6-yl)methyl)tetrahydro-2H-pyran-4-carboxamide

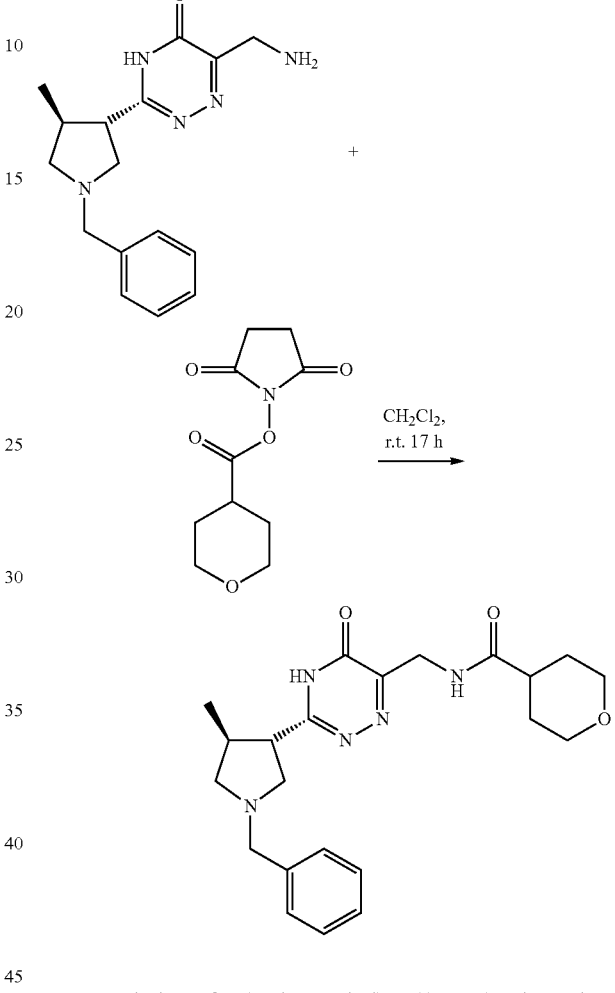

To a solution of 6-(aminomethyl)-3-((3S,4S)-1-benzyl-4-methylpyrrolidin-3-yl)-1,2,4-triazin-5(4H)-one (1.10 g, 3.68 mmol) in CH$_2$Cl$_2$ (60 mL) was added 2,5-dioxopyrrolidin-1-yl tetrahydro-2H-pyran-4-carboxylate (1.30 g, 5.51 mmol) at RT. The resulting solution was stirred at room temperature for 20 h. The reaction mixture was filtered. The filtrate was washed with sat. NaHCO$_3$ (2×20 mL). The aqueous phase was extracted with CHCl$_3$ (2×20 mL). The combined organic phase was dried over MgSO$_4$. Concentration and purification by flash chromatography over silica gel column (0.1/1.5/98.4-1/15/84 NH$_4$OH/MeOH/CH$_2$Cl$_2$) to give N-((3-((3S,4S)-1-benzyl-4-methylpyrrolidin-3-yl)-5-oxo-4,5-dihydro-1,2,4-triazin-6-yl)methyl)tetrahydro-2H-pyran-4-carboxamide (1.07 g, 71%) as a yellow solid. $^1$H NMR (300 MHz, CDCl$_3$) δ 7.46-7.30 (m, 5H), 7.00 (br s, 1H), 6.84 (br s, 1H), 4.52 (br s, 2H), 4.08-3.82 (m, 4H), 3.48-3.38 (m, 3H), 3.29 (br s, 1H), 3.22-3.04 (m, 2H), 2.70-2.38 (m, 3H), 1.92-1.77 (m, 4H), 1.06 (d, 3H, J=6.3 Hz); $^{13}$C NMR (75 MHz, CDCl$_3$) δ 174.3, 165.3, 162.7, 150.7, 134.2, 129.2, 128.7, 128.4, 67.2, 60.4, 59.6, 56.6, 50.3, 42.0, 39.7, 38.6, 29.2, 18.3.

Synthesis of 2-((3S,4S)-1-benzyl-4-methylpyrrolidin-3-yl)-7-(tetrahydro-2H-pyran-4-yl)imidazo[1,5-f][1,2,4]triazin-4(3H)-one ii. Racemic synthesis of (+/−)-2-((3,4-trans)-1-benzyl-4-methylpyrrolidin-3-yl)-7-(tetrahydro-2H-pyran-4-yl)imidazo[5,1-f][1,2,4]triazin-4(3H)-one

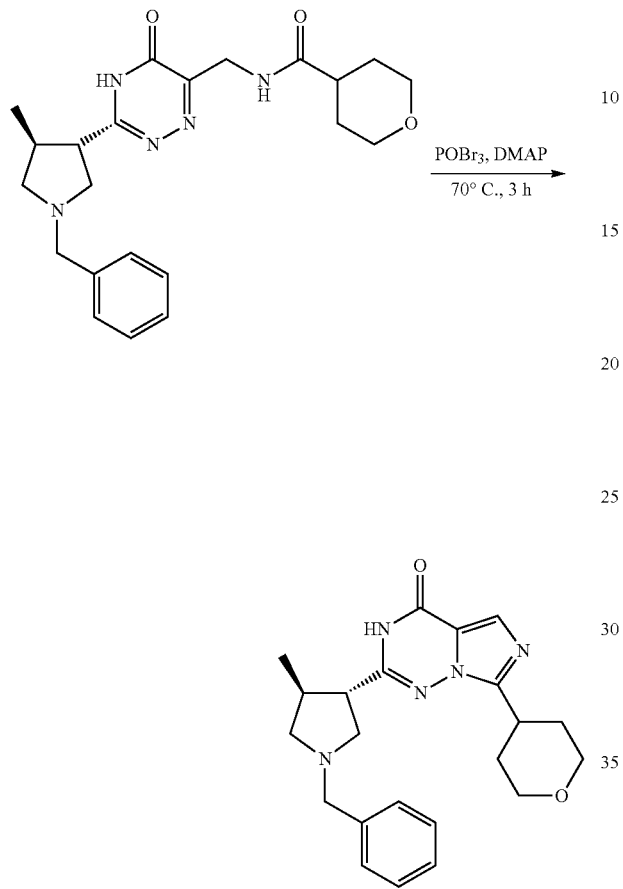

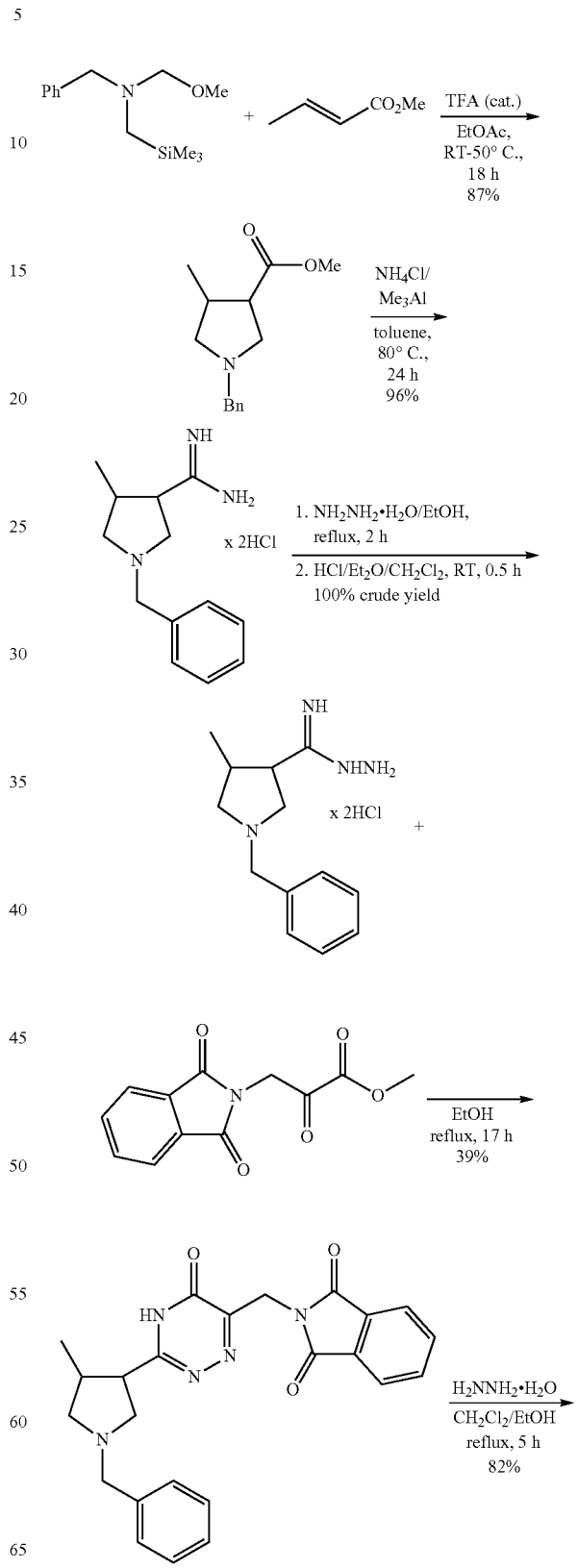

To a solution of N-((3-((3S,4S)-1-benzyl-4-methylpyrrolidin-3-yl)-5-oxo-4,5-dihydro-1,2,4-triazin-6-yl)methyl)tetrahydro-2H-pyran-4-carboxamide (1.04 g, 2.53 mmol), DMAP (34 mg, 0.25 mmol) in acetonitrile (65 mL) was added a solution of $POBr_3$ (2.18 g, 7.61 mmol) in acetonitrile (25 mL) at RT, and the resulting suspension was heated to 70° C. for 3 h. After the mixture was cooled to room temperature, it was poured into saturated $NaHCO_3$ solution (200 mL), and stirred vigorously for 0.5 h, then extracted with $CH_2Cl_2$ (1×90 mL, 2×40 mL). The organic extract was dried over $MgSO_4$ and concentrated under reduced pressure. The residue was purified by flash chromatography over silica gel (0.1/1.5/98.4-0.3/4.5/95.2 $NH_4OH/MeOH/CH_2Cl_2$) to furnish 2-((3S,4S)-1-benzyl-4-methylpyrrolidin-3-yl)-7-(tetrahydro-2H-pyran-4-yl)imidazo[1,5-f][1,2,4]triazin-4(3H)-one (0.72 g, 70%) as a white wax. $^1H$ NMR (300 MHz, $CDCl_3$/TMS) δ δ 8.33 (br s, 1H), 7.78 (s, 1H), 7.42-7.22 (m, 5H), 4.13-4.02 (m, 2H), 3.81 (d, 1H, J=12.6 Hz), 3.65-3.52 (m, 3H), 3.50-3.34 (m, 2H), 2.99 (d, 1H, J=9.9 Hz), 2.83-2.75 (m, 1H), 2.57 (dd, 1H, J=9.9, 6.3 Hz), 2.52-2.40 (m, 1H), 2.19-1.84 (m, 5H), 1.23 (d, 3H, J=6.9 Hz); $^{13}C$ NMR (75 MHz, $CDCl_3$/TMS) δ 154.25, 153.53, 148.32, 137.16, 128.49, 128.44, 127.34, 127.22, 118.67, 67.42, 67.38, 60.95, 59.15, 55.93, 47.78, 38.15, 32.47, 30.23, 29.97, 19.97.

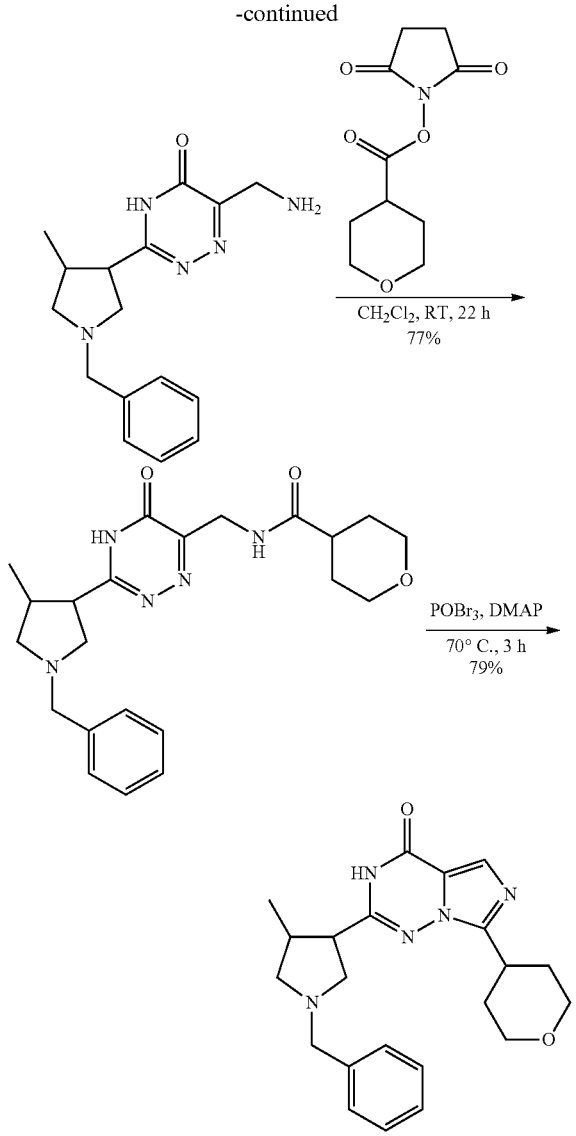

Synthesis of (+/−)-(3,4-trans)-methyl 1-benzyl-4-methylpyrrolidine-3-carboxylate

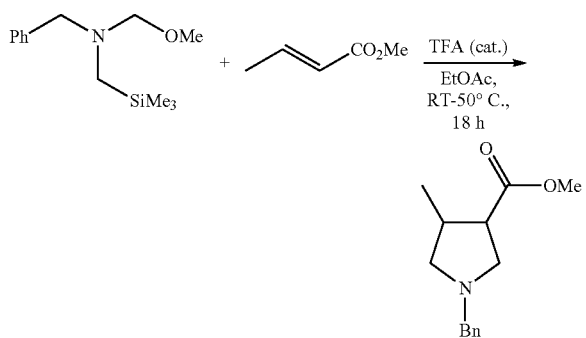

Benzylmethoxymethyl-trimethylsilanylmethylamine (118.71 g, 500 mmole) was added drop-wise to a stirred solution of methyl trans-2-pentenoate (50.00 g, 500 mmol) and TFA (1.0 mL) in dry ethyl acetate (1000 mL) at a rate to maintain the temperature below 50° C. After the addition was complete, the reaction mixture was stirred at room temperature under argon for 5 hours. Saturated NaHCO₃ (200 mL) was added and the mixture was stirred for 0.5 hour. The organic phase was separated from aqueous phase, and the latter was extracted with EtOAc (150 mL). The combined organic phases were washed with brine (100 mL), dried over magnesium sulfate. The solvent was removed under reduced pressure to give crude product as yellowish oil, which was purified by chromatography (1/20/79-1/30/69 Et₃N/EtOAc/heptane) to obtain 101.37 g of (+/−)-(3 (3,4-trans)-methyl 1-benzyl-4-methylpyrrolidine-3-carboxylate as light yellow oil (87%). ¹H NMR (300 MHz, CDCl₃/TMS): δ 7.35-7.18 (m, 5H), 3.68 (s, 3H), 3.64 (d, 1H, J=12.9 Hz), 3.56 (d, 1H, J=12.9 Hz), 2.95-2.74 (m, 3H), 2.60-2.44 (m, 2H), 2.25-2.18 (m, 1H), 1.13 (d, 3H, J=6.6 Hz); ¹³C NMR (75 MHz, CDCl₃/TMS): δ 174.9, 138.8, 128.5, 128.1, 126.8, 61.6, 60.1, 56.6, 51.7, 50.5, 36.8, 19.8.

Synthesis of (+/−)-(3,4-trans)-1-benzyl-4-methylpyrrolidine-3-carboximidamide hydricholoride

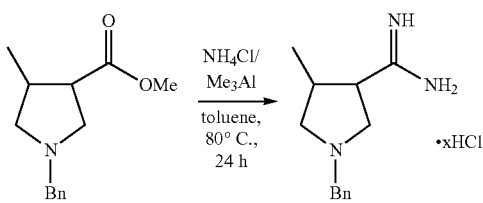 [SMILES: COC(=O)C1CN(Cc2ccccc2)CC1C ; CC1CN(Cc2ccccc2)CC1C(=N)N]

Ammonium chloride (26.75 g, 500 mmol) was suspended in dry toluene (600 mL) and the mixture was then cooled to 0° C. A solution of trimethylaluminum in hexane (250 mL, 2.0 M, 500 mmol) was added drop-wise and the resulting mixture was stirred at room temperature until no more evolution of gas was observed (about 3 hours). (+/−)-(3 (3,4-Trans)-methyl 1-benzyl-4-methylpyrrolidine-3-carboxylate (23.33 g, 100 mmol) was added and the resulting mixture was heated at 80° C. for 24 h. After cooling to 0° C., the reaction mixture was quenched by slow addition of methanol (500 mL) and then stirred vigorously at room temperature for one hour. The mixture was filtered and the filter cake was washed with methanol (3×150 mL). The combined filtrates were concentrated under reduced pressure to give a yellow solid. The solid was triturated with dichloromethane/methanol (1:1, 300 mL). The filtrate was concentrated under reduced pressure to give (+/−)-(3,4-trans)-1-benzyl-4-methylpyrrolidine-3-carboximidamide hydrochloride as a yellow wax (28.00 g, 96%). This compound was used for next step without further purification. ¹H NMR (300 MHz, CDCl₃): δ 7.60-7.25 (m, 5H), 4.08 (br s, 2H), 3.46-3.16 (m, 3H), 3.03-2.90 (m, 1H), 2.72-2.50 (m, 2H), 1.19 (d, 3H, J=6.3 Hz); ¹³C NMR (75 MHz, CDCl₃) δ 173.2, 135.7, 130.8, 129.9, 129.7, 61.2, 60.0, 57.2, 50.0, 40.3, 18.0.

Synthesis of (+/−)-(3,4-trans)-1-benzyl-4-methylpyrrolidine-3-carboximidhydrazide hydrochloride

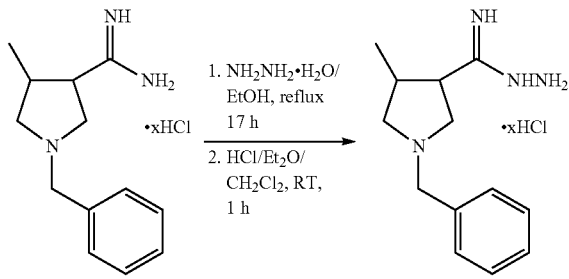 [SMILES: CC1CN(Cc2ccccc2)CC1C(=N)N ; "·xHCl" ; CC1CN(Cc2ccccc2)CC1C(=N)NN ; "·xHCl"]

A solution of hydrazine monohydrate (2.62 g, 52.4 mmol) in EtOH (20 mL) was added slowly to a solution of (+/−)-(3,4-trans)-1-benzyl-4-methylpyrrolidine-3-carboximidamide hydrochloride (15.21 g, 52.4 mmol) in ethanol (200 mL). The resulting white suspension was stirred at reflux for 2 h. The reaction mixture was cooled to RT and the white solid was filtered. The filtrate was concentrated under reduced pressure to give a light pink wax. The material was dissolved in a minimum CH$_2$Cl$_2$ (20 mL), and to this stick solution was added 2M HCl in ether (70 mL) dropwise at RT with stirring. Then anhydrous ether (50 mL) was added. The resulting yellow suspension was stirred at RT under argon for 0.5 h. The solid was filtered and rinsed with ether, dried over high vacuum to provide crude salt (+/−)-(3,4-trans)-1-benzyl-4-methylpyrrolidine-3-carboximidhydrazide hydrochloride (16.50 g, 103%). This material was used for next step without further purification.

Synthesis of (+/−)-2-((3-((3,4-trans)-1-benzyl-4-methylpyrrolidin-3-yl)-5-oxo-4,5-dihydro-1,2,4-triazin-6-yl)methyl)isoindoline-1,3-dione

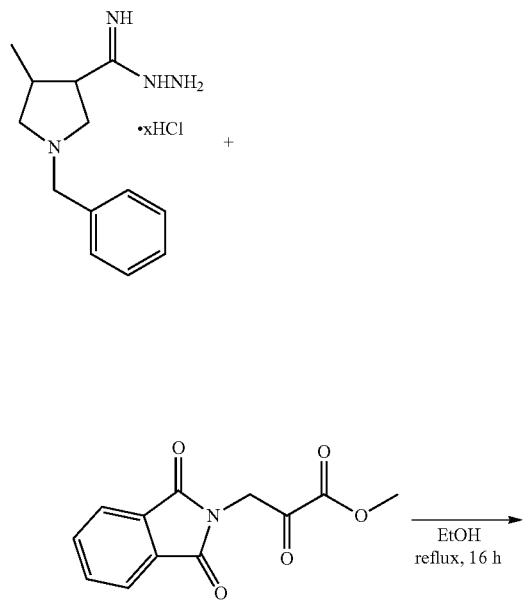

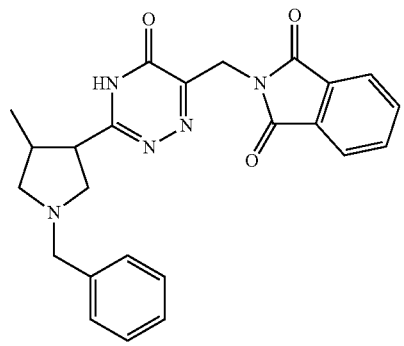

The mixture of (+/−)-(3,4-trans)-1-benzyl-4-methylpyrrolidine-3-carboximidhydrazide hydrochloride (2.69 g, 8.8 mmol) and methyl 3-(1,3-dioxoisoindolin-2-yl)-2-oxopropanoate (2.18 g, 8.8 mmol) in anhydrous ethanol (25 mL) was heated under reflux and argon for 17 h. The cooled reaction mixture was concentrated under reduced pressure and the residue was triturated with 2% MeOH/CH$_2$Cl$_2$ (20 mL) to give a yellow solid. The solid was suspended in CHCl$_3$ (25 mL) and the pH value was adjusted to 8 with saturated NaHCO$_3$. The organic phase was separated from aqueous phase, and the latter was extracted with CHCl$_3$ (2×10 mL). The combined organic phase was dried over MgSO$_4$. After concentration the residue purified by flash chromatography over silica gel column (0.1/1.5/98.4-0.6/9/90.4 NH$_4$OH/MeOH/CH$_2$Cl$_2$) to give (+/−)-2-((3-(3,4-trans)-1-benzyl-4-methylpyrrolidin-3-yl)-5-oxo-4,5-dihydro-1,2,4-triazin-6-yl)methyl)isoindoline-1,3-dione (1.46 g, 39%) as light yellow solid. $^1$H NMR (300 MHz, CD$_3$OD/CDCl$_3$) δ 7.92-7.85 (m, 2H), 7.81-7.74 (m, 2H), 7.34 (m, 5H), 4.97 (s, 2H), 3.98 (d, 1H, J=12.3 Hz), 3.89 (d, 1H, J=12.3 Hz), 3.40-3.24 (m, 1H), 3.22-3.17 (m, 2H), 3.08-2.98 (m, 1H), 2.65-2.50 (m, 2H), 1.03 (d, 3H, J=6.0 Hz); $^{13}$C NMR (75 MHz, CD$_3$OD/CDCl$_3$) δ 168.3, 165.7, 163.7, 148.6, 134.3, 134.0, 132.2, 129.6, 128.9, 128.7, 123.4, 60.6, 59.6, 57.4, 50.3, 38.8, 37.7, 17.6.

Synthesis of (+/−)-6-(aminomethyl)-3-((3,4-trans)-1-benzyl-4-methylpyrrolidin-3-yl)-1,2,4-triazin-5(4H)-one

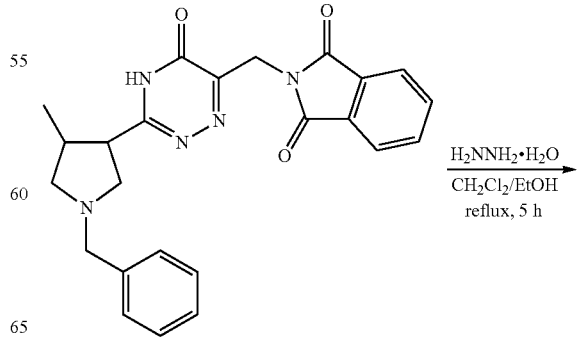

85

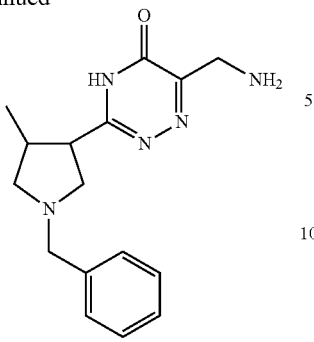

To a mixture of (+/−)-2-((3-(3,4-trans)-1-benzyl-4-methylpyrrolidin-3-yl)-5-oxo-4,5-dihydro-1,2,4-triazin-6-yl)methyl)isoindoline-1,3-dione (2.19 g, 5.1 mmol) in dichloromethane/ethanol (1:1, 80 mL) was added hydrazine monohydrate (0.64 g, 12.7 mmol) at RT, and the resulting suspension was stirred and heated to reflux for 5 h. The cooled reaction mixture was filtered and the filter cake was rinsed with dichloromethane/ethanol (1:1, 80 mL). The combined filtrates were concentrated under reduced pressure to give crude mixture, which was purified by flash chromatography column (0.5/7.5/92-1/15/84 NH$_4$OH/MeOH/CH$_2$Cl$_2$) to provide (+/−)-6-(aminomethyl)-3-((3,4-trans)-1-benzyl-4-methylpyrrolidin-3-yl)-1,2,4-triazin-5(4H)-one (1.25 g, 82%) as off-white wax. $^1$H NMR (300 MHz, CD$_3$OD) δ 7.45-7.27 (m, 5H), 4.04 (br s, 2H), 3.88 (d, 1H, J=12.6 Hz), 3.80 (d, 1H, J=12.6 Hz), 3.20-2.92 (m, 4H), 2.63-2.55 (m, 2H), 1.08 (d, 3H, J=5.7 Hz); $^{13}$C NMR (75 MHz, CD$_3$OD) δ 170.0, 166.5, 150.1, 137.8, 130.6, 129.6, 128.9, 62.4, 61.3, 60.1, 53.2, 41.3, 39.9, 18.8.

Synthesis of (+/−)-N-((3-((3,4-trans)-1-benzyl-4-methylpyrrolidin-3-yl)-5-oxo-4,5-dihydro-1,2,4-triazin-6-yl)methyl)tetrahydro-2H-pyran-4-carboxamide

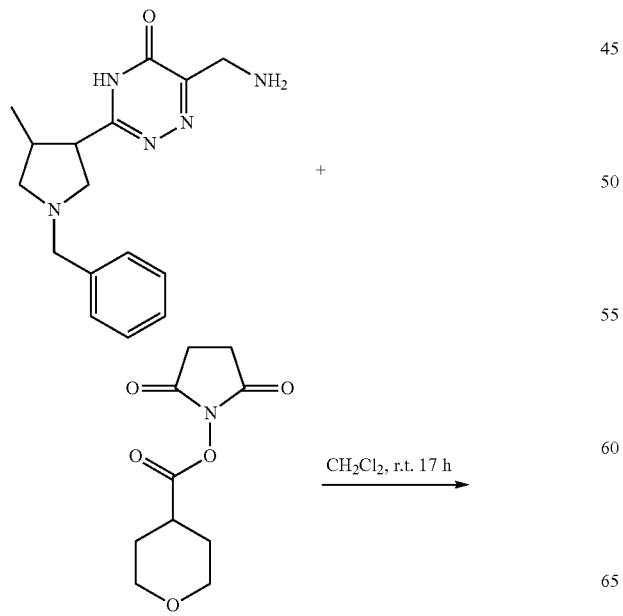

86

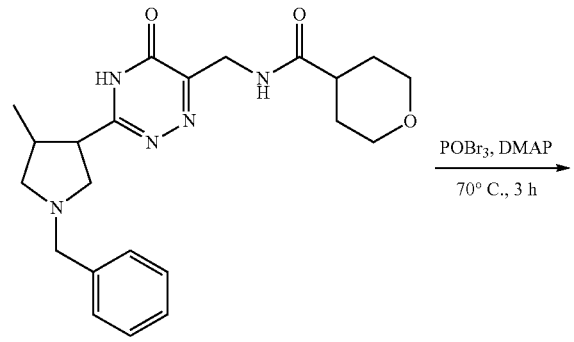

To a suspension of (+/−)-6-(aminomethyl)-3-((3,4-trans)-1-benzyl-4-methylpyrrolidin-3-yl)-1,2,4-triazin-5(4H)-one (1.00 g, 3.34 mmol) in CH$_2$Cl$_2$ (45 mL) was added 2,5-dioxopyrrolidin-1-yl tetrahydro-2H-pyran-4-carboxylate (1.19 g, 5.01 mmol) at room temperature. The resulting solution was stirred at room temperature for 22 h. The reaction mixture was filtered. The filtrate was washed with sat. NaHCO$_3$ (2×10 mL). The aqueous phase was extracted with CHCl$_2$ (3×10 mL). The combined organic phase was dried over MgSO$_4$. Concentration and purification by flash chromatography over silica gel column (0.1/1.5/98.4-1/15/84 NH$_4$OH/MeOH/CH$_2$Cl$_2$) to give (+/−)-N-((3-((3,4-trans)-1-benzyl-4-methylpyrrolidin-3-yl)-5-oxo-4,5-dihydro-1,2,4-triazin-6-yl)methyl)tetrahydro-2H-pyran-4-carboxamide (1.06 g, 77%) as a yellow solid. $^1$H NMR (300 MHz, CDCl$_3$) δ 9.99 (br s, 1H, br), 7.36-7.26 (m, 5H), 6.81 (br s, 1H), 4.50 (d, 2H, =4.5 Hz), 4.04-3.78 (m, 4H), 3.46-3.37 (m, 3H), 3.20 (br s, 1H), 3.04-2.75 (m, 2H), 2.60-2.28 (m, 2H), 2.28-2.15 (m, 1H), 1.91-1.77 (m, 4H), 1.13 (d, 3H, 1=6.3 Hz); $^{13}$C NMR (75 MHz, CDCl$_3$) δ 174.2, 165.8, 162.3, 151.0, 134.8, 129.0, 128.8, 128.2, 67.3, 60.5, 59.6, 56.4, 50.0, 42.2, 39.9, 38.8, 29.2, 19.5.

Synthesis of (+)-2-((3,4-trans)-1-benzyl-4-methylpyrrolidin-3-yl)-7-(tetrahydro-2H-pyran-4-yl)imidazo[1,5-f][1,2,4]triazin-4(3H)-one and (−)-2-((3,4-trans)-1-benzyl-4-methylpyrrolidin-3-yl)-7-(tetrahydro-2H-pyran-4-yl)imidazo[1,5-f][1,2,4]triazin-4(3H)-one

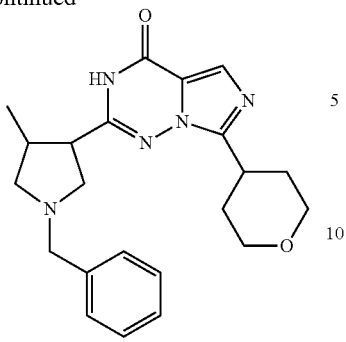

To a solution of (+/−)-N-((3-((3,4-trans)-1-benzyl-4-methylpyrrolidin-3-yl)-5-oxo-4,5-dihydro-1,2,4-triazin-6-yl)methyl)tetrahydro-2H-pyran-4-carboxamide (500 mg, 1.2 mmol), DMAP (15 mg, 0.12 mmol) in acetonitrile (25 mL) was added a solution of POBr$_3$ (1045 mg, 3.6 mmol) in acetonitrile (5 mL) at RT, and the resulting suspension was heated to 70° C. for 3 h. After the mixture was cooled to room temperature, it was poured into saturated NaHCO$_3$ solution (100 mL), and stirred vigorously for 0.5 h, then extracted with CH$_2$Cl$_2$ (3×25 mL). The organic extract was dried over MgSO$_4$ and concentrated under reduced pressure. The residue was purified by flash chromatography over silica gel (0.1/1.5/98.4-0.5/7.5/92 NH$_4$OH/MeOH/CH$_2$Cl$_2$) to furnish (+/−)-2-((3,4-trans)-1-benzyl-4-methylpyrrolidin-3-yl)-7-(tetrahydro-2H-pyran-4-yl)imidazo[1,5-f][1,2,4]triazin-4(3H)-one (380 mg, 79%) as a yellow wax.

Racemic (+/−)-2-((3,4-trans)-1-benzyl-4-methylpyrrolidin-3-yl)-7-(tetrahydro-2H-pyran-4-yl)imidazo[1,5-f][1,2,4]triazin-4(3H)-one was purified by Chiralpak IA, 250×20 mm, 5 um (100 mg loading; 0.1% TEA in n-Hexane: IPA (90:10) as mobile phase) to obtain (−)-2-((3,4-trans)-1-benzyl-4-methylpyrrolidin-3-yl)-7-(tetrahydro-2H-pyran-4-yl)imidazo[1,5-f][1,2,4]triazin-4(3H)-one and (+)-2-((3,4-trans)-1-benzyl-4-methylpyrrolidin-3-yl)-7-(tetrahydro-2H-pyran-4-yl)imidazo[1,5-f][1,2,4]triazin-4(3H)-one.

(−)-2-((3,4-trans)-1-benzyl-4-methylpyrrolidin-3-yl)-7-(tetrahydro-2H-pyran-4-yl)imidazo[1,5-f][1,2,4]triazin-4(3H)-one: H-NMR (DMSO d$_6$, 400 MHz): δ 7.65 (s, 1H), 7.34-7.29 (m, 4H), 7.24-7.21 (m, 1H), 3.94-3.92 (m, 2H), 3.68-3.64 (m, 2H), 3.52-3.47 (m, 4H), 2.98-2.87 (m, 4H), 2.64-2.61 (m, 1H), 2.28-2.24 (m, 1H), 1.89-1.82 (m, 4H), 1.09 (d, 3H); Mass (ESI): 394 [M$^+$+1]; UPLC (purity): 99.07%; (column; Acquity BEH C-18, 50×2.1 mm, 1.7μ; RT 1.42 min. 0.025% TFA (Aq): ACN:Water; 0.50 ml/min.; Chiral HPLC: 99.34% ee R$_t$=17.21 min (Chiralpak IA, 250×4.6 mm, 5μ; mobile phase (A) 0.1% TEA in n-Hexane (B) Ethanol (A:B: 90:10); flow Rate: 1.00 mL/min); Optical rotation [α]$_D^{27}$: −22.72° (c=0.25, DCM).

(+)-2-((3,4-trans)-1-benzyl-4-methylpyrrolidin-3-yl)-7-(tetrahydro-2H-pyran-4-yl)imidazo[1,5-f][1,2,4]triazin-4(3H)-one: H-NMR (DMSO d$_6$, 400 MHz): δ 7.64 (s, 1H), 7.32-7.29 (m, 4H), 7.24-7.21 (m, 1H), 3.94-3.92 (m, 2H), 3.68-3.64 (m, 2H), 3.52-3.47 (m, 2H), 3.42-3.39 (m, 2H), 2.94-2.91 (m, 2H), 2.82-2.78 (m, 2H), 2.68-2.64 (m, 1H), 2.32-2.27 (m, 1H), 1.92-1.87 (m, 4H), 1.09 (d, 3H); Mass (ESI): 394 [M$^+$+1]; UPLC (purity): 99.73%; (column; Acquity BEH C-18, 50×2.1 mm, 1.7μ; RT 1.42 min. 0.025% TFA (Aq): ACN:Water; 0.50 ml/min.; Chiral HPLC: 99.55% ee R$_t$=21.37 min (Chiralpak IA, 250×4.6 mm, 5μ; mobile phase (A) 0.1% TEA in n-Hexane (B) Ethanol (A:B: 90:10); flow Rate: 1.00 mL/min); Optical rotation [α]$_D^{27}$: +22.22° (c=0.25, DCM).

iii. Synthesis of (+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one

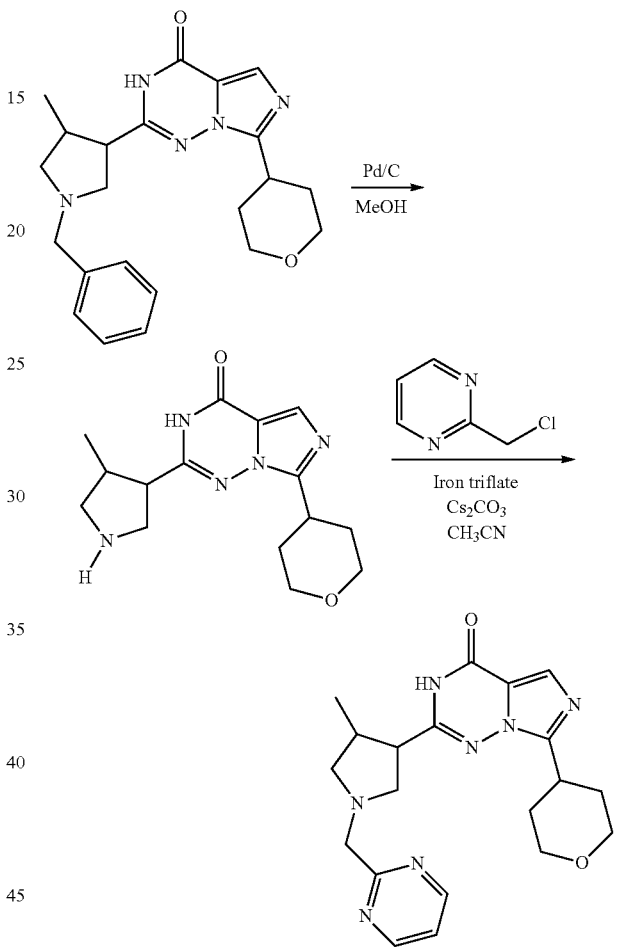

Synthesis of (−)-2-((3,4-trans)-4-methylpyrrolidin-3-yl)-7-(tetrahydro-2H-pyran-4-yl)imidazo[5,1-f][1,2,4]triazin-4(3H)-one

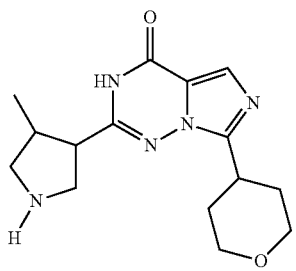 [SMILES: CC1CNCC1c1nn2c(C3CCOCC3)ncc2c(=O)[nH]1]

To a stirred solution of (−)-2-((3,4-trans)-1-benzyl-4-methylpyrrolidin-3-yl)-7-(tetrahydro-2H-pyran-4-yl)imidazo[1,5-f][1,2,4]triazin-4(3H)-one (0.5 g 1.27 mmol) in MeOH (30 mL) was added 10% Pd—C (150 mg) and stirred at RT for 16 h under H$_2$ atmosphere (balloon pressure). The reaction mixture was passed through a pad of celite and dried in vacuo to obtain crude. The crude material was triturated with pentane to afford (−)-2-((3,4-trans)-4-methylpyrrolidin-3-yl)-7-(tetrahydro-2H-pyran-4-yl)imidazo[5,1-f][1,2,4]triazin-4(3H)-one (360 mg, 1.18 mmol, 94%) as an off-white solid. $^1$H-NMR (DMSO d$_6$, 400 MHz): δ 7.58 (s, 1H), 3.95-3.85 (m, 4H), 3.54-3.48 (m, 2H), 3.38-3.32 (m, 1H), 3.24-3.22 (m, 2H), 3.07-3.02 (m, 1H), 2.68-2.64 (m, 1H), 2.44-2.41 (m, 2H), 1.87-1.82 (m, 4H), 1.04 (d, 3H); Mass (ESI): 304 [M$^+$+1]; LC-MS: 98.57%; 304 (M$^+$+1); (column; X-bridge C-18, (50×3.0 mm, 3.5μ); RT 1.77 min. 5 mM NH$_4$OAc: ACN; 0.8 ml/min); UPLC (purity): 97.43%; (column; Acquity UPLC HSS T3, 2.1×100 mm, 1.7μ; RT 2.83 min. 0.025% aqueous TFA: ACN:Water; 0.3 ml/min.; TLC: 10% MeOH/CH$_2$Cl$_2$ (Rf: 0.2); Optical rotation [α]$_D^{27}$: −69° (c=0.25, DMF).

Synthesis of (+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one

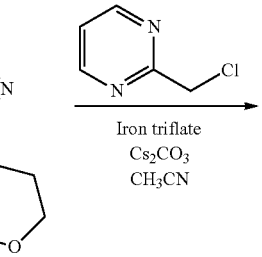

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 2-(chloromethyl)pyrimidine (46.46 mg, 0.36 mmol), iron triflate (33.20 mg, 0.066 mmol) and Cs$_2$CO$_3$ (236 mg, 0.72 mmol) at RT under inert atmosphere. The reaction mixture was heated to 70° C. and stirred for 4 h, After completion of starting material (by TLC), the reaction mixture was diluted with water and extracted with EtOAc (3×25 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one (60 mg, 46%) as an off-white solid. $^1$H-NMR (DMSO d$_6$, 500 MHz): δ 8.78 (d, 2H), 7.62 (s, 1H), 7.29 (t, 1H), 4.02-3.98 (m, 1H), 3.94-3.87 (m, 2H), 3.85-3.82 (m, 1H), 3.48-3.42 (m, 2H), 3.38-3.34 (m, 2H), 3.18-3.12 (m, 1H), 2.29-2.27 (m, 2H), 2.81-2.76 (m, 1H), 2.62-2.59 (m, 1H), 2.18-2.16 (m, 1H), 1.84-1.79 (m, 4H), 1.04 (d, 3H); Mass (ESI): 396.5 [M$^+$+1]; LC-MS: 95.73%; 396.4 (M$^+$+1); (column; X-bridge C-18, (50×3.0 mm, 3.5μ); RT 2.91 min. 5 mM NH$_4$OAc: ACN; 0.8 ml/min); UPLC (purity): 99.06%; (column; Acquity UPLC HSS T3, 2.1×100 mm, 1.7μ; RT 2.75 min. 0.025% TFA (Aq): ACN:Water; 0.3 ml/min.; Chiral HPLC: 100% ee R$_1$=26.48 min (Chiralpak IC, 250× 4.6 mm, 5μ; mobile phase (A) 0.1% TEA in n-Hexane (B) ethanol (A:B: 50:50); flow Rate: 1.00 mL/min); Optical rotation [α]$_D^{25}$: +115.88° (c=0.5, DCM); TLC: 10% MeOH/DCM (Rf: 0.7).

iv. Synthesis of (−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one

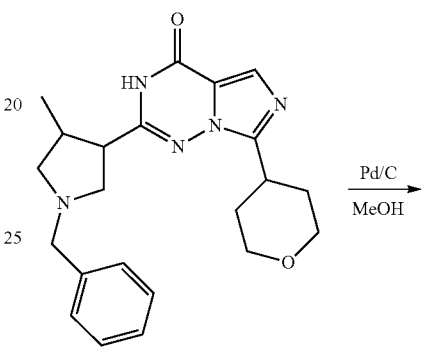

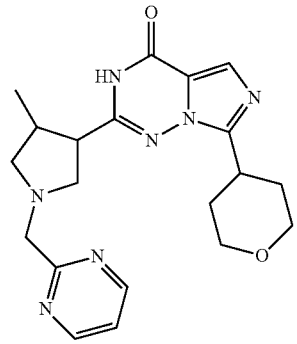 [SMILES: CC1CN(Cc2ncccn2)CC1c1nn2c(C3CCOCC3)ncc2c(=O)[nH]1]

Synthesis of (+)-2-((3,4-trans)-4-methylpyrrolidin-3-yl)-7-(tetrahydro-2H-pyran-4-yl)imidazo[5,1-f][1,2,4]triazin-4(3H)-one

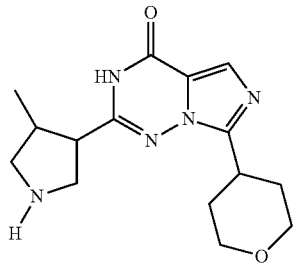 [SMILES: CC1CNCC1c1nn2c(C3CCOCC3)ncc2c(=O)[nH]1]

To a stirred solution of (+)-2-((3,4-trans)-1-benzyl-4-methylpyrrolidin-3-yl)-7-(tetrahydro-2H-pyran-4-yl)imidazo[5,1-f][1,2,4]triazin-4(3H)-one (0.5 g 1.27 mmol) in MeOH (30 mL) was added 10% Pd—C (150 mg) and stirred at RT for 16 h under $H_2$ atmosphere (balloon pressure). The reaction mixture was passed through a pad of celite and dried in vacuo to obtain crude. The crude material was triturated with n-pentane to afford (+)-2-((3,4-trans)-4-methylpyrrolidin-3-yl)-7-(tetrahydro-2H-pyran-4-yl)imidazo[5,1-f][1,2,4]triazin-4(3H)-one (365 mg, 1.20 mmol, 95%) as an off-white solid. $^1$H-NMR (DMSO $d_6$, 400 MHz): δ 7.56 (s, 1H), 3.96-3.87 (m, 5H), 3.52-3.48 (m, 3H), 3.42-3.37 (m, 1H), 3.28-3.21 (m, 2H), 3.18-3.14 (m, 1H), 2.67-2.64 (m, 1H), 2.42-2.38 (m, 2H), 1.89-1.86 (m, 2H), 0.96 (d, 3H); LC-MS: 98.34%; 304.8 (M$^+$+1); (column; Chromolith RP-18e, (100×4.6 mm); RT 3.47 min. 5 mM NH$_4$OAc: ACN; 1.0 ml/min); UPLC (purity): 98.81%; (column; Acquity HSS T3, 2.1×100 mm, 1.7µ; RT 2.77 min. 0.025% aqueous TFA: ACN:Water; 0.3 ml/min.; TLC: 10% MeOH/CH$_2$Cl$_2$ (Rf: 0.2); Optical rotation $[α]_D^{27}$: +61° (c=0.25, DMF).

Synthesis of (−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one

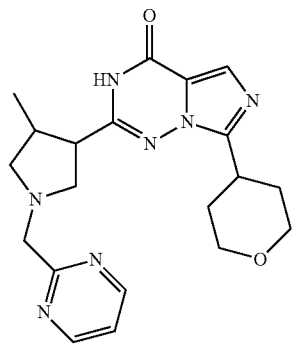 [SMILES: CC1CN(Cc2ncccn2)CC1c1nn2c(C3CCOCC3)ncc2c(=O)[nH]1]

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added 2-(chloromethyl)pyrimidine (34 mg, 0.27 mmol), iron triflate (24 mg, 0.047 mmol) and Cs$_2$CO$_3$ (161 mg, 0.49 mmol) at RT under inert atmosphere. The reaction mixture was heated to 70° C. and stirred for 4 h. After completion of starting material (by TLC), the reaction mixture was diluted with water and extracted with EtOAc (3×25 mL). Combined organic layer was dried over sodium sulphate, filtered and concentrated in vacuo to obtain the crude product. The crude material was purified by silica gel column chromatography and then further washed with pentane to afford (−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one (50 mg, 52%) as an off-white solid. $^1$H-NMR (DMSO $d_6$, 400 MHz): δ 11.67 (br s, 1H), 8.79 (s, 2H), 7.62 (s, 1H), 7.42 (t, 1H), 4.18-4.12 (m, 1H), 3.96-3.92 (m, 2H), 3.82-3.78 (m, 1H), 3.52-3.48 (m, 2H), 3.41-3.38 (m, 2H), 3.18-3.14 (m, 1H), 3.06-2.98 (m, 2H), 2.82-2.78 (m, 1H), 2.62-2.59 (m, 1H), 1.86-1.82 (m, 4H), 1.14 (d, 3H); Mass (ESI): 396 [M$^+$+1]; LC-MS: 96.67%; 396 (M$^+$+1); (column; X-bridge C-18, (50×3.0 mm, 3.5µ); RT 2.64 min. 5 mM NH$_4$OAc: ACN; 0.8 ml/min); UPLC (purity): 99.80%; (column; Acquity UPLC HSS T3, 2.1×100 mm, 1.7µ; RT 2.94 min. 0.025% TFA (Aq): ACN:Water; 0.3 ml/min.; Chiral HPLC: 99.35% ee R$_t$=41.20 min (Chiralpak IC, 250×4.6 mm, 5µ; mobile phase (A) 0.1% TEA in n-Hexane (B) ethanol (A:B: 50:50); flow Rate: 1.00 mL/min); Optical rotation $[α]_D^{24}$: −116.01° (c=0.5, DCM); TLC: 10% MeOH/DCM (Rf: 0.5).

v. Synthesis of (+)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one

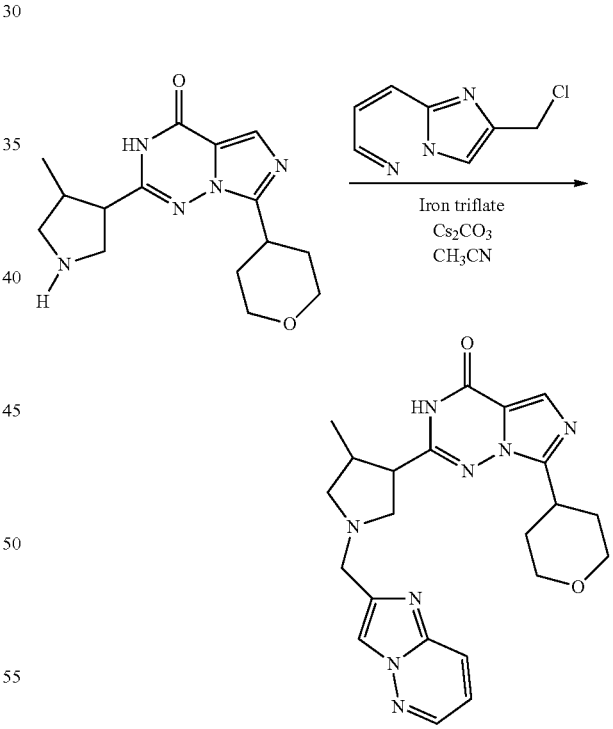

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (0.1 g, 0.33 mmol) in ACN (10 mL) were added 2-(chloromethyl)imidazo[1,2-b]pyridazine (60.62 mg, 0.36 mmol), iron triflate (33.20 mg, 0.066 mmol) and Cs$_2$CO$_3$ (236 mg, 0.72 mmol) at RT under inert atmosphere. The reaction mixture was heated to 70° C. and stirred for 4 h. After completion of starting material (by TLC), the reaction mixture was cooled to RT; diluted with water and extracted with EtOAc (3×25 mL). Combined organic layer was dried over sodium sulphate, filtered and concentrated in vacuo to obtain the crude product. The crude material was purified by silica gel column chromatography to afford (+)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one (70 mg, 51.95%) as an off-white solid. $^1$H-NMR (DMSO d$_6$, 400 MHz): δ 8.45 (d, 1H), 8.14 (s, 1H), 8.02 (d, 1H), 7.64 (s, 1H), 7.18-7.12 (m, 1H), 3.92-3.84 (m, 5H), 3.08-3.04 (m, 4H), 2.94-2.91 (m, 2H), 2.82-238 (m, 1H), 2.69-2.64 (m, 1H), 2.34-2.31 (m, 1H), 1.87-1.82 (m, 4H), 1.08 (d, 3H); Mass (ESI): 435 [M$^+$+1]; LC-MS: 93.22%; 435 (M$^+$+1); (column; X-bridge C-18, (50×3.0 mm, 3.5μ); RT 2.62 min. 5 mM NH$_4$OAc: ACN; 0.8 ml/min); HPLC (purity): 99.91%; (column; Acquity BEH C-18, 50×2.1 mm, 1.7μ; RT 1.21 min. 0.025% TFA (Aq): ACN:Water; 0.50 ml/min.; Chiral HPLC: 99.14% ee R$_t$=22.18 min (Chiralpak IC, 250×4.6 mm, 5μ; mobile phase (A) 0.1% TEA in n-Hexane (B) ethanol (A:B: 40:60); flow Rate: 1.00 mL/min); Optical rotation [α]$_D^{25}$: +48.76° (c=0.5, DCM); TLC: 10% MeOH/DCM (Rf: 0.5).

vi. Synthesis of (−)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one gel column chromatography and then further triturated with n-pentane to afford (−)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one (78 mg, 36%) as an off-white solid. $^1$H-NMR (DMSO d$_6$, 400 MHz): 8.48 (t, 1H), 8.16 (s, 1H), 8.04 (d, 1H), 7.64 (s, 1H), 7.21-7.16 (m, 1H), 3.46-3.34 (m, 6H), 3.12-3.04 (m, 3H), 2.96-2.94 (m, 1H), 2.84-2.78 (m, 1H), 2.69-2.64 (m, 1H), 2.41-2.36 (m, 1H), 1.86-1.82 (m, 4H), 1.09 (d, 3H); Mass (ESI): 435 [M$^+$+1]; LC-MS: 97.00%; 435 (M$^+$+1); (column; X-bridge C-18, (50×3.0 mm, 3.5μ); RT 2.54 min. 5 mM NH$_4$OAc: ACN; 0.8 ml/min); UPLC (purity): 99.79%; (column; Acquity BEH C-18, 50×2.1 mm, 1.7μ; RT 1.20 min. 0.025% TFA (Aq): ACN:Water; 0.50 ml/min.; Chiral HPLC: 99.32% ee R$_t$=36.69 min (Chiralpak IC, 250×4.6 mm, 5μ; mobile phase (A) 0.1% TEA in n-Hexane (B) ethanol (A:B: 40:60); flow Rate: 1.00 mL/min); Optical rotation [α]$_D^{25}$: −45.21° (c=0.5, DCM). TLC: 10% MeOH/DCM (Rf: 0.5).

v. (−)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one

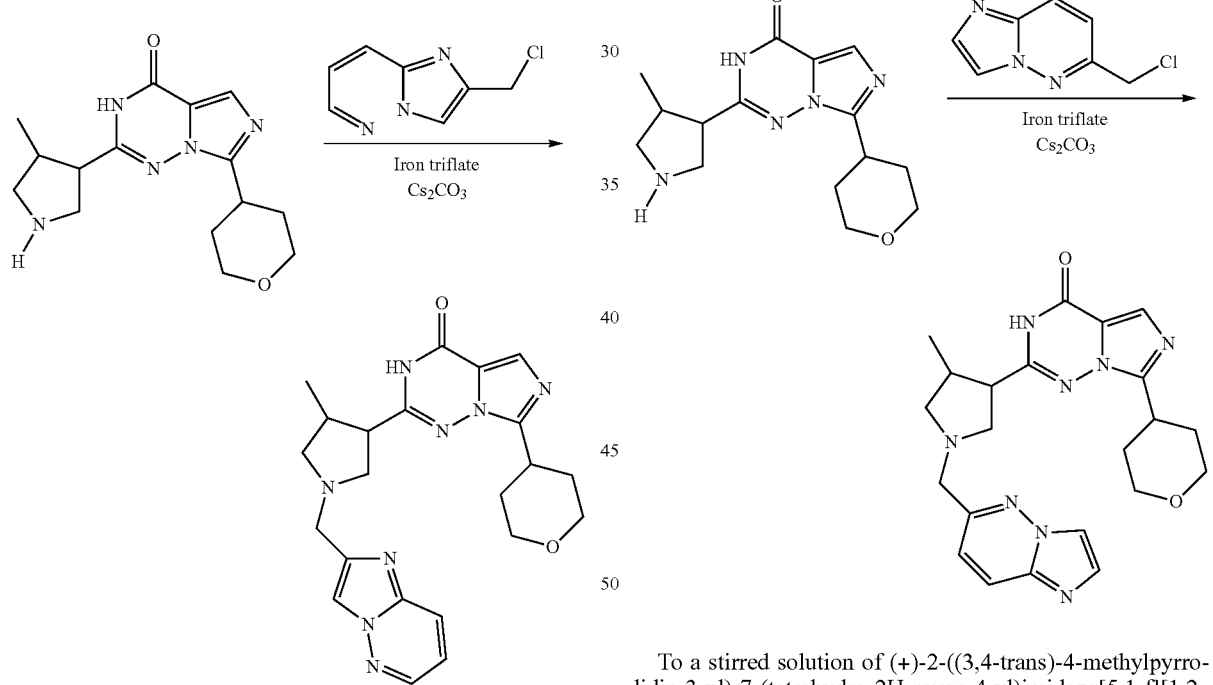

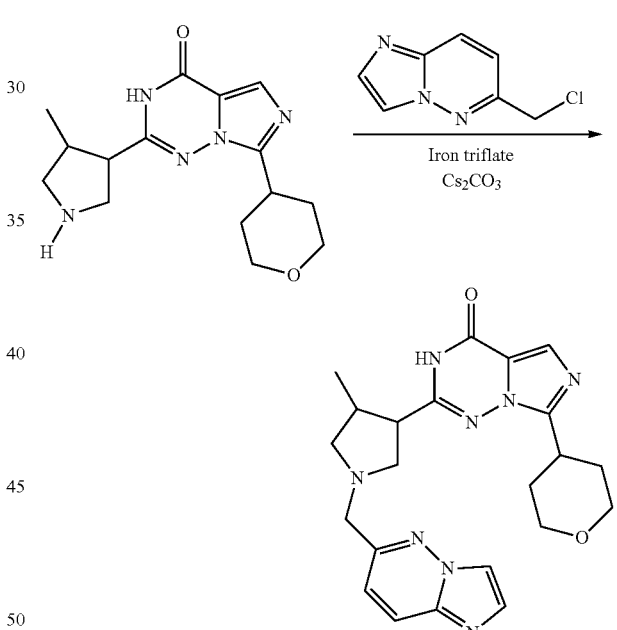

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in ACN (20 mL) were added 2-(chloromethyl)imidazo[1,2-b]pyridazine (90 mg, 0.54 mmol), iron triflate (48 mg, 0.095 mmol) and Cs$_2$CO$_3$ (322 mg, 0.99 mmol) at RT under inert atmosphere. The reaction mixture was heated to 70° C. and stirred for 4 h. After completion of starting material (by TLC), the reaction mixture was diluted with water and extracted with EtOAc (3×25 mL). Combined organic layer was dried over sodium sulphate, filtered and concentrated in vacuo to obtain the crude product. The crude material was purified by silica To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 6-(chloromethyl)imidazo[1,2-b]pyridazine (60.6 mg, 0.33 mmol), iron triflate (33.2 mg, 0.066 mmol) and Cs$_2$CO$_3$ (215 mg, 0.66 mmol) at RT under inert atmosphere. The reaction mixture was heated to 70° C. and stirred for 4 h. After completed consumption of starting material (by TLC), the reaction mixture was diluted with water and extracted with EtOAc (3×25 mL), The combined organic layers were dried over sodium sulfate, filtered and concentrated in vacuo to obtain the crude product. The crude material was purified by silica gel column chromatography and then further washed with 20% DCM/ether to afford (−)-2-((3,4-trans)-1-(imidazo[1,2-b]pyridazin-6-ylmethyl)-

4-methylpyrrolidin-3-yl)-7-(tetrahydro-2H-pyran-4-yl)imidazo[5,1-f][1,2,4]triazin-4(3H)-one (55 mg, 38%) as an off-white solid. $^1$H-NMR (DMSO d$_6$, 400 MHz): δ 11.67 (br s, 1H), 8.21 (s, 1H), 8.06 (d, 1H), 7.74 (s, 1H), 7.64 (s, 1H), 7.21 (d, 1H), 3.94-3.78 (m, 4H), 3.52-3.48 (m, 3H), 3.18-2.82 (m, 4H), 2.72-2.68 (m, 1H), 2.38-2.32 (m, 1H), 1.92-1.84 (m, 4H), 1.12 (d, 3H); Mass (ESI): 435.5 [M$^+$+1]; LC-MS: 96.67%; 435.6 (M$^+$+1); (column; X-Select C-18, (50×3.0 mm, 3.5μ); RT 2.54 min. 5 mM NH$_4$OAc in water: ACN; 0.8 ml/min); UPLC (purity): 95.02%; (column; Acquity UPLC HSS T3, 2.1×100 mm, 17μ; RT 2.86 min. 0.025% TFA (Aq): ACN:Water; 0.3 ml/min.; Chiral HPLC: 100% ec R$_t$=35.95 min (Chiralpak IC, 250×4.6 mm, 5μ; mobile phase (A) 0.1% TEA in n-Hexane (B) ethanol (A:B: 25:75); flow Rate: 1.00 mL/min); Optical rotation [α]$_D$25: −101.22° (c=0.5, DCM). TLC: 10% MeOH/DCM (Rf: 0.5).

vi. (+)-2-((3,4-trans)-1-(imidazol[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one 1H), 8.04 (d, 1H), 7.72 (s, 1H), 7.68 (s, 1H), 7.25 (d, 1H), 3.92-3.74 (m, 4H), 3.52-3.49 (m, 2H), 3.47-3.42 (m, 4H), 3.04-2.97 (m, 4H), 2.68-2.62 (m, 1H), 2.34-2.32 (m, 1H), 1.89-1.84 (m, 4H), 1.04 (d, 3H); Mass (ESI): 435.5 [M$^+$+1]; LC-MS: 94.75%; 435.5 (M$^+$+1); (column; X-bridge C-18, (50×3.0 mm, 3.5μ); RT 3.04 min. 5 mM NH$_4$OAc in water: ACN; 0.8 ml/min); UPLC (purity): 97.45%; (column; Acquity UPLC HSS T3, 2.1×100 mm, 1.7μ; RT 2.89 min. 0.025% TFA (Aq): ACN: Water; 0.3 ml/min.; Chiral HPLC: 98.98% ee R$_t$=53.89 min (Chiralpak IC, 250×4.6 mm, 5μ; mobile phase (A) 0.1% TEA in n-Hexane (B) ethanol (A:B: 25:75); flow Rate: 1.00 mL/min); Optical rotation [α]$_D$$^{24}$: +118.00° (c=0.5, DCM); TLC: 10% MeOH/DCM (Rf: 0.54).

vii. Scheme X: (+)-2-((3,4-trans)-1-((6-methoxy-pyridin-2-yl)methyl)-4-methylpyrrolidin-3-yl)-7-(tetrahydro-2H-pyran-4-yl)imidazol[5,1-f][1,2,4]triazin-4(3H)-one

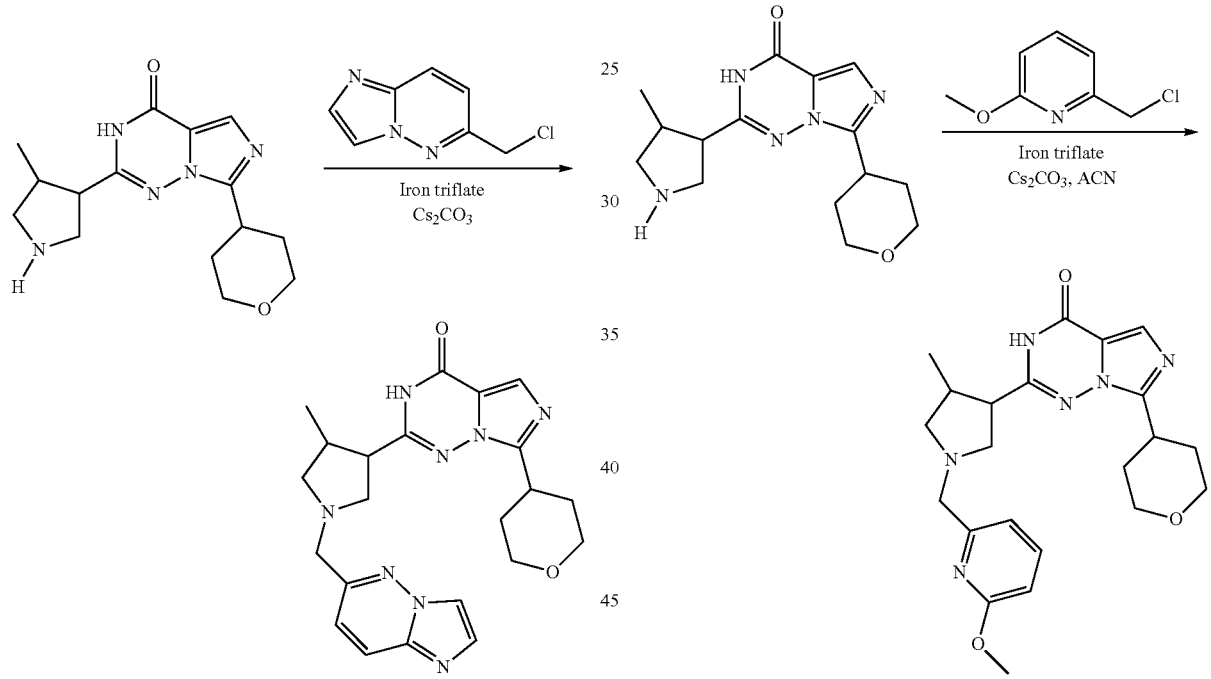

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 6-(chloromethyl)imidazo[1,2-b]pyridazine (60.62 mg, 0.36 mmol), iron triflate (33.2 mg, 0.066 mmol) and Cs$_2$CO$_3$ (236 mg, 0.72 mmol) at RT under inert atmosphere. The reaction mixture was heated to 70° C. and stirred for 4 h. After full consumption of starting material (by TLC), the reaction mixture was diluted with water and extracted with EtOAc (3×25 mL). The combined organic layers were dried over sodium sulfate, filtered and concentrated in vacuo to obtain the crude product. The crude material was purified by silica gel column chromatography and then further washed with 20% DCM/ether to afford (+)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one (70 mg, 49%) as an off-white solid. $^1$H-NMR (DMSO d$_6$, 400 MHz): δ 11.62 (br s, 1H), 8.21 (s, To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added 2-(chloromethyl)-6-methoxypyridine (39 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×15 mL). Combined organic layer was dried over sodium sulphate, filtered and concentrated in vacuo to obtain the crude product. The crude material was purified by silica gel column chromatography to afford (+)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4 (3H)-one (55 mg, 52%) as pale green solid. $^1$H-NMR (DMSO d$_6$, 400 MHz): δ 11.48 (br s, 1H), 7.68-7.61 (m, 2H), 7.02 (d, 1H), 6.68 (d, 1H), 3.94-3.92 (m, 2H), 3.84 (s, 3H), 3.78-3.72 (m, 2H), 3.51-3.48 (m, 2H), 3.42-3.39 (m, 1H), 3.07-3.00 (m, 2H), 2.98-2.97 (m, 1H), 2.89-2.85 (m, 1H), 2.64-2.62 (m, 1H), 2.38-2.28 (m, 1H), 1.92-1.87 (m, 4H), 1.14 (d, 3H); Mass (ESI): 425.4 [M$^+$+1]; LC-MS: 95.85%; 425 (M$^+$+1); (column; X-bridge C-18, (50×3.0 mm, 3.5μ); RT 3.05 min. 5 mM NH$_4$OAc: ACN; 0.8 ml/min); UPLC (purity): 97.10%; (column; Acquity UPLC BEH C-18, (2.1×50 mm, 1.7μ); RT 1.35 min, 0.025% TFA (Aq): ACN:Water; 0.5 ml/min.; Chiral HPLC: 95.11% ee, R$_t$=12.04 min (Chiralpak IC, 250×4.6 mm, 5μ; mobile phase (A) 0.1% TEA in n-Hexane (B) ethanol (A:B: 50:50); flow Rate: 1.00 mL/min); Optical rotation [α]$_D^{25}$: +7.28° (c=0.5, DCM), TLC: 10% MeOH/DCM (Rf: 0.6).

viii. (−)-2-((3,4-trans)-4-methyl-1-((R)-1-phenyl-ethyl)pyrrolidin-3-yl)-7-(tetrahydro-2H-pyran-4-yl)imidazo[5,1-f][1,2,4]triazin-4(3H)-one

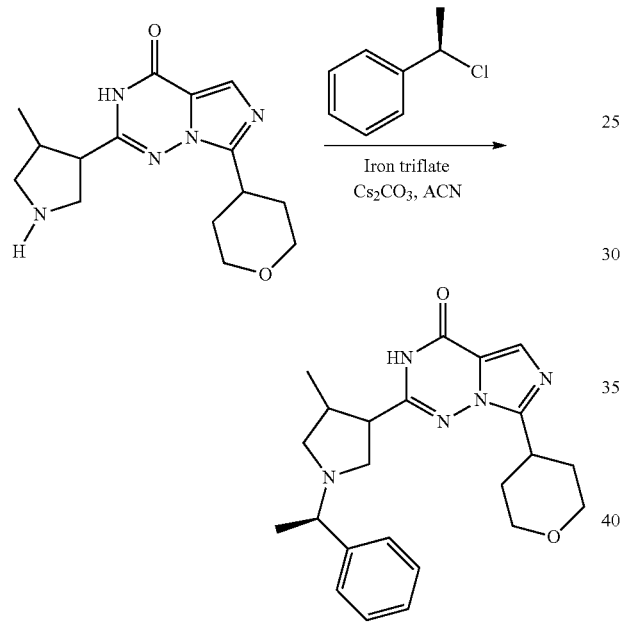

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added (R)-(1-Chloroethyl)benzene (38 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×25 mL). Combined organic layer was dried over sodium sulphate, filtered and concentrated in vacuo to obtain the crude product. The crude material was purified by silica gel column chromatography to afford the desired product as a racemic mixture, which upon chiral preparative HPLC purification to afforded (−)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one (9 mg, 9%) as an off-white solid. $^1$H-NMR (DMSO d$_6$, 400 MHz): δ 7.62 (s, 1H), 7.34-7.29 (m, 4H), 7.21-7.18 (m, 1H), 3.97-3.93 (m, 2H), 3.54-3.47 (m, 4H), 3.34-3.31 (m, 2H), 2.84-2.81 (m, 4H), 2.78-2.72 (m, 1H), 2.31-2.27 (m, 1H), 1.89-1.82 (m, 4H), 1.28 (d, 3H), 1.07 (d, 3H); Mass (ESI): 406 [M$^-$−1]; LC-MS: 86.11%; 408.5 (M$^+$+1); (column; X-bridge C-18, (50×3.0 mm, 3.5μ); RT 2.69 min. 0.1% Aq TFA: ACN; 0.8 ml/min); UPLC (purity): 87.57%; (column; Acquity UPLC BEH C-18, 2.1×50 mm, 1.7μ; RT 1.43 min. 0.025% TFA (Aq): ACN:Water; 0.50 ml/min; Chiral HPLC: 100% ee R$_t$=8.82 min (Chiralpak IC, 250×4.6 mm, 5μ; mobile phase (A) 0.1% TEA in n-Hexane (B) ethanol (A:B: 50:50); flow Rate: 1.00 mL/min); Optical rotation [α]$_D^{24}$: −85.66° (c=0.5, DCM). TLC: 10% MeOH/DCM (Rf: 0.6).

ix. (+)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one

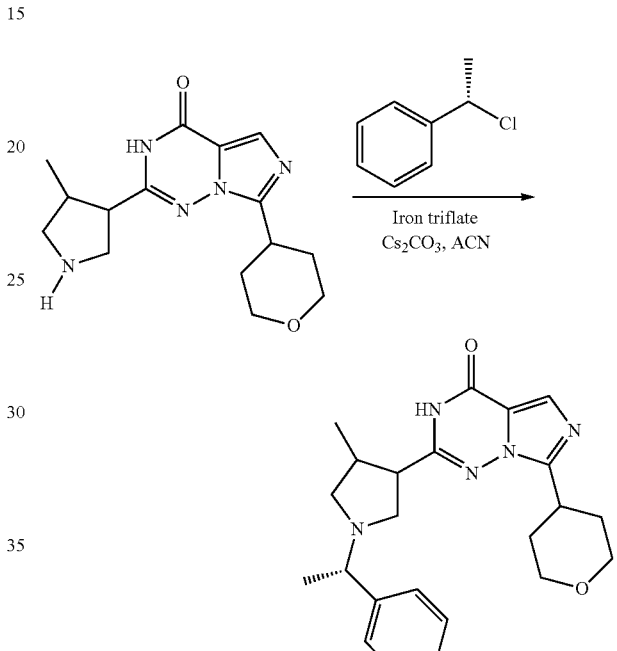

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added (S)-(1-chloroethyl)benzene (38 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×15 mL). Combined organic layer was dried over sodium sulphate, filtered and concentrated in vacuo to obtain the crude product. The crude material was purified by silica gel column chromatography to afford the desired product as a racemic mixture, which upon chiral preparative HPLC purification to afforded (+)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one (12 mg, 12%) as an off-white solid. $^1$H-NMR (DMSO d$_6$, 400 MHz): δ 7.64 (s, 1H), 7.34-7.31 (m, 4H), 7.21-7.18 (m, 1H), 3.56-3.52 (m, 3H), 3.42-3.37 (m, 4H), 2.94 (t, 2H), 2.75-2.71 (m, 1H), 2.68-2.65 (m, 1H), 2.61-2.58 (m, 1H), 2.14-2.11 (m, 1H), 1.89-1.82 (m, 4H), 1.32 (d, 3H), 1.04 (d, 3H); Mass (ESI): 408 [M$^+$+1]; LC-MS: 86.88%; 408.5 (M$^+$+1); (column; X-bridge C-18, (50×3.0 mm, 3.5μ); RT 2.67 min. 0.1% Aq TFA: ACN; 0.8 ml/min); UPLC (purity): 87.11%; (column; Acquity UPLC BEH C-18, 2.1×50 mm, 1.7μ; RT 1.42 min.

0.025% TFA (Aq): ACN:Water; 0.50 ml/min.; Chiral HPLC: 99.44% ee $R_t$=11.01 min (Chiralpak IC, 250×4.6 mm, 5µ; mobile phase (A) 0.1% TEA in n-Hexane (B) ethanol (A:B: 50:50); flow Rate: 1.00 mL/min); Optical rotation $[\alpha]_D^{25}$: +96.90° (c=0.5, DCM). TLC: 10% MeOH/DCM (Rf: 0.4).

x. (−)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one

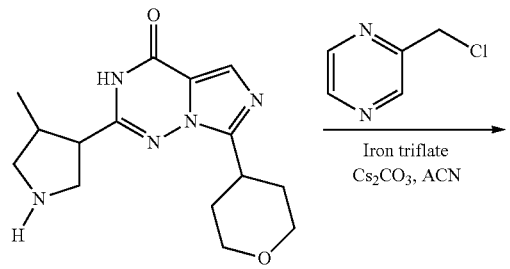

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(chloromethyl)pyrazine (34.85 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (3×25 mL). Combined organic layer was dried over sodium sulphate, filtered and concentrated in vacuo to obtain the crude product. The crude material was purified by silica gel column chromatography to afford (−)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one (45 mg, 46%) as an off-white solid. $^1$H-NMR (DMSO d$_6$, 400 MHz): δ 11.78 (br s, 1H), 8.72 (s, 1H), 8.58-8.54 (m, 2H), 7.61 (s, 1H), 3.97-3.94 (m, 3H), 3.81-3.76 (m, 1H), 3.52-3.47 (m, 2H), 3.41-3.37 (m, 1H), 3.02-2.94 (m, 4H), 2.67-2.62 (m, 1H), 2.34-2.31 (m, 1H), 1.89-1.74 (m, 4H), 1.04 (d, 3H); Mass (ESI): 396 [M$^+$+1]; LC-MS: 97.39%; 396 (M$^+$+1); (column; X-bridge C-18, (50×3.0 mm, 3.5µ); RT 2.44 min. 5 mM NH$_4$OAc: ACN; 0.8 ml/min); UPLC (purity): 98.61%; (column; Acquity UPLC HSS T3 (2.1×100 mm, 1.70; RT 2.89 min. 0.025% TFA (Aq): ACN:Water; 0.3 ml/min.; Chiral HPLC: 99.90% ee $R_t$=38.93 min (Chiralpak IC, 250×4.6 mm, 5µ); mobile phase (A) 0.1% TEA in n-Hexane (B) ethanol (A:B: 50:50); flow Rate: 1.00 mL/min); Optical rotation $[\alpha]_D^{24}$: −67.24° (c=0.5, DCM); TLC: 10% MeOH/DCM (Rf: 0.46).

xi. (+)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one

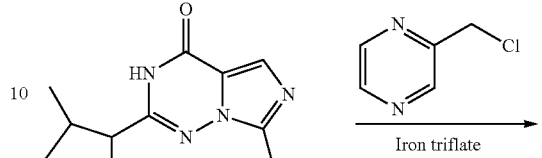

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(chloromethyl)pyrazine (34.85 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (3×25 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one (42 mg, 43%) as an off-white solid. $^1$H-NMR (DMSO d$_6$, 400 MHz): δ 11.67 (br s, 1H), 8.72 (s, 1H), 8.54 (d, 2H), 7.64 (s, 1H), 3.94-3.91 (m, 3H), 3.81-3.77 (m, 1H), 3.42-3.38 (m, 2H), 3.04-3.01 (m, 2H), 2.94-2.92 (m, 2H), 2.84-2.81 (m, 1H), 2.67-2.62 (m, 1H), 2.34-2.31 (m, 1H), 1.89-1.82 (m, 4H), 1.04 (d, 3H); Mass (ESI): 396 [M$^+$+1]; LC-MS: 94.22%; 396 (M$^+$+1); (column; Eclipse XDB C-18, (150×4.6 mm, 5.0µ); RT 5.35 min. 5 mM NH$_4$OAc: ACN; 1.0 ml/min); UPLC (purity): 95.66%; (column; Acquity BEH C-18 (50×2.1 mm, 1.7µ; RT 1.11 min. 0.025% TFA (Aq): ACN:Water; 0.50 ml/min.; Chiral HPLC: 100% ee $R_t$=25.25 min (Chiralpak IC, 250×4.6 mm, 5µ; mobile phase (A) 0.1% TEA in n-Hexane (B) ethanol (A:B: 50:50); flow Rate: 1.00 mL/min); Optical rotation $[\alpha]_D^{26}$: +60.52° (c=0.5, DCM); TLC: 10% MeOH/DCM (Rf: 0.46).

xii. (+)-2-((3,4-trans)-1-(2-fluorobenzyl)-4-methyl-pyrrolidin-3-yl)-7-(tetrahydro-2H-pyran-4-yl)imidazo[5,1-f][1,2,4]triazin-4(3H)-one

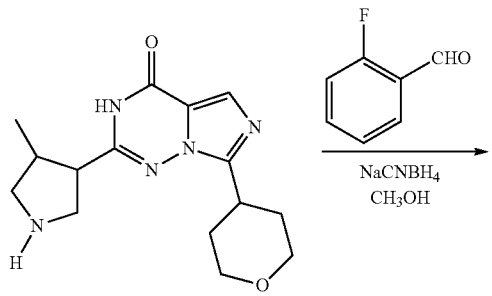

xiii. (−)-2-((3,4-trans)-1-(3-fluorobenzyl)-4-methyl-pyrrolidin-3-yl)-7-(tetrahydro-2H-pyran-4-yl)imidazo[5,1-f][1,2,4]triazin-4(3H)-one

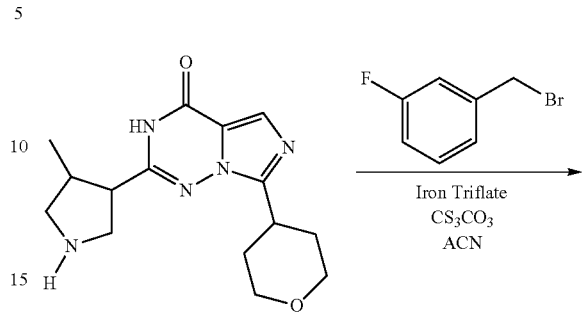

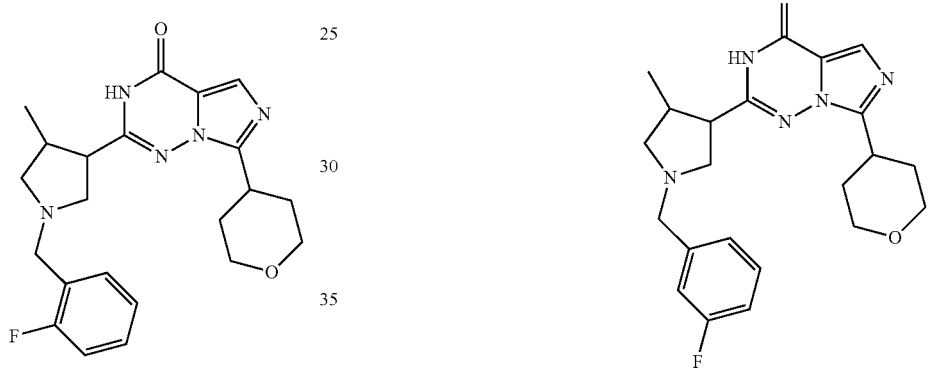

A mixture of (−)-2-((3,4-trans)-4-methylpyrrolidin-3-yl)-7-(tetrahydro-2H-pyran-4-yl)imidazo[5,1-f][1,2,4]triazin-4(3H)-one (60 mg, 0.198 mmol) and 2-fluorobenzaldehyde (27 mg, 0.22 mmol) in MeOH (5 mL) at RT and stirred for 2 h under inert atmosphere. To this NaCNBH$_4$ (37 mg, 0.59 mmol) was added and stirring was continued for another 6 h at RT. After completion of starting material (by TLC), the volatiles were evaporated under reduced pressure. The residue was diluted with water and extracted with DCM (2×15 mL). Combined organic layer was dried over sodium sulphate, filtered and concentrated in vacuo to obtain the crude product. The crude material was purified by silica gel column chromatography to afford (+)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one (0.06 g, 75%) as sticky solid. $^1$H-NMR (DMSO d$_6$, 400 MHz): δ 7.67 (s, 1H), 7.46-7.42 (m, 1H), 7.34-7.31 (m, 1H), 7.21-7.18 (m, 2H), 3.68 (s, 2H), 3.53-3.49 (m, 3H), 3.41-3.37 (m, 3H), 2.99-2.97 (m, 1H), 2.94-2.91 (m, 1H), 2.87-2.82 (m, 2H), 2.65-2.63 (m, 1H), 2.34-2.32 (m, 1H), 1.84-1.81 (m, 4H), 1.07 (d, 3H); Mass (ESI): 412.4 [M$^+$+1]; LC-MS: 97.97%; 412.6 (M$^+$+1); (column; X-bridge C-18, (50×4.6 mm, 5.0μ); RT 2.55 min 0.1% TFA: ACN; 0.8 ml/min); UPLC (purity): 96.92%; (column; Acquity UPLC BEH C-18, (2.1×50 mm, 1.7μ); RT 1.37 min. 0.025% TFA (Aq); ACN:Water; 0.5 ml/min.; Optical rotation $[α]_D^{25}$: +14.83° (c=0.5, DCM). TLC: 5% MeOH/DCM (Rf: 0.7).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one hydrochloride (50 mg, 0.16 mmol) in ACN (5 mL) were added 1-(bromomethyl)-3-fluorobenzene (37.7 mg, 0.19 mmol), iron triflate (16.6 mg, 0.03 mmol) and Cs$_2$CO$_3$ (118 mg, 0.36 mmol) at RT under inert atmosphere. The reaction mixture was heated to 70° C. and stirred for 12 h. After completion of starting material (by TLC), the reaction mixture was diluted with water and extracted with EtOAc (2×15 mL). Combined organic layer was dried over sodium sulphate, filtered and concentrated in vacuo to obtain the crude product. The crude material was purified by preparative HPLC to afford (−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one (15 mg, 22%) as sticky solid. $^1$H-NMR (DMSO d$_5$, 400 MHz): δ 7.64 (s, 1H), 7.39-7.34 (m, 1H), 7.18-7.09 (m, 3H), 3.92-3.89 (m, 2H), 3.67-3.61 (m, 2H), 3.52-3.48 (m, 3H), 2.94-2.91 (m, 3H), 2.81-2.78 (m, 2H), 2.68-2.64 (m, 1H), 2.29-2.26 (m, 1H), 1.89-1.87 (m, 4H), 1.07 (d, 3H); Mass (ESI): 412.5 [M$^+$+1]; LC-MS: 94.10%; 412.4 (M$^+$+1); (column; X-bridge C-18, (50×3.0 mm, 3.54 RT 3.87 min. 5 mM NH$_4$OAc: ACN; 0.8 ml/min); UPLC (purity): 96.81%; (column; Acquity UPLC BEH C-18, (50×2.1 mm, 1.7μ); RT 1.41 min. 0.025% TFA (Aq): ACN:Water; 0.50 ml/min.; Optical rotation $[α]_D^{25}$: −1.216° (c=0.5, MeOH). TLC: 5% MeOH/DCM (Rf: 0.6).

xiv. (+)-2-((3,4-trans)-1-(4-fluorobenzyl)-4-methyl-pyrrolidin-3-yl)-7-(tetrahydro-2H-pyran-4-yl)imidazo[5,1-f][1,2,4]triazin-4(3H)-one xv. (+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile

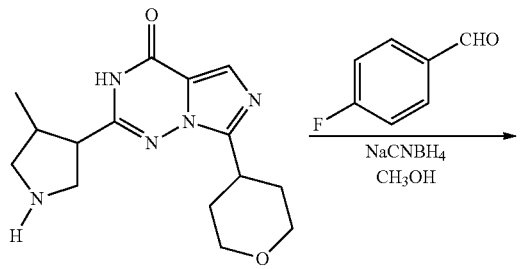

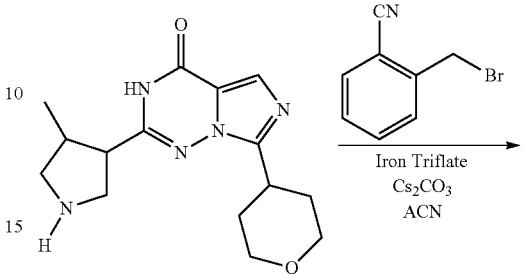

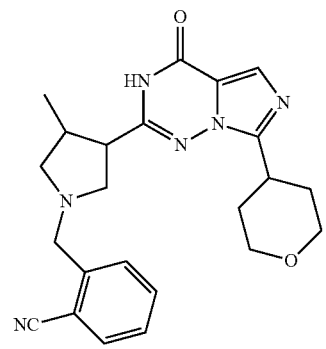

A mixture of (−)-2-((3,4-trans)-4-methylpyrrolidin-3-yl)-7-(tetrahydro-2H-pyran-4-yl)imidazo[5,1-f][1,2,4]triazin-4(3H)-one (50 mg, 0.16 mmol) and 4-fluorobenzaldehyde (22.5 mg, 0.18 mmol) in MeOH (5 mL) at RT and stirred for 2 h under inert atmosphere. To this NaCNBH$_4$ (31 mg, 0.49 mmol) was added and stirring was continued for another 6 h at RT. After completion of starting material (by TLC), the volatiles were evaporated under reduced pressure. The residue was diluted with ice cold water and extracted with DCM (2×15 mL). Combined organic layer was dried over sodium sulphate, filtered and concentrated in vacuo to obtain the crude product. The crude material was purified by silica gel column chromatography then triturated with n-pentane to afford (+)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one (45 mg, 66%) as an off-white solid. $^1$H-NMR (DMSO d$_6$, 400 MHz): δ 7.62 (s, 1H), 7.38-7.32 (m, 2H), 7.17-7.12 (m, 2H), 3.96-3.94 (m, 2H), 3.67-3.64 (m, 2H), 3.57-3.55 (m, 2H), 3.42-3.36 (m, 4H), 2.95-2.93 (m, 1H), 2.84-2.79 (m, 1H), 2.64-2.62 (m, 1H), 2.24-2.21 (m, 1H), 1.92-1.87 (m, 4H), 1.07 (d, 3H); LC-MS: 94.33%; 412.5 (M$^+$+1); (column; X-bridge C-18, (50×3.0 mm, 3.5μ); RT 2.71 min. 0.1% TFA: ACN; 0.8 ml/min); UPLC (purity): 95.95%; (column; Acquity BEH C-18, (50×2.1 mm, 1.7μ); RT 1.51 min. 0.025% TFA (Aq): ACN:Water; 0.50 ml/min.; Optical rotation [α]$_D^{24}$: +16.44° (c=0.5, DCM). TLC: 5% MeOH/DCM (Rf: 0.8).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(bromomethyl)benzonitrile (53.37 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile (35 mg, 34%) as an off-white solid. $^1$H-NMR (DMSO d$_6$, 500 MHz): δ 11.62 (br s, 1H), 7.87-7.84 (m, 1H), 7.72-7.67 (m, 2H), 7.62-7.58 (m, 1H), 7.52-7.47 (m, 1H), 3.97-3.92 (m, 2H), 3.84-3.82 (m, 2H), 3.53-3.49 (m, 2H), 3.41-3.37 (m, 1H), 3.04-3.00 (m, 1H), 2.96-2.92 (m, 2H), 2.87-2.84 (m, 1H), 2.68-2.64 (m, 1H), 2.37-2.34 (m, 1H), 1.86-1.81 (m, 4H), 1.04 (d, 3H); Mass (ESI): 419.4 [M$^+$+1]; LC-MS: 95.93%; 419.7 (M$^+$+1); (column; Eclipse XDB C-18, (150×4.6 mm, 5.0μ); RT 7.21 min. 5 mM NH$_4$OAc: ACN; 1.0 ml/min); UPLC (purity): 99.32%; (column; Acquity BEH C-18 (50×2.1 mm, 1.7μ); RT 1.41 min. 0.025% TFA (Aq): ACN:Water; 0.50 ml/min.; Optical rotation [α]$_D^{25}$: +7.28° (c=0.5, DCM). TLC: 5% MeOH/DCM (Rf: 0.5).

xvi. (+)-3-(((3,4-trans)-3-methyl-4-(4-oxo-7-(tetra-hydro-2H-pyran-4-yl)-3,4-dihydroimidazo[5,1-f][1,2,4]triazin-2-yl)pyrrolidin-1-yl)methyl)benzonitrile xvii. (−)-4(((3,4-trans)-3-methyl-4-(4-oxo-7-(tetra-hydro-2H-pyran-4-yl)-3,4-dihydroimidazo[5,1-f][1,2,4]triazin-2-yl)pyrrolidin-1-yl)methylbenzonitrile

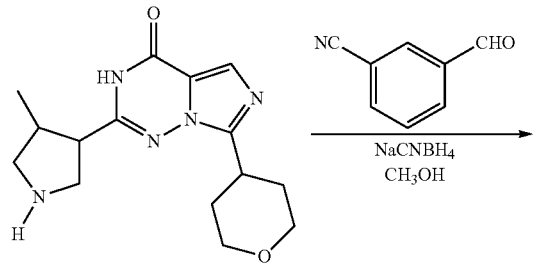

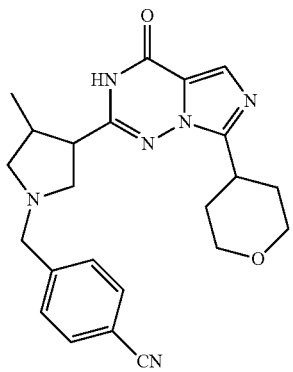

A mixture of (−)-2-((3,4-trans)-4-methylpyrrolidin-3-yl)-7-(tetrahydro-2H-pyran-4-yl)imidazo[5,1-f][1,2,4]triazin-4(3H)-one (50 mg, 0.16 mmol) and 3-formylbenzonitrile (23.7 mg, 0.18 mmol) in MeOH (5 mL) at RT and stirred for 2 h under inert atmosphere. To this NaCNBH$_4$ (31 mg, 0.49 mmol) was added and stirring was continued for another 6 h at RT. After completion of starting material (by TLC), the volatiles were evaporated under reduced pressure. The residue was diluted with ice cold water and extracted with DCM (2×15 mL). Combined organic layer was dried over sodium sulphate, filtered and concentrated in vacuo to obtain the crude product. The crude material was purified by preparative HPLC to afford (+)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile (40 mg, 58%) as an off-white solid. $^1$H-NMR (DMSO d$_6$, 400 MHz): δ 7.78-7.74 (m, 1H), 7.72-7.68 (m, 1H), 7.64 (s, 2H), 7.56-7.51 (m, 1H), 3.97-3.94 (m, 2H), 3.71 (s, 2H), 3.52-3.47 (m, 2H), 3.42-3.38 (m, 2H), 2.97-2.94 (m, 1H), 2.89-2.87 (m, 1H), 2.81-2.77 (m, 2H), 2.68-2.64 (m, 1H), 2.31-2.27 (m, 1H), 1.87-1.82 (m, 4H), 1.12 (d, 3H); LC-MS: 97.10%; 419.7 (M$^+$+1); (column; X-bridge C-18, (50×4.6 mm, 5μ); RT 2.49 min. 0.1% TFA: ACN; 0.8 ml/min); UPLC (purity): 96.81%; (column; Acquity BEH C-18, (50×2.1 mm, 1.7μ); RT 1.44 min. 0.025% TFA (Aq): ACN:Water; 0.50 ml/min.; Optical rotation [α]$_D^{23}$: +5.11° (c=0.5, DCM). TLC: 5% MeOH/DCM (Rf: 0.8).

A mixture of (−)-2-((3,4-trans)-4-methylpyrrolidin-3-yl)-7-(tetrahydro-2H-pyran-4-yl)imidazo[5,1-f][1,2,4]triazin-4(3H)-one (50 mg, 0.16 mmol) and 4-formylbenzonitrile (23.7 mg, 0.18 mmol) in MeOH (5 mL) at RT and stirred for 2 h under inert atmosphere. To this NaCNBH$_4$ (31 mg, 0.49 mmol) was added and stirring was continued for another 6 h at RT. After completion of starting material (by TLC), the volatiles were evaporated under reduced pressure. The residue was diluted with ice cold water and extracted with DCM (2×15 mL). Combined organic layer was dried over sodium sulphate, filtered and concentrated in vacuo to obtain the crude product. The crude material was purified by preparative HPLC to afford (−)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile (40 mg, 58%) as an off-white solid. $^1$H-NMR (DMSO d$_6$, 400 MHz): δ 7.78 (d, 2H), 7.68 (s, 1H), 7.54 (d, 2H), 4.95-4.91 (m, 2H), 3.78-3.72 (m, 2H), 3.54-3.51 (m, 2H), 3.42-3.37 (m, 2H), 2.99-2.97 (m, 1H), 2.87-2.81 (m, 3H), 2.68-2.64 (m, 1H), 2.34-2.28 (m, 1H), 1.87-1.82 (m, 4H), 1.12 (d, 3H); Mass (ESI): 419.5 [M$^+$+1]; LC-MS: 97.59%; 419.6 (M$^+$+1); (column; X-bridge C-18, (50×3.0 mm, 3.5μ); RT 2.46 min. 0.1% TFA: ACN; 0.8 ml/min); UPLC (purity): 98.56%; (column; Acquity BEH C-18, (50×2.1 mm, 1.7μ); RT 1.43 min. 0.025% TFA (Aq): ACN:Water; 0.50 ml/min.; Optical rotation [α]$_D^{23}$: −5.368° (c=0.5, DCM). TLC: 5% MeOH/DCM (Rf: 0.7).

xviii. (+)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one xix. (−)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one

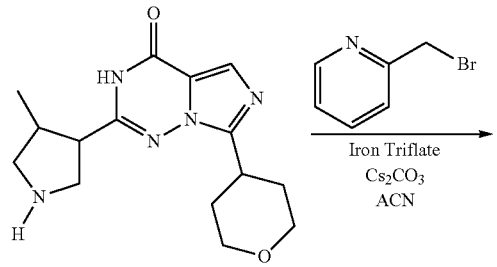

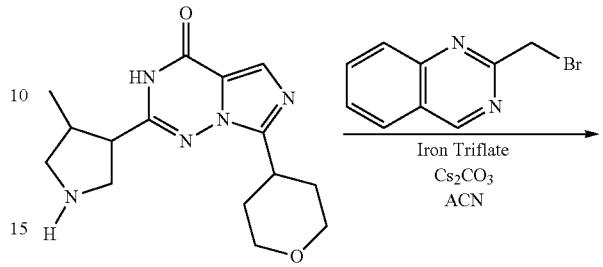

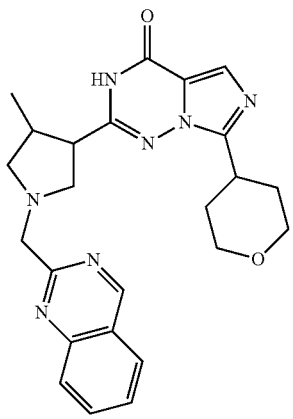

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(chloromethyl)pyridine (44.46 mg, 0.27 mmol), iron triflate (24.90 mg, 0.049 mmol) and $Cs_2CO_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one (20 mg, 20%) as sticky solid. $^1$H-NMR (DMSO d$_6$, 500 MHz): δ 8.47 (d, 1H), 7.78-7.74 (m, 1H), 7.68 (s, 1H), 7.42 (d, 1H), 7.24-7.21 (m, 1H), 3.96-3.92 (m, 2H), 3.84-3.81 (m, 1H), 3.74-3.68 (m, 1H), 3.54-3.48 (m, 2H), 3.42-3.38 (m, 2H), 3.01-3.27 (m, 2H), 2.87-2.79 (m, 2H), 2.64-2.62 (m, 1H), 2.37-2.34 (m, 1H), 1.85-1.82 (m, 4H), 1.12 (d, 3H); Mass (ESI): 395.3 [M$^+$+1]; LC-MS: 98.60%; 395.2 (M$^+$+1); (column; X-bridge C-18, (50×3.0 mm, 3.5μ); RT 2.16 min. 0.1% TFA in water: ACN; 0.50 ml/min); UPLC (purity): 97.79%; (column; Acquity UPLC BEH C-18 (2.1×50 mm, 1.70; RT 1.23 min. 0.025% TFA (Aq): ACN:Water; 0.5 ml/min.; Optical rotation [α]$_D^{25}$: +11.24° (c=0.5, DCM). TLC: 10% MeOH/DCM (Rf: 0.6).

To a stirred solution of compound (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.247 mmol) in ACN (5 mL) were added 2-(chloromethyl)quinazoline (48.6 mg, 0.272 mmol), iron triflate (24.9 mg, 0.049 mmol) and $Cs_2CO_3$ (177.5 mg, 0.54 mmol) at RT under inert atmosphere. The resultant reaction mixture was heated to 70° C. and stirred for 6 h. After completion of starting material (by TLC), the reaction mixture was diluted with water and extracted with EtOAc (3×25 mL). Combined organic layers were dried over anhydrous sodium sulphate, filtered and concentrated in vacuo to obtain the crude product. The crude material was purified by silica gel column chromatography to afford (−)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one (50 mg, 45%) as an off-white solid. $^1$H-NMR (DMSO d$_6$, 400 MHz): δ 9.63 (s, 1H), 8.18 (d, 1H), 8.09-8.01 (m, 2H), 7.77 (t, 2H), 4.24 (d, 1H), 4.01-3.92 (m, 3H), 3.52 (t, 2H), 3.25-3.20 (m, 2H), 3.14 (t, 1H), 2.98 (t, 1H), 2.81 (q, 1H), 2.63-2.59 (m, 1H), 2.41 (t, 1H), 1.85 (s, 4H), 1.14 (d, 3H); Mass (ESI): 446 [M$^+$+1]; LC-MS: 97.83%; 447.1 (M$^+$+1); (column; XDB C-18, (150× 4.6 mm, 5 um); RT 5.04 min. 0.1% TFA in water: ACN; 1.0 ml/min); UPLC (purity): 99.01%; (column; Acquity BEH C-18, 50×2.1 mm, 1.7μ; RT 1.42 min. 0.025% TFA (Aq): ACN:DMSO; 0.50 ml/min.; TLC: 5% MeOH/DCM (Rf: 0.5). Chiral HPLC: 96.49% ec R$_t$=43.76 min (Chiralpak IC, 250×4.6 mm, 5μ; mobile phase (A) 0.1% TEA in n-Hexane (B) ethanol (A:B: 50:50); flow Rate: 1.00 mL/min); Optical rotation [α]$_D^{24}$: −128.77° (c=0.5, DCM).

xx. (+)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one xxi. (−)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one

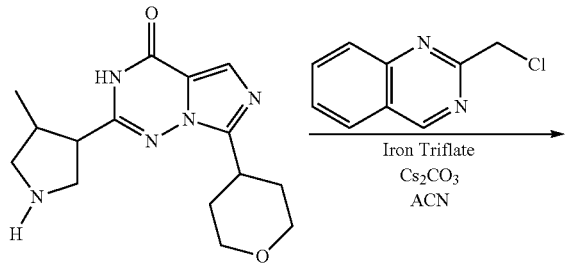

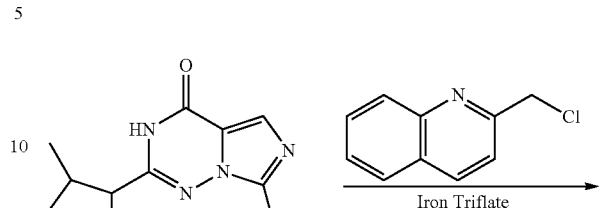

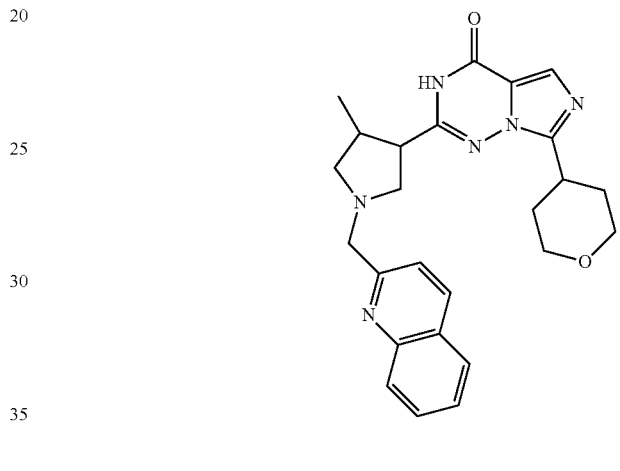

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(chloromethyl)quinazoline (48.46 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one (40.2 mg, 37%) as an off-white solid. $^1$H-NMR (DMSO d$_6$, 400 MHz): δ 9.58 (s, 1H), 8.14 (d, 1H), 8.07-8.02 (m, 2H), 7.78-7.65 (m, 2H), 4.24-4.21 (m, 1H), 4.01-3.95 (m, 3H), 3.52-3.48 (m, 2H), 3.28-3.24 (m, 2H), 3.14-3.11 (m, 1H), 2.98-2.94 (m, 1H), 2.87-2.85 (m, 1H), 2.67-2.64 (m, 1H), 2.42-2.37 (m, 1H), 1.94-1.87 (m, 4H), 1.12 (d, 3H); Mass (ESI): 446.3 [M$^+$+1]; LC-MS: 96.13%; 446.6 (M$^+$+1); (column; Eclipse XDB C-18, (150×4.6 mm, 5μ); RT 6.84 min. 5.0 mM NH$_4$OAc: ACN; 1.0 ml/min); UPLC (purity): 97.52%; (column; Acquity BEH C-18 (50×2.1 mm, 1.7μ); RT 1.46 min. 0.025% TFA (Aq): ACN:Water; 0.50 ml/min.; Optical rotation [α]$_D^{25}$: +130.89° (c=0.5, DCM). TLC: 10% MeOH/DCM (Rf: 0.7).

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.247 mmol) in ACN (10 mL) were added 2-(chloromethyl)quinoline (58.3 mg, 0.272 mmol), Iron triflate (24 mg, 0.049 mmol) and Cs$_2$CO$_3$ (177 mg, 0.54 mmol) at RT under inert atmosphere. The resultant reaction mixture was heated to 70° C. and stirred for 6 h. After completion of the reaction, the reaction mixture was diluted with water and extracted with EtOAc (3×25 mL). Combined organic layers were dried over anhydrous sodium sulphate, filtered and concentrated in vacuo to obtain the crude product. The crude material was purified by silica gel column chromatography to afford (−)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one (50 mg, 42%) as an off-white solid. $^1$H-NMR (DMSO d$_6$, 400 MHz): 8.33 (d, 1H), 8.01-7.98 (m, 2H), 7.77-7.52 (m, 4H), 4.01-3.97 (m, 4H), 3.52-3.48 (m, 4H), 3.04 (t, 2H), 2.85 (q, 1H), 2.75 (t, 1H), 2.71-2.69 (m, 1H), 2.39 (t, 1H), 1.82 (s, 3H), 1.12 (d, 3H); Mass (ESI): 445 [M$^+$+1]; LC-MS: 93.62%; 445.5 (M$^+$+1); (column; XDB C-18, (150×4.6 mm, 3.5 um); RT 5.39 min. 0.1% Aqueous TFA: ACN; 1.0 ml/min); UPLC (purity): 96.63%; (column; Acquity BEH C-18, 50×2.1 mm, 1.7μ; RT 1.59 min. 0.025% TFA (Aq): ACN:Water; 0.50 ml/min.; TLC: 5% MeOH/DCM (Rf: 0.5). Chiral HPLC: 99.12% ee R$_t$=20.83 min (Chiralpak IC, 250×4.6 mm, 5μ; mobile phase (A) 0.1% TEA in n-Hexane (B) ethanol (A:B: 50:50); flow Rate: 1.00 mL/min); Optical rotation [α]$_D^{24}$: −87.99° (c=0.5, DCM).

xxii. (+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one

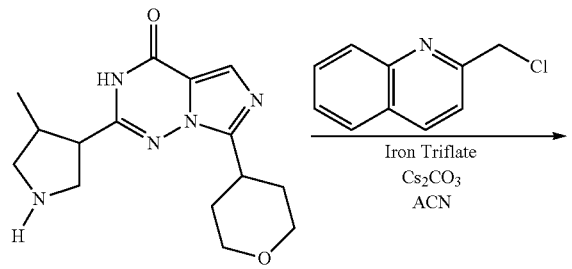

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(chloromethyl)quinoline (63 mg, 0.29 mmol), iron triflate (24 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one (65 mg, 59%) as sticky solid. $^1$H-NMR (DMSO d$_6$, 400 MHz): δ 8.32 (d, 1H), 8.07-7.95 (m, 2H), 7.76 (t, 1H), 7.68 (s, 1H), 7.64-7.61 (m, 1H), 7.59-7.57 (m, 1H), 4.08-3.92 (m, 4H), 3.57-3.47 (m, 2H), 3.42-3.38 (m, 2H), 3.06-3.02 (m, 2H), 2.87-2.84 (m, 1H), 2.71-2.65 (m, 1H), 2.37-2.34 (m, 1H), 1.92-1.84 (m, 4H), 1.12 (d, 3H); Mass (ESI): 445.7 [M$^+$+1]; LC-MS: 94.58%; 445.2 (M$^+$+1); (column; X-bridge C-18, (50×3.0 mm, 3.5μ); RT 2.21 min. 0.1% TFA in water: ACN; 0.80 ml/min); UPLC (purity): 94.28%; (column; Acquity BEH C-18 (50×2.1 mm, 1.7μ); RT 1.56 min. 0.025% TFA (Aq): ACN:Water; 0.50 ml/min.; Optical rotation [α]$_D^{21}$: +78.42° (c=0.5, DCM). TLC: 5% MeOH/DCM (Rf: 0.6).

xxiii. (+)-7-(1s,3R)-adamantan-1-yl)-2-((3,4-trans)-1-benzyl-4-methylpyrrolidin-3-yl)imidazo[5,1-f][1,2,4]triazin-4(3H)-one and (−)-7-((1s,3R)-adamantan-1-yl)-2-((3,4-trans)-1-benzyl-4-methylpyrrolidin-3-yl)imidazo[5,1-f][1,2,4]triazin-4(3H)-one

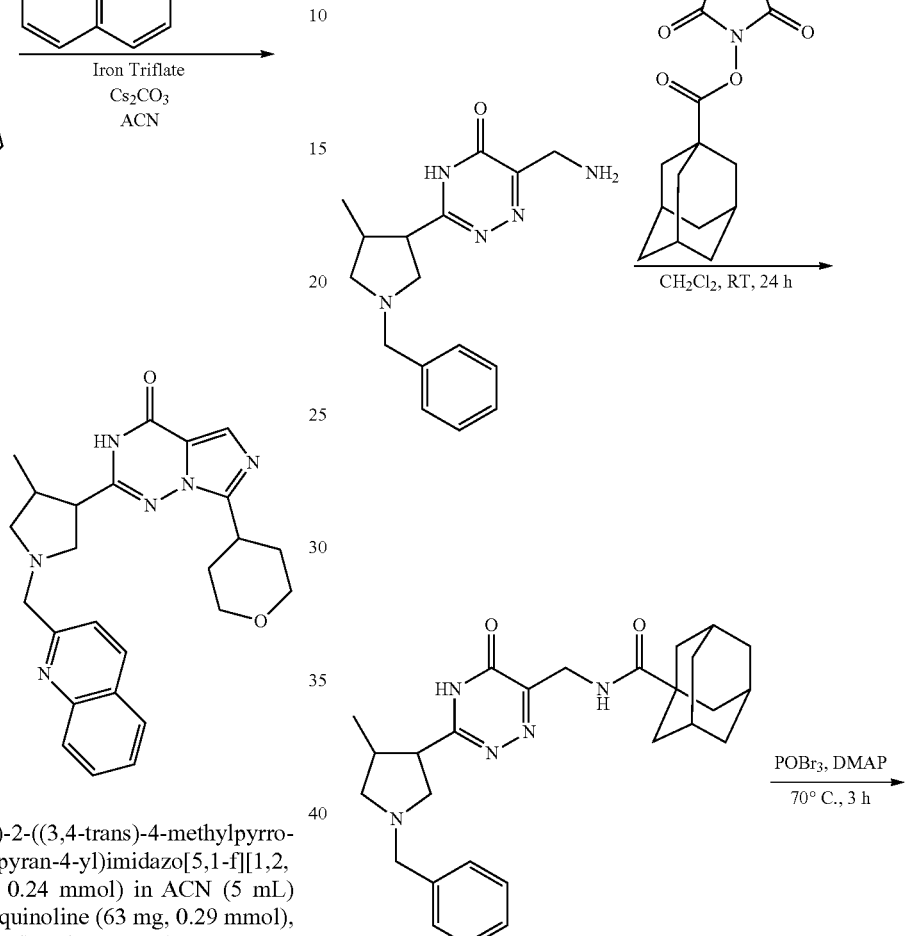

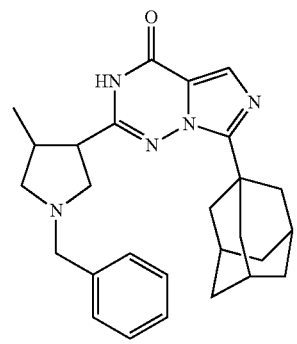

Synthesis of (+/−)-(3S,5S,7S)—N-((3-((3,4-trans)-1-benzyl-4-methylpyrrolidin-3-yl)-5-oxo-4,5-dihydro-1,2,4-triazin-6-yl)methyl)adamantane-1-carboxamide

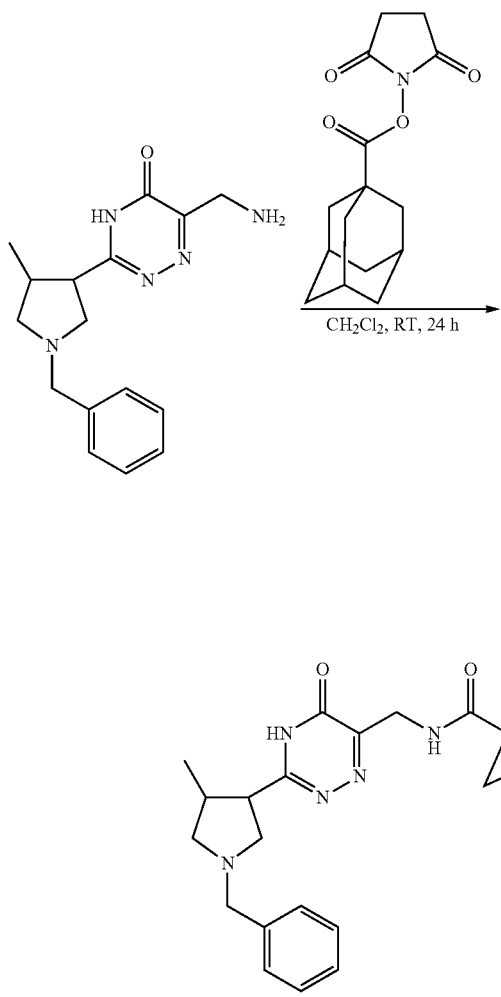

To a suspension of (+/−)-6-(aminomethyl)-3-((3,4-trans)-1-benzyl-4-methylpyrrolidin-3-yl)-1,2,4-triazin-5(4H)-one (1.05 g, 3.51 mmol) in $CH_2Cl_2$ (45 mL) was added (3r,5r,7r)-2,5-dioxopyrrolidin-1-yl adamantine-1-carboxylate (1.46 g, 5.26 mmol) at RT. The resulting solution was stirred at room temperature for 24 h. The solvent was removed under reduced pressure to give a yellow solid. Flash chromatography over silica gel column (0.1/1.5/98.4-1/15/84 $NH_4OH/MeOH/CH_2Cl_2$) provided (+/−)-(3S,5S,7S)—N-((3-((3,4-trans)-1-benzyl-4-methylpyrrolidin-3-yl)-5-oxo-4,5-dihydro-1,2,4-triazin-6-yl)methyl)adamantane-1-carboxamide (1.19 g, 74% yield) as a yellow solid. $^1$H NMR (300 MHz, $CDCl_3$) δ 10.41 (br s, 1H), 7.38-7.30 (m, 5H), 7.07 (br s, 1H), 4.49 (d, 2H, J=4.8 Hz), 4.04 (d, 1H, J=12.6 Hz); 3.92 (d, 1H, J=12.9 Hz), 3.45-3.37 (m, 1H), 3.34-3.22 (m, 1H), 3.22-3.10 (m, 2H), 2.70-2.45 (m, 2H), 2.03 (br s, 3H), 1.90 (br s, 6H), 1.72 (br s, 6H), 1.08 (d, 3H, J=6.3 Hz); $^{13}$C NMR (75 MHz, $CDCl_3$) δ 178.0, 165.1, 162.8, 150.7, 134.3, 131.9, 129.2, 128.6, 128.3, 60.3, 59.5, 56.8, 50.1, 40.7, 39.7, 39.1, 38.5, 36.4, 28.0, 18.3.

Synthesis of (+)-7-((1s,3R)-adamantan-1-yl)-2-((3,4-trans)-1-benzyl-4-methylpyrrolidin-3-yl)imidazo[5,1-f][1,2,4]triazin-4(3H)-one and (−)-7-((1s,3R)-adamantan-1-yl)-2-((3,4-trans)-1-benzyl-4-methylpyrrolidin-3-yl)imidazo[5,1-f][1,2,4]triazin-4(3H)-one

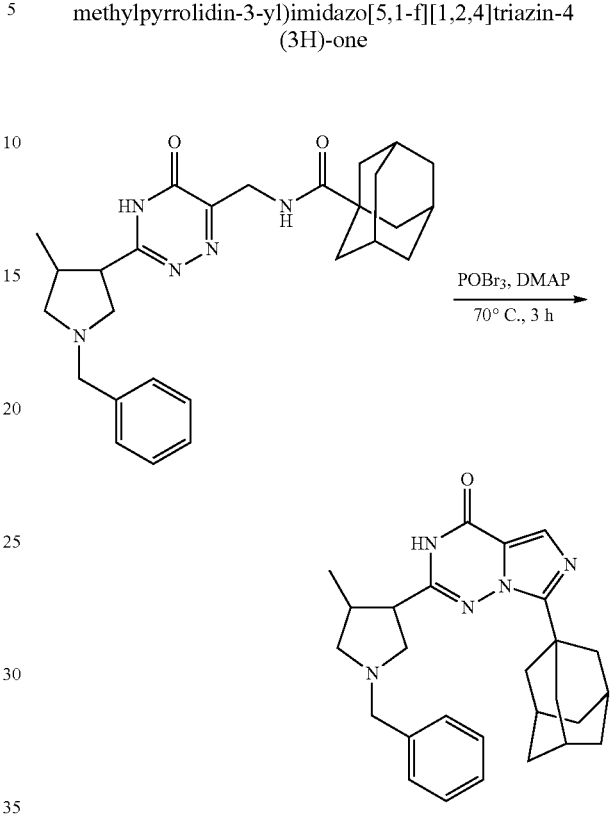

To a solution of (+/−)-(3S,5S,7S)—N-((3-((3,4-trans)-1-benzyl-4-methylpyrrolidin-3-yl)-5-oxo-4,5-dihydro-1,2,4-triazin-6-yl)methyl)adamantane-1-carboxamide (200 mg, 0.43 mmol), DMAP (5 mg, 0.04 mmol) in acetonitrile (8 mL) was added a solution of $POBr_3$ (373 mg, 1.3 mmol) in acetonitrile (2 mL) at RT, and the resulting suspension was heated to 70° C. for 3 h. After the mixture was cooled to room temperature, it was poured into cold saturated $NaHCO_3$ solution (30 mL), and stirred vigorously for 0.5 h, then extracted with $CH_2Cl_2$ (3×10 mL). The organic extract was dried over $MgSO_4$ and concentrated under reduced pressure. The residue was purified by flash chromatography over silica gel (0.1/1.5/98.4-0.3/4.5/95.2 $NH_4OH/MeOH/CH_2Cl_2$) to furnish (+/−)-7-((1s,3R)-adamantan-1-yl)-2-((3,4-trans)-1-benzyl-4-methylpyrrolidin-3-yl)imidazo[5,1-f][1,2,4]triazin-4(3H)-one (120 mg, 62% yield) as a white foam. Purity (HPLC): 96.1%; $^1$H NMR (300 MHz, $CDCl_3$/TMS) δ 9.10 (br s, 1H), 7.76 (s, 1H), 7.50-7.24 (m, 5H), 3.81 (d, 0.1=12.3 Hz, 1H), 3.57 (d, J=12.6 Hz, 1H), 3.36 (t, J=8.5 Hz, 1H), 2.99 (d, J=10.2 Hz, 1H), 2.76 (dd, J=6.2, 2.4 Hz, 1H), 2.55 (dd, J=9.9, 6.6 Hz, 1H), 2.52-2.40 (m, 1H), 2.26 (br s, 6H), 2.08 (br s, 3H), 2.02-1.93 (m, 1H), 1.80 (br s, 6H), 1.22 (d, J=6.6 Hz, 3H); $^{13}$C NMR (75 MHz, $CDCl_3$/TMS) δ 154.61, 152.15, 151.79, 137.29, 128.53, 128.50, 127.40, 126.89, 119.35, 61.12, 59.32, 56.10, 48.15, 39.09, 38.24, 36.71, 36.06, 28.25, 20.14; HRMS: calculated for $C_{27}H_{34}N_5O_2$ ($MH^+$), 444.2758. found, 444.2768. Racemic (+/−)-7-((1s,3R)-adamantan-1-yl)-2-((3,4-trans)-1-benzyl-4-methy 1pyrrolidin-3-yl)imidazo[5,1-f][1,2,4]triazin-4 (3H)-one was purified by Chiralpak IC, 250×20 mm, 5 um (80 mg loading; 0.1% TEA in n-Hexane: Ethanol (90:10) as mobile phase) to obtain pure fraction 1 ((+)-7-((1s,3R)-adamantan-1-yl)-2-((3,4-trans)-1-benzyl-4-methylpyrrolidin-3-yl)imidazo[5,1-f][1,2,4]triazin-4(3H)-one) and pure fraction 2 ((−)-7-((1s,3R)-adamantan-1-yl)-2-((3,4-trans)-1-benzyl-4-methylpyrrolidin-3-yl)imidazo[5,1-f][1,2,4]triazin-4(3H)-one). Characterization details of are as follows:

(+)-7-((1s,3R)-adamantan-1-yl)-2-((3,4-trans)-1-benzyl-4-methylpyrrolidin-3-yl)imidazo[5,1-f][1,2,4]triazin-4(3H)-one: H-NMR (DMSO $d_6$, 400 MHz): δ 7.62 (s, 1H), 7.34-7.29 (m, 4H), 7.24-7.21 (m, 1H), 3.64-3.62 (m, 2H), 3.08-3.02 (m, 2H), 2.82-2.78 (m, 3H), 2.65-2.62 (m, 1H), 2.28-2.25 (m, 6H), 2.09-2.07 (m, 3H), 1.78-1.74 (m, 6H), 1.14 (d, 3H); Mass (ESI): 444 [M$^+$+1]; LC-MS: 97.86%; 444 (M$^+$+1); (column; X-bridge C-18, (50×3.0 mm, 3.5μ); RT 4.44 min. 5 mM NH$_4$OAc: ACN; 0.8 ml/min); UPLC (purity): 99.51%; (column; Acquity BEH C-18, 50×2.1 mm, 1.7μ; RT 2.00 min. 0.025% TFA (Aq): ACN:Water; 0.50 ml/min.; Chiral HPLC: 99.73% ee $R_t$=9.70 min (Chiralpak IC, 250×4.6 mm, 5μ; mobile phase (A) 0.1% TEA in n-Hexane (B) ethanol (A:B: 80:20); flow Rate: 1.00 mL/min); Optical rotation $[α]_D^{24}$: +16.15° (c=0.5, DCM). 16874

(−)-7-((1s,3R)-adamantan-1-yl)-2-((3,4-trans)-1-benzyl-4-methylpyrrolidin-3-yl)imidazo[5,1-f][1,2,4]triazin-4(3H)-one: H-NMR (DMSO $d_6$, 400 MHz): δ 7.62 (s, 1H), 7.34-7.29 (m, 4H), 7.24-7.21 (m, 1H), 4.34-4.28 (m, 1H), 3.68-3.64 (m, 2H), 3.48-3.42 (m, 2H), 3.02-2.98 (m, 1H), 2.89-2.81 (m, 3H), 2.68-2.62 (m, 1H), 2.28-2.23 (m, 1H), 2.24-2.18 (m, 6H), 2.07-2.02 (m, 3H), 1.78-1.74 (m, 4H), 1.18 (d, 3H); Mass (ESI): 444 [M$^+$+1]; LC-MS: 98.74%; 444 (M$^+$+1); (column; X-bridge C-18, (50×3.0 mm, 3.5μ); RT 4.43 min. 5 mM NH$_4$OAc: ACN; 0.8 ml/min); UPLC (purity): 99.17%; (column; Acquity BEH C-18, 50×2.1 mm, 1.7μ; RT 1.99 min. 0.025% TFA (Aq): ACN:Water; 0.50 ml/min.; Chiral HPLC: 98.98% ee $R_t$=12.32 min (Chiralpak IC, 250×4.6 mm, 5μ; mobile phase (A) 0.1% TEA in n-Hexane (B) ethanol (A:B: 80:20); flow Rate: 1.00 mL/min); Optical rotation $[α]_D^{25}$: −20.78° (c=0.5, DCM). 16875 xxiv. (+)-7-((1s,3R)-adamantan-1-yl)-2-((3,4-trans)-4-methyl-1-(pyrimidin-2-ylmethyl)pyrrolidin-3-yl)imidazo[5,1-f][1,2,4]triazin-4(3H)-one

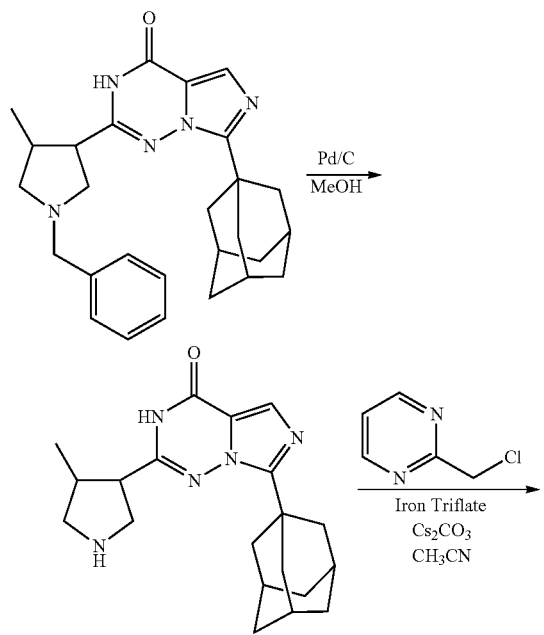

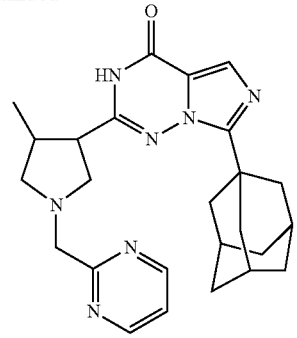

To a stirred solution of (+)-7-((1s,3R)-adamantan-1-yl)-2-((3,4-trans)-1-benzyl-4-methylpyrrolidin-3-yl)imidazo[5,1-f][1,2,4]triazin-4(3H)-one (160 mg, 0.36 mmol) in MeOH (10 mL) was added Pd/C (55 mg, catalytic) under N$_2$ atmosphere. The reaction was stirred at RT for 16 h under H$_2$ atmosphere (balloon pressure). The reaction mixture was passed through a pad of celite and volatiles were dried in vacuo. Obtained residue was washed with n-pentane (2 times) and dried under reduced pressure to afford 7-((1s,3R)-adamantan-1-yl)-2-((3,4-trans)-4-methylpyrrolidin-3-yl)imidazo[5,1-f][1,2,4]triazin-4(3H)-one (95 mg, 75%) as off-white solid. $^1$H-NMR (DMSO $d_6$, 400 MHz): δ 7.59 (s, 1H), 3.31 (t, 1H), 3.25 (t, 1H), 3.02-2.99 (m, 1H), 2.71 (q, 1H), 2.21 (s, 6H), 2.05 (s, 3H), 1.76 (s, 6H), 1.05 (d, 3H); LC-MS: 92.03%; 355.5 [(M$^+$+2)]; (column; Eclipse XDBC-18, (150×4.6 mm, 5 um); RT 5.35 min. 0.1% Aqueous TFA: ACN; 1.0 ml/min); UPLC (purity): 96.4%; (column; Acquity BEH C18, 2.1×50 mm, 1.7μ; RT 1.61 min. 0.025% aqueous TFA: ACN:Water; 0.5 ml/min.; TLC: 5% MeOH/CH$_2$Cl$_2$ (Rf 0.1). To a stirred solution of 7-((1s,3R)-adamantan-1-yl)-2-((3,4-trans)-4-methylpyrrolidin-3-yl)imidazo[5,1-f][1,2,4]triazin-4(3H)-one (50 mg, 0.14 mmol) in ACN (5 mL) was added 2-(chloromethyl)pyrimidine (19 mg, 0.1 mmol), iron triflate (14 mg, 0.02 mmol) followed by Cs$_2$CO$_3$ (92 mg, 0.2 mmol) at RT under inert atmosphere. The reaction mixture was heated to 70° C. and stirred for 4 h. After consumption of starting material (by TLC), the reaction was diluted with water and extracted with EtOAc (2×30 mL). Combined organic layers were dried over anhydrous sodium sulphate, filtered and concentrated in vacuo to obtain the crude product. The crude material was purified by silica gel column chromatography to afford (+)-7-((1s,3R)-adamantan-1-yl)-2-((3,4-trans)-4-methyl-1-(pyrimidin-2-ylmethyl)pyrrolidin-3-yl)imidazo[5,1-f][1,2,4]triazin-4(3H)-one (20 mg, 32%) as an off-white solid. $^1$H-NMR (DMSO $d_6$, 400 MHz): δ 8.79 (d, 2H), 7.61 (s, 1H), 7.42 (t, 1H), 3.99 (d, 1H), 3.85 (d, 1H), 3.09 (q, 2H), 2.98 (t, 1H), 2.80 (q, 1H), 2.62-2.58 (m, 1H), 2.42 (t, 1H), 2.19 (s, 6H), 2.04 (br s, 3H), 1.75 (s, 6H), 1.12 (d, 3H); Mass (ESI): 446 [(M$^+$+1)]; LC-MS: 97.27%; 446 [(M$^+$+1)]; (column; X-bridge C-18, (50×3.0 mm, 3.5μ); RT 3.91 min. 5 mM NH4OAc: ACN; 0.8 ml/min); UPLC (purity): 97.78%; (column; Acquity UPLC BEH C18, 2.1×50 mm, 1.7μ; RT 1.63 min. 0.025% aqueous TFA: ACN:Water; 0.5 ml/min.; Chiral HPLC: 99.28% ee $R_t$=10.92 min (Chiralpak IC, 250×4.6 mm, 5μ; mobile phase (A) 0.1% TEA in n-Hexane (B) ethanol (A:B: 50:50); flow Rate: 1.00 mL/min); Optical rotation $[α]_D^{25}$: +98.4° (c=0.5, DCM).

xxv. (+)-2-((3,4-trans)-1-benzyl-4-methylpyrrolidin-3-yl)-7-(5-chloro-2-methylphenyl)imidazo[5,1-f][1,2,4]triazin-4(3H)-one and (−)-2-((3,4-trans)-1-benzyl-4-methylpyrrolidin-3-yl)-7-(5-chloro-2-methylphenyl)imidazo[5,1-f][1,2,4]triazin-4(3H)-one Synthesis of (+/−)-N-((3-((3,4-trans)-1-benzyl-4-methylpyrrolidin-3-yl)-5-oxo-4,5-dihydro-1,2,4-triazin-6-yl)methyl)-5-chloro-2-methylbenzamide

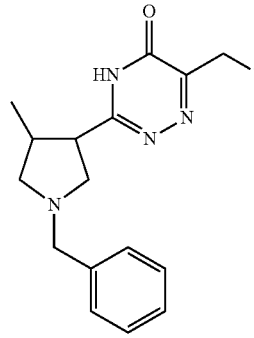

+

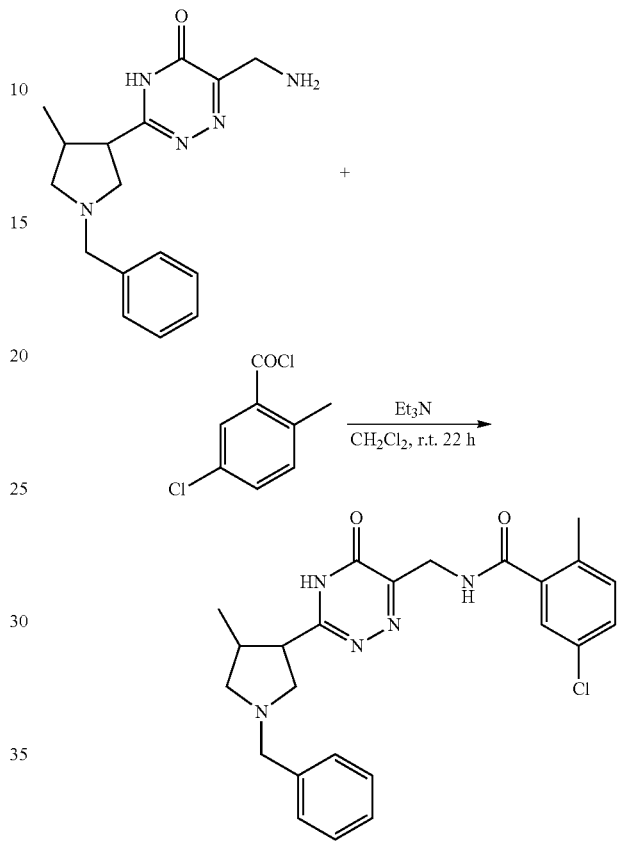

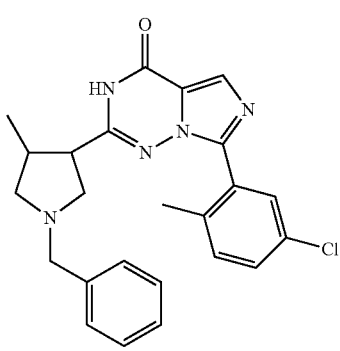

To a suspension of (+/−)-6-(aminomethyl)-3-((3,4-trans)-1-benzyl-4-methylpyrrolidin-3-yl)-1,2,4-triazin-5(4H)-one (1.02 g, 3.41 mmol) and triethylamine (1.04 g, 10.23 mmol) in $CH_2Cl_2$ (45 mL) was added 5-chloro-2-methylbenzoyl chloride (0.97 g, 5.11 mmol) drop-wise at RT. The resulting solution was stirred at room temperature for 22 h. After which time the precipitate was filtered and the filter cake was washed with $CHCl_3$. The filtrated was mixed with saturated $NaHCO_3$ (30 mL). The organic phase was separated from the aqueous phase, and the latter was extracted with $CHCl_3$ (20 mL). The combined organic phase was dried over $MgSO_4$. Filtration and concentration gave a yellow foam. Flash chromatography over silica gel column (0.1/1.5/98.4-1/15/84 $NH_4OH/MeOH/CH_2Cl_2$) provided (+/−)-N-((3-((3,4-trans)-1-benzyl-4-methylpyrrolidin-3-yl)-5-oxo-4,5-dihydro-1,2,4-triazin-6-yl)methyl)-5-chloro-2-methylbenzamide (1.10 g, 71% yield) as a yellow solid. $^1H$ NMR (300 MHz, $CDCl_3$) δ 7.41 (d, 1H, J=1.8 Hz), 7.38-7.30 (m, 5H), 7.24 (dd, 1H, J=7.8, 2.1 Hz), 7.14 (d, 1H, J=7.8 Hz), 6.97 (br s, 1H), 4.66 (d, 2H, J=5.1 Hz), 3.91 (d, 1H, J=12.3 Hz), 3.78 (d, 1H, J=12.3 Hz), 3.48-3.37 (m, 1H), 3.25-3.14 (m, 1H), 3.05-2.78 (m, 2H), 2.58-2.42 (m, 1H), 2.41 (s, 3H), 2.30-2.14 (m, 1H), 1.13 (d, 3H, J=6.6 Hz); $^{13}C$ NMR (75 MHz, $CDCl_3$) δ 168.3, 165.8, 160.7, 151.0, 1137.3, 135.9, 134.6, 132.2, 131.3, 129.8, 128.8, 128.7, 128.0, 126.9, 60.6, 59.5, 56.3, 49.8, 40.1, 389, 19.8, 19.4.

Synthesis of (+)-2-((3,4-trans)-1-benzyl-4-methyl-pyrrolidin-3-yl)-7-(5-chloro-2-methylphenyl)imidazo[5,1-f][1,2,4]triazin-4(3H)-one and (−)-2-((3,4-trans)-1-benzyl-4-methylpyrrolidin-3-yl)-7-(5-chloro-2-methylphenyl)imidazo[5,1-f][1,2,4]triazin-4(3H)-one

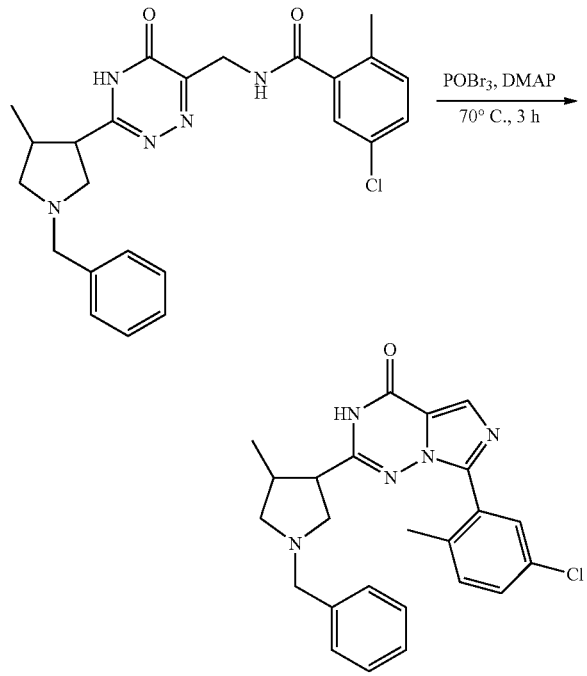

To a solution of (+/−)-N-((3-((3,4-trans)-1-benzyl-4-methylpyrrolidin-3-yl)-5-oxo-4,5-dihydro-1,2,4-triazin-6-yl)methyl)-5-chloro-2-methylbenzamide (110 mg, 0.24 mmol), DMAP (4 mg, 0.03 mmol) in acetonitrile (5 mL) was added a solution of POBr$_3$ (210 mg, 0.73 mmol) in acetonitrile (1 mL) at RT, and the resulting suspension was heated to 70° C. for 3 h. After the mixture was cooled to room temperature, it was poured into cold saturated NaHCO$_3$ solution (20 mL), and stirred vigorously for 0.5 h, then extracted with CH$_2$Cl$_2$ (3×10 mL). The organic extract was dried over MgSO$_4$ and concentrated under reduced pressure. The residue was purified by flash chromatography over silica gel (0.05/0.75/99.2-0.3/4.5/95.2 NH$_4$OH/MeOH/CH$_2$Cl$_2$) to furnish (+/−)-2-((3,4-trans)-1-benzyl-4-methyl-pyrrolidin-3-yl)-7-(5-chloro-2-methylphenyl)imidazo[5,1-f][1,2,4]triazin-4(3H)-one (68 mg, 64% yield) as a white foam. Purity (HPLC): 97.2%; $^1$H NMR (300 MHz, CDCl$_3$/TMS) δ 7.98 (s, 1H), 7.54 (d, J=1.8 Hz, 1H) 7.42-7.21 (m, 7H), 3.82 (d, J=12.3 Hz, 1H), 3.57 (d, J=12.6 Hz, 1H), 3.40 (t, J=8.6 Hz, 1H), 2.97 (d, J=10.5 Hz, 1H), 2.72-2.68 (m, 1H), 2.52-2.37 (m, 2H), 2.30 (s, 3H), 1.92 (t, J=8.7 Hz, 1H), 1.17 (d, J=7.2 Hz, 3H); $^{13}$C NMR (75 MHz, CDCl$_3$/TMS) δ 154.51, 154.25, 143.18, 137.17, 136.86, 131.73, 130.92, 130.66, 129.68, 129.49, 128.70, 128.67, 128.49, 127.65, 119.30, 61.10, 59.32, 55.96, 47.75, 38.50, 20.25, 20.00; HRMS: calculated for C$_{24}$H$_{25}$ClN$_5$O (MH$^+$), 434.1742. found, 434.1742.

(+/−)-2-((3,4-trans)-1-benzyl-4-methylpyrrolidin-3-yl)-7-(5-chloro-2-methylphenyl)imidazo[5,1-f][1,2,4]triazin-4(3H)-one was purified by Chiralpak AD-H, 250×20 mm, 5 um (160 mg loading; 0.1% TEA in n-Hexane: Ethanol (95:05) as mobile phase) to obtain pure fraction 1 ((−)-2-((3,4-trans)-1-benzyl-4-methylpyrrolidin-3-yl)-7-(5-chloro-2-methylphenyl)imidazo[5,1-f][1,2,4]triazin-4(3H)-one) and pure fraction 2 ((+)-2-((3,4-trans)-1-benzyl-4-methyl-pyrrolidin-3-yl)-7-(5-chloro-2-methylphenyl)imidazo[5,1-f][1,2,4]triazin-4(3H)-one). Characterization details of both fractions are as follows:

(−)-2-((3,4-trans)-1-benzyl-4-methylpyrrolidin-3-yl)-7-(5-chloro-2-methylphenyl)imidazo[5,1-f][1,2,4]triazin-4(3H)-one: H-NMR (DMSO d$_6$, 400 MHz): δ 7.92 (s, 1H), 7.68 (s, 1H), 7.48 (d, 1H), 7.42 (d, 1H), 7.32-7.29 (m, 5H), 3.62-3.57 (m, 4H), 2.94-2.91 (m, 1H), 2.82-2.78 (m, 3H), 2.34 (s, 3H), 2.22-2.18 (m, 1H), 1.07 (d, 3H); Mass (ESI): 434 [M$^+$+1]; LC-MS: 96.91%; 434 (M$^+$+1); (column; X-bridge C-18, (50×3.0 mm, 3.5μ); RT 3.71 min, 5 mM NH$_4$OAc: ACN; 0.8 ml/min); UPLC (purity): 99.01%; (column; Acquity BEH C-18, 50×2.1 mm, 1.7μ; RT 1.95 min. 0.025% TFA (Aq): ACN:Water; 0.50 ml/min.; Chiral HPLC: 99.65% ee R$_t$=10.64 min (Chiralpak AD-H, 250×4.6 mm, 5μ; mobile phase (A) 0.1% TEA in n-Hexane (B) Ethanol (A:B: 90:10); flow Rate: 1.00 mL/min); Optical rotation [α]$_D^{25}$: −28.52° (c=0.5, DCM).

(+)-2-((3,4-trans)-1-benzyl-4-methylpyrrolidin-3-yl)-7-(5-chloro-2-methylphenyl)imidazo[5,1-f][1,2,4]triazin-4(3H)-one: H-NMR (DMSO d$_6$, 400 MHz): δ 7.92 (s, 1H), 7.69 (s, 1H), 7.48 (d, 1H), 7.42 (d, 1H), 7.36-7.29 (m, 5H), 3.62-3.57 (m, 4H), 2.94-2.91 (m, 1H), 2.82-2.777 (m, 3H), 2.34 (s, 3H), 2.24-2.21 (m, 1H), 1.07 (d, 3H); Mass (ESI): 434 [M$^+$+1]; LC-MS: 95.15%; 434 (M$^+$+1); (column; X-bridge C-18, (50×3.0 mm, 3.5μ); RT 3.71 min. 5 mM NH$_4$OAc: ACN; 0.8 ml/min); UPLC (purity): 98.14%; (column; Acquity BEH C-18, 50×2.1 mm, 1.7μ; RT 1.95 min. 0.025% TFA (Aq): ACN:Water; 0.50 ml/min.; Chiral HPLC: 99.94% ee R$_t$=18.33 min (Chiralpak AD-H, 250×4.6 mm, 5μ; mobile phase (A) 0.1% TEA in n-Hexane (B) Ethanol (A:B: 90:10); flow Rate: 1.00 mL/min); Optical rotation [α]$_D^{25}$: +23.42° (c=0.5, DCM).

xxvi. (−)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one

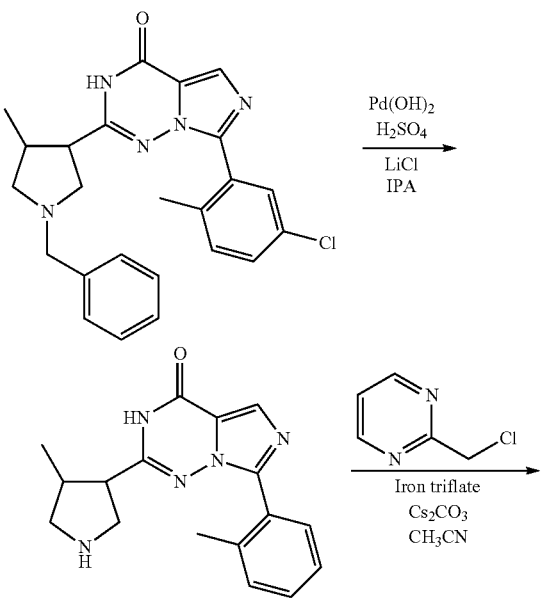

-continued

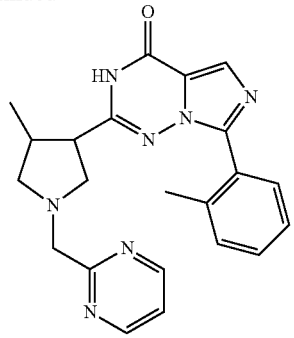

To a stirred solution of (−)-2-((3,4-trans)-1-benzyl-4-methylpyrrolidin-3-yl)-7-(5-chloro-2-methylphenyl)imidazo[5,1-f][1,2,4]triazin-4(3H)-one (150 mg, 0.34 mmol) in MeOH (10 mL) was added Pd/C (50 mg) under $N_2$ atmosphere. The reaction was stirred at RT for 3 h under $H_2$ atmosphere (balloon pressure). The reaction mixture was passed through a pad of celite and volatiles were dried in vacuo. Obtained residue was washed with n-pentane (2 times) to afford 2-((3,4-trans)-4-methylpyrrolidin-3-yl)-7-(o-tolyl)imidazo[5,1-f][1,2,4]triazin-4(3H)-one (100 mg, 94%) as solid. $^1$H-NMR (DMSO $d_6$, 400 MHz): δ 12.34 (br s, 1H), 9.65 (br s, 1H), 7.92 (s, 1H), 7.60 (d, 1H), 7.55-7.32 (m, 3H), 3.65 (t, 1H), 3.46-3.40 (m, 2H), 3.01 (q, 1H), 2.83 (t, 1H), 2.61-2.57 (m, 1H), 2.34 (s, 3H), 1.09 (d, 3H); LC-MS: 91.38%; 310 (M$^+$+1); (column; Eclipse XDB C-18, (150×4.6 mm, 5.0μ); RT 5.30 min. 5 mM NH4Oac: ACN; 1.0 ml/min); TLC: 5% MeOH/CH$_2$Cl$_2$ (Rf 0.1).

To a stirred solution of 2-((3,4-trans)-4-methylpyrrolidin-3-yl)-7-(o-tolyl)imidazo[5,1-f][1,2,4]triazin-4(3H)-one (100 mg, 0.29 mmol) in ACN (10 mL) was added 2-(chloromethyl)pyrimidine (41 mg, 0.32 mmol), Irontriflate (29.32 mg, 0.06 mmol) followed by Cs$_2$CO$_3$ (209 mg, 0.641 mmol) at RT under inert atmosphere The reaction mixture was heated to 70° C. and stirred for 3 h. After consumption of starting material (by TLC), the reaction was diluted with water and extracted with EtOAc (2×30 ml). Combined organic layers were dried over anhydrous sodium sulphate, filtered and concentrated in vacuo to obtain the crude product. The crude material was purified by silica gel column chromatography and further purified by preparative to afford (−)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one (42 mg, 36%) as an off-white solid. $^1$H-NMR (DMSO $d_6$, 400 MHz): δ 8.79 (d, 2H), 7.90 (s, 1H), 7.53 (d, 1H), 7.41-7.25 (m, 4H), 3.98 (d, 1H), 3.82 (d, 1H), 3.09 (t, 2H), 2.99-2.90 (m, 3H), 2.72 (q, 1H), 2.34 (d, 1H), 2.28 (s, 3H), 1.05 (d, 3H); Mass (ESI): 402 [(M$^+$+1)]; LC-MS: 97.87%; 403.7 [(M$^+$+2)]; (column; X-bridge C-18, (50×3.0 mm, 3.5μ); RT 2.66 min. 0.1% aq. TFA: ACN; 0.8 ml/min); UPLC (purity): 98.7%; (column; Acquity UPLC BEH C18, 2.1×50 mm, 1.7μ; RT 1.41 min. 0.025% aqueous TFA: ACN:Water; 0.5 ml/min.; Chiral HPLC: 100% ee $R_t$=33.0 min (Chiralpak IC, 250×4.6 mm, 5 g; mobile phase (A) 0.1% TEA in n-Hexane (B) ethanol (A:B: 50:50); flow Rate: 1.00 mL/min); Optical rotation $[α]_D^{24}$: −86.78° (c=0.5, DCM). TLC: 10% MeOH/CH$_2$Cl$_2$ (Rf 0.5).

xxvii. (−)-7-(5-chloro-2-methylphenyl)-2-((3,4-trans)-4-methylpyrrolidin-3-yl)imidazo[5,1-f][1,2,4]triazin-4(3H)-one

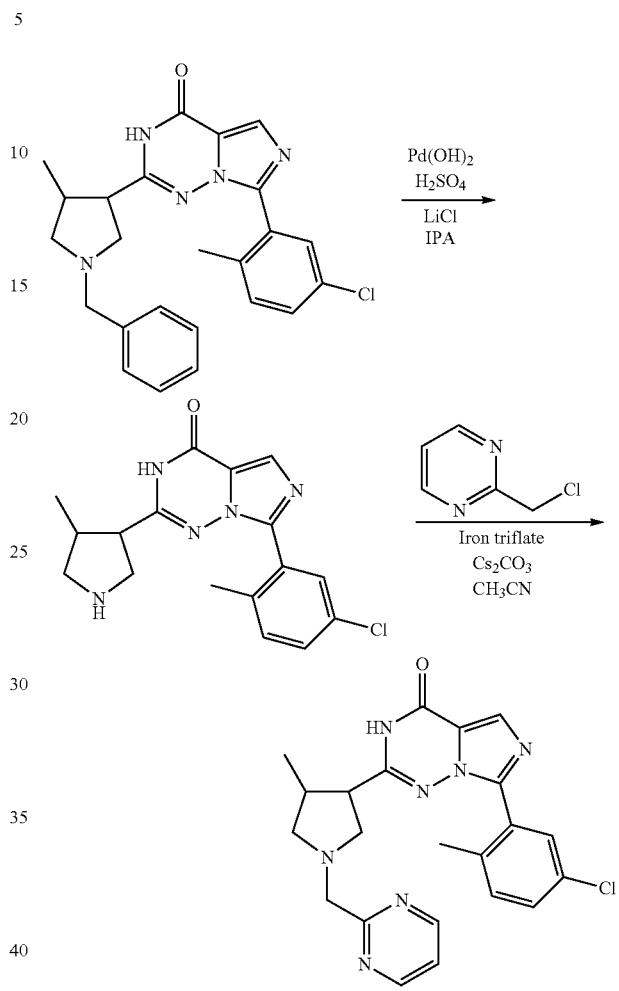

To a stirred solution of (−)-2-((3,4-trans)-1-benzyl-4-methylpyrrolidin-3-yl)-7-(5-chloro-2-methylphenyl)imidazo[5,1-f][1,2,4]triazin-4(3H)-one (120 mg, 0.276 mmol) in IPA (20 mL) were added LiCl (24 mg), Pd(OH)$_2$ (36 mg) followed by H$_2$SO$_4$ (36 mg) under $N_2$ atmosphere. The reaction was stirred at RT for 8 h under $H_2$ atmosphere (balloon pressure). The reaction mixture was passed through a pad of celite and volatiles were dried in vacuo. Obtained residue was co-distilled with PhCH$_3$ (2×20 ml) to afford 7-(5-chloro-2-methylphenyl)-2-((3,4-trans)-4-methylpyrrolidin-3-yl)imidazo[5,1-f][1,2,4]triazin-4(3H)-one (140 mg, crude) as solid. This was directly used for the next step without further purification. Mass (ESI): 344 [M$^+$+1]; LC-MS: 34.66%; 344.9 (M$^+$+1); (column; X-bridge C-18, (50× 3.0 mm, 3.5μ); RT 2.94 min. 0.1% TFA: ACN; 0.8 ml/min); UPLC (purity): 37.41%; (column; Acquity BEH C18, 2.1× 100 mm, 1.7μ; RT 1.63 min. 0.025% aqueous TFA: ACN: Water; 0.5 ml/min.; TLC: 10% MeOH/CH$_2$Cl$_2$ (Rf 0.2).

To a stirred solution of 7-(5-chloro-2-methylphenyl)-2-((3,4-trans)-4-methylpyrrolidin-3-yl)imidazo[5,1-f][1,2,4]triazin-4(3H)-one (60 mg, 0.174 mmol) in ACN (10 mL) was added 2-(chloromethyl)pyrimidine (24.6 mg, 0.19 mmol), iron triflate (17.5 mg, 0.03 mmol) followed by Cs$_2$CO$_3$ (114 mg, 0.34 mmol) at RT under inert atmosphere.

The reaction mixture was heated to 70° C. and stirred for 4 h. After consumption of starting material (by TLC), the reaction was diluted with water and extracted with EtOAc. Combined organic layers were dried over anhydrous sodium sulphate, filtered and concentrated in vacuo to obtain the crude product. The crude material was purified by silica gel column chromatography and further purified by preparative to afford (−)-7-(5-chloro-2-methylphenyl)-2-((3,4-trans)-4-methylpyrrolidin-3-yl)imidazo[5,1-f][1,2,4]triazin-4(3H)-one (12 mg, 16%) as an off-white solid. $^1$H-NMR (DMSO d$_6$, 500 MHz): δ 8.79 (s, 2H), 7.95 (s, 1H), 7.64 (s, 1H), 7.46 (d, 1H), 7.41 (d, 2H), 4.03 (d, 1H), 3.82-3.80 (m, 1H), 3.54 (s, 1H), 3.15 (t, 1H), 3.03-2.97 (m, 3H), 2.79 (q, 1H), 2.38 (t, 1H), 2.09 (s, 3H), 1.05 (d, 3H); Mass (ESI): 436 [M$^+$]; LC-MS: 87.85%; 436 (M$^+$); (column; X-bridge C-18, (50× 3.0 mm, 3.5μ); RT 3.68 min. 5 mM NH4OAc: ACN; 0.8 ml/min); UPLC (purity): 87.41%; (column; Acquity BEH C18, 2.1×100 mm, 1.7μ; RT 1.66 min. 0.025% aqueous TFA: ACN:Water; 0.5 nal/min.; Chiral HPLC: 98.3% ee R$_t$=23.57 min (Chiralpak IC, 250×4.6 mm, 5μ; mobile phase (A) 0.1% TEA in n-Hexane (B) ethanol (A:B: 40:60); flow Rate: 1.00 mL/min); Optical rotation [α]$_D^{25}$: −64.53° (c=0.25, DCM). TLC: 5% MeOH/CH$_2$Cl$_2$ (Rf 0.35).

xxviii. (+)-2-((3,4-trans)-1-benzyl-4-methylpyrrolidin-3-yl)-7-(4-fluoro-2-methylphenyl)imidazo[5,1-f][1,2,4]triazin-4(3H)-one and (−)-2-((3,4-trans)-1-benzyl-4-methylpyrrolidin-3-yl)-7-(4-fluoro-2-methylphenyl)imidazo[5,1-f][1,2,4]triazin-4(3H)-one

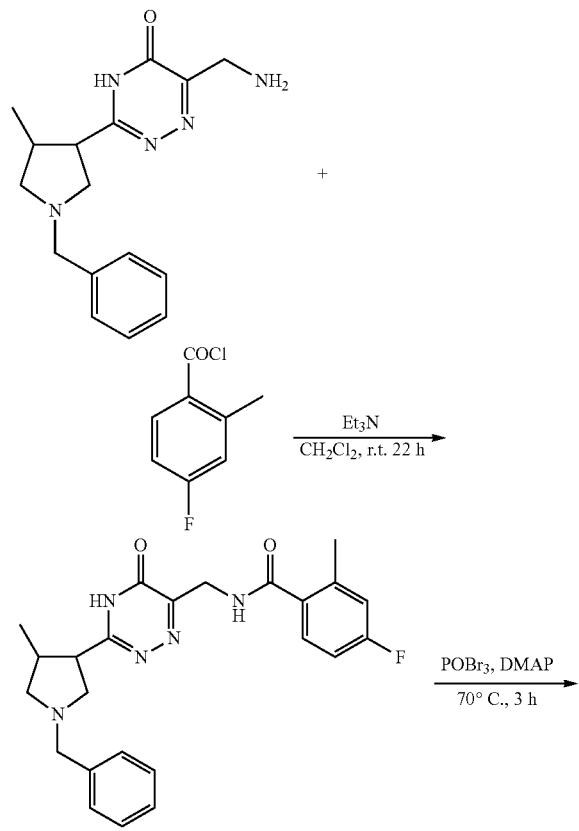

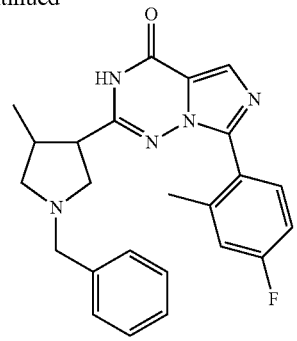

Synthesis of (+/−)-N-((3-((3,4-trans)-1-benzyl-4-methylpyrrolidin-3-yl)-5-oxo-4,5-dihydro-1,2,4-triazin-6-yl)methyl)-4-fluoro-2-methylbenzamide

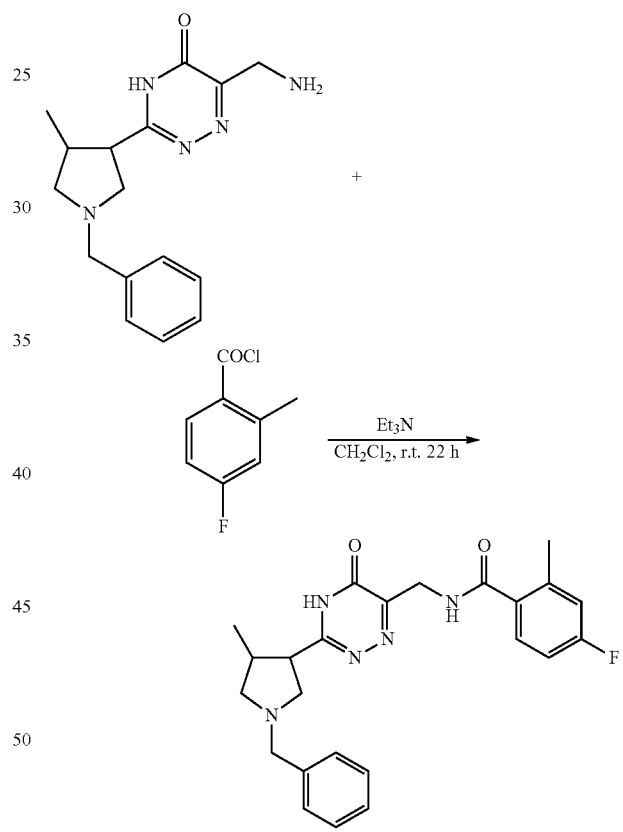

To a suspension of (+/−)-6-(aminomethyl)-3-((3,4-trans)-1-benzyl-4-methylpyrrolidin-3-yl)-1,2,4-triazin-5(4H)-one (1.02 g, 3.41 mmol) and triethylamine (1.04 g, 10.23 mmol) in CH$_2$Cl$_2$ (40 mL) was added a solution of 4-fluoro-2-methylbenzoyl chloride (0.88 g, 5.11 mmol) in CH$_2$Cl$_2$ (5 mL) drop-wise at RT. The resulting solution was stirred at room temperature for 17 h. After which time the precipitate was filtered and the filter cake was washed with CHCl$_3$. The filtrated was concentrated to give a yellow solid. Flash chromatography over silica gel column (0.1/1.5/98.4-0.8/12/87.2 NH$_4$OH/MeOH/CH$_2$Cl$_2$) provided (+/−)-N-((3-((3,4-trans)-1-benzyl-4-methylpyrrolidin-3-yl)-5-oxo-4,5-dihydro-1,2,4-triazin-6-yl)methyl)-4-fluoro-2-methylbenzamide (1.17 g, 79% yield) as a yellow solid. $^1$H NMR (300 MHz, CDCl$_3$) δ 9.43 (br s, 1H), 7.45 (dd, 1H, J=8.4, 6.0 Hz), 7.40-7.26 (m, 5H), 7.05 (br s, 1H), 6.94-6.82 (m, 2H), 4.67 (d, 2H, J=5.4 Hz), 3.96 (d, 1H, J=11.4 Hz), 3.84 (d, 1H, J=11.4 Hz), 3.48-3.37 (m, 1H), 3.30-3.20 (m, 1H), 3.15-2.85 (m, 2H), 2.60-2.45 (m, 1H), 2.48 (s, 3H), 2.39-2.25 (m, 1H), 1.11 (d, 3H, J=6.9 Hz); $^{13}$C NMR (75 MHz, CDCl$_3$) δ 168.9, 165.5, 163.1 (d, J=247 Hz), 150.8, 139.4 (d, J=8.4 Hz), 131.8, 129.0, 128.7, 128.3, 117.6 (d, J=22 Hz), 112.4 (d, J=21 Hz), 60.4, 59.5, 56.4, 49.9, 40.2, 38.7, 20.2, 19.0.

Synthesis of (+)-2-((3,4-trans)-1-benzyl-4-methylpyrrolidin-3-yl)-7-(4-fluoro-2-methylphenyl)imidazo[5,1-f][1,2,4]triazin-4(3H)-one and (−)-2-((3,4-trans)-1-benzyl-4-methylpyrrolidin-3-yl)-7-(4-fluoro-2-methylphenyl)imidazo[5,1-f][1,2,4]triazin-4(3H)-one

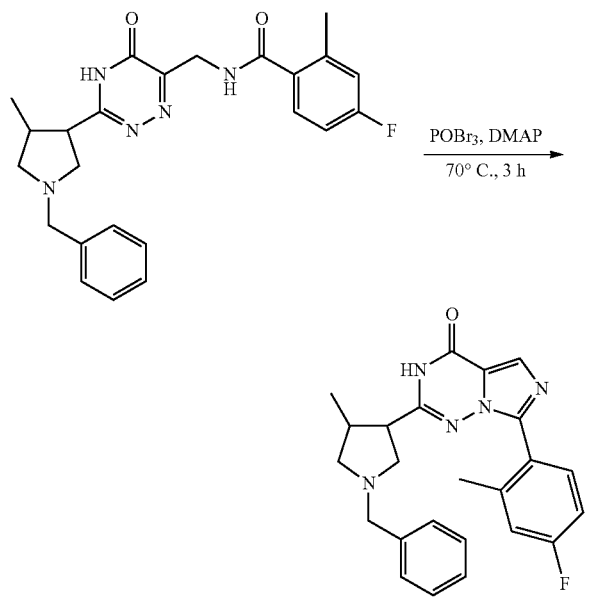

To a solution of (+/−)-N-((3-((3,4-trans)-1-benzyl-4-methylpyrrolidin-3-yl)-5-oxo-4,5-dihydro-1,2,4-triazin-6-yl)methyl)-4-fluoro-2-methylbenzamide (1.17 g, 2.69 mmol), DMAP (33 mg, 0.27 mmol) in acetonitrile (50 mL) was added a solution of POBr$_3$ (2.31 g, 8.06 mmol) in acetonitrile (10 mL) at RT, and the resulting suspension was heated to 70° C. for 3 h. After the mixture was cooled to room temperature, it was poured into cold saturated NaHCO$_3$ solution (200 mL), and stirred vigorously for 0.5 h, then extracted with CH$_2$Cl$_2$ (3×60 mL). The organic extract was dried over MgSO$_4$ and concentrated under reduced pressure. The residue was purified by flash chromatography over silica gel (0.05/0.75/99.2-0.3/4.5/95.2 NH$_4$OH/MeOH/CH$_2$Cl$_2$) to furnish (+/−)-2-((3,4-trans)-1-benzyl-4-methylpyrrolidin-3-yl)-7-(4-fluoro-2-methylphenyl)imidazo[5,1-f][1,2,4]triazin-4(3H)-one (0.72 g, 64% yield) as a white foam. Purity (HPLC): 96.9%; $^1$H NMR (300 MHz, CDCl$_3$/TMS) δ 7.98 (s, 1H), 7.51 (dd, J=8.4, 6.0 Hz, 1H) 7.44-7.24 (m, 5H), 7.06-6.94 (m, 2H), 3.82 (d, J=12.3 Hz, 1H), 3.56 (m, J=12.9 Hz, 1H), 3.39 (t, J=8.3 Hz, 1H), 2.96 (d, J=9.9 Hz, 1H), 2.72-2.66 (m, 1H), 2.52-2.37 (m, 2H), 2.33 (s, 3H), 1.91 (t, J=8.7 Hz, 1H), 1.16 (d, J=7.2 Hz, 3H); $^{13}$C NMR (75 MHz, CDCl$_3$/TMS) δ 163.12 (d, J=247 Hz), 154.22, 143.73, 141.20 (d, J=8.4 Hz), 137.13, 132.62 (d, J=9.0 Hz), 128.62, 128.58, 128.33, 127.55, 124.41, 119.12, 117.10 (d, J=21.5 Hz), 112.39 (d, J=21.5 Hz), 61.07, 59.27, 55.94, 47.84, 38.44, 20.47, 20.11; HRMS: calculated for C$_{24}$H$_{25}$FN$_5$O (MH$^+$), 418.2038. found, 418.2043.

(+/−)-2-((3,4-trans)-1-benzyl-4-methylpyrrolidin-3-yl)-7-(4-fluoro-2-methylphenyl)imidazo[5,1-f][1,2,4]triazin-4(3H)-one was purified by Chiralpak AD-H, 250×20 mm, 5 um (135 mg loading; 0.1% TEA in n-Hexane: Ethanol (90:10) as mobile phase) to obtain pure fraction 1 ((+)-2-((3,4-trans)-1-benzyl-4-methylpyrrolidin-3-yl)-7-(4-fluoro-2-methylphenyl)imidazo[5,1-f][1,2,4]triazin-4(3H)-one) and pure fraction 2 ((−)-2-((3,4-trans)-1-benzyl-4-methylpyrrolidin-3-yl)-7-(4-fluoro-2-methylphenyl)imidazo[5,1-f][1,2,4]triazin-4(3H)-one). Characterization details of both fractions are as follows:

(+)-2-((3,4-trans)-1-benzyl-4-methylpyrrolidin-3-yl)-7-(4-fluoro-2-methylphenyl)imidazo[5,1-f][1,2,4]triazin-4(3H)-one: H-NMR (DMSO d$_6$, 400 MHz): δ 7.89 (s, 1H), 7.64-7.61 (m, 1H), 7.34-7.29 (m, 6H), 7.21-7.16 (m, 1H), 3.64-3.58 (m, 3H), 2.92-2.87 (m, 1H), 2.82-2.74 (m, 3H), 2.57-2.52 (m, 1H), 232 (s, 3H), 2.23-2.18 (m, 1H), 1.07 (d, 3H); Mass (ESI): 418 [M$^+$+1]; LC-MS: 95.17%; 418 (M$^+$+1); (column; X-bridge C-18, (50×3.0 mm, 3.5μ); RT 3.44 min. 5 mM NH$_4$OAc: ACN; 0.8 ml/min); UPLC (purity): 97.01%; (column; Acquity BEH C-18, 50×2.1 mm, 1.7μ; RT 1.83 min. 0.025% TFA (Aq): ACN:Water; 0.50 ml/min.; Chiral HPLC: 100% ee R$_t$=27.33 min (Chiralpak IA, 250× 4.6 mm, 5μ; mobile phase (A) 0.1% TEA in n-Hexane (B) IPA (A:B: 95:05); flow Rate: 1.00 mL/min); Optical rotation [α]$_D^{24}$: +11.61° (c=0.5, DCM).

(−)-2-((3,4-trans)-1-benzyl-4-methylpyrrolidin-3-yl)-7-(4-fluoro-2-methylphenyl)imidazo[5,1-f][1,2,4]triazin-4(3H)-one: H-NMR (DMSO d$_6$, 400 MHz): δ 7.89 (s, 1H), 7.62-7.57 (m, 1H), 7.34-7.29 (m, 6H), 7.19-7.14 (m, 1H), 3.64-3.58 (m, 3H), 2.92-2.87 (m, 1H), 2.82-2.76 (m, 3H), 2.57-2.52 (m, 1H), 2.32 (s, 3H), 2.21-2.17 (m, 1H), 1.04 (d, 3H); Mass (ESI): 418 [M$^+$+1]; LC-MS: 97.42%; 418 (M$^+$+1); (column; X-bridge C-18, (50×3.0 mm, 3.5μ); RT 3.44 min. 5 mM NH$_4$OAc: ACN; 0.8 ml/min); UPLC (purity): 99.30%; (column; Acquity BEH C-18, 50×2.1 mm, 1.7μ; RT 1.83 min. 0.025% TFA (Aq): ACN:Water; 0.50 ml/min.; Chiral HPLC: 100% ee R$_t$=34.31 min (Chiralpak IA, 250× 4.6 mm, 5μ; mobile phase (A) 0.1% TEA in n-Hexane (B) IPA (A:B: 95:05); flow Rate: 1.00 mL/min); Optical rotation [α]$_D^{24}$: −19.16° (c=0.5, DCM).

xxix. (−)-7-(4-fluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one

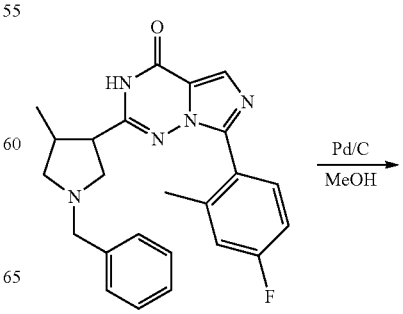

127

-continued

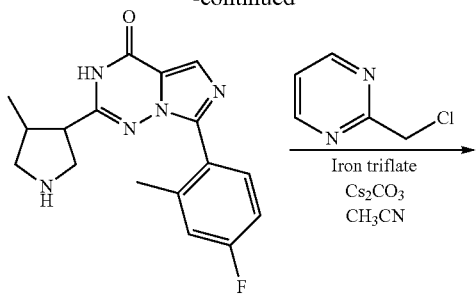

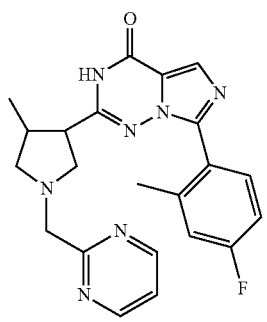

To a stirred solution of (+)-2-((3,4-trans)-1-benzyl-4-methylpyrrolidin-3-yl)-7-(4-fluoro-2-methylphenyl)imidazo[5,1-f][1,2,4]triazin-4(3H)-one (100 mg, 0.24 mmol) in MeOH (5 mL) was added dry Pd/C (30 mg) under $N_2$ atmosphere. The reaction was stirred at RT for 8 h under $H_2$ atmosphere (balloon pressure). The reaction mixture was passed through a pad of celite; the bed was washed with MeOH/$CH_2Cl_2$ and volatiles were dried in vacuo. Obtained residue was washed with n-pentane (2 times) to afford compound 7-(4-fluoro-2-methylphenyl)-2-((3,4-trans)-4-methylpyrrolidin-3-yl)imidazo[5,1-f][1,2,4]triazin-4(3H)-one (75 mg, 96%) as off-white solid. $^1$H-NMR (DMSO $d_6$, 400 MHz): δ 7.73 (s, 1H), 7.67 (t, 1H), 7.21 (dd, 2H), 3.31-3.20 (m, 4H), 2.67-2.55 (m, 1H), 2.47-2.38 (m, 2H), 2.34 (s, 3H), 1.02 (d, 3H); LC-MS: 93.25%; 328 [(M$^+$+1)]; (column; X-Bridge C-18, (50×3.0 mm, 5.0µ); RT 2.36 min. 5 mM NH4Oac: ACN; 0.8 ml/min); TLC: 5% MeOH/$CH_2Cl_2$ (Rf 0.05).

To a stirred solution of compound 7-(4-fluoro-2-methylphenyl)-2-((3,4-trans)-4-methylpyrrolidin-3-yl)imidazo[5,1-f][1,2,4]triazin-4(3H)-one (75 mg, 0.23 mmol) in ACN (10 mL) was added 2-(chloromethyl)pyrimidine (32.29 mg, 0.253 mmol), iron triflate (23 mg, 0.045 mmol) followed by $Cs_2CO_3$ (164 mg, 0.504 mmol) at RT under inert atmosphere. The reaction mixture was heated to 70° C. and stirred for 4 h. After consumption of starting material (by TLC), the reaction was diluted with water and extracted with EtOAc (2×30 ml). Combined organic layers were dried over anhydrous sodium sulphate, filtered and concentrated in vacuo to obtain the crude product. The crude material was purified by silica gel column chromatography to afford (−)-7-(4-fluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one (60 mg, 63%) as an off-white solid. $^1$H-NMR (DMSO $d_6$, 400 MHz): δ 8.83 (d, 2H), 7.92 (s, 1H), 7.65 (t, 1H), 7.44 (t, 1H), 7.29 (dd, 1H), 7.20 (t, 1H), 4.01 (d, 1H), 3.85 (d, 1H), 3.13 (t, 1H), 2.99-2.90 (m, 2H), 2.79 (q, 1H), 2.59 (d, 4H), 2.35 (s, 4H), 1.12 (d, 3H); Mass (ESI): 420 [(M$^+$+1)]; LC-MS: 97.74%; 420 [(M$^+$+1)]; (column; X-bridge C-18, (50×3.0 mm, 3.5µ); RT 3.24 min. 5.0 mM NH4OAc: ACN; 0.8 ml/min); UPLC (purity): 99.07%;

128

(column; Acquity UPLC BEH C18, 2.1×50 mm, 1.7µ; RT 1.51 min. 0.025% aqueous TFA: ACN:Water; 0.5 ml/min.; Chiral HPLC: 98.87% ee R$_t$=17.71 min (Chiralpak IC, 250×4.6 mm, 5µ; mobile phase (A) 0.1% TEA in n-Hexane (B) ethanol (A:B: 50:50); flow Rate: 1.00 mL/min); Optical rotation [α]$_D^{24}$: −70.93° (c=0.5, DCM). TLC: 10% MeOH/$CH_2Cl_2$ (Rf 0.55).

xxx. (+)-2-((3,4-trans)-1-benzyl-4-methylpyrrolidin-3-yl)-7-(4,4-difluorocyclohexyl)imidazo[5,1-f][1,2,4]triazin-4(3H)-one and (−)-2-((3,4-trans)-1-benzyl-4-methylpyrrolidin-3-yl)-7-(4,4-difluorocyclohexyl)imidazo[5,1-f][1,2,4]triazin-4(3H)-one

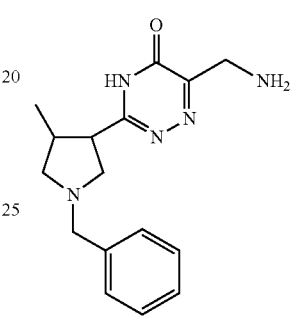

+

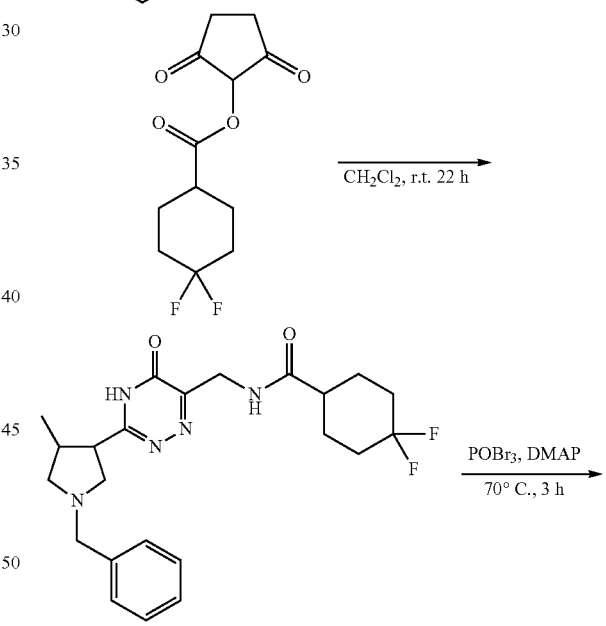

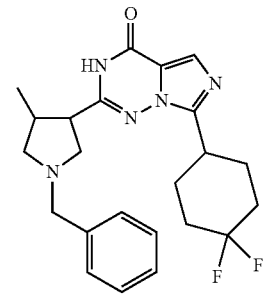

Synthesis of (+/−)-N-((3-((3,4-trans)-1-benzyl-4-methylpyrrolidin-3-yl)-5-oxo-4,5-dihydro-1,2,4-triazin-6-yl)methyl)-4,4-difluorocyclohexanecarboxamide Synthesis of (+)-2-((3,4-trans)-1-benzyl-4-methylpyrrolidin-3-yl)-7-(4,4-difluorocyclohexyl)imidazo[5,1-f][1,2,4]triazin-4(3H)-one and (−)-2-((3,4-trans)-1-benzyl-4-methylpyrrolidin-3-yl)-7-(4,4-difluorocyclohexyl)imidazo[5,1-f][1,2,4]triazin-4(3H)-one

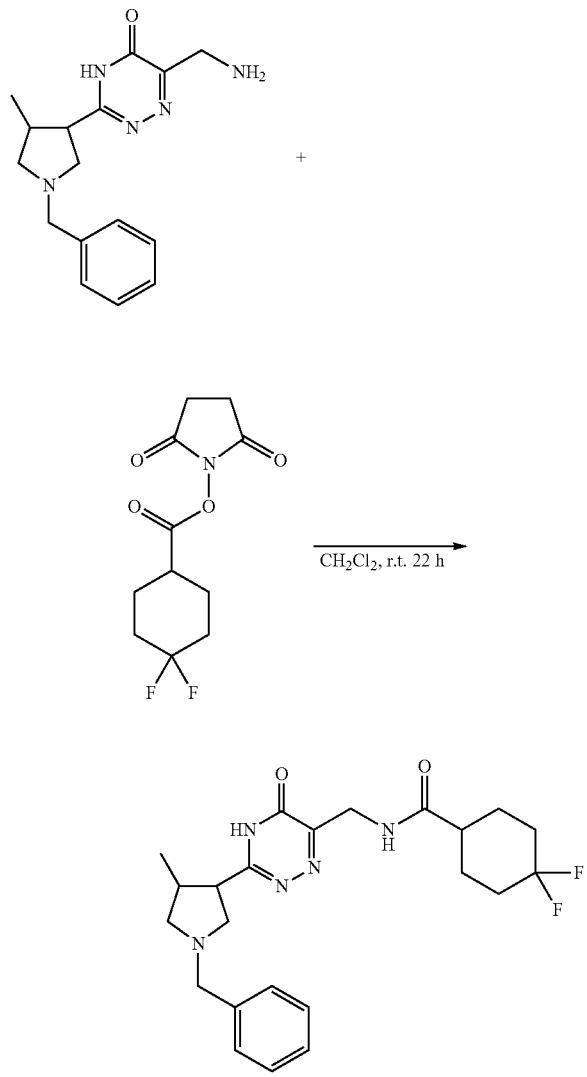

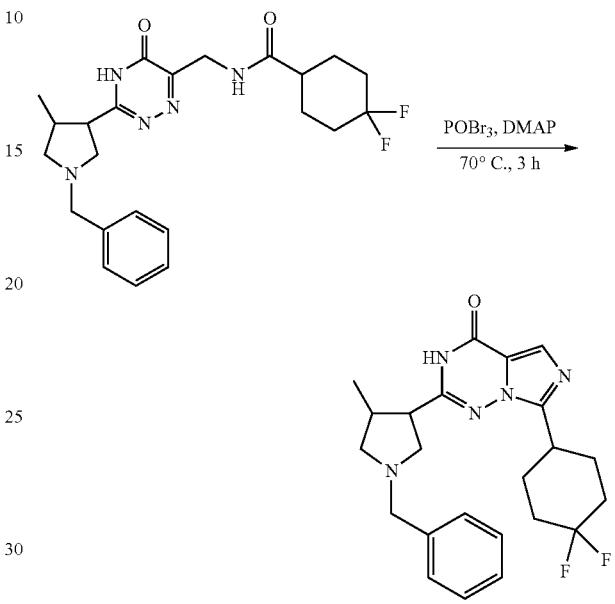

The mixture of (+/−)-6-(aminomethyl)-3-((3,4-trans)-1-benzyl-4-methylpyrrolidin-3-yl)-1,2,4-triazin-5(4H)-one (1.0 g, 3.3 mmol) and 2,5-dioxopyrrolidin-1-yl 4,4-difluorocyclohexanecarboxylate (1.0 g, 3.8 mmol) in CH$_2$Cl$_2$ (50 mL) was stirred at room temperature over night. The precipitate was filtered and the filtrate was washed with water. The aqueous solution was extracted with chloroform (4×100 ml). The CH$_2$Cl$_2$ solution and chloroform extracts were combined and the solvents were evaporated. The residue was purified by column chromatography (silica gel, CH$_2$Cl$_2$/MeOH/NH$_4$OH, 10:1:0.5%) to prepare (+/−)-N-((3-((3,4-trans)-1-benzyl-4-methylpyrrolidin-3-yl)-5-oxo-4,5-dihydro-1,2,4-triazin-6-yl)methyl)-4,4-difluorocyclohexanecarboxamide (670 mg, 45% yield). $^1$H NMR (300 MHz, CDCl$_3$/TMS): δ 7.31 (m, 5H), 4.46 (d, J=4 Hz, 2H), 4.00 (d, J=12 Hz, 1H), 3.86 (d, J=12 Hz, 1H), 3.39 (t, J=9 Hz, 1H), 3.25 (m, 1H), 3.08 (m, 2H), 2.53-2.43 (m, 2H), 2.25 (m, 1H), 2.13-1.60 (m, 9H), 1.04 (d, J=7 Hz, 3H).

Phosphorus oxybromide (1.26 g, 4.4 mmol) was dissolved in MeCN (10 mL) and the solution was added to (+/−)-N-((3-((3,4-trans)-1-benzyl-4-methylpyrrolidin-3-yl)-5-oxo-4,5-dihydro-1,2,4-triazin-6-yl)methyl)-4,4-difluorocyclohexanecarboxamide (670 mg, 1.5 mmol) and DMAP (50 mg) in MeCN (30 mL) at room temperature drop wise. The reaction mixture was heat up to 70° C. and stirred for 3 h. The reaction mixture was purred into the cold concentrated aqueous solution of NaHCO$_3$ (100 mL). The organics were extracted with CH$_2$Cl$_2$ (3×50 mL). The organic solution was washed with brine and dried over MgSO$_4$. The solvent was evaporated and residue was purified by column chromatography (silica gel, CH$_2$Cl$_2$/MeOH/NH$_4$OH, 10:1:1%) to prepare (+/−)-2-((3,4-trans)-1-benzyl-4-methylpyrrolidin-3-yl)-7-(4,4-difluoro cyclohexyl)imidazo[5,1-f][1,2,4]triazin-4(3H)-one (380 mg, 59% yield). Purity (HPLC): 97.2%; $^1$H NMR (300 MHz, CDCl$_3$/TMS): δ 7.75 (s, 1H), 7.34-7.24 (m, 5H), 3.80 (d, J=12.6 Hz, 1H), 3.54 (d, J=12.6 Hz, 1H), 3.37 (t, J=8.5 Hz, 1H), 3.23 (m, 1H), 2.95 (d, J 9.0 Hz, 1H), 2.73-2.72 (m, 1H), 2.53-2.38 (m, 2H), 2.24-1.81 (m, 9H), 1.19 (d, J=7.0 Hz, 3H); $^{13}$C NMR (75 MHz, CDCl$_3$/TMS): δ 154.6, 154.2, 148.3, 137.5, 128.9, 127.9, 127.7, 123.1 (t, J=241. Hz), 119.2, 61.4, 59.6, 56.3, 48.2, 38.7, 33.8, 33.5, 33.1, 27.0 (dd, J=9.0 Hz, J=10.0 Hz), 20.5; $^{19}$F NMR (282 MHz, CDCl$_3$/TMS): δ—93.10 (d, J=236 Hz), 101.1 (d, J=236 Hz).

(+/−)-2-((3,4-trans)-1-benzyl-4-methylpyrrolidin-3-yl)-7-(4,4-difluorocyclohexyl)imidazo[5,1-f][1,2,4]triazin-4(3H)-one was purified by Chiralpak IC, 250×20 mm, 5 um (45 mg loading; 0.1% TEA in n-Hexane: Ethanol (90:10) as mobile phase) to obtain pure fraction 1 ((+)-2-((3,4-trans)-1-benzyl-4-methylpyrrolidin-3-yl)-7-(4,4-difluorocyclohexyl)imidazo[5,1-f][1,2,4]triazin-4(3H)-one) and pure fraction 2 ((−)-2-((3,4-trans)-1-benzyl-4-methylpyrrolidin-3-yl)-7-(4, 4-difluorocyclohexyl)imidazo[5,1-f][1,2,4]triazin-4(3H)-one). Characterization details of both fractions are as follows:

(+)-2-(3,4-trans)-1-benzyl-4-methylpyrrolidin-3-yl)-7-(4,4-difluorocyclohexyl)imidazo[5,1-f][1,2,4]triazin-4(3H)-one: H-NMR (DMSO $d_6$, 400 MHz): δ 7.64 (s, 1H), 7.34-7.29 (m, 4H), 7.24-7.21 (m, 1H), 3.68-3.62 (m, 3H), 3.38-3.32 (m, 3H), 2.98-2.96 (m, 1H), 2.87-2.82 (m, 1H), 2.79-2.74 (m, 2H), 2.65-2.62 (m, 1H), 2.18-2.15 (m, 2H), 2.08-1.96 (m, 4H), 1.07 (d, 3H); Mass (ESI): 428 [M$^+$+1]; LC-MS: 97.43%; 428 (M$^+$+1); (column; X-bridge C-18, (50×3.0 mm, 3.5µ); RT 3.40 min. 5 mM NH$_4$OAc: ACN; 0.8 ml/min); UPLC (purity): 99.76%; (column; Acquity BEH C-18, 50×2.1 mm, 1.7µ; RT 1.81 min. 0.025% TFA (Aq): ACN:Water; 0.50 ml/min.; Chiral HPLC: 100% ee $R_t$=24.69 min (Chiralpak IC, 250×4.6 mm, 5µ; mobile phase (A) 0.1% TEA in n-Hexane (B) Ethanol (A:B: 90:10); flow Rate: 1.00 mL/min); Optical rotation $[α]_D^{24}$: +20.19° (c=0.5, DCM).

(−)-2-((3,4-trans)-1-benzyl-4-methylpyrrolidin-3-yl)-7-(4,4-difluorocyclohexyl)imidazo[5,1-f][1,2,4]triazin-4(3H)-one: H-NMR (DMSO $d_6$, 400 MHz): δ 7.62 (s, 1H), 7.37-7.29 (m, 4H), 7.24-7.21 (m, 1H), 3.68-3.61 (m, 3H), 3.34-3.31 (m, 3H), 2.98-2.96 (m, 1H), 2.86-2.84 (m, 1H), 2.79-2.74 (m, 2H), 2.65-2.63 (m, 1H), 2.28-2.26 (m, 114), 2.18-2.14 (m, 2H), 2.09-1.97 (m, 4H), 1.09 (d, 3H); Mass (ESI): 428 [M$^+$+1]; LC-MS: 98.16%; 428 (M$^+$+1); (column; X-bridge C-18, (50×3.0 mm, 3.5µ); RT 3.42 min. 5 mM NH$_4$OAc: ACN; 0.8 ml/min); UPLC (purity): 99.58%; (column; Acquity BEH C-18, 50×2.1 mm, RT 1.81 min. 0.025% TFA (Aq): ACN:Water; 0.50 ml/min.; Chiral HPLC: 98.94% ee $R_t$=28.81 min (Chiralpak IC, 250×4.6 mm, 5µ; mobile phase (A) 0.1% TEA in n-Hexane (B) Ethanol (A:B: 90:10); flow Rate: 1.00 mL/min); Optical rotation $[α]_D^{24}$: −24.91° (c=0.5, DCM).

xxxi. (+)-7-(4,4-difluorocyclohexyl)-2-((3,4-trans)-4-methyl-1-(pyrimidin-2-ylmethyl)pyrrolidin-3-yl)imidazo[5,1-f][1,2,4]triazin-4(3H)-one

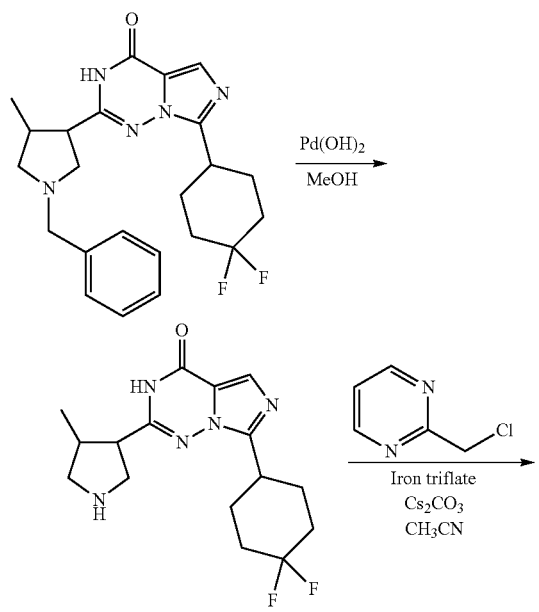

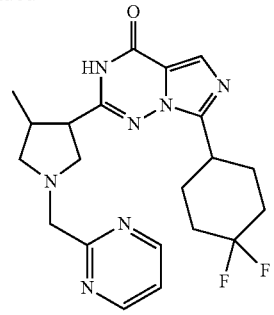

To a stirred solution of (+)-2-((3,4-trans)-1-benzyl-4-methylpyrrolidin-3-yl)-7-(4,4-difluorocyclohexyl)imidazo[5,1-f][1,2,4]triazin-4(3H)-one (125 mg, 0.3 mmol) in MeOH (15 mL) was added 10% Pd(OH)$_2$ (38 mg, catalytic) under N$_2$ atmosphere. The reaction was stirred at RT for 8 h under H$_2$ atmosphere (balloon pressure). The reaction mixture was passed through a pad of celite; the bed was washed with MeOH & CH$_2$Cl$_2$ and volatiles were dried in vacuo. Obtained residue was washed with n-pentane (2 times) and dried under reduced pressure to afford 7-(4,4-difluorocyclohexyl)-2-((3,4-trans)-4-methylpyrrolidin-3-yl)imidazo[5,1-f][1,2,4]triazin-4(3H)-one as off-white solid (95 mg, 97%). LC-MS: 77.88%; 338 [(M$^4$+1)]; (column; X-Bridge C-18, (50×3.0 mm, 3.5 um); RT 2.38 min. 5 mM NH4Oac: ACN; 0.8 ml/min); UPLC (purity): 96.84%; (column; Acquity UPLC BEH C18, 2.1×50 mm, 1.7µ; RT 1.35 min. 0.025% aqueous TFA: ACN:Water; 0.5 ml/min.; TLC: 10% MeOH/ CH$_2$Cl$_2$ (Rf 0.1).

To a stirred solution of 7-(4,4-difluorocyclohexyl)-2-((3,4-trans)-4-methylpyrrolidin-3-yl)imidazo[5,1-f][1,2,4]triazin-4(3H)-one (75 mg, 0.22 mmol) in ACN (10 mL) was added 2-(chloromethyl)pyrimidine (31.33 mg, 0.24 mmol), iron triflate (22.4 mg, 0.04 mmol) followed by Cs$_2$CO$_3$ (145 mg, 0.4 mmol) at RT under inert atmosphere. The reaction mixture was heated to 70° C. and stirred for 3 h. After consumption of starting material (by TLC), the reaction was diluted with water and extracted with EtOAc (3×25 mL). Combined organic layers were dried over anhydrous sodium sulphate, filtered and concentrated in vacuo to obtain the crude product. The crude material was purified by silica gel column chromatography to afford (+)-7-(4,4-difluorocyclohexyl)-2-((3,4-trans)-4-methyl-1-(pyrimidin-2-ylmethyl)pyrrolidin-3-yl)imidazo[5,1-f][1,2,4]triazin-4(3H)-one (50 mg, 53%) as an off-white solid. $^1$H-NMR (DMSO $d_6$, 400 MHz): δ 8.79 (d, 2H), 7.68 (s, 1H), 7.44 (t, 1H), 4.04 (d, 1H), 3.85 (d, 1H), 3.15 (t, 1H), 3.02-2.98 (m, 2H), 2.78 (q, 1H), 2.63-2.58 (m, 1H), 2.38 (t, 1H), 2.21-1.98 (m, 9H), 1.13 (d, 3H); Mass (ESI): 430 [(M$^+$+1)]; LC-MS: 99.05%; 430.9 [(M$^+$+1)]; (column; X-bridge C-18, (50×3.0 mm, 3.5µ); RT 2.67 min. 0.1% TFA: ACN; 0.8 ml/min); UPLC (purity): 99.04%; (column; Acquity BEH C18, 2.1×50 mm, 1.7µ; RT 1.56 min. 0.025% aqueous TFA: ACN:Water; 0.5 ml/min.; Chiral HPLC: 100% ee $R_t$=9.04 min (Chiralpak IC, 250×4.6 mm, 5µ; mobile phase (A) 0.1% TEA in n-Hexane (B) ethanol (A:B: 40:60); flow Rate: 1.00 mL/min); Optical rotation $[α]_D^{25}$: +103.4° (c=0.5, DCM), TLC: 10% MeOH/ CH$_2$Cl$_2$ (Rf 0.5).

133 xxxii. (+)-2-((3,4-trans)-1-benzyl-4-methylpyrrolidin-3-yl)-7-(furan-3-yl)imidazo[5,1-f][1,2,4]triazin-4(3H)-one and (−)-2-(3,4-trans)-1-benzyl-4-methylpyrrolidin-3-yl)-7-(furan-3-yl)imidazo[5,1-f][1,2,4]triazin-4(3H)-one

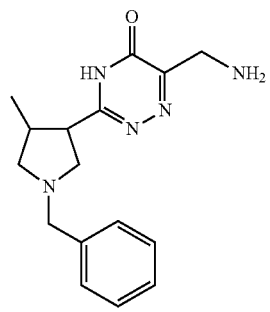

+

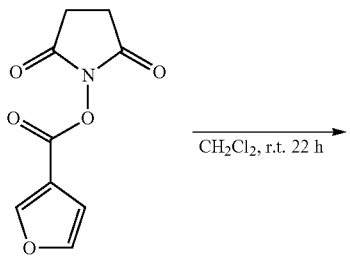

POBr₃, DMAP
70° C., 3 h
→

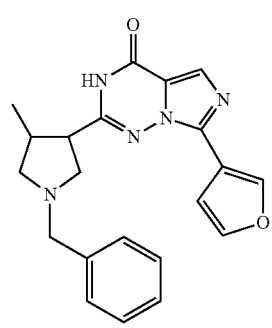

134

Synthesis of (+/−)-N-((3-((3,4-trans)-1-benzyl-4-methylpyrrolidin-3-yl)-5-oxo-4,5-dihydro-1,2,4-triazin-6-yl)methyl)furan-3-carboxamide

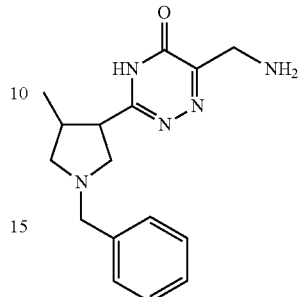

+

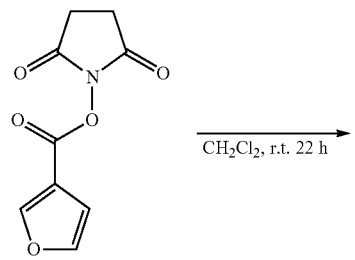

CH₂Cl₂, r.t. 22 h
→

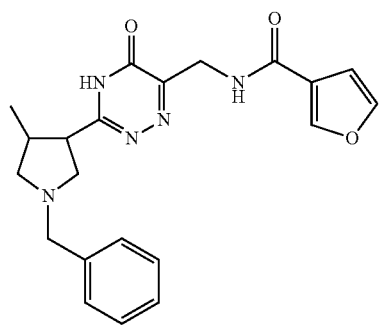

The mixture of (+/−)-6-(aminomethyl)-3-((3,4-trans)-1-benzyl-4-methylpyrrolidin-3-yl)-1,2,4-triazin-5(4H)-one (1.5 g, 5.0 mmol) and furan-2,5-dioxopyrrolidin-1-yl furan-3-carboxylate (1.15 g, 5.5 mmol) in CH₂Cl₂ (50 mL) was stirred at room temperature overnight. The precipitate was filtered and the filtrate was washed with water. The aqueous solution was extracted with chloroform (4×100 mL). The CH₂Cl₂ solution and chloroform extracts were combined and the solvents were evaporated and the residue was purified by column chromatography (silica gel, CH₂Cl₂/MeOH/NH₄OH, 10:1:0.5%) to prepare (+/−)-N-((3-((3,4-trans)-1-benzyl-4-methylpyrrolidin-3-yl)-5-oxo-4,5-dihydro-1,2,4-triazin-6-yl)methyl)furan-3-carboxamide (1.05 g, 45% yield). $^1$H NMR (300 MHz, CDCl₃/TMS): δ 7.98 (s, 1H), 7.54 (s, 1H), 7.36-7.26 (m, 5H), 6.70 (s, 1H), 4.60 (d, J=4 Hz, 2H), 4.00 (d, J=12 Hz, 1H), 3.90 (d, J=12 Hz, 1H), 3.44-3.13 (m, 4H), 2.60-2.45 (m, 2H), 1.02 (d, J=6 Hz, 3H).

Synthesis of (+)-2-((3,4-trans)-1-benzyl-4-methyl-pyrrolidin-3-yl)-7-(furan-3-yl)imidazo[5,1-f][1,2,4]triazin-4(3H)-one and (−)-2-((3,4-trans)-1-benzyl-4-methylpyrrolidin-3-yl)-7-(furan-3-yl)imidazo[5,1-f][1,2,4]triazin-4(3H)-one

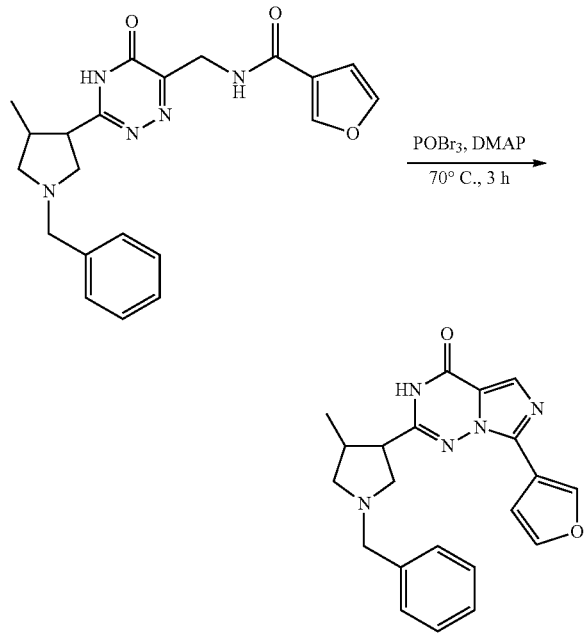

Phosphorus oxybromide (2.31 g, 8.0 mmol) was dissolved in acetonitrile (20 mL) and the solution was added to (+/−)-N-((3-((3,4-trans)-1-benzyl-4-methylpyrrolidin-3-yl)-5-oxo-4,5-dihydro-1,2,4-triazin-6-yl)methyl)furan-3-carboxamide (1.05 g, 2.7 mmol) and DMAP (50 mg) in acetonitrile (40 mL) at room temperature drop wise. The reaction mixture was heat up to 70° C. and stirred for 3 h. The reaction mixture was purred into the cold concentrated aqueous solution of NaHCO$_3$ (100 mL). The organics were extracted with CH$_2$Cl$_2$ (3×50 mL), the organic solution was washed with brine and dried over MgSO$_4$, the solvent was evaporated and residue was purified by column chromatography (silicagel, CH$_2$Cl$_2$/MeOH/NH$_4$OH, 30:1:1%) to obtain (+/−)-2-(3,4-trans)-1-benzyl-4-methylpyrrolidin-3-yl)-7-(furan-3-yl)imidazo[5,1-f][1,2,4]triazin-4(3H)-one (370 mg, 37% yield). Purity by HPLC: 97.3%; $^1$H NMR (300 MHz, CDCl$_3$/TMS): δ 8.39 (s, 1H), 7.90 (s, 1H), 7.49 (s, 1H), 7.37-7.28 (m, 5H), 7.12 (s, 1H), 3.81 (d, J=12 Hz, 1H), 3.58 (d, 0.1=12 Hz, 1H), 3.39 (t, =8 Hz, 1H), 3.00 (d, 0.1=10 Hz, 1H), 2.77 (m, 1H), 2.56-2.42 (m, 2H), 1.93 (t, J=10 Hz, 1H), 1.21 (d, J=7 Hz, 3H); $^{13}$C NMR (75 MHz, CDCl$_3$/TMS): δ 154.4, 154.0, 142.8, 142.6, 138.7, 137.0, 128.8, 128.6, 127.5, 119.2, 115.4, 109.2, 60.9, 59.2, 55.9, 48.1, 38.4, 20.2.

(+/−)-2-((3,4-trans)-1-benzyl-4-methylpyrrolidin-3-yl)-7-(furan-3-yl)imidazo[5,1-f][1,2,4]triazin-4(3H)-one was purified by Chiralpak IC, 250×20 mm, 5 um (20 mg loading; 0.1% TEA in n-Hexane: ethanol (70:30) as mobile phase) to obtain pure fraction 1 ((+)-2-((3,4-trans)-1-benzyl-4-methylpyrrolidin-3-yl)-7-(furan-3-yl)imidazo[5,1-f][1,2,4]triazin-4(3H)-one) and pure fraction 2 ((−)-2-((3,4-trans)-1-benzyl-4-methylpyrrolidin-3-yl)-7-(furan-3-yl)imidazo[5,1-f][1,2,4]triazin-4(3H)-one).

Characterization details of both fractions are as follows:

(+)-2-((3,4-trans)-1-benzyl-4-methylpyrrolidin-3-yl)-7-(furan-3-yl)imidazo[5,1-f][1,2,4]triazin-4(3H)-one:
$^1$H-NMR (DMSO d$_6$, 500 MHz): δ 8.43 (s, 1H), 7.86 (s, 1H), 7.82 (s, 1H), 7.34 (s, 4H), 7.24 (br s, 1H), 7.13 (s, 1H), 3.63 (q, 2H), 2.99 (t, 1H), 2.90-2.83 (m, 4H), 2.73-2.65 (m, 1H), 2.29 (t, 1H), 1.16 (d, 3H); LC-MS: 99.09%; 376.5 (M$^+$+1); (column; X select C-18, (50×3.0 mm, 3.5μ); RT 3.43 min. ACN: 5 mM NH$_4$OAc in water; 0.8 ml/min); UPLC (purity): 99.9%; (column; Acquity BEH C-18, 50×2.1 mm, 1.7μ; RT 1.62 min. 0.025% TFA (Aq): ACN:Water; 0.50 ml/min.; Chiral HPLC: 98.99% ee R$_t$=8.18 min (Chiralpak IC, 250× 4.6 mm, 5μ; mobile phase (A) 0.1% TEA in n-Hexane (B) Ethanol (A:B: 70:30); flow Rate: 1.00 mL/min); Optical rotation [α]$_D^{25}$: +28.12° (c=0.25, DCM).

(−)-2-((3,4-trans)-1-benzyl-4-methylpyrrolidin-3-yl)-7-(furan-3-yl)imidazo[5,1-f][1,2,4]triazin-4(3H)-one:
$^1$H-NMR (DMSO d$_6$, 400 MHz): δ 12.72-10.80 (m, 1H), 8.45 (s, 1H), 7.89 (s, 1H), 7.80 (s, 1H), 7.34 (s, 4H), 7.34 (br s, 1H), 7.10 (s, 1H), 3.62 (q, 2H), 2.99-2.79 (m, 4H), 2.71-2.60 (m, 1H), 2.29 (t, 1H), 1.13 (d, 3H); LC-MS: 95.47%; 376.5 (M$^+$+1); (column; X-bridge C-18, (50×3.0 mm, 3.5μ); RT 5.19 min. 5 mM NH$_4$OAc: ACN; 0.8 ml/min); UPLC (purity): 99.94%; (column; Acquity BEH C-18, 50×2.1 mm, 1.7μ; RT 1.60 min. 0.025% TFA (Aq): ACN:Water; 0.50 ml/min.; Chiral HPLC: 99.29% ee R$_t$=10.3 min (Chiralpak IC, 250×4.6 mm, 5μ; mobile phase (A) 0.1% TEA in n-Hexane (B) Ethanol (A:B: 70:30); flow Rate: 1.00 mL/min); Optical rotation [α]$_D^{24}$: −36.51° (c=0.25, DCM).

xxxiii. (+)-7-(1-acetylpiperidin-4-yl)-2-((3,4-trans)-1-benzyl-4-methylpyrrolidin-3-yl)imidazo[5,1-f][1,2,4]triazin-4(3H)-one and (−)-7-(1-acetylpiperidin-4-yl)-2-((3,4-trans)-1-benzyl-4-methylpyrrolidin-3-yl)imidazo[5,1-f][1,2,4]triazin-4(3H)-one

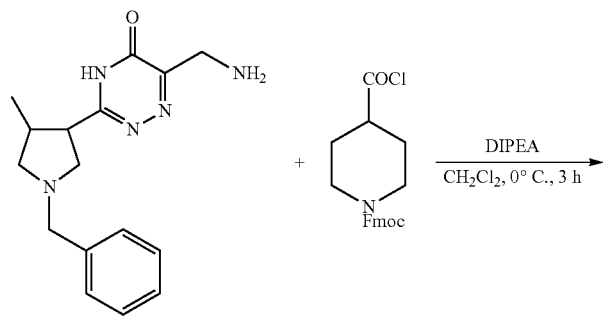

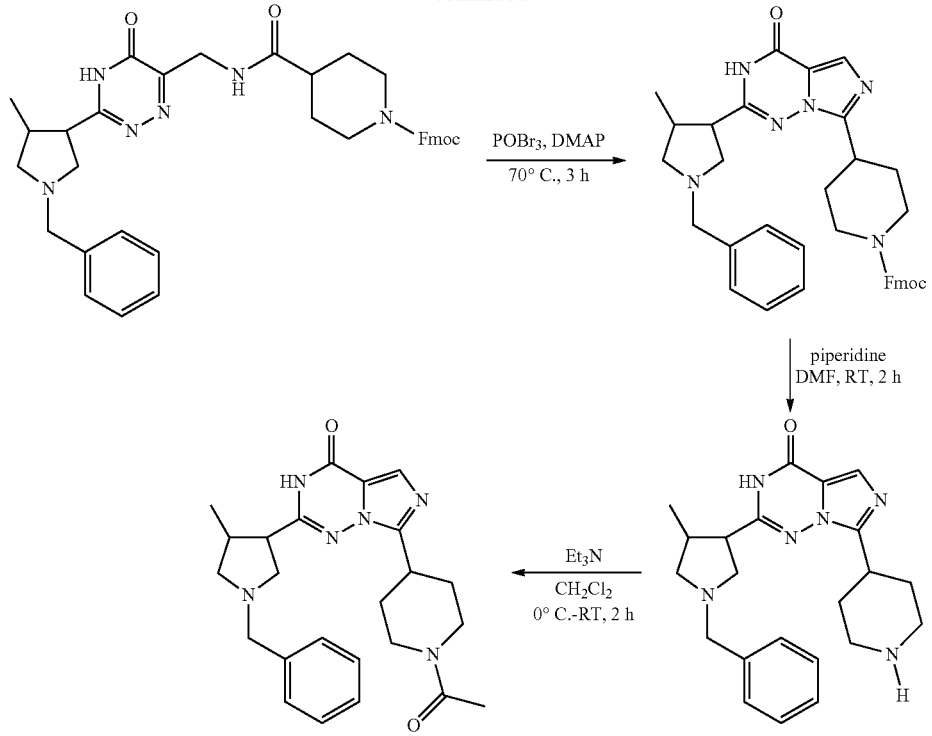

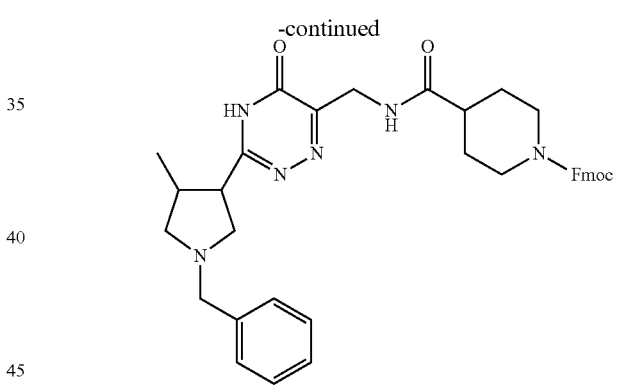

Synthesis of (+/−)-(9H-fluoren-9-yl)methyl 4-(((3-((3,4-trans)-1-benzyl-4-methylpyrrolidin-3-yl)-5-oxo-4,5-dihydro-1,2,4-triazin-6-yl)methyl)carbamoyl)piperidine-1-carboxylate

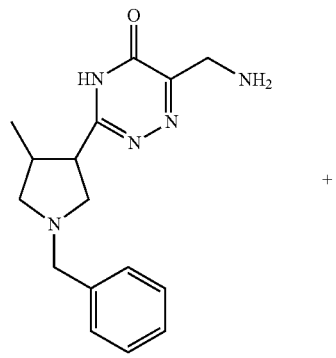

+

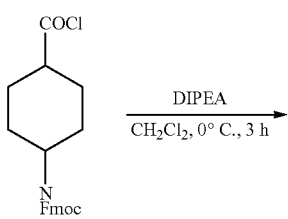

To a solution of (9H-fluoren-9-yl)methyl 4-(chlorocarbonyl)piperidine-1-carboxylate (2.45 g, 6.6 mmol) in $CH_2Cl_2$ (75 mL) was added a solution of (+/−)-6-(aminomethyl)-3-((3,4-trans)-1-benzyl-4-methylpyrrolidin-3-yl)-1,2,4-triazin-5(4H)-one (1.80 g, 6.0 mmol) and diisopropylethylamine (0.93 g, 7.2 mmol) in $CH_2Cl_2$ (75 mL) drop-wise at 0° C. The resulting solution was stirred at this temperature for 3 h. After which time the precipitate was filtered and the filter cake was washed with $CHCl_3$. The filtrated was treated with saturated $NaHCO_3$ (50 mL). The phases were separated, and the aqueous phase was extracted with $CHCl_3$ (2×20 mL). The combined organic phase was dried over $MgSO_4$. Concentration and purification by chromatography (0-10% $MeOH/CH_2Cl_2$) provided (+/−)-(9H-fluoren-9-yl)methyl 4-(((3-((3,4-trans)-1-benzyl-4-methylpyrrolidin-3-yl)-5-oxo-4,5-dihydro-1,2,4-triazin-6-yl)methyl)carbamoyl)piperidine-1-carboxylate (2.06 g, 54% yield) as a yellow solid. $^1$H NMR (300 MHz, $CDCl_3$) δ 7.76 (d, 2H, =7.5 Hz), 7.57 (d, 2H, J=7.8 Hz), 7.43-7.24 (m, 9H), 6.74 (br s, 1H), 4.55-4.35 (m, 4H), 4.28-4.05 (m, 3H), 3.90-3.70 (m, 2H, 3.45-3.35 (m, 1H), 3.20-3.10 (m, 1H), 2.98-2.70 (m, 4H), 2.55-2.40 (m, 1H), 2.38-2.27 (m, 1H), 2.25-2.00 (m, 1H), 1.90-1.80 (m, 2H), 1.74-1.58 (m, 2H), 1.15 (d, 3H, J=6.3 Hz); $^{13}$C NMR (75 MHz, CDCl$_3$) δ 174.1, 165.3, 162.6, 154.8, 150.5, 143.7, 141.0, 134.3, 129.2, 128.7, 128.3, 127.4, 126.8, 124.7, 119.7, 67.2, 60.3, 59.5, 56.6, 50.2, 47.2, 43.3, 42.8, 39.7, 38.5, 28.4, 18.4.

Synthesis of (+/−)-(9H-fluoren-9-yl)methyl 4-(2-((3,4-trans)-1-benzyl-4-methylpyrrolidin-3-yl)-4-oxo-3,4-dihydroimidazo[5,1-f][1,2,4]triazin-7-yl)piperidine-1-carboxylate

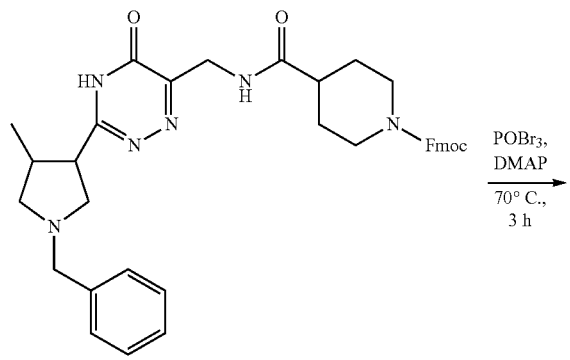

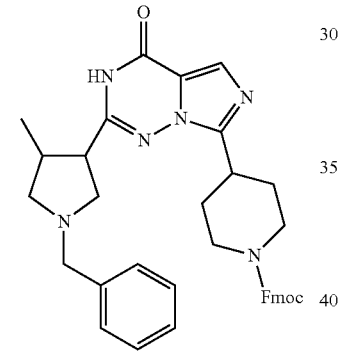

To a solution of (+/−)-(9H-fluoren-9-yl)methyl 4-(((3-((3,4-trans)-1-benzyl-4-methylpyrrolidin-3-yl)-5-oxo-4,5-dihydro-1,2,4-triazin-6-yl)methyl)carbamoyl)piperidine-1-carboxylate (2.14 g, 3.38 mmol) and DMAP (40 mg, 0.34 mmol) in acetonitrile (100 mL) was added a solution of POBr$_3$ (2.91 g, 10.15 mmol) in acetonitrile (70 mL) at RT, and the resulting suspension was heated to 70° C. for 3 h. After the mixture was cooled to room temperature, it was poured into cold saturated NaHCO$_3$ solution (250 mL), and stirred vigorously for 0.5 h, then extracted with CH$_2$Cl$_2$ (1×150 mL, 2×50 mL). The combined organic extracts were dried over MgSO$_4$ and concentrated under reduced pressure. The residue was purified by gradient flash chromatography over silica gel (0-10% MeOH/CH$_2$Cl$_2$) to furnish (+/−)-(9H-fluoren-9-yl)methyl 4-(2-((3,4-trans)-1-benzyl-4-methylpyrrolidin-3-yl)-4-oxo-3,4-dihydroimidazo[5,1-f][1,2,4]triazin-7-yl)piperidine-1-carboxylate (1.67 g, 80% yield) as a white foam. $^1$H NMR (300 MHz, CDCl$_3$/TMS) δ 9.40 (br s, 1H), 7.79 (s, 1H), 7.74 (d, J=7.8 Hz, 2H), 7.58 (d, J=7.5 Hz, 2H), 7.44-7.22 (m, 9H), 4.52-4.16 (m, 5H), 3.79 (d, J=12.3 Hz, 1H), 3.53 (d, J=12.6 Hz, 1H), 3.35 (t, J=8.3 Hz, 2H), 3.20-2.88 (m, 3H), 2.80-2.64 (m, 1H), 2.60-2.34 (m, 2H), 2.14-1.80 (m, 5H), 1.19 (d, J=6.9 Hz, 3H); $^{13}$C NMR (75 MHz, CDCl$_3$/TMS) δ 154.8, 154.1, 153.7, 148.0, 143.8, 141.0, 137.1, 128.5, 127.4, 127.3, 126.8, 124.7, 119.7, 118.8, 67.2, 60.9, 59.1, 55.8, 47.7, 47.2, 43.6, 38.2, 33.1, 29.4, 29.1, 20.1.

Synthesis of (+/−)-2-((3,4-trans)-1-benzyl-4-methylpyrrolidin-3-yl)-7-(piperidin-4-yl)imidazo[5,1-f][1,2,4]triazin-4(3H)-one

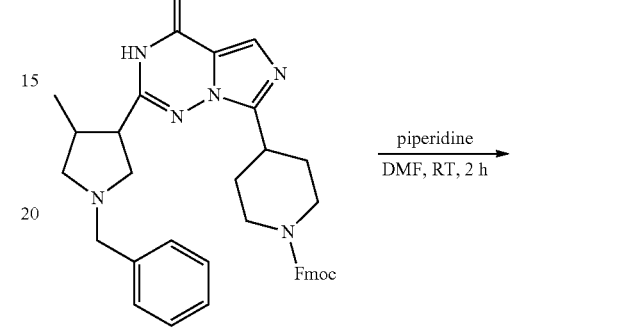

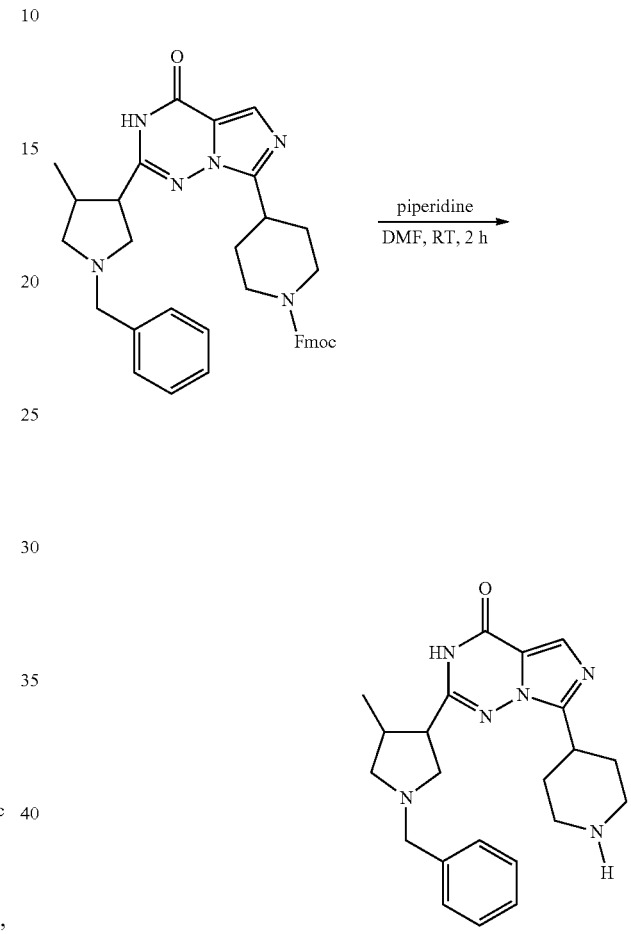

To a solution of (+/−)-(9H-fluoren-9-yl)methyl 4-(2-((3,4-trans)-1-benzyl-4-methylpyrrolidin-3-yl)-4-oxo-3,4-dihydroimidazo[5,1-f][1,2,4]triazin-7-yl)piperidine-1-carboxylate (1.67 g, 3.24 mmol) in DMF (50 mL) was added piperidine (5.53 g, 64.90 mmol) at RT, and the resulting solution was stirred at RT for 2 h. The solvent and excess piperidine was removed under reduced pressure. The residue was purified by flash chromatography over silica gel (0.1/1.5/98.4-1/15/84 NH$_4$OH/MeOH/CH$_2$Cl$_2$) to furnish (+/−)-2-((3,4-trans)-1-benzyl-4-methylpyrrolidin-3-yl)-7-(piperidin-4-yl)imidazo[5,1-f][1,2,4]triazin-4(3H)-one (0.75 g, 70% yield) as an off-white foam. Purity (HPLC): 99.5%; $^1$H NMR (300 MHz, CDCl$_3$/TMS) δ 7.78 (s, 1H), 7.40-7.24 (m, 5H), 5.25 (br s, 2H), 3.82 (d, 1H, J=12.6 Hz), 3.57 (d, 1H, J=12.6 Hz), 3.42-3.16 (m, 4H), 2.97 (d, 1H, J=9.9 Hz), 2.87-2.72 (m, 3H), 2.58-2.36 (m, 2H), 2.02-1.76 (m, 5H), 1.22 (d, 3H, J=7.2 Hz); $^{13}$C NMR (75 MHz, CDCl$_3$/TMS) δ 154.35, 153.55, 149.11, 137.14, 128.54, 127.47, 127.42, 118.57, 61.07, 59.25, 55.95, 47.80, 46.17, 38.27, 33.72, 30.89, 30.63, 20.11; HRMS: calculated for C$_{22}$H$_{29}$N$_6$O (MH$^+$), 393.2397. found: 393.2410.

Synthesis of (+)-7-(1-acetylpiperidin-4-yl)-2-((3,4-trans)-1-benzyl-4-methylpyrrolidin-3-yl)imidazo[5,1-f][1,2,4]triazin-4(3H)-one and (−)-7-(1-acetylpiperidin-4-yl)-2-((3,4-trans)-1-benzyl-4-methylpyrrolidin-3-yl)imidazo[5,1-f][1,2,4]triazin-4(3H)-one

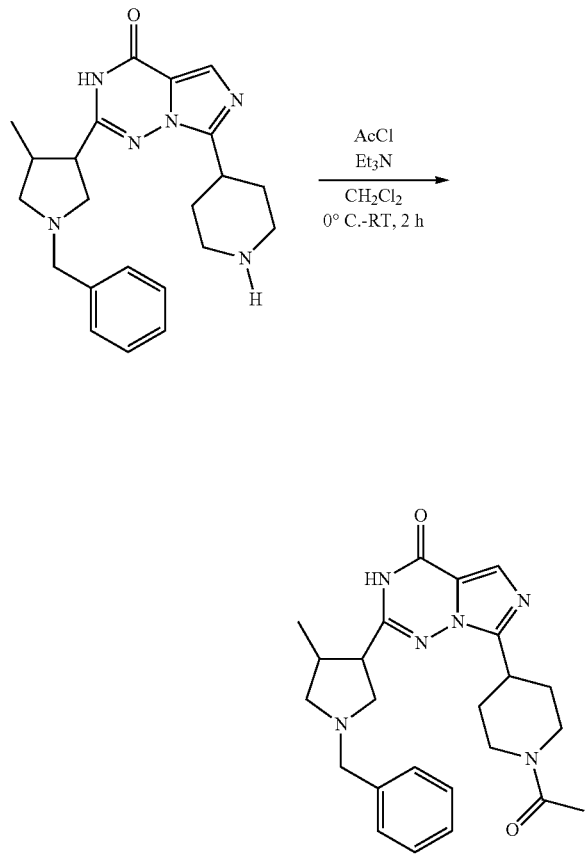 [SMILES: CC1CN(Cc2ccccc2)CC1c1nn2c(C3CCNCC3)ncc2c(=O)[nH]1 ; CC(=O)N1CCC(c2ncc3c(=O)[nH]c(C4CN(Cc5ccccc5)CC4C)nn23)CC1]

To a solution of (+/−)-2-((3,4-trans)-1-benzyl-4-methylpyrrolidin-3-yl)-7-(piperidin-4-yl)imidazo[5,1-f][1,2,4]triazin-4(3H)-one (0.30 g, 0.76 mmol) and triethylamine (0.23 g, 2.29 mmol) in $CH_2Cl_2$ (5 mL) was added acetyl chloride (0.09 g, 1.15 mmol) drop-wise at 0° C. After complete of addition, the ice-water bath was removed and the reaction mixture was stirred at RT for 2 h. The reaction mixture was diluted with $CH_2Cl_2$ (15 mL) and washed with saturated $NaHCO_3$ (5 mL), dried over $MgSO_4$. Concentration and purification by flash chromatography over silica gel (0.1/1.5/98.4-0.4/6.0/93.6 $NH_4OH/MeOH/CH_2Cl_2$) to furnish (+/−)-7-(1-acetylpiperidin-4-yl)-2-((3,4-trans)-1-benzyl-4-methylpyrrolidin-3-yl)imidazo[5,1-f][1,2,4]triazin-4(3H)-one (0.29 g, 87% yield) as a colorless wax. Purity (HPLC): 99.3%; $^1$H NMR (300 MHz, $CDCl_3$/TMS) 8.58 (br s, 1H), 7.76 (s, 1H), 7.42-7.23 (m, 5H), 4.62 (t, 1H, J=12.3 Hz), 3.94 (t, 1H, J=11.3 Hz), 3.82 (d, 1H, J=12.6 Hz), 3.57 (d, 1H, J=12.6 Hz), 3.50-3.34 (m, 2H), 3.32-3.18 (m, 1H), 2.98 (d, 1H, J=9.9 Hz), 2.90-2.74 (m, 2H), 2.60-2.52 (m, 1H), 2.50-2.40 (m, 1H), 2.12 (s, 3H), 2.08-1.72 (m, 5H), 1.23 (d, 3H, J=6.9 Hz); $^{13}$C NMR (75 MHz, $CDCl_3$/TMS) δ 168.54, 154.16, 153.80, 147.83, 137.15, 128.49, 127.40, 127.29, 118.78, 60.97, 59.17, 55.92, 47.75, 46.11, 41.16, 38.19, 33.11, 29.88, 29.59, 29.48, 29.23, 21.40, 20.09.

(+/−)-7-(1-acetylpiperidin-4-yl)-2-((3,4-trans)-1-benzyl-4-methylpyrrolidin-3-yl)imidazo[5,1-f][1,2,4]triazin-4(3H)-one was purified by Chiralcel OJ-H, 250×20 mm, 5 um (30 mg loading; 0.1% TEA in n-Hexane: Ethanol (90:10) as mobile phase) to obtain pure fraction 1 ((−)-7-(1-acetylpiperidin-4-yl)-2-(3,4-trans)-1-benzyl-4-methylpyrrolidin-3-yl)imidazo[5,1-f][1,2,4]triazin-4(3H)-one) and pure fraction 2 ((+)-7-(1-acetylpiperidin-4-yl)-2-((3,4-trans)-1-benzyl-4-methylpyrrolidin-3-yl)imidazo[5,1-f][1,2,4]triazin-4(3H)-one). Characterization details of both fractions are as follows:

(−)-7-(1-acetylpiperidin-4-yl)-2-((3,4-trans)-1-benzyl-4-methylpyrrolidin-3-yl)imidazo[5,1-f][1,2,4]triazin-4(3H)-one: H-NMR (DMSO $d_6$, 400 MHz): δ 7.64 (s, 1H), 7.37-7.32 (m, 4H), 7.24-7.21 (m, 1H), 4.39-4.32 (m, 1H), 3.92-3.86 (m, 1H), 3.67-3.62 (m, 2H), 3.48-3.47 (m, 1H), 2.98-2.94 (m, 6H), 2.72-2.67 (m, 2H), 2.34-2.31 (m, 1H), 2.04 (s, 3H), 1.98-1.96 (m, 2H), 1.84-1.81 (m, 1H), 1.68-1.62 (m, 1H), 1.09 (d, 3H); LC-MS: 93.15%; 435 ($M^+$+1); (column; X-bridge C-18, (50×3.0 mm, 3.5μ); RT 2.86 min. 5 mM $NH_4OAc$: ACN; 0.8 ml/min); UPLC (purity): 100%; (column; Acquity BEH C-18, 50×2.1 mm, 1.7μ; RT 1.36 min. 0.025% TFA (Aq): ACN:Water; 0.50 ml/min.; Chiral HPLC: 100% ee $R_t$=38.92 min (Chiralcel OJ-H, 250×4.6 mm, 5 g; mobile phase (A) 0.1% TEA in n-Hexane (B) ethanol (A:B: 90:10); flow Rate: 1.00 mL/min); Optical rotation $[\alpha]_D^{25}$: −25.72° (c=0.25, DCM).

(+)-7-(1-acetylpiperidin-4-yl)-2-((3,4-trans)-1-benzyl-4-methylpyrrolidin-3-yl)imidazo[5,1-f][1,2,4]triazin-4(3H)-one: H-NMR (DMSO $d_6$, 400 MHz): δ 7.62 (s, 1H), 7.34-7.29 (m, 4H), 7.24-7.22 (m, 1H), 4.36-4.34 (m, 1H), 3.92-3.89 (m, 1H), 3.68-3.62 (m, 2H), 3.47-3.41 (m, 2H), 3.28-3.26 (m, 2H), 2.98-2.96 (m, 1H), 2.67-2.63 (m, 2H), 2.29-2.27 (m, 1H), 2.02 (s, 3H), 1.98-1.94 (m, 2H), 1.84-1.82 (m, 1H), 1.64-1.61 (m, 1H), 1.08 (d, 3H); LC-MS: 91.25%; 435 ($M^+$+1); (column; X-bridge C-18, (50×3.0 mm, 3.5μ); RT 2.85 min. 5 mM $NH_4OAc$: ACN; 0.8 ml/min); UPLC (purity): 99.35%; (column; Acquity BEH C-18, 50×2.1 mm, 1.7μ; RT 1.35 min. 0.025% TFA (Aq): ACN:Water; 0.50 ml/min.; Chiral HPLC: 100% ee $R_t$=45.10 min (Chiralcel OJ-H, 250×4.6 mm, 5μ; mobile phase (A) 0.1% TEA in n-Hexane (B) ethanol (A:B: 90:10); flow Rate: 1.00 mL/min); Optical rotation $[\alpha]_D^{25}$: +26.38° (c=0.25, DCM).

xxxiv. (−)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one

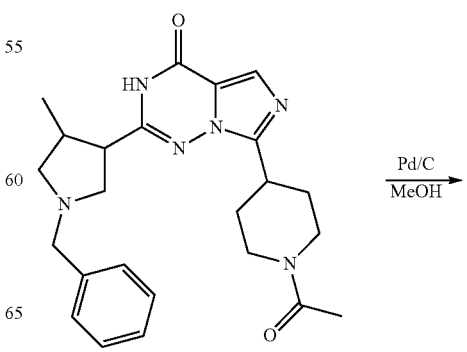

-continued

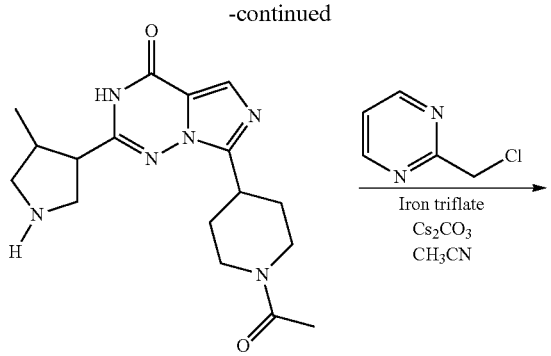

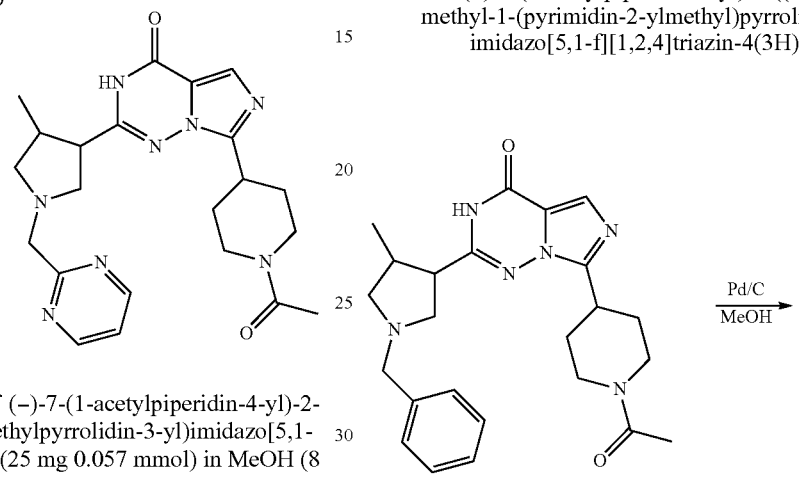

To a stirred solution of (−)-7-(1-acetylpiperidin-4-yl)-2-((3,4-trans)-1-benzyl-4-methylpyrrolidin-3-yl)imidazo[5,1-f][1,2,4]triazin-4(3H)-one (25 mg 0.057 mmol) in MeOH (8 mL) was added 10% Pd—C (6 mg) under a $N_2$ atmosphere. The reaction mixture was stirred at RT for 10 h under $H_2$ atmosphere (balloon pressure). The reaction mixture was passed through a pad of celite and dried in vacuo to obtain crude. The crude material was washed with n-pentane to afford 7-(1-acetylpiperidin-4-yl)-2-((3,4-trans)-4-methylpyrrolidin-3-yl)imidazo[5,1-f][1,2,4]triazin-4(3H)-one (16 mg, crude) as an off-white solid. $^1$H-NMR (DMSO $d_6$, 400 MHz): δ 7.65 (s, 1H), 7.47 (br s, 1H), 4.76 (q, 1H), 4.41-4.35 (m, 1H), 3.85-3.80 (m, 1H), 3.35-3.30 (m, 3H), 2.97 (d, 1H), 2.82 (t, 2H), 2.64-2.60 (m, 1H), 2.46-2.41 (m, 1H), 2.01 (s, 3H), 1.91-1.80 (m, 2H), 1.72-1.70 (m, 2H), 1.01 (s, 3H); Mass (ESI): 345 [(M$^+$+1)]; LC-MS: 48.83%; 345 (M$^+$+1); (column; X-bridge C-18, (50×3.0 mm, 3.5 um); RT 1.69 min. 5 mM NH$_4$OAc: ACN; 0.8 ml/min); TLC: 10% MeOH/CH$_2$Cl$_2$ (Rf 0.1).

To a stirred solution of 7-(1-acetylpiperidin-4-yl)-2-((3,4-trans)-4-methylpyrrolidin-3-yl)imidazo[5,1-f][1,2,4]triazin-4(3H)-one (35 mg, 0.1 mmol) in ACN (10 mL) were added 2-(chloromethyl)pyrimidine (14.3 mg, 0.11 mmol), iron triflate (10 mg, 0.02 mmol) and Cs$_2$CO$_3$ (66 mg, 0.2 mmol) at RT under inert atmosphere. The resultant reaction mixture was heated at 70° C. and stirred for 3 h. After full consumption of starting material (by TLC), the reaction mixture was diluted with water and extracted with EtOAc (2×25 mL). Combined organic layers were dried over anhydrous sodium sulfate, filtered and concentrated in vacuo to obtain the crude product. The crude material was purified by silica gel column chromatography to afford (−)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one (20 mg, 22%) as an off-white solid. $^1$H-NMR (DMSO $d_6$, 400 MHz): δ 8.79 (d, 2H), 7.68 (s, 1H), 7.44 (t, 1H), 4.39-4.30 (m, 1H), 4.02 (d, 1H), 3.89 (d, 2H), 3.45-3.40 (m, 1H), 3.28-3.25 (m, 1H), 3.14 (t, 2H), 3.03-2.97 (m, 2H), 2.81-2.76 (m, 2H), 2.64-2.60 (m, 1H), 2.38 (t, 1H), 2.02 (s, 3H), 1.95 (t, 2H), 1.80-1.72 (m, 2H), 1.11 (d, 3H); Mass (ESI): 437.6 [M$^+$+1]; LC-MS: 97.43%; 437.5 (1\e+1); (column; Xbridge C-18, (50×3.0 mm, 3.5 um); RT 2.73 min. 5 mM NH4OAC: ACN; 0.8 ml/min); UPLC (purity): 96.67%; (column; Acquity UPLC HSS T3, 100×2.1 mm, 1.7µ; RT 2.95 min. 0.025% TFA (Aq): ACN:Water; 0.3 ml/min.; TLC: 10% MeOH/DCM (Rf: 0.5). Chiral HPLC: 99.44% ee R$_t$=14.61 min (Chiralpak IA, 250×4.6 mm, 5 um; mobile phase (A) 0.1% DBA in n-Hexane (B) IPA (A:B: 60:40); flow Rate: 1.00 mL/min); Optical rotation [α]$_D^{23}$: −29.92° (c=0.125, DCM).

xxxv. (+)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one

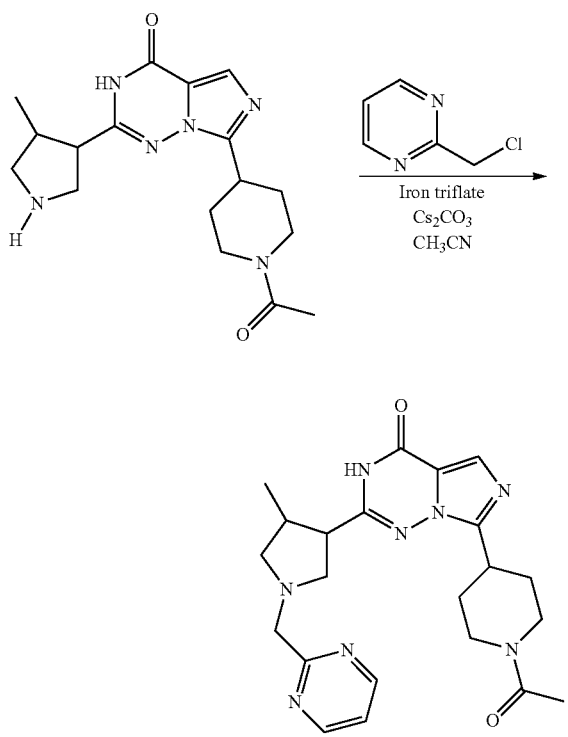

To a stirred solution of (+)-7-(1-acetylpiperidin-4-yl)-2-((3,4-trans)-1-benzyl-4-methylpyrrolidin-3-yl)imidazo[5,1-f][1,2,4]triazin-4(3H)-one (90 mg 0.207 mmol) in MeOH (10 mL) was added 10% Pd—C (25 mg) under $N_2$ atmosphere. The reaction mixture was stirred at RT for 10 h under H₂ atmosphere (balloon pressure). The reaction mixture was passed through a pad of celite and dried in vacuo to obtain crude 7-(1-acetylpiperidin-4-yl)-2-((3,4-trans)-4-methylpyrrolidin-3-yl)imidazo[5,1-f][1,2,4]triazin-4(3H)-one (75 mg, crude) as an off-white solid. Mass (ESI): 345 [(M⁺+1)]; LC-MS: 87.06%; 345 (M⁺+1); (column; X-bridge C-18, (50×3.0 mm, 3.5 um); RT 1.82 min. 5 mM NH₄OAc: ACN; 0.8 ml/min); TLC: 5% MeOH/CH₂Cl₂ (Rf 0.1).

To a stirred solution of 7-(1-acetylpiperidin-4-yl)-2-((3,4-trans)-4-methylpyrrolidin-3-yl)imidazo[5,1-f][1,2,4]triazin-4(3H)-one (75 mg, 0.2 mmol) in ACN (5 mL) were added 2-(chloromethyl)pyrimidine (30 mg, 0.23 mmol), iron triflate (21 mg, 0.04 mmol) and Cs₂CO₃ (142 mg, 0.4 mmol) at RT under inert atmosphere. The resultant reaction mixture was heated to 70° C. and stirred for 4 h. After full consumption of starting material (by TLC), the reaction mixture was diluted with water and extracted with EtOAc (3×25 mL). Combined organic layers were dried over anhydrous sodium sulphate, filtered and concentrated in vacuo to obtain the crude product. The crude material was purified by silica gel column chromatography to afford (+)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one (20 mg, 21%) as an off-white solid. ¹H-NMR (DMSO d₆, 400 MHz): δ 8.79 (d, 2H), 7.68 (s, 1H), 7.44 (t, 1H), 4.39-4.30 (m, 1H), 4.02 (d, 1H), 3.89 (d, 2H), 3.45-3.40 (m, 1H), 3.14 (t, 1H), 3.03-2.97 (m, 2H), 2.81-2.76 (m, 2H), 2.64-2.60 (m, 2H), 2.38 (t, 1H), 2.02 (s, 3H), 1.95 (t, 2H), 1.80-1.72 (m, 2H), 1.11 (d, 3H); Mass (ESI): 437.6 [M⁺+1]; LC-MS: 95.86%; 437.6 (M⁺+1); (column; Xbridge C-18, (50×3.0 mm, 3.5 um); RT 2.78 min. 0.1% Aqueous TFA: ACN; 0.8 ml/min); HPLC (purity): 96.55%; (column; Eclipse XDB C-18, 150× 3.0 mm, 3 um; RT 7.42 min. ACN: 5 mM NH4OAC: ACN:Water; 1.0 ml/min.; TLC: 5% MeOH/DCM (Rf: 0.4). Chiral HPLC: 98.67% ee R$_t$=11.24 min (Chiralpak IA, 250×4.6 mm, 5 um; mobile phase (A) 0.1% DBA in n-Hexane (B) IPA (A:B: 60:40); flow Rate: 1.00 mL/min); Optical rotation [α]$_D^{23}$: +140.64° (c=0.125, DCM).

xxxvi. (+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one and (−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one

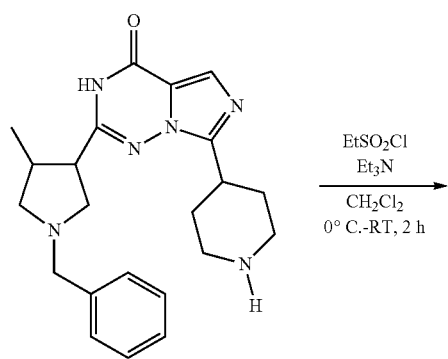

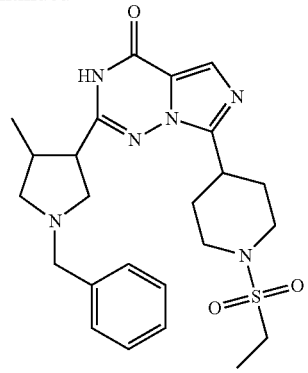

To a solution of (+/−)-2-((3,4-trans)-1-benzyl-4-methylpyrrolidin-3-yl)-7-(piperidin-4-yl)imidazo[5,1-f][1,2,4]triazin-4(3H)-one (0.31 g, 0.79 mmol) and triethylamine (0.24 g, 2.37 mmol) in CH₂Cl₂ (5 mL) was added ethanesulfonyl chloride (0.15 g, 1.18 mmol) drop-wise at 0° C. After complete of addition, the ice-water bath was removed and the reaction mixture was stirred at RT for 2 h. The reaction mixture was diluted with CH₂Cl₂ (15 mL) and washed with saturated NaHCO₃ (5 mL), dried over MgSO₄. Concentration and purification by flash chromatography over silica gel (0.1/1.5/98.4-0.3/4.5/95.2 NH₄OH/MeOH/CH₂Cl₂) gave (+/−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one (0.33 g, 86% yield) as a white foam. HPLC: 98.0% (rt=11.09 min); NMR (300 MHz, CDCl₃/TMS) δ 7.78 (s, 1H), 7.47-7.24 (m, 5H), 4.00-3.79 (m, 3H), 3.56 (d, 1H, J=12.3 Hz), 3.45-3.25 (m, 2H), 3.15-2.94 (m, 5H), 2.82-2.72 (m, 1H), 2.60-2.46 (m, 2H), 2.20-1.90 (m, 5H), 1.39 (t, 3H, 1=7.4 Hz) 1.22 (d, 3H, J=6.6 Hz); ¹³C NMR (75 MHz, CDCl₃/TMS) δ 154.12, 153.94, 147.55, 137.07, 128.57, 127.52, 127.41, 118.92, 61.02, 59.20, 55.86, 47.77, 45.34, 45.31, 44.54, 38.31, 32.60, 29.49, 29.20, 20.16, 7.98.

(+/−)-2-((3,4-Trans)-1-benzyl-4-methylpyrrolidin-3-yl)-7-(1-(ethylsulfonyl)piperidin-4-yl)imidazo[5,1-f][1,2,4]triazin-4(3H)-one was purified by Chiralcel OJ-H, 250×20 mm, 5 um (40 mg loading; 0.1% TEA in n-Hexane: Ethanol (50:50) as mobile phase) to obtain pure fraction 1 ((+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one) and pure fraction 2 ((−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one). Characterization details of both fractions are as follows:

(+)-2-((3,4-trans)-1-benzyl-4-methy 1pyrrolidin-3-yl)-7-(1-(ethylsulfonyl)piperidin-4-yl)imidazo[5,1-f][1,2,4]triazin-4(3H)-one: H-NMR (DMSO d₆, 400 MHz): δ 7.58 (s, 1H), 7.34-7.28 (m, 4H), 7.24-7.21 (m, 1H), 3.68-3.62 (m, 4H), 3.18-3.14 (m, 4H), 3.94-3.92 (m, 2H), 3.87-3.84 (m, 1H), 2.79-2.74 (m, 2H), 2.68-2.62 (m, 1H), 2.24-2.21 (m, 1H), 2.02-1.97 (m, 2H), 1.89-1.82 (m, 2H), 1.24 (t, 3H), 1.08 (d, 3H); Mass (ESI): 485 [M⁺+1]; LC-MS: 97.97%; 485 (M⁺+1); (column; X-bridge C-18, (50×3.0 mm, 3.5μ); RT 3.34 min, 5 mM NH₄OAc: ACN: 0.8 ml/min); UPLC (purity): 99.85%; (column; Acquity BEH C-18, 50×2.1 mm, 1.7μ; RT 1.56 min. 0.025% TFA (Aq): ACN:Water; 0.50 ml/min.; Chiral HPLC: 100% ee R$_t$=13.31 min (Chiralcel OJ-H, 250×4.6 mm, 5μ; mobile phase (A) 0.1% TEA in n-Hexane (B) ethanol (A:B: 50:50); flow Rate: 1.00 mL/min); Optical rotation [α]$_D^{24}$: +18.32° (c=0.25, DCM).

(−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one: H-NMR (DMSO d$_6$, 400 MHz): δ 7.68 (s, 1H), 7.34-7.29 (m, 4H), 7.24-7.21 (m, 1H), 3.72-3.65 (m, 4H), 3.38-3.32 (m, 1H), 3.12-3.07 (m, 4H), 2.98-2.96 (m, 1H), 2.87-2.84 (m, 1H), 2.79-2.77 (m, 2H), 2.64-2.62 (m, 1H), 2.29-2.27 (m, 1H), 2.07-2.03 (m, 2H), 1.89-1.84 (m, 2H), 1.26 (t, 3H), 1.07 (d, 3H); Mass (ESI): 485 [M$^+$+1]; LC-MS: 94.38%; 485 (M$^+$+1); (column; X-bridge C-18, (50×3.0 mm, 3.5μ); RT 3.28 min, 5 mM NH$_4$OAc: ACN; 0.8 ml/min); UPLC (purity): 99.05%; (column; Acquity BEH C-18, 50×2.1 mm, 1.7 g; RT 1.58 min. 0.025% TFA (Aq): ACN:Water; 0.50 ml/min.; Chiral HPLC: 98.67% cc R$_t$=20.84 min (Chiralcel OJ-H, 250×4.6 mm, 5μ; mobile phase (A) 0.1% TEA in n-Hexane (B) ethanol (A:B: 50:50); flow Rate: 1.00 mL/min); Optical rotation [α]$_D^{25}$: −21.98° (c=0.25, DCM).

xxxvii. (+)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one

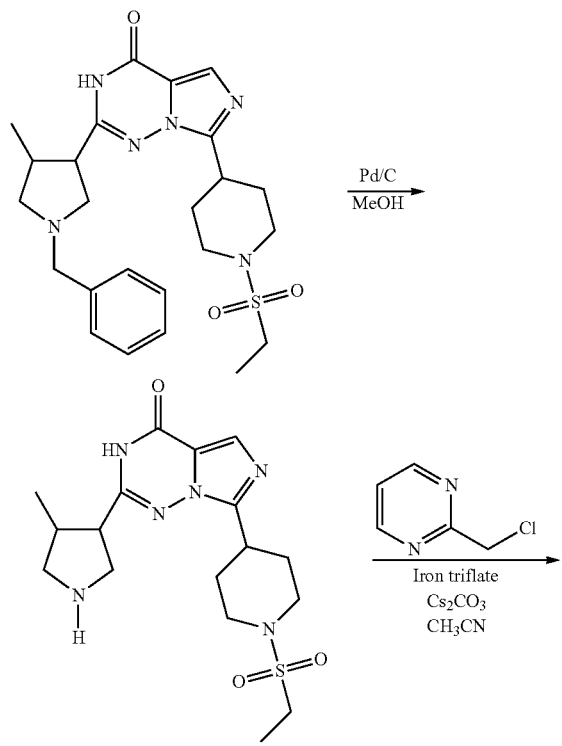

To a stirred solution of (+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one (80 mg 0.165 mmol) in MeOH (10 mL) was added 10% Pd—C (25 mg) under N$_2$ atmosphere. The reaction mixture was stirred at RT for 10 h under H$_2$ atmosphere (balloon pressure). The reaction mixture was passed through a pad of celite and dried in vacuo to obtain crude 7-(1-(ethylsulfonyl)piperidin-4-yl)-2-((3,4-trans)-4-methylpyrrolidin-3-yl)imidazo[5,1-f][1,2,4]triazin-4(3H)-one (100 mg, crude) as an off-white solid. LC-MS: 88.31%; 395.5 (M$^+$+1); (column; X-bridge C-18, (50×3.0 mm, 3.5 um); RT 2.16 min. 5 mM NH$_4$OAc: ACN; 0.8 ml/min); TLC: 10% MeOH/CH$_2$Cl$_2$ (Rf 0.1).

To a stirred solution of 7-(1-(ethylsulfonyl)piperidin-4-yl)-2-((3,4-trans)-4-methylpyrrolidin-3-yl)imidazo[5,1-f][1,2,4]triazin-4(3H)-one (100 mg, 0.2 mmol) in ACN (10 mL) were added 2-(chloromethyl)pyrimidine (35 mg, 0.27 mmol), iron triflate (25 mg, 0.05 mmol) and Cs$_2$CO$_3$ (165 mg, 0.5 mmol) at RT under inert atmosphere. The resultant reaction mixture was heated at 70° C. and stirred for 4 h. After full consumption of starting material (by TLC), the reaction mixture was diluted with water and extracted with EtOAc (3×25 mL). Combined organic layers were dried over anhydrous sodium sulphate, filtered and concentrated in vacuo to obtain the crude product. The crude material was purified by silica gel column chromatography and further purified by preparative to afford (+)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one (20 mg, 16%) as semi solid. $^1$H-NMR (DMSO d$_6$, 400 MHz): δ 8.79 (d, 2H), 7.68 (s, 1H), 7.44 (t, 1H), 4.02 (d, 1H), 3.89 (d, 1H), 3.71-3.65 (m, 2H), 3.39-3.20 (m, 1H), 3.18-3.10 (m, 3H), 2.78 (q, 1H), 2.67-2.60 (m, 1H), 2.61-2.55 (m, 1H), 2.37 (t, 1H), 2.01 (d, 2H), 1.85-1.80 (m, 2H), 1.52 (t, 2H), 1.34-1.30 (m, 2H), 1.25 (s, 3H), 1.12 (d, 31-1); Mass (ESI): 487.6 [M$^+$+1]; LC-MS: 96.31%; 487.9 (M$^+$+1); (column; Xbridge C-18, (50×3.0 mm, 3.5 um); RT 2.45 min. 0.1% Aqueous TFA: ACN; 0.8 ml/min); UPLC (purity): 96.89%; (column; Aquity BEH C-18, 50×2.1 mm, 1.7μ; RT 1.34 min. ACN: 0.025% Aqueous TFA: ACN:Water; 0.5 ml/min.; TLC: 5% MeOH/DCM (Rf: 0.4). Chiral UPLC: 99.63% ee R$_t$=12.15 min (Chiralpak IA, 250×4.6 mm, 5 um; mobile phase (A) 0.1% DBA in n-Hexane (B) IPA (A:B: 60:40); flow Rate: 1.00 mL/min); Optical rotation [α]$_D^{24}$: +53.12° (c=0.125, DCM).

xxxviii. (−)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one

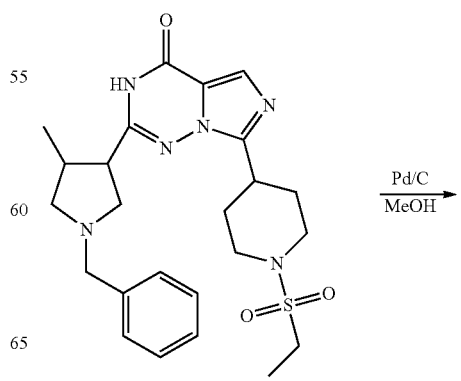

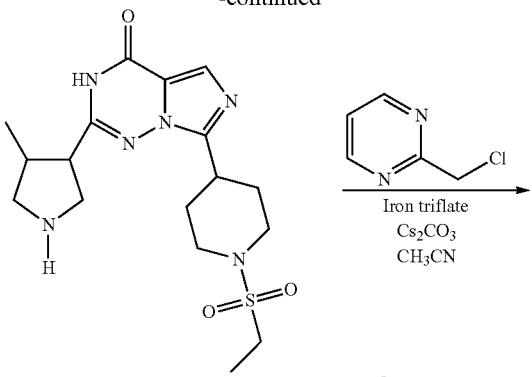

To a stirred solution of (−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one (90 mg, 0.185 mmol) in MeOH (10 mL) was added 10% Pd—C (25 mg) under $N_2$ atmosphere. The reaction mixture was stirred at RT for 10 h under $H_2$ atmosphere (balloon pressure). The reaction mixture was passed through a pad of celite and dried in vacuo to obtain crude 7-(1-(ethylsulfonyl)piperidin-4-yl)-2-((3,4-trans)-4-methylpyrrolidin-3-yl)imidazo[5,1-f][1,2,4]triazin-4(3H)-one (80 mg, crude) as an off-white solid. LC-MS: 47.32%; 395 (M+1); (column; X-bridge C-18, (50×3.0 mm, 3.5 um); RT 2.04 min. 5 mM $NH_4OAc$: ACN; 0.8 ml/min); TLC: 5% $MeOH/CH_2Cl_2$ (Rf 0.1).

To a stirred solution of 7-(1-(ethylsulfonyl)piperidin-4-yl)-2-((3,4-trans)-4-methylpyrrolidin-3-yl)imidazo[5,1-f][1,2,4]triazin-4(3H)-one (80 mg, 0.2 mmol) in ACN (5 mL) were added 2-(chloromethyl)pyrimidine (28 mg, 0.22 mmol), iron triflate (20 mg, 0.04 mmol) and $Cs_2CO_3$ (132 mg, 0.4 mmol) at RT. The resultant reaction mixture was heated up to 70° C. and stirred for 4 h. After full consumption of starting material (by TLC), the reaction mixture was diluted with water and extracted with EtOAc (2×25 mL) & $CH_2Cl_2$ (2×25 mL). Combined organic layers were dried over anhydrous sodium sulphate, filtered and concentrated in vacuo to obtain the crude product. The crude material was purified by silica gel column chromatography to afford (−)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one (22 mg, 22%) as an off-white solid. $^1$H-NMR (DMSO $d_6$, 400 MHz): δ 8.79 (d, 2H), 7.68 (s, 1H), 7.44 (t, 1H), 4.02 (d, 1H), 3.89 (d, 1H), 3.71-3.65 (m, 2H), 3.29-3.19 (m, 8H), 2.78 (q, 1H), 2.67-2.60 (m, 1H), 2.41 (t, 1H), 2.02 (d, 2H), 1.85-1.80 (m, 2H), 1.25 (t, 4H), 1.12 (d, 3H); Mass (ESI): 487 [M$^+$+1]; LC-MS: 96.21%; 487.6 (M$^+$+1); (column; Xbridge C-18, (50×3.0 mm, 3.5 um); RT 3.22 min. 5 mM NH4OAC: ACN; 0.8 ml/min); HPLC (purity): 98.53%; (column; Eclipse XDB C-18, 150× 4.6 mm, 5 um; RT 8.29 min. ACN: 5 mM NH4OAC: ACN:Water; 1.0 ml/min.; TLC: 5% MeOH/DCM (Rf: 0.45). Chiral HPLC: 99.12% ee $R_t$=16.93 min (Chiralpak IA, 250×4.6 mm, 5 um; mobile phase (A) 0.1% DBA in n-Hexane (B) IPA (A:B: 60:40); flow Rate: 1.00 mL/min); Optical rotation $[α]_D^{26}$: −83.3° (c=0.125, DCM).

xxxix. (+)-2-((3,4-trans)-1-benzyl-4-methylpyrrolidin-3-yl)-7-(2-hydroxypropan-2-yl)imidazo[5,1-f][1,2,4]triazin-4(3H)-one and (−)-2-((3,4-trans)-1-benzyl-4-methylpyrrolidin-3-yl)-7-(2-hydroxypropan-2-yl)imidazol[5,1-f][1,2,4]triazin-4(3H)-one

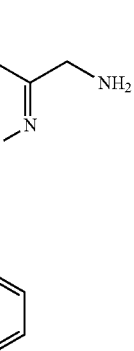

+

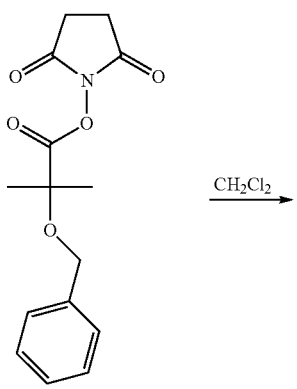

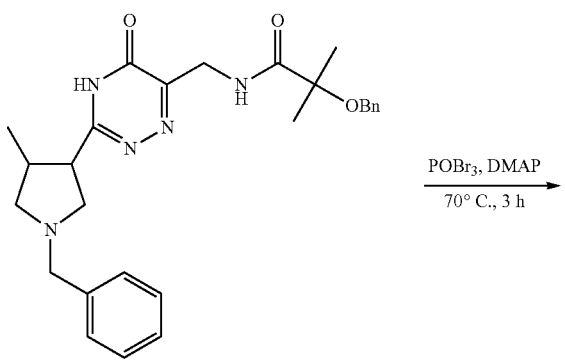

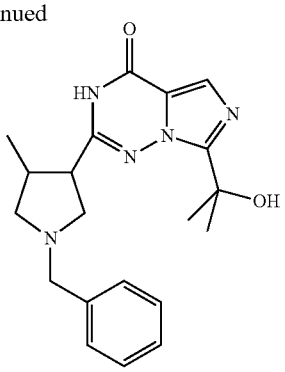

Synthesis of (+/−)-N-((3-((3,4-trans)-1-benzyl-4-methylpyrrolidin-3-yl)-5-oxo-4,5-dihydro-1,2,4-triazin-6-yl)methyl)-2-(benzyloxy)-2-methylpropanamide

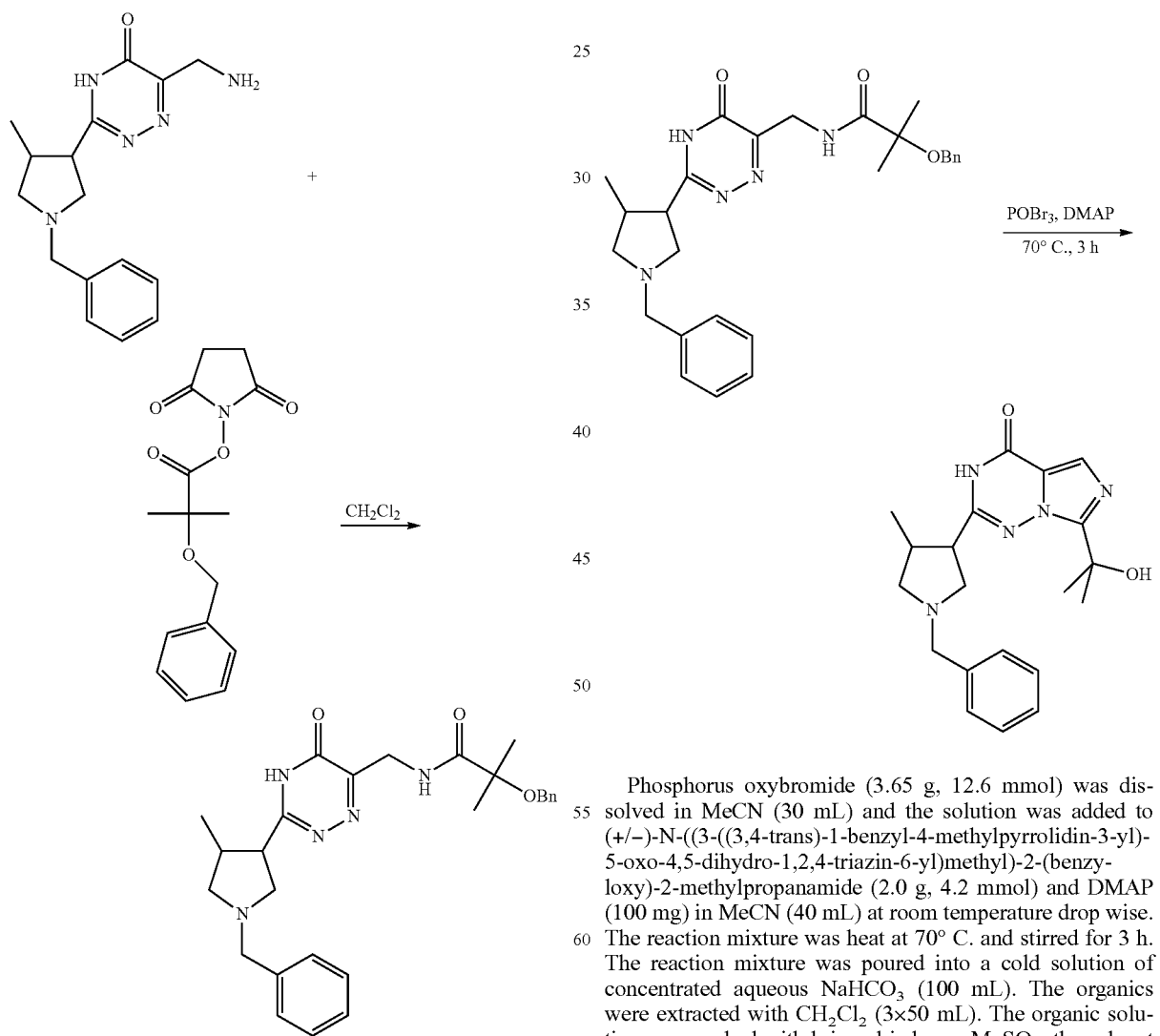

The mixture of (+/−)-6-(aminomethyl)-3-((3,4-trans)-1-benzyl-4-methylpyrrolidin-3-yl)-1,2,4-triazin-5(4H)-one (1.3 g, 4.3 mmol) and 2,5-dioxopyrrolidin-1-yl 2-(benzyloxy)-2-methylpropanoate (1.4 g, 4.8 mmol) in $CH_2Cl_2$ (50 mL) was stirred at room temperature overnight. The precipitate was filtered and the filtrate was washed with water. The aqueous solution was extracted with chloroform (4×100 ml). The $CH_2Cl_2$ solution and chloroform extracts were combined, the solvents were evaporated, and the residue was purified by column chromatography (silica gel, $CH_2Cl_2$/MeOH/$NH_4OH$, 10:1:0.5%) to prepare (+/−)-N-((3-((3,4-trans)-1-benzyl-4-methylpyrrolidin-3-yl)-5-oxo-4,5-dihydro-1,2,4-triazin-6-yl)methyl)-2-(benzyloxy)-2-methylpropanamide (2.0 g, 100% yield). $^1H$ NMR (300 MHz, $CDCl_3$/TMS): δ 8.4 (br s, 1H), 7.34-7.22 (m, 10H), 4.50 (s, 2H), 4.02 (s, 2H), 3.44-3.30 (m, 4H), 2.69 (m, 1H), 1.48 (s, 3H), 1.48 (s, 6H), 1.09 (s, 3H).

Synthesis of (+)-2-((3,4-trans)-1-benzyl-4-methylpyrrolidin-3-yl)-7-(2-hydroxypropan-2-yl)imidazo[5,1-f][1,2,4]triazin-4(3H)-one and (−)-2-((3,4-trans)-1-benzyl-4-methylpyrrolidin-3-yl)-7-(2-hydroxypropan-2-yl)imidazo[5,1-f][1,2,4]triazin-4(3H)-one

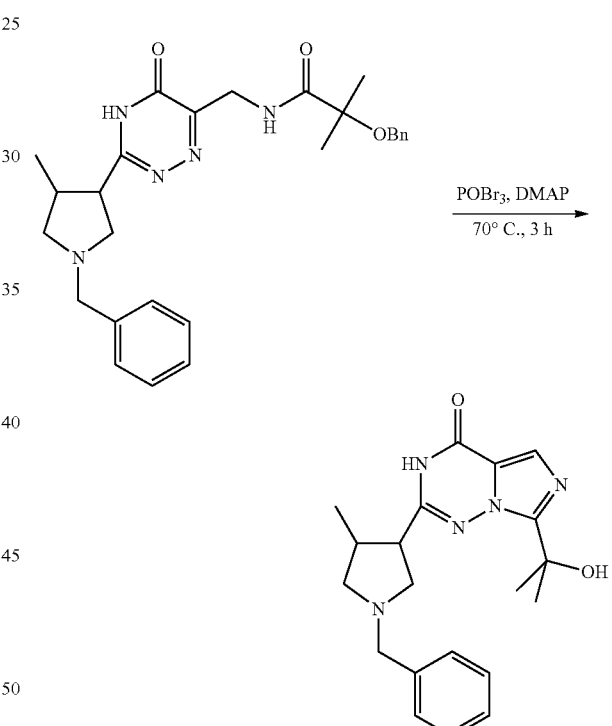

Phosphorus oxybromide (3.65 g, 12.6 mmol) was dissolved in MeCN (30 mL) and the solution was added to (+/−)-N-((3-((3,4-trans)-1-benzyl-4-methylpyrrolidin-3-yl)-5-oxo-4,5-dihydro-1,2,4-triazin-6-yl)methyl)-2-(benzyloxy)-2-methylpropanamide (2.0 g, 4.2 mmol) and DMAP (100 mg) in MeCN (40 mL) at room temperature drop wise. The reaction mixture was heat at 70° C. and stirred for 3 h. The reaction mixture was poured into a cold solution of concentrated aqueous $NaHCO_3$ (100 mL). The organics were extracted with $CH_2Cl_2$ (3×50 mL). The organic solution was washed with brine, dried over $MgSO_4$, the solvent was evaporated, and residue was purified by column chromatography (silica gel, $CH_2Cl_2$/MeOH/$NH_4OH$, 30:1:0.5%) to prepare (+/−)-2-((3,4-trans)-1-benzyl-4-methylpyrrolidin-3-yl)-7-(2-hydroxypropan-2-yl)imidazo[5,1-f][1,2,4]triazin-4(3H)-one (135 mg, 9% yield). Purity (HPLC): 96.6%; $^{1}$H NMR (300 MHz, CDCl$_3$/TMS): δ 7.77 (s, 1H), 7.39-7.29 (m, 5H), 3.85 (d, J=12 Hz, 1H), 3.58 (d, J=12 Hz, 1H), 3.42 (t, J=8 Hz, 1H), 3.01 (d, J=10 Hz, 1H), 2.76-2.74 (m, 1H), 2.57-2.43 (m, 2H), 1.96 (t, J=10 Hz, 1H), 1.72 (d, 5 Hz, 6H), 1.22 (d, J=7 Hz, 3H); $^{13}$C NMR (75 MHz, CDCl$_3$/TMS): δ 153.9, 149.4, 136.9, 128.6, 128.5, 127.5, 126.8, 119.4, 70.4, 60.9, 59.1, 55.8, 53.3, 47.8, 38.4, 28.5, 28.3, 20.1.

(+/−)-2-((3,4-trans)-1-benzyl-4-methylpyrrolidin-3-yl)-7-(2-hydroxypropan-2-yl)imidazo[5,1-f][1,2,4]triazin-4(3H)-one was purified by Chiralcel OJ-H, 250×20 mm, 5 um (15 mg loading; 0.1% TEA in n-Hexane: Ethanol (90:10) as mobile phase) to obtain pure fraction 1 ((−)-2-((3,4-trans)-1-benzyl-4-methylpyrrolidin-3-yl)-7-(2-hydroxypropan-2-yl)imidazo[5,1-f][1,2,4]triazin-4(3H)-one) and pure fraction 2 ((+)-2-((3,4-trans)-1-benzyl-4-methylpyrrolidin-3-yl)-7-(2-hydroxypropan-2-yl)imidazo[5,1-f][1,2,4]triazin-4(3H)-one). Characterization details of both fractions are as follows:

(−)-2-((3,4-trans)-1-benzyl-4-methylpyrrolidin-3-yl)-7-(2-hydroxypropan-2-yl)imidazo[5,1-f][1,2,4]triazin-4(3H)-one: $^{1}$H-NMR (DMSO d$_6$, 400 MHz): δ 7.65 (s, 1H), 7.32 (s, 5H), 5.15 (br s, 1H), 3.66 (q, 2H), 2.99 (t, 1H), 2.85-2.60 (m, 3H), 2.59-2.50 (m, 1H), 2.25 (t, 1H), 1.63 (s, 6H), 1.12 (d, 3H); Mass (ESI): 368.5 [M$^+$+1]; LC-MS: 98.01%; 368.5 (M$^4$+1); (column; X Select C-18, (50×3.0 mm, 3.5µ); RT 2.81 min. ACN: 5 mM NH$_4$OAc; 0.8 ml/min); UPLC (purity): 98.29%; (column; Acquity BEH C-18, 50×2.1 mm, 1.7 g; RT 1.36 min. 0.025% TFA (Aq): ACN:Water; 0.50 ml/min.; Chiral HPLC: 100% ee R$_t$=14.72 min (Chiralcel OJ-H, 250×4.6 mm, 5µ; mobile phase (A) 0.1% TEA in n-Hexane (B) ethanol (A:B: 90:10); flow Rate: 1.00 mL/min); Optical rotation [α]$_D^{21}$: −12.64° (c=0.125, DCM).

(+)-2-((3,4-trans)-1-benzyl-4-methylpyrrolidin-3-yl)-7-(2-hydroxypropan-2-yl)imidazo[5,1-f][1,2,4]triazin-4(3H)-one: $^{1}$H-NMR (DMSO d$_6$, 400 MHz): δ 7.65 (s, 1H), 7.32 (s, 5H), 5.15 (br s, 1H), 3.66 (q, 2H), 2.99 (t, 1H), 2.85-2.60 (m, 4H), 2.25 (t, 1H), 1.63 (s, 6H), 1.12 (d, 3H); Mass (ESI): 368.5 [M$^+$+1]; LC-MS: 98.81%; 368.5 (M$^+$+1); (column; X select C-18, (50×3.0 mm, 3.5µ); RT 2.82 min. ACN: 5 mM NH$_4$OAc; 0.8 ml/min); UPLC (purity): 97.17%; (column; Acquity BEH C-18, 50×2.1 mm, 1.7µ; RT 1.36 min. 0.025% TFA (Aq): ACN:Water; 0.50 ml/min.; Chiral HPLC: 96.74% ee R$_t$=16.74 min (Chiralcel 250×4.6 mm, 5µ; mobile phase (A) 0.1% TEA in n-Hexane (B) ethanol (A:B: 90:10); flow Rate: 1.00 mL/min); Optical rotation [α]$_D^{21}$: 21.44° (c=0.125, DCM).

xxxx. 2-((3,4-trans)-1-benzyl-4-methylpyrrolidin-3-yl)-7-(tetrahydro-2H-pyran-3-yl)imidazo[5,1-f][1,2,4]triazin-4(3H)-one

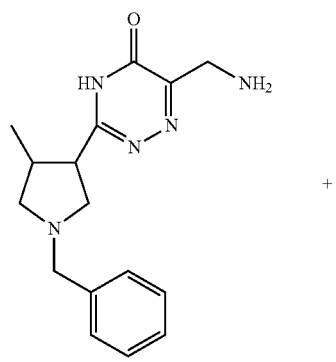

+

Synthesis of N-((3-((3,4-trans)-1-benzyl-4-methylpyrrolidin-3-yl)-5-oxo-4,5-dihydro-1,2,4-triazin-6-yl)methyl)tetrahydro-2H-pyran-3-carboxamide

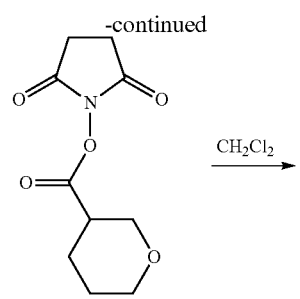

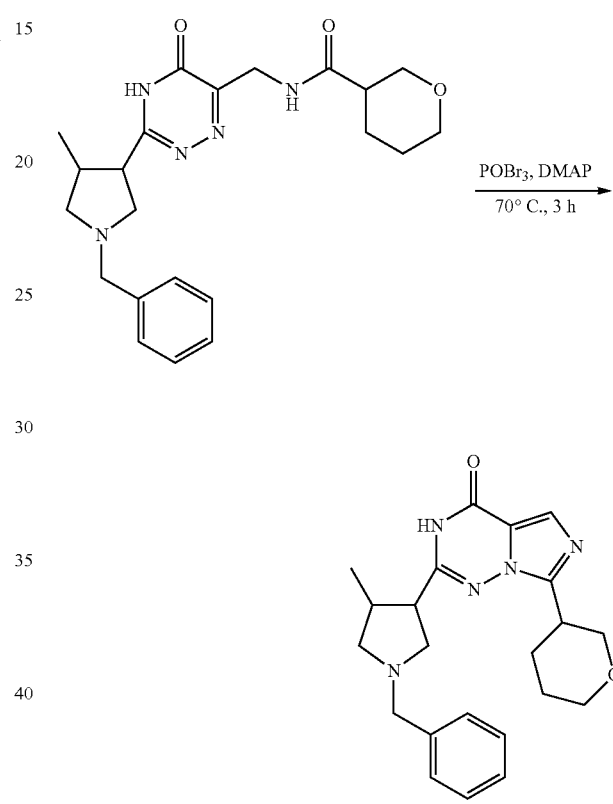

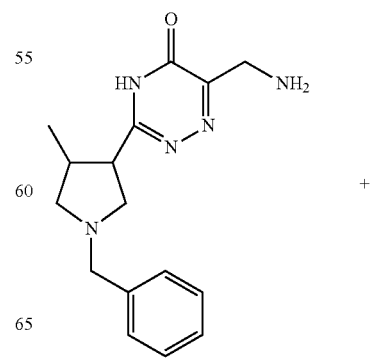

+

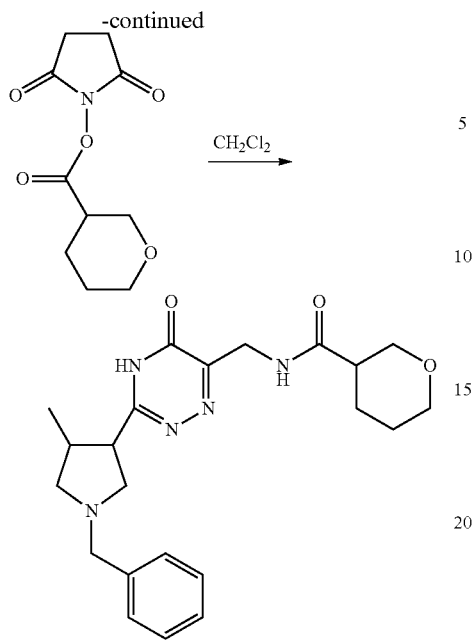

The mixture of (+/−)-6-(aminomethyl)-3-((3,4-trans)-1-benzyl-4-methylpyrrolidin-3-yl)-1,2,4-triazin-5(4H)-one (1.0 g, 3.3 mmol) and 2,5-dioxopyrrolidin-1-yl tetrahydro-2H-pyran-3-carboxylate (0.99 g, 4.4 mmol) in CH$_2$Cl$_2$ (50 mL) was stirred at room temperature overnight. The precipitate was filtered, the filtrate was concentrated and the residue was purified by column chromatography (silica gel, CH$_2$Cl$_2$/MeOH, 10:1). The obtained product (1.63 g) was dissolved in CH$_2$Cl$_2$ (50 mL) and washed with water (3×20 mL). The aqueous solution was extracted with chloroform (4×100 mL). The CH$_2$Cl$_2$ solution and chloroform extracts were combined and the solvents were evaporated to prepare N-((3-((3,4-trans)-1-benzyl-4-methylpyrrolidin-3-yl)-5-oxo-4,5-dihydro-1,2,4-triazin-6-yl)methyl)tetrahydro-2H-pyran-3-carboxamide (750 mg, 55% yield). $^1$H NMR (300 MHz, CDCl$_3$/TMS): δ 7.42-7.34 (m, 5H), 4.37 (d, 2 Hz, 1H), 4.07-3.58 (m, 4H), 3.51-3.27 (m, 6H), 3.00 (m, 1H), 2.63 (m, 1H), 2.55 (m, 2H), 2.00-1.50 (m, 5H), 1.09 (d, J=6 Hz, 3H).

Synthesis of 2-((3,4-trans)-1-benzyl-4-methylpyrrolidin-3-yl)-7-(tetrahydro-2H-pyran-3-yl)imidazo[5,1-f][1,2,4]triazin-4(3H)-one

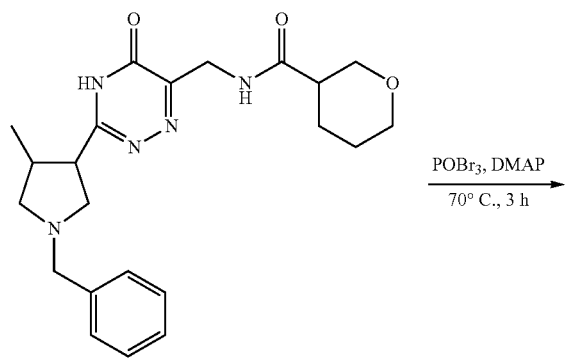

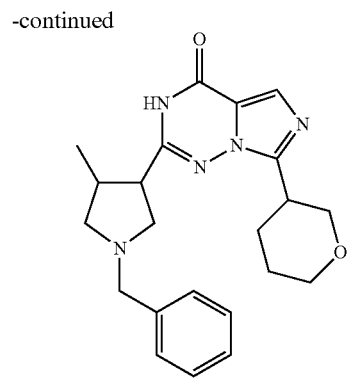

Phosphorous oxybromide (1.57 g, 5.4 mmol) was dissolved in MeCN (10 mL) and the solution was added to N-((3-((3,4-trans)-1-benzyl-4-methylpyrrolidin-3-yl)-5-oxo-4,5-dihydro-1,2,4-triazin-6-yl)methyl)tetrahydro-2H-pyran-3-carboxamide (750 mg, 1.8 mmol) and DMAP (50 mg) in MeCN (30 mL) at room temperature drop-wise. The reaction mixture was heat up to 70° C. and stirred for 3 h. The reaction mixture was purred into the ice-cold concentrated aqueous solution of NaHCO$_3$ (100 mL). The organics were extracted with CH$_2$Cl$_2$ (3×50 mL), washed with brine, and dried over MgSO$_4$. The CH$_2$Cl$_2$ solvent was evaporated and residue was purified by column chromatography (silica gel, CH$_2$Cl$_2$/MeOH/NH$_4$OH, 10:1:1%) to prepare 2-((3,4-trans)-1-benzyl-4-methylpyrrolidin-3-yl)-7-(tetrahydro-2H-pyran-3-yl)imidazo[5,1-f][1,2,4]triazin-4 (3H)-one as a colorless glass (330 mg, 46% yield). Purity by HPLC: 95.9%; $^1$H NMR (300 MHz, CDCl$_3$/TMS): δ 7.73 (s, 1H), 7.73-7.21 (m, 5H), 4.07 (m, 1H), 3.96-3.93 (m, 1H), 3.79-3.74 (m, 1H), 3.63-3.43 (m, 4H), 3.28 (t, J=8.5 Hz, 1H), 2.94 (d, J=9.9 Hz, 1H4), 2.71 (m, 1H), 2.58 (m, 1H), 2.41-2.39 (m, 1H), 2.09-1.88 (m, 3H), 1.77-1.72 (m, 2H), 1.16 (d, =8.8 Hz, 3H); $^{13}$C NMR (75 MHz, CDCl$_3$/TMS): δ 148.9, 148.4, 140.9, 140.8, 131.8, 123.2, 123.1, 122.1, 113.4, 64.8, 64.7, 62.8, 55.7, 53.9, 50.6, 42.5, 32.9, 28.7, 28.6, 22.2, 21.9, 20.1, 14.7 (mixture of four stereoisomers).

2-((3,4-trans)-1-benzyl-4-methylpyrrolidin-3-yl)-7-(tetrahydro-2H-pyran-3-yl)imidazo[5,1-f][1,2,4]triazin-4(3H)-one was purified by Chiralpak AD-H, 250×20 mm, 5 um (35 mg loading; 0.1% TEA in n-Hexane: Ethanol (90:10) as mobile phase) to obtain pure fraction 1 (2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 1), pure fraction 2 (2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 2) and fraction 3 (2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 3). Characterization details of all fractions are as follows:

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 1:
$^1$H-NMR (CDCl3, 400 MHz): δ 7.79 (s, 1H), 7.37 (s, 4H), 7.29 (s, 1H), 4.13 (t, 1H), 4.01 (d, 1H), 3.83 (d, 1H), 3.71 (t, 1H), 3.58-3.50 (m, 3H), 3.41 (t, 1H), 2.99 (d, 1H), 2.75 (d, 1H), 2.52-2.49 (m, 1H), 2.41 (q, 1H), 2.16-2.02 (m, 2H), 1.91 (t, 1H), 1.87-1.70 (m, 3H), 1.20 (d, 3H); Chiral HPLC: 100% ee R$_f$=21.15 min (Chiralpak IC, 250×4.6 mm, 5μ; mobile phase (A) 0.1% TEA in n-Hexane (B) ethanol (A:B: 80:20); flow Rate: 1.00 mL/min); Optical rotation [α]$_D^{25}$: +19.71° (c=0.5, DCM).

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 2:

$^1$H-NMR (CDCl$_3$, 400 MHz): δ 7.79 (s, 1H), 7.37 (s, 4H), 7.29 (s, 1H), 4.13 (dd, 1H), 4.01 (d, 1H), 3.83 (d, 1H), 3.71 (t, 1H), 3.58-3.50 (m, 3H), 3.41 (t, 1H), 2.99 (d, 1H), 2.75 (d, 1H), 2.52-2.49 (m, 1H), 2.41 (q, 1H), 2.16-2.02 (m, 2H), 1.91 (t, 1H), 1.87-1.70 (m, 3H), 1.20 (d, 3H); Chiral HPLC: 98.44% ee R$_t$=22.79 min (Chiralpak IC, 250×4.6 mm, 5μ; mobile phase (A) 0.1% TEA in n-Hexane (B) ethanol (A:B: 80:20); flow Rate: 1.00 mL/min); Optical rotation [α]$_D^{25}$: −15.46° (c=0.5, DCM).

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 3:

$^1$H-NMR (CDCl$_3$, 400 MHz): δ 7.79 (s, 1H), 7.37 (s, 4H), 7.29-2.5 (m, 2H), 4.13 (dd, 1H), 4.01 (d, 1H), 3.83 (d, 1H), 3.61-3.40 (m, 5H), 2.99 (d, 1H), 2.75 (d, 1H), 2.52-2.49 (m, 1H), 2.41 (q, 1H), 2.16-2.02 (m, 2H), 1.91 (t, 1H), 1.87-1.70 (m, 2H), 1.20 (d, 3H), 0.01 (s, 2H); Chiral HPLC: 96.69% ee R$_t$=24.95 min (Chiralpak IC, 250×4.6 mm, 5μ; mobile phase (A) 0.1% TEA in n-Hexane (B) ethanol (A:B: 80:20); flow Rate: 1.00 mL/min); Optical rotation [α]$_D^{25}$: −17.65° (c=0.5, DCM).

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. (+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one or a pharmaceutically acceptable salt thereof.

* * * * *